US006518256B1

(12) United States Patent
Wang et al.

(10) Patent No.: US 6,518,256 B1
(45) Date of Patent: Feb. 11, 2003

(54) COMPOUNDS AND METHODS FOR THERAPY AND DIAGNOSIS OF LUNG CANCER

(75) Inventors: Tongtong Wang, Medina, WA (US); Liqun Fan, Bellevue, WA (US); Michael D. Kalos, Seattle, WA (US); Chaitanya S. Bangur, Seattle, WA (US); Nancy A. Hosken, Seattle, WA (US); Gary R. Fanger, Mill Creek, WA (US)

(73) Assignee: Corixa Corporation, Seattle, WA (US)

( * ) Notice: Subject to any disclaimer, the term of this patent is extended or adjusted under 35 U.S.C. 154(b) by 0 days.

(21) Appl. No.: 09/542,615

(22) Filed: Apr. 4, 2000

Related U.S. Application Data

(63) Continuation-in-part of application No. 09/510,376, filed on Feb. 22, 2000, which is a continuation-in-part of application No. 09/480,884, filed on Jan. 10, 2000, which is a continuation-in-part of application No. 09/476,496, filed on Dec. 30, 1999, which is a continuation-in-part of application No. 09/466,396, filed on Dec. 17, 1999, which is a continuation-in-part of application No. 09/285,479, filed on Apr. 2, 1999, and a continuation of application No. PCT/US99/05798, filed on Mar. 17, 1999, which is a continuation-in-part of application No. 09/221,107, filed on Dec. 22, 1998, which is a continuation-in-part of application No. 09/123,912, filed on Jul. 27, 1998, now Pat. No. 6,312,695, which is a continuation-in-part of application No. 09/040,802, filed on Mar. 18, 1998, now abandoned.

(51) Int. Cl.[7] .................. A01N 43/04; C12N 15/63; C12N 5/00; C07H 21/04; A61K 39/00

(52) U.S. Cl. ............... 514/44; 435/320.1; 435/325; 435/455; 536/23.1; 536/23.5; 424/184.1

(58) Field of Search .................. 435/320.1, 325, 435/455; 536/23.1, 23.5; 514/44; 424/184.1, 93.2

(56) References Cited

U.S. PATENT DOCUMENTS

| 5,705,159 A | 1/1998 | Irie et al. ............... 424/185.1 |
| 5,783,422 A | 7/1998 | Suminami et al. .......... 435/69.3 |
| 6,297,364 B1 | 10/2001 | Chen et al. ................ 536/23.1 |

FOREIGN PATENT DOCUMENTS

| EP | 0695760 A1 | 2/1996 |
| WO | WO 91/18926 | 12/1991 |
| WO | WO 94/06929 | 3/1994 |
| WO | WO 95/21862 | 8/1995 |
| WO | WO96/02552 | 2/1996 |
| WO | WO 96/28473 | 9/1996 |
| WO | WO96/30389 | 10/1996 |
| WO | WO 97/07244 | 2/1997 |
| WO | WO 98/35985 | 8/1998 |
| WO | WO 98/46788 | 10/1998 |
| WO | WO 99/38973 | 8/1999 |
| WO | WO 99/47674 | 9/1999 |

OTHER PUBLICATIONS

Rudinger et al., Characteristics of the amino acids as components of a peptide hormone sequence, 1976, Peptide Hormones, pp. 1–7.*
Kaye et al., A single amino acid substitution results in a retinoblastoma protein defective in phosphylation and oncoprotein binding, Sep. 1990, Proc. Natl. Acad. Sci., vol. 87, pp. 6922–6926.*
Deonarain, Ligand–targeted receptor–mediated vectors for gene delivery, 1998, Exp. Opin. Ther., vol. 8, No. 1, pp. 53–69.*
Verma et al., Gene therapy–promises, problems, and prospects, Sep. 18, 1997, Nature, vol. 389, pp. 239–242.*
Crystal et al., Transfer of Genes to Humans: Early Lessons and Obstacles to Success, 1995, Science, vol. 270, pp. 404–410.*
Eck et al., Gene–Based Therapy, 1996, Goodman & Gilman's, Ninth Edition, pp. 77–101.*
Ohgi et al., Expression of RNase Rh from Rhizopus niveus in Yest and Characterization of the Secreted Proteins, 1991, J. Biochem., vol. 109, pp. 776–785.*
Mueller–Pillasch et al., Jul. 1997, AC:000425.*
Mueller–Pillasch et al., Sep. 1998, AC: U97188.*
Geneseq Accession No. AAC66035, Feb. 21, 2001.
Geneseq Accession No. AAZ36150, Dec. 7, 1999.
Jolly, D., "Viral vector systems for gene therapy," *Cancer Gene Therapy* 1(1):51–64, 1994.
GenBank Accession No. AF043977, Jun. 23, 1999.
GenBank Accession No. U85946, Jul. 30, 1999.
Geneseq Accession No. AAZ24653, Dec. 7, 1999.
Gruber et al., "Molecular cloning and transmembrane structure of hCLCA2 from human lung, trachea, and mammary gland," *Am. J. Physiol.* 276(Cell Physiol 45):C1261–C1270, 1999.
Guo et al., "Identification and characterization of homologues of the Exocyst component Sec10p," *FEBS Letters* 404(2–3):135–139, 1997.
Brass et al., "Translation initiation factor eIF–4gamma is encoded by an amplified gene and induces an immune response in squamous cell lung carcinoma," *Human Molecular Genetics*, 6(1): 33–39, 1997.
Database EMBLest17 Accession No. AA340797:EST46165 Fetal kidney II *Homo sapiens* cDNA 3' end, Apr. 18, 1997.
Database EMBLest17 Accession No. W22264:Human retina cDNATsp–509I–cleaved sublibrary *Homo sapiens* cDNA not directional, May 9, 1996.

(List continued on next page.)

Primary Examiner—Scott D. Priebe
Assistant Examiner—Shin-Lin Chen
(74) Attorney, Agent, or Firm—SEED Intellectual Property Law Group PLLC

(57) ABSTRACT

Compounds and methods for the treatment and diagnosis of lung cancer are provided. The inventive compounds include polypeptides containing at least a portion of a lung tumor protein. Vaccines and pharmaceutical compositions for immunotherapy of lung cancer comprising such polypeptides, or DNA molecules encoding such polypeptides, are also provided, together with DNA molecules for preparing the inventive polypeptides.

9 Claims, No Drawings

OTHER PUBLICATIONS

Finch et al., "Identification of a cloned sequence activated during multi-stage carcinogenesis in mouse skin," *Carcinogenesis,* 12(8):1519–1522, Aug. 1991.

Gerhold and Caskey, "It's the genes! EST access to human genome content," *BioEssays* 18(12):973–981, 1996.

Russell and Barton, "Structural features can be unconserved in proteins with similar folds," *J. Mol. Biol.* 244:332–350, 1994.

Wells and Peitsch, "The chemokine information source: identification and characterization of novel chemokines using the WorldWideWeb and expressed sequence tag databases," *Journal of Leukocyte Biology* 61:545–550, May 1997.

Baldi et al., "Differential expression of Rb2/p130 and p107 in normal human tissues and in primary lung cancer," *Clinical Cancer Research* 3(10):1691–1697, Oct. 1997.

Database EMBL Nucleotide and Protein Sequence, Accession No. AI468638, Mar. 17, 1999.

Davidson et al., "Lung tumours immunoreactive for parathyroid hormone related peptide: analysis of serum calcium levels and tumour type," *Journal of Pathology* 178:398–401, Jan. 1996.

Hara et al., "Characterization of cell phenotype by a novel cDNA library subtraction system:expression of CD8α in a mast cell–derived interleukin–4–dependent cell line," *Blood* 84(1):189–199, Jul. 1, 1994.

Henderson et al., "Identification of lung tumor antigens for cancer immunotherapy: immunological and molecular approaches," *Immunological Investigation* 29(2):87–91, May 2000.

Hogan et al., "The peptide recognized by HLA–A68.2–restricted, squamous cell carcinoma of the lung–specific cytotoxic T lymphocytes is derived from a mutated elongation factor 2 gene," *Cancer Research* 58(22):5144–5150, Nov. 15, 1998.

Hu et al., "A small proline–rich protein, spr1: specific marker for squamous lung carcinoma," *Lung Cancer* 20:25–30, 1998.

Lelievre et al., "Structural properties of chimeric peptides containing a T–cell epitope linked to a fusion peptide and their importance for in vivo induction of cytotoxic T–cell responses," *European Journal of Biochemistry* 249(3):895–904, 1997.

Marshall and Hodgson, "DNA chips: an array of possibilities," *Nature Biotechnology* 16:27, 31 Jan. 1998.

Pastor et al., "Diagnostic value of SCC, CEA and CYFRA 21.1 in lung cancer: a Bayesian analysis," *Eur. Respir J.* 10(3):603–609, Mar. 1997.

Rammensee et al., "MHC ligands and peptide motifs: first listing," *Immunogenetics* 41:178–228, 1995.

Ramsay, G., "DNA chips: state–of–the art," *Nature Biotechnology* 16:40–44, Jan. 1998.

Ruppert et al., "Prominent role of secondary anchor residues in peptide binding to HLA–A2.1 molecules," *Cell* 74:929–937, Sep. 10, 1993.

Skeiky et al., "Cloning, expression and immunological evaluation of two putative secreted serine protease antigens of *Mycobacterium tuberculosis*," *Infection and Immunity* 67(8):3998–4007, Aug. 1999.

Theobald et al., "Targeting p53 as a general tumor antigen," *Proc. Natl. Acad. Sci. USA* 92:11993–11997, Dec. 1995.

Visseren et al., "Indentification of HLA–A *0201–restricted CTL epitopes encoded by the tumor–specific MAGE–2 gene product," *International Journal of Cancer* 73(1):125–130, 1997.

Wang et al., "Identification of genes differentially over–expressed in lung squamous cell carcinoma using combination of cDNA subtraction and microarray analysis," *Oncogene* 19(12):1519–1528, Mar. 16, 2000.

\* cited by examiner

COMPOUNDS AND METHODS FOR THERAPY AND DIAGNOSIS OF LUNG CANCER

REFERENCE TO RELATED APPLICATIONS

This application is a continuation-in-part of U.S. patent application Ser. No. 09/510,376, filed Feb. 22, 2000, which is a continuation-in-part of U.S. patent application Ser. No. 09/480,884, filed Jan. 10, 2000, which is a continuation-in-part of U.S. patent application Ser. No. 09/476,496, filed Dec. 30, 1999, which is a continuation-in-part of U.S. patent application Ser. No. 09/466,396, filed Dec. 17, 1999, which is a continuation-in-part of U.S. patent application Ser. No. 09/285,479, filed Apr. 2, 1999, and is a continuation of and claims prority from PCT Application No. PCT/US99/05798, filed Mar. 17, 1999, which is a continuation-in-part and claims prority from U.S. patent application Ser. No. 09/221,107, filed Dec. 22, 1998, which is a continuation-in-part of U.S. patent application Ser. No. 09/123,912, filed Jul. 27, 1998 now U.S. Pat. No. 6,312,695, which is a continuation-in-part of U.S. patent application Ser. No. 09/040,802, filed Mar. 18, 1998 abandoned May 23, 2001.

TECHNICAL FIELD

The present invention relates generally to therapy and diagnoses of cancer, such as lung cancer. The invention is more specifically related to polypeptides comprising at least a portion of a lung tumor protein, and to polynucleotides encoding such polypeptidies. Such polypeptides and polynucleotides may be used in vaccines and pharmaceutical compositions for prevention and treatment of lung cancer, and for the diagnosis and monitoring of such cancers.

BACKGROUND OF THE INVENTION

Lung cancer is the primary cause of cancer death among both men and women in the U.S., with an estimated 172,000 new cases being reported in 1994. The five-year survival rate among all lung cancer patients, regardless of the stage of disease at diagnosis, is only 13%. This contrasts with a five-year survival rate of 46% among cases detected while the disease is still localized. However, only 16% of lung cancers are discovered before the disease has spread.

Early detection is difficult since clinical symptoms are often not seen until the disease has reached an advanced stage. Currently, diagnosis is aided by the use of chest x-rays, analysis of the type of cells contained in sputum and fiberoptic examination of the bronchial passages. Treatment regimens are determined by the type and stage of the cancer, and include surgery, radiation therapy and/or chemotherapy. In spite of considerable research into therapies for the disease, lung cancer remains difficult to treat.

Accordingly, there remains a need in the art for improved vaccines, treatment methods and diagnostic techniques for lung cancer.

SUMMARY OF THE INVENTION

Briefly stated, the present invention provides compositions and methods for the diagnosis and therapy of cancer, such as lung cancer. In one aspect, the present invention provides polypeptides comprising at least a portion of a lung tumor protein, or a variant thereof. Certain portions and other variants are immunogenic, such that the ability of the variant to react with antigen-specific antisera is not substantially diminished. Within certain embodiments, the polypeptide comprises a sequence that is encoded by a polynucleotide sequence selected from the group consisting of: (a) sequences recited in any one of SEQ ID NO: 1–3, 6–8, 10–13, 15–27, 29, 30, 32, 34–49, 51, 52, 54, 55, 57–59, 61–69, 71, 73, 74, 77, 78, 80–82, 84, 86–96, 107–109, 111, 113, 125, 127, 128, 129, 131–133, 142, 144, 148–151, 153, 154, 157, 158, 160, 167, 168, 171, 179, 182, 184–186, 188–191, 193, 194, 198–207, 209, 210, 213, 214, 217, 220–224, 253–337, 345, 347 and 349; (b) variants of a sequence recited in any one of SEQ ID NO: 1–3, 6–8, 10–13, 15–27, 29, 30, 32, 34–49, 51, 52, 54, 55, 57–59, 61–69, 71, 73, 74, 77, 78, 80–82, 84, 86–96, 107–109, 111, 113, 125, 127, 128, 129, 131–133, 142, 144, 148–151, 153, 154, 157, 158, 160, 167, 168, 171, 179, 182, 184–186, 188–191, 193, 194, 198–207, 209, 210, 213, 214, 217, 220–224, 253–337, 345, 347 and 349; and (c) complements of a sequence of (a) or (b). In specific embodiments, the polypeptides of the present invention comprise at least a portion of a tumor protein that includes an amino acid sequence selected from the group consisting of sequences recited in any one of SEQ ID NO: 152, 155, 156, 165, 166, 169, 170, 172, 174, 176, 226–252, 338–344 and 346, and variants thereof.

The present invention further provides polynucleotides that encode a polypeptide as described above, or a portion thereof (such as a portion encoding at least 15 amino acid residues of a lung tumor protein), expression vectors comprising such polynucleotides and host cells transformed or transfected with such expression vectors.

Within other aspects, the present invention provides pharmaceutical compositions comprising a polypeptide or polynucleotide as described above and a physiologically acceptable carrier.

Within a related aspect of the present invention, vaccines for prophylactic or therapeutic use are provided. Such vaccines comprise a polypeptide or polynucleotide as described above and an immunostimulant.

The present invention further provides pharmaceutical compositions that comprise: (a) an antibody or antigen-binding fragment thereof that specifically binds to a lung tumor protein; and (b) a physiologically acceptable carrier.

Within further aspects, the present invention provides pharmaceutical compositions comprising: (a) an antigen presenting cell that expresses a polypeptide as described above and (b) a pharmaceutically acceptable carrier or excipient. Antigen presenting cells include dendritic cells, macrophages, monocytes, fibroblasts and B cells.

Within related aspects, vaccines are provided that comprise: (a) an antigen presenting cell that expresses a polypeptide as described above, and (b) an immunostimulant.

The present invention further provides, in other aspects, fusion proteins that comprise at least one polypeptide as described above, as well as polynucleotides encoding such fusion proteins.

Within related aspects, pharmaceutical compositions comprising a fusion protein, or a polynucleotide encoding a fusion protein, in combination with a physiologically acceptable carrier are provided.

Vaccines are further provided, within other aspects, that comprise a fusion protein, or a polynucleotide encoding a fusion protein, in combination with an immunostimulant.

Within further aspects, the present invention provides methods for inhibiting the development of a cancer in a patient, comprising administering to a patient a pharmaceutical composition or vaccine as recited above.

The present invention further provides, within other aspects, methods for removing tumor cells from a biological sample, comprising contacting a biological sample with T cells that specifically react with a lung tumor protein, wherein the step of contacting is performed under conditions and for a time sufficient to permit the removal of cells expressing the protein from the sample.

Within related aspects, methods are provided for inhibiting the development of a cancer in a patient, comprising administering to a patient a biological sample treated as described above.

Methods are further provided, within other aspects, for stimulating and/or expanding T cells specific for a lung tumor protein, comprising contacting T cells with one or more of: (i) a polypeptide as described above; (ii) a polynucleotide encoding such a polypeptide; and/or (iii) an antigen presenting cell that expresses such a polypeptide; under conditions and for a time sufficient to permit the stimulation and/or expansion of T cells. Determined T cell populations comprising T cells prepared as described above are also provided.

Within further aspects, the present invention provides methods for inhibiting the development of a cancer in a patient, comprising administering to a patient an effective amount of a T cell population as described above.

The present invention further provides methods for inhibiting the development of a cancer in a patient, comprising the steps of: (a) incubating CD4$^+$ and/or CD8$^+$ T cells determined from a patient with one or more of: (i) a polypeptide comprising at least an immunogenic portion of a lung tumor protein; (ii) a polynucleotide encoding such a polypeptide; and (iii) an antigen-presenting cell that expressed such a polypeptide; and (b) administering to the patient an effective amount of the proliferated T cells, and thereby inhibiting the development of a cancer in the patient. Proliferated cells may, but need not, be cloned prior to administration to the patient.

Within further aspects, the present invention provides methods for determining the presence or absence of a cancer in a patient, comprising: (a) contacting a biological sample obtained from a patient with a binding agent that binds to a polypeptide as recited above; (b) detecting in the sample an amount of polypeptide that binds to the binding agent; and (c) comparing the amount of polypeptide with a predetermined cut-off value, and therefrom determining the presence or absence of a cancer in the patient. Within preferred embodiments, the binding agent is an antibody, more preferably a monoclonal antibody. The cancer may be lung cancer.

The present invention also provides, within other aspects, methods for monitoring A) the progression of a cancer in a patient. Such methods comprise the steps of: (a) contacting a biological sample obtained from a patient at a first point in time with a binding agent that binds to a polypeptide as recited above; (b) detecting in the sample an amount of polypeptide that binds to the binding agent; (c) repeating steps (a) and (b) using a biological sample obtained from the patient at a subsequent point in time; and (d) comparing the amount of polypeptide detected in step (c) with the amount detected in step (b) and therefrom monitoring the progression of the cancer in the patient.

The present invention further provides, within other aspects, methods for determining the presence or absence of a cancer in a patient, comprising the steps of: (a) contacting a biological sample obtained from a patient with an oligonucleotide that hybridizes to a polynucleotide that encodes a lung tumor protein; (b) detecting in the sample a level of a polynucleotide, preferably mRNA, that hybridizes to the oligonucleotide; and (c) comparing the level of polynucleotide that hybridizes to the oligonucleotide with a predetermined cut-off value, and therefrom determining the presence or absence of a cancer in the patient. Within certain embodiments, the amount of mRNA is detected via polymerase chain reaction using, for example, at least one oligonucleotide primer that hybridizes to a polynucleotide encoding a polypeptide as recited above, or a complement of such a polynucleotide. Within other embodiments, the amount of mRNA is detected using a hybridization technique, employing an oligonucleotide probe that hybridizes to a polynucleotide that encodes a polypeptide as recited above, or a complement of such a polynucleotide.

In related aspects, methods are provided for monitoring the progression of a cancer in a patient, comprising the steps of: (a) contacting a biological sample obtained from a patient with an oligonucleotide that hybridizes to a polynucleotide that encodes a lung tumor protein; (b) detecting in the sample an amount of a polynucleotide that hybridizes to the oligonucleotide; (c) repeating steps (a) and (b) using a biological sample obtained from the patient at a subsequent point in time; and (d) comparing the amount of polynucleotide detected in step (c) with the amount detected in step (b) and therefrom monitoring the progression of the cancer in the patient.

Within further aspects, the present invention provides antibodies, such as monoclonal antibodies, that bind to a polypeptide as described above, as well as diagnostic kits comprising such antibodies. Diagnostic kits comprising one or more oligonucleotide probes or primers as described above are also provided. These and other aspects of the present invention will become apparent upon reference to the following detailed description and attached drawings. All references disclosed herein are hereby incorporated by reference in their entirety as if each was incorporated individually.

Sequence Identifiers

SEQ ID NO: 1 is the determined cDNA sequence for LST-S-1-2.
SEQ ID NO: 2 is the determined cDNA sequence for LST-S-1-28.
SEQ ID NO: 3 is the determined cDNA sequence for LST-S-1-90.
SEQ ID NO: 4 is the determined cDNA sequence for LST-S-1-144.
SEQ ID NO: 5 is the determined cDNA sequence for LST-S-1-133.
SEQ ID NO: 6 is the determined cDNA sequence for LST-S-1-169.
SEQ ID NO: 7 is the determined cDNA sequence for LST-S-2-6.
SEQ ID NO: 8 is the determined cDNA sequence for LST-S-2-11.
SEQ ID NO: 9 is the determined cDNA sequence for LST-S-2-17.
SEQ ID NO: 10 is the determined cDNA sequence for LST-S-2-25.
SEQ ID NO: 11 is the determined cDNA sequence for LST-S-2-39.
SEQ ID NO: 12 is a first determined cDNA sequence for LST-S-2-43.
SEQ ID NO: 13 is a second determined cDNA sequence for LST-S-2-43.
SEQ ID NO: 14 is the determined cDNA sequence for LST-S-2-65.
SEQ ID NO: 15 is the determined cDNA sequence for LST-S-2-68.

SEQ ID NO: 16 is the determined cDNA sequence for LST-S-2-72.
SEQ ID NO: 17 is the determined cDNA sequence for LST-S-2-74.
SEQ ID NO: 18 is the determined cDNA sequence for LST-S-2-103.
SEQ ID NO: 19 is the determined cDNA sequence for LST-S-2-N1-1F.
SEQ ID NO: 20 is the determined cDNA sequence for LST-S-2-N1-2A.
SEQ ID NO: 21 is the determined cDNA sequence for LST-S-2-N1-4H.
SEQ ID NO: 22 is the determined cDNA sequence for LST-S-2-N1-5A.
SEQ ID NO: 23 is the determined cDNA sequence for LST-S-2-N1-6B.
SEQ ID NO: 24 is the determined cDNA sequence for LST-S-2-N1-7B.
SEQ ID NO: 25 is the determined cDNA sequence for LST-S-2-N1-7H.
SEQ ID NO: 26 is the determined cDNA sequence for LST-S-2-N1-8A.
SEQ ID NO: 27 is the determined cDNA sequence for LST-S-2-N1-8D.
SEQ ID NO: 28 is the determined cDNA sequence for LST-S-2-N1-9A.
SEQ ID NO: 29 is the determined cDNA sequence for LST-S-2-N1-98.
SEQ ID NO: 30 is the determined cDNA sequence for LST-S-2-N1-10A.
SEQ ID NO: 31 is the determined cDNA sequence for LST-S-2-N1-11G.
SEQ ID NO: 32 is the determined cDNA sequence for LST-S-2-N1-11A.
SEQ ID NO: 33 is the determined cDNA sequence for LST-S-2-N1-12C.
SEQ ID NO: 34 is the determined cDNA sequence for LST-S-2-N1-12E.
SEQ ID NO: 35 is the determined cDNA sequence for LST-S-2-B1-3D.
SEQ ID NO: 36 is the determined cDNA sequence for LST-S-2-B1-6C.
SEQ ID NO: 37 is the determined cDNA sequence for LST-S-2-B1-5D.
SEQ ID NO: 38 is the determined cDNA sequence for LST-S-2-B1-5F.
SEQ ID NO: 39 is the determined cDNA sequence for LST-S-2-B1-6G.
SEQ ID NO: 40 is the determined cDNA sequence for LST-S-2-B1-8A.
SEQ ID NO: 41 is the determined cDNA sequence for LST-S-2-B1-8D.
SEQ ID NO: 42 is the determined cDNA sequence for LST-S-2-B1-10A.
SEQ ID NO: 43 is the determined cDNA sequence for LST-S-2-B1-9B.
SEQ ID NO: 44 is the determined cDNA sequence for LST-S-2-B1-9F.
SEQ ID NO: 45 is the determined cDNA sequence for LST-S-2-B1-12D.
SEQ ID NO: 46 is the determined cDNA sequence for LST-S-2-I2-2B.
SEQ ID NO: 47 is the determined cDNA sequence for LST-S-2-I2-5F.
SEQ ID NO: 48 is the determined cDNA sequence for LST-S-2-I2-6B.
SEQ ID NO: 49 is the determined cDNA sequence for LST-S-2-I2-7F.
SEQ ID NO: 50 is the determined cDNA sequence for LST-S-2-I2-8G.
SEQ ID NO: 51 is the determined cDNA sequence for LST-S-2-I2-9E.
SEQ ID NO: 52 is the determined cDNA sequence for LST-S-2-I2-12B.
SEQ ID NO: 53 is the determined cDNA sequence for LST-S-2-H2-2C.
SEQ ID NO: 54 is the determined cDNA sequence for LST-S-2-H2-1G.
SEQ ID NO: 55 is the determined cDNA sequence for LST-S-2-H2-4G.
SEQ ID NO: 56 is the determined cDNA sequence for LST-S-2-H2-3H.
SEQ ID NO: 57 is the determined cDNA sequence for LST-S-2-H2-5G.
SEQ ID NO: 58 is the determined cDNA sequence for LST-S-2-H2-9B.
SEQ ID NO: 59 is the determined cDNA sequence for LST-S-2-H2-10H.
SEQ ID NO: 60 is the determined cDNA sequence for LST-S-2-H2-12D.
SEQ ID NO: 61 is the determined cDNA sequence for LST-S-3-2.
SEQ ID NO: 62 is the determined cDNA sequence for LST-S-3-4.
SEQ ID NO: 63 is the determined cDNA sequence for LST-S-3-7.
SEQ ID NO: 64 is the determined cDNA sequence for LST-S-3-8.
SEQ ID NO: 65 is the determined cDNA sequence for LST-S-3-12.
SEQ ID NO: 66 is the determined cDNA sequence for LST-S-3-13.
SEQ ID NO: 67 is the determined cDNA sequence for LST-S-3-14.
SEQ ID NO: 68 is the determined cDNA sequence for LST-S-3-16.
SEQ ID NO: 69 is the determined cDNA sequence for LST-S-3-21.
SEQ ID NO: 70 is the determined cDNA sequence for LST-S-3-22.
SEQ ID NO: 71 is the determined cDNA sequence for LST-S-1-7.
SEQ ID NO: 72 is the determined cDNA sequence for LST-S-1-A-1E.
SEQ ID NO: 73 is the determined cDNA sequence for LST-S-1-A-1G.
SEQ ID NO: 74 is the determined cDNA sequence for LST-S-1-A-3E.
SEQ ID NO: 75 is the determined cDNA sequence for LST-S-1-A-4E.
SEQ ID NO: 76 is the determined cDNA sequence for LST-S-1-A-6D.
SEQ ID NO: 77 is the determined cDNA sequence for LST-S-1-A-8D.
SEQ ID NO: 78 is the determined cDNA sequence for LST-S-1-A-10A.
SEQ ID NO: 79 is the determined cDNA sequence for LST-S-1-A-10C.
SEQ ID NO: 80 is the determined cDNA sequence for LST-S-1-A-9D.
SEQ ID NO: 81 is the determined cDNA sequence for LST-S-1-A-10D.
SEQ ID NO: 82 is the determined cDNA sequence for LST-S-1-A-9H.
SEQ ID NO: 83 is the determined cDNA sequence for LST-S-1-A-11D.

SEQ ID NO: 84 is the determined cDNA sequence for LST-S-1-A-12D.
SEQ ID NO: 85 is the determined cDNA sequence for LST-S-1-A-11E.
SEQ ID NO: 86 is the determined cDNA sequence for LST-S-1-A-12E.
SEQ ID NO: 87 is the determined cDNA sequence for L513S (T3).
SEQ ID NO: 88 is the determined cDNA sequence for L513S contig 1.
SEQ ID NO: 89 is a first determined cDNA sequence for L514S.
SEQ ID NO: 90 is a second determined cDNA sequence for L514S.
SEQ ID NO: 91 is a first determined cDNA sequence for L516S.
SEQ ID NO: 92 is a second determined cDNA sequence for L516S.
SEQ ID NO: 93 is the determined cDNA sequence for L517S.
SEQ ID NO: 94 is the extended cDNA sequence for LST-S-1-169 (also known as L519S).
SEQ ID NO: 95 is a first determined cDNA sequence for L520S.
SEQ ID NO: 96 is a second determined cDNA sequence for L520S.
SEQ ID NO: 97 is a first determined cDNA sequence for L521S.
SEQ ID NO: 98 is a second determined cDNA sequence for L521S.
SEQ ID NO: 99 is the determined cDNA sequence for L522S.
SEQ ID NO: 100 is the determined cDNA sequence for L523S.
SEQ ID NO: 101 is the determined cDNA sequence for L524S.
SEQ ID NO: 102 is the determined cDNA sequence for L525S.
SEQ ID NO: 103 is the determined cDNA sequence for L526S.
SEQ ID NO: 104 is the determined cDNA sequence for L527S.
SEQ ID NO: 105 is the determined cDNA sequence for L528S.
SEQ ID NO: 106 is the determined cDNA sequence for L529S.
SEQ ID NO: 107 is a first determined cDNA sequence for L530S.
SEQ ID NO: 108 is a second determined cDNA sequence for L530S.
SEQ ID NO: 109 is the determined full-length cDNA sequence for L531S short form.
SEQ ID NO: 110 is the predicted amino acid sequence encoded by SEQ ID NO: 109.
SEQ ID NO: 111 is the determined full-length cDNA sequence for L531S long form.
SEQ ID NO: 112 is the predicted amino acid sequence encoded by SEQ ID NO: 111.
SEQ ID NO: 113 is the determined full-length cDNA sequence for L520S.
SEQ ID NO: 114 is the predicted amino acid sequence encoded by SEQ ID NO: 113.
SEQ ID NO: 115 is the determined cDNA sequence for contig 1.
SEQ ID NO: 116 is the determined cDNA sequence for contig 3.
SEQ ID NO: 117 is the determined cDNA sequence for contig 4.
SEQ ID NO: 118 is the determined cDNA sequence for contig 5.
SEQ ID NO: 119 is the determined cDNA sequence for contig 7.
SEQ ID NO: 120 is the determined cDNA sequence for contig 8.
SEQ ID NO: 121 is the determined cDNA sequence for contig 9.
SEQ ID NO: 122 is the determined cDNA sequence for contig 10.
SEQ ID NO: 123 is the determined cDNA sequence for contig 12.
SEQ ID NO: 124 is the determined cDNA sequence for contig 11.
SEQ ID NO: 125 is the determined cDNA sequence for contig 13.
SEQ ID NO: 126 is the determined cDNA sequence for contig 15.
SEQ ID NO: 127 is the determined cDNA sequence for contig 16.
SEQ ID NO: 128 is the determined cDNA sequence for contig 17.
SEQ ID NO: 129 is the determined cDNA sequence for contig 19.
SEQ ID NO: 129 is the determined cDNA sequence for contig 20.
SEQ ID NO: 131 is the determined cDNA sequence for contig 22.
SEQ ID NO: 132 is the determined cDNA sequence for contig 24.
SEQ ID NO: 133 is the determined cDNA sequence for contig 29.
SEQ ID NO: 134 is the determined cDNA sequence for contig 31.
SEQ ID NO: 135 is the determined cDNA sequence for contig 33.
SEQ ID NO: 136 is the determined cDNA sequence for contig 38.
SEQ ID NO: 137 is the determined cDNA sequence for contig 39.
SEQ ID NO: 138 is the determined cDNA sequence for contig 41.
SEQ ID NO: 139 is the determined cDNA sequence for contig 43.
SEQ ID NO: 140 is the determined cDNA sequence for contig 44.
SEQ ID NO: 140 is the determined cDNA sequence for contig 44.
SEQ ID NO: 142 is the determined cDNA sequence for contig 47.
SEQ ID NO: 143 is the determined cDNA sequence for contig 48.
SEQ ID NO: 144 is the determined cDNA sequence for contig 49.
SEQ ID NO: 145 is the determined cDNA sequence for contig 49.
SEQ ID NO: 146 is the determined cDNA sequence for contig 53.
SEQ ID NO: 147 is the determined cDNA sequence for contig 54.
SEQ ID NO: 148 is the determined cDNA sequence for contig 56.
SEQ ID NO: 149 is the determined cDNA sequence for contig 57.
SEQ ID NO: 150 is the determined cDNA sequence for contig 58.
SEQ ID NO: 151 is the full-length cDNA sequence for L530S.

SEQ ID NO: 152 is the amino acid sequence encoded by SEQ ID NO: 151.
SEQ ID NO: 153 is the full-length cDNA sequence of a first variant of L514S.
SEQ ID NO: 154 is the full-length cDNA sequence of a second variant of L514S.
SEQ ID NO: 155 is the amino acid sequence encoded by SEQ ID NO: 153.
SEQ ID NO: 156 is the amino acid sequence encoded by SEQ ID NO: 154.
SEQ ID NO: 157 is the determined cDNA sequence for contig 59.
SEQ ID NO: 158 is the full-length cDNA sequence for L763P (also referred to as contig 22).
SEQ ID NO: 159 is the amino acid sequence encoded by SEQ ID NO: 158.
SEQ ID NO: 160 is the full-length cDNA sequence for L762P (also referred to as contig 17).
SEQ ID NO: 161 is the amino acid sequence encoded by SEQ ID NO: 160.
SEQ ID NO: 162 is the determined cDNA sequence for L515S.
SEQ ID NO: 163 is the full-length cDNA sequence of a first variant of L524S.
SEQ ID NO: 164 is the fall-length cDNA sequence of a second variant of L524S.
SEQ ID NO: 165 is the amino acid sequence encoded by SEQ ID NO: 163.
SEQ ID NO: 166 is the amino acid sequence encoded by SEQ ID NO: 164.
SEQ ID NO: 167 is the full-length cDNA sequence of a first variant of L762P.
SEQ ID NO: 168 is the full-length cDNA sequence of a second variant of L762P.
SEQ ID NO: 169 is the amino acid sequence encoded by SEQ ID NO: 167.
SEQ ID NO: 170 is the amino acid sequence encoded by SEQ ID NO: 168.
SEQ ID NO: 171 is the full-length cDNA sequence for L773P (also referred to as contig 56).
SEQ ID NO: 172 is the amino acid sequence encoded by SEQ ID NO: 171.
SEQ ID NO: 173 is an extended cDNA sequence for L519S.
SEQ ID NO: 174 is the predicted amino acid sequence encoded by SEQ ID NO: 174.
SEQ ID NO: 175 is the full-length cDNA sequence for L523S.
SEQ ID NO: 176 is the predicted amino acid sequence encoded by SEQ ID NO: 175.
SEQ ID NO: 177 is the determined cDNA sequence for LST-sub5-7A.
SEQ ID NO: 178 is the determined cDNA sequence for LST-sub5-8G.
SEQ ID NO: 179 is the determined cDNA sequence for LST-sub5-8H.
SEQ ID NO: 180 is the determined cDNA sequence for LST-sub5-10B.
SEQ ID NO: 181 is the determined cDNA sequence for LST-sub5-10H.
SEQ ID NO: 182 is the determined cDNA sequence for LST-sub5-12B.
SEQ ID NO: 183 is the determined cDNA sequence for LST-sub5-11C.
SEQ ID NO: 184 is the determined cDNA sequence for LST-sub6-1c.
SEQ ID NO: 185 is the determined cDNA sequence for LST-sub6-2f.
SEQ ID NO: 186 is the determined cDNA sequence for LST-sub6-2G.
SEQ ID NO: 187 is the determined cDNA sequence for LST-sub6-4d.
SEQ ID NO: 188 is the determined cDNA sequence for LST-sub6-4e.
SEQ ID NO: 189 is the determined cDNA sequence for LST-sub6-4f.
SEQ ID NO: 190 is the determined cDNA sequence for LST-sub6-3h.
SEQ ID NO: 191 is the determined cDNA sequence for LST-sub6-3d.
SEQ ID NO: 192 is the determined cDNA sequence for LST-sub6-5h.
SEQ ID NO: 192 is the determined cDNA sequence for LST-sub6-6h.
SEQ ID NO: 194 is the determined cDNA sequence for LST-sub6-7a.
SEQ ID NO: 195 is the determined cDNA sequence for LST-sub6-8a.
SEQ ID NO: 196 is the determined cDNA sequence for LST-sub6-7d.
SEQ ID NO: 197 is the determined cDNA sequence for LST-sub6-7e.
SEQ ID NO: 198 is the determined cDNA sequence for LST-sub6-8e.
SEQ ID NO: 199 is the determined cDNA sequence for LST-sub6-9f.
SEQ ID NO: 201 is the determined cDNA sequence for LST-sub6-9h.
SEQ ID NO: 202 is the determined cDNA sequence for LST-sub6-11b.
SEQ ID NO: 203 is the determined cDNA sequence for LST-sub6-11c.
SEQ ID NO: 204 is the determined cDNA sequence for LST-sub6-12c.
SEQ ID NO: 205 is the determined cDNA sequence for LST-sub6-12e.
SEQ ID NO: 206 is the determined cDNA sequence for LST-sub6-12f.
SEQ ID NO: 207 is the determined cDNA sequence for LST-sub6-11g.
SEQ ID NO: 208 is the determined cDNA sequence for LST-sub6-12g.
SEQ ID NO: 209 is the determined cDNA sequence for LST-sub6-12h.
SEQ ID NO: 210 is the determined cDNA sequence for LST-sub6-II-1a.
SEQ ID NO: 211 is the determined cDNA sequence for LST-sub6-II-2b.
SEQ ID NO: 212 is the determined cDNA sequence for LST-sub6-II-2g.
SEQ ID NO: 213 is the determined cDNA sequence for LST-sub6-II-1h.
SEQ ID NO: 214 is the determined cDNA sequence for LST-sub6-II-4a.
SEQ ID NO: 215 is the determined cDNA sequence for LST-sub6-II-4b.
SEQ ID NO: 216 is the determined cDNA sequence for LST-sub6-II-3e.
SEQ ID NO: 217 is the determined cDNA sequence for LST-sub6-II-4f.
SEQ ID NO: 218 is the determined cDNA sequence for LST-sub6-II-4g.
SEQ ID NO: 219 is the determined cDNA sequence for LST-sub6-II-4h.
SEQ ID NO: 220 is the determined cDNA sequence for LST-sub6-II-5c.

SEQ ID NO: 221 is the determined cDNA sequence for LST-sub6-II-5e.
SEQ ID NO: 222 is the determined cDNA sequence for LST-sub6-II-6f.
SEQ ID NO: 223 is the determined cDNA sequence for LST-sub6-II-5g.
SEQ ID NO: 224 is the determined cDNA sequence for LST-sub6-II-6g.
SEQ ID NO: 225 is the amino acid sequence for L528S.
SEQ ID NO: 226–251 are synthetic peptides derived from L762P.
SEQ ID NO: 252 is the expressed amino acid sequence of L514S.
SEQ ID NO: 253 is the DNA sequence corresponding to SEQ ID NO: 252.
SEQ ID NO: 254 is the DNA sequence of a L762P expression construct.
SEQ ID NO: 255 is the determined cDNA sequence for clone 23785.
SEQ ID NO: 256 is the determined cDNA sequence for clone 23786.
SEQ ID NO: 257 is the determined cDNA sequence for clone 23788.
SEQ ID NO: 258 is the determined cDNA sequence for clone 23790.
SEQ ID NO: 259 is the determined cDNA sequence for clone 23793.
SEQ ID NO: 260 is the determined cDNA sequence for clone 23794.
SEQ ID NO: 261 is the determined cDNA sequence for clone 23795.
SEQ ID NO: 262 is the determined cDNA sequence for clone 23796.
SEQ ID NO: 263 is the determined cDNA sequence for clone 23797.
SEQ ID NO: 264 is the determined cDNA sequence for clone 23798.
SEQ ID NO: 265 is the determined cDNA sequence for clone 23799.
SEQ ID NO: 266 is the determined cDNA sequence for clone 23800.
SEQ ID NO: 267 is the determined cDNA sequence for clone 23802.
SEQ ID NO: 268 is the determined cDNA sequence for clone 23803.
SEQ ID NO: 269 is the determined cDNA sequence for clone 23804.
SEQ ID NO: 270 is the determined cDNA sequence for clone 23805.
SEQ ID NO: 271 is the determined cDNA sequence for clone 23806.
SEQ ID NO: 272 is the determined cDNA sequence for clone 23807.
SEQ ID NO: 273 is the determined cDNA sequence for clone 23808.
SEQ ID NO: 274 is the determined cDNA sequence for clone 23809.
SEQ ID NO: 275 is the determined cDNA sequence for clone 23810.
SEQ ID NO: 276 is the determined cDNA sequence for clone 23811.
SEQ ID NO: 277 is the determined cDNA sequence for clone 23812.
SEQ ID NO: 278 is the determined cDNA sequence for clone 23813.
SEQ ID NO: 279 is the determined cDNA sequence for clone 23815.
SEQ ID NO: 280 is the determined cDNA sequence for clone 25298.
SEQ ID NO: 281 is the determined cDNA sequence for clone 25299.
SEQ ID NO: 282 is the determined cDNA sequence for clone 25300.
SEQ ID NO: 283 is the determined cDNA sequence for clone 25301.
SEQ ID NO: 284 is the determined cDNA sequence for clone 25304.
SEQ ID NO: 285 is the determined cDNA sequence for clone 25309.
SEQ ID NO: 286 is the determined cDNA sequence for clone 25312.
SEQ ID NO: 287 is the determined cDNA sequence for clone 25317.
SEQ ID NO: 288 is the determined cDNA sequence for clone 25321.
SEQ ID NO: 289 is the determined cDNA sequence for clone 25323.
SEQ ID NO: 290 is the determined cDNA sequence for clone 25327.
SEQ ID NO: 291 is the determined cDNA sequence for clone 25328.
SEQ ID NO: 292 is the determined cDNA sequence for clone 25332.
SEQ ID NO: 293 is the determined cDNA sequence for clone 25333.
SEQ ID NO: 294 is the determined cDNA sequence for clone 25336.
SEQ ID NO: 295 is the determined cDNA sequence for clone 25340.
SEQ ID NO: 296 is the determined cDNA sequence for clone 25342.
SEQ ID NO: 297 is the determined cDNA sequence for clone 25356.
SEQ ID NO: 298 is the determined cDNA sequence for clone 25357.
SEQ ID NO: 299 is the determined cDNA sequence for clone 25361.
SEQ ID NO: 300 is the determined cDNA sequence for clone 25363.
SEQ ID NO: 301 is the determined cDNA sequence for clone 25397.
SEQ ID NO: 302 is the determined cDNA sequence for clone 25402.
SEQ ID NO: 303 is the determined cDNA sequence for clone 25403.
SEQ ID NO: 304 is the determined cDNA sequence for clone 25405.
SEQ ID NO: 305 is the determined cDNA sequence for clone 25407.
SEQ ID NO: 306 is the determined cDNA sequence for clone 25409.
SEQ ID NO: 307 is the determined cDNA sequence for clone 25396.
SEQ ID NO: 308 is the determined cDNA sequence for clone 25414.
SEQ ID NO: 309 is the determined cDNA sequence for clone 25410.
SEQ ID NO: 310 is the determined cDNA sequence for clone 25406.
SEQ ID NO: 311 is the determined cDNA sequence for clone 25306.
SEQ ID NO: 312 is the determined cDNA sequence for clone 25362.
SEQ ID NO: 313 is the determined cDNA sequence for clone 25360.

SEQ ID NO: 314 is the determined cDNA sequence for clone 25398.
SEQ ID NO: 315 is the determined cDNA sequence for clone 25355.
SEQ ID NO: 316 is the determined cDNA sequence for clone 25351.
SEQ ID NO: 317 is the determined cDNA sequence for clone 25331.
SEQ ID NO: 318 is the determined cDNA sequence for clone 25338.
SEQ ID NO: 319 is the determined cDNA sequence for clone 25335.
SEQ ID NO: 320 is the determined cDNA sequence for clone 25329.
SEQ ID NO: 321 is the determined cDNA sequence for clone 25324.
SEQ ID NO: 322 is the determined cDNA sequence for clone 25322.
SEQ ID NO: 323 is the determined cDNA sequence for clone 25319.
SEQ ID NO: 324 is the determined cDNA sequence for clone 25316.
SEQ ID NO: 325 is the determined cDNA sequence for clone 25311.
SEQ ID NO: 326 is the determined cDNA sequence for clone 25310.
SEQ ID NO: 327 is the determined cDNA sequence for clone 25302.
SEQ ID NO: 328 is the determined cDNA sequence for clone 25315.
SEQ ID NO: 329 is the determined cDNA sequence for clone 25308.
SEQ ID NO: 330 is the determined cDNA sequence for clone 25303.
SEQ ID NO: 331–337 are the cDNA sequences of isoforms of the p53 tumor suppressor homologue, p63 (also referred to as L530S).
SEQ ID NO: 338–344 are the amino acid sequences encoded by SEQ ID NO: 331–337, respectively.
SEQ ID NO: 345 is a second cDNA sequence for the antigen L763P.
SEQ ID NO: 346 is the amino acid sequence encoded by the sequence of SEQ ID NO: 345.
SEQ ID NO: 347 is a determined full-length cDNA sequence for L523S.
SEQ ID NO: 348 is the predicted amino acid sequence encoded by SEQ ID NO: 347.
SEQ ID NO: 349 is the cDNA sequence encoding the N-terminal portion of L773P.
SEQ ID NO: 350 is the amino acid sequence of the N-terminal portion of L773P.

DETAILED DESCRIPTION OF THE INVENTION

As noted above, the present invention is generally directed to compositions and methods for the therapy and diagnosis of cancer, such as lung cancer. The compositions described herein may include lung tumor polypeptides, polynucleotides encoding such polypeptides, binding agents such as antibodies, antigen presenting cells (APCs) and/or immune system cells (e.g., T cells). Polypeptides of the present invention generally comprise at least a portion (such as an immunogenic portion) of a lung tumor protein or a variant thereof. A "lung tumor protein" is a protein that is expressed in lung tumor cells at a level that is at least two fold, and preferably at least five fold, greater than the level of expression in a normal tissue, as determined using a representative assay provided herein. Certain lung tumor proteins are tumor proteins that react detectably (within an immunoassay, such as an ELISA or Western blot) with antisera of a patient afflicted with lung cancer. Polynucleotides of the subject invention generally comprise a DNA or RNA sequence that encodes all or a portion of such a polypeptide, or that is complementary to such a sequence. Antibodies are generally immune system proteins. or antigen-binding fragments thereof, that are capable of binding to a polypeptide as described above. Antigen presenting cells include dendritic cells, macrophages, monocytes, fibroblasts and B-cells that express a polypeptide as described above. T cells that may be employed within such compositions are generally T cells that are specific for a polypeptide as described above.

The present invention is based on the discovery human lung tumor proteins. Sequences of polynucleotides encoding specific tumor proteins are provided in SEQ ID NO: 1–109, 111, 113, 115–151, 153, 154,157, 158, 160, 162–164, 167, 168, 171, 173, 175, 177–224, 255–337, 345, 347 and 349.

Lung Tumor Protein Polynucleotides

Any polynucleotide that encodes a lung tumor protein or a portion or other variant thereof as described herein is encompassed by the present invention. Preferred polynucleotides comprise at least 15 consecutive nucleotides, preferably at least 30 consecutive nucleotides and more preferably at least 45 consecutive nucleotides, that encode a portion of a lung tumor protein. More preferably, a polynucleotide encodes an immunogenic portion of a lung tumor protein. Polynucleotides complementary to any such sequences are also encompassed by the present invention. Polynucleotides may be single-stranded (coding or antisense) or double-stranded, and may be DNA (genomic, cDNA or synthetic) or RNA molecules. RNA molecules include HnRNA molecules, which contain introns and correspond to a DNA molecule in a one-to-one manner, and mRNA molecules, which do not contain introns. Additional coding or non-coding sequences may, but need not, be present within a polynucleotide of the present invention, and a polynucleotide may, but need not, be linked to other molecules and/or support materials.

Polynucleotides may comprise a native sequence (i.e., an endogenous sequence that encodes a lung tumor protein or a portion thereof) or may comprise a variant of such a sequence. Polynucleotide variants may contain one or more substitutions, additions, deletions and/or insertions such that the immunogenicity of the encoded polypeptide is not diminished, relative to a native tumor protein. The effect on the immunogenicity of the encoded polypeptide may generally be assessed as described herein. Variants preferably exhibit at least about 70% identity, more preferably at least about 80% identity and most preferably at least about 90% identity to a polynucleotide sequence that encodes a native lung tumor protein or a portion thereof. The term "variants" also encompasses homologous genes of xenogenic origin.

Two polynucleotide or polypeptide sequences are said to be "identical" if the sequence of nucleotides or amino acids in the two sequences is the same when aligned for maximum correspondence as described below. Comparisons between two sequences are typically performed by comparing the sequences over a comparison window to identify and compare local regions of sequence similarity. A "comparison window" as used herein, refers to a segment of at least about 20 contiguous positions, usually 30 to about 75, 40 to about 50, in which a sequence may be compared to a reference sequence of the same number of contiguous positions after the two sequences are optimally aligned.

Optimal alignment of sequences for comparison may be conducted using the Megalign program in the Lasergene suite of bioinformatics software (DNASTAR, Inc., Madison, Wis.), using default parameters. This program embodies several alignment schemes described in the following references: Dayhoff, M. O. (1978) A model of evolutionary change in proteins—Matrices for detecting distant relationships. In Dayhoff, M. O. (ed.) Atlas of Protein Sequence and Structure, National Biomedical Research Foundation, Washington D.C. Vol. 5, Suppl. 3, pp. 345–358; Hein J. (1990) Unified Approach to Alignment and Phylogenes pp. 626–645 *Methods in Enzymology* vol. 183, Academic Press, Inc., San Diego, Calif.; Higgins, D. G. and Sharp, P. M. (1989) *CABIOS* 5:151–153; Myers, E. W. and Muller W. (1988) *CABIOS* 4:11–17; Robinson, E. D. (1971) *Comb. Theor* 11:105; Santou, N. Nes, M. (1987) *Mol. Biol. Evol.* 4:406–425; Sneath, P. H. A. and Sokal, R. R. (1973) *Numerical Taxonomy—the Principles and Practice of Numerical Taxonomy*, Freeman Press, San Francisco, Calif.; Wilbur, W. J. and Lipman, D. J. (1983) *Proc. Natl. Acad., Sci. USA* 80:726–730.

Preferably, the "percentage of sequence identity" is determined by comparing two optimally aligned sequences over a window of comparison of at least 20 positions, wherein the portion of the polynucleotide or polypeptide sequence in the comparison window may comprise additions or deletions (i.e. gaps) of 20 percent or less, usually 5 to 15 percent, or 10 to 12 percent, as compared to the reference sequences (which does not comprise additions or deletions) for optimal alignment of the two sequences. The percentage is calculated by determining the number of positions at which the identical nucleic acid bases or amino acid residue occurs in both sequences to yield the number of matched positions, dividing the number of matched positions by the total number of positions in the reference sequence (i.e. the window size) and multiplying the results by 100 to yield the percentage of sequence identity.

Variants may also, or alternatively, be substantially homologous to a native gene, or a portion or complement thereof. Such polynucleotide variants are capable of hybridizing under moderately stringent conditions to a naturally occurring DNA sequence encoding a native lung tumor protein (or a complementary sequence). Suitable moderately stringent conditions include prewashing in a solution of 5×SSC, 0.5% SDS, 1.0 mM EDTA (pH 8.0); hybridizing at 50° C.–65° C., 5×SSC, overnight; followed by washing twice at 65° C. for 20 minutes with each of 2×, 0.5× and 0.2×SSC containing 0.1% SDS.

It will be appreciated by those of ordinary skill in the art that, as a result of the degeneracy of the genetic code, there are many nucleotide sequences that encode a polypeptide as described herein. Some of these polynucleotides bear minimal homology to the nucleotide sequence of any native gene. Nonetheless, polynucleotides that vary due to differences in codon usage are specifically contemplated by the present invention. Further, alleles of the genes comprising the polynucleotide sequences provided herein are within the scope of the present invention. Alleles are endogenous genes that are altered as a result of one or more mutations, such as deletions, additions and/or substitutions of nucleotides. The resulting MnRNA and protein may, but need. not, have an altered structure or function. Alleles may be identified using standard techniques (such as hybridization, amplification and/or database sequence comparison).

Polynucleotides may be prepared using any of a variety of techniques. For example, a polynucleotide may be identified, as described in more detail below, by screening a microarray of cDNAs for tumor-associated expression (i.e., expression that is at least two fold greater in a lung tumor than in normal tissue, as determined using a representative assay provided herein). Such screens may be performed using a Synteni microarray (Palo Alto, Calif.) according to the manufacturer's instructions (and essentially as described by Schena et al., *Proc. Natl. Acad. Sci. USA* 93:10614–10619, 1996 and Heller et al., *Proc. Natl. Acad. Sci. USA* 94:2150–2155, 1997). Alternatively, polypeptides may be amplified from cDNA prepared from cells expressing the proteins described herein, such as lung tumor cells. Such polynucleotides may be amplified via polymerase chain reaction (PCR). For this approach, sequence-specific primers may be designed based on the sequences provided herein, and may be purchased or synthesized.

An amplified portion may be used to isolate a full length gene from a suitable library (e.g., a lung tumor cDNA library) using well known techniques. Within such techniques, a library (cDNA. or genomic) is screened using one or more polynucleotide probes or primers suitable for amplification. Preferably, a library is size-selected to include larger molecules. Random primed libraries may also be preferred for identifying 5' and upstream regions of genes. Genomic libraries are preferred for obtaining introns and extending 5' sequences.

For hybridization techniques, a partial sequence may be labeled (e.g., by nick-translation or end-labeling with $^{32}P$) using well known techniques. A bacterial or bacteriophage library is then screened by hybridizing filters containing denatured bacterial colonies (or lawns containing phage plaques) with the labeled probe (see Sambrook et al., *Molecular Cloning: A Laboratory Manual,* Cold Spring Harbor Laboratories, Cold Spring Harbor, N.Y., 1989). Hybridizing colonies or plaques are selected and expanded, and the DNA is isolated for further analysis. cDNA clones may be analyzed to determine the amount of additional sequence by, for example, PCR using a primer from the partial sequence and a primer from the vector. Restriction maps and partial sequences may be generated to identify one or more overlapping clones. The complete sequence may then be determined using standard techniques, which may involve generating a series of deletion clones. The resulting overlapping sequences are then assembled into a single contiguous sequence. A full length cDNA molecule can be generated by ligating suitable fragments, using well known techniques.

Alternatively, there are numerous amplification techniques for obtaining a full length coding sequence from a partial cDNA sequence. Within such techniques, amplification is generally performed via PCR. Any of a variety of commercially available kits may be used to perform the amplification step. Primers may be designed using, for example, software well known in the art. Primers are preferably 22.30 nucleotides in length, have a GC content of at least 50% and anneal to the target sequence at temperatures of about 68° C. to 72° C. The amplified region may be sequenced as described above, and overlapping sequences assembled into a contiguous sequence.

One such amplification technique is inverse PCR (see Triglia et al., *Nucl. Acids Res.* 16:8186, 1988), which uses restriction enzymes to generate a fragment in the known region of the gene. The fragment is then circularized by intramolecular ligation and used as a template for PCR with divergent primers derived from the known region. Within an alternative approach, sequences adjacent to a partial sequence may be retrieved by amplification with a primer to a linker sequence and a primer specific to a known region.

The amplified sequences are typically subjected to a second round of amplification with the same linker primer and a second primer specific to the known region. A variation on this procedure, which employs two primers that initiate extension in opposite directions from the known sequence, is described in WO 96/38591. Another such technique is known as "rapid amplification of cDNA ends" or RACE. This technique involves the use of an internal primer and an external primer, which hybridizes to a polyA region or vector sequence, to identify sequences that are 5' and 3' of a known sequence. Additional techniques include capture PCR (Lagerstrom et al., *PCR Methods Applic.* 1:111–19, 1991) and walking PCR (Parker et al., *Nucl. Acids. Res.* 19:3055–60, 1991). Other methods employing amplification may also be employed to obtain a full length cDNA sequence.

In certain instances, it is possible to obtain a full length cDNA sequence by analysis of sequences provided in an expressed sequence tag (EST) database, such as that available from GenBank. Searches for overlapping ESTs may generally be performed using well known programs (e.g., NCBI BLAST searches). and such ESTs may be used to generate a contiguous full length sequence. Full length DNA sequences may also be obtained by analysis of genomic fragments.

Certain nucleic acid sequences of cDNA molecules encoding portions of lung tumor proteins are provided in SEQ ID NO: 1–109, 111, 113, 115–151, 153, 154,157, 158, 160, 162–164, 167, 168, 171, 173, 175, 177–224, 255–347, 345, 347 and 349.

Polynucleotide variants may generally be prepared by any method known in the art, including chemical synthesis by, for example, solid phase phosphoramidite chemical synthesis. Modifications in a polynucleotide sequence may also be introduced using standard mutagenesis techniques, such as oligonucleotide-directed site-specific mutagenesis (see Adelman et al., *DNA* 2:183, 1983). Alternatively, RNA molecules may be generated by in vitro or in vivo transcription of DNA sequences encoding a lung tumor protein, or portion thereof, provided that the DNA is incorporated into a vector with a suitable RNA polymerase promoter (such as T7 or SP6). Certain portions may be used to prepare an encoded polypeptide, as described herein. In addition, or alternatively, a portion may be administered to a patient such that the encoded polypeptide is generated in vivo (e.g., by transfecting antigen-presenting cells, such as dendritic cells, with a cDNA construct encoding a lung tumor polypeptide, and administering the transfected cells to the patient).

A portion of a sequence complementary to a coding sequence (ie., an antisense polynucleotide) may also be used as a probe or to modulate gene expression. cDNA constructs that can be transcribed into antisense RNA may also be introduced into cells of tissues to facilitate the production of antisense RNA. An antisense polynucleotide may be used, as described herein, to inhibit expression of a tumor protein. Antisense technology can be used to control gene expression through triple-helix formation, which compromises the ability of the double helix to open sufficiently for the binding of polymerases, transcription factors or regulatory molecules (see Gee et al., In Huber and Carr, *Molecular and Immunologic Approaches,* Futura Publishing Co. (Mt. Kisco, N.Y.; 1994)). Alternatively, an antisense molecule may be designed to hybridize with a control region of a gene (e.g., promoter, enhancer or transcription initiation site), and block transcription of the gene; or to block translation by inhibiting binding of a transcript to ribosomes.

A portion of a coding sequence, or of a complementary sequence, may also be designed as a probe or primer to detect gene expression. Probes may be labeled with a variety of reporter groups, such as radionuclides and enzymes, and are preferably at least 10 nucleotides in length, more preferably at least 20 nucleotides in length and still more preferably at least 30 nucleotides in length. Primers, as noted above, are preferably 22–30 nucleotides in length.

Any polynucleotide may be further modified to increase stability in vivo. Possible modifications include, but are not limited to, the addition of flanking sequences at the 5' and/or 3'-ends; the use of phosphorothioate or 2' O-methyl rather than phosphodiesterase linkages in the backbone; and/or the inclusion of nontraditional bases such as inosine, queosine and wybutosine, as well as acetyl- methyl-, thio- and other modified forms of adenine, cytidine, guanine, thymine and uridine.

Nucleotide sequences as described herein may be joined to a variety of other nucleotide sequences using established recombinant DNA techniques. For example, a polynucleotide may be cloned into any of a variety of cloning vectors, including plasmids, phagemids, lambda phage derivatives and cosmids. Vectors of particular interest include expression vectors, replication vectors, probe generation vectors and sequencing vectors. In general, a vector will contain an origin of replication functional in at least one organism, convenient restriction endonuclease sites and one or more selectable markers. Other elements will depend upon the desired use, and will be apparent to those of ordinary skill in the art.

Within certain embodiments, polynucleotides may be formulated so as to permit entry into a cell of a mammal, and expression therein. Such formulations are particularly useful for therapeutic purposes, as described below. Those of ordinary skill in the art will appreciate that there are many ways to achieve expression of a polynucleotide in a target cell, and any suitable method may be employed. For example, a polynucleotide may be incorporated into a viral vector such as, but not limited to, adenovirus, adeno-associated virus, retrovirus, or vaccinia or other pox virus (e.g, avian pox virus).). The polynucleotides may also be administered as naked plasmid vectors. Techniques for incorporating DNA into such vectors are well known to those of ordinary skill in the art. A retroviral vector may additionally transfer or incorporate a gene for a selectable marker (to aid in the identification or selection of transduced cells) and/or a targeting moiety, such as a gene that encodes a ligand for a receptor on a specific target cell, to render the vector target specific. Targeting may also be accomplished using an antibody, by methods known to those of ordinary skill in the art.

Other formulations for therapeutic purposes include colloidal dispersion systems, such as macromolecule complexes, nanocapsules, microspheres, beads, and lipid-based systems including oil-in-water emulsions, micelles, mixed micelles, and liposomes. A preferred colloidal system for use as a delivery vehicle in vitro and in vivo is a liposome (i.e. an artificial membrane vesicle). The preparation and use of such systems is well known in the art.

Lung Tumor Polypeptides

Within the context of the present invention, polypeptides may comprise at least an immunogenic portion of a lung tumor protein or a variant thereof, as described herein. As noted above, a "lung tumor protein" is a protein that is expressed by lung tumor cells. Proteins that are lung tumor proteins also react detectably within an immunoassay (such as an ELISA) with antisera from a patient with lung cancer. Polypeptides as described herein may be of any length. Additional sequences derived from the native protein and/or heterologous sequences may be present, and such sequences may (but need not) possess further immunogenic or antigenic properties.

An "immunogenic portion," as used herein is a portion of a protein that is recognized (i.e., specifically bound) by a B-cell and/or T-cell surface antigen receptor. Such immunogenic portions generally comprise at least 5 amino acid residues, more preferably at least 10, and still more preferably at least 20 amino acid residues of a lung tumor protein or a variant thereof. Certain preferred immunogenic portions include peptides in which an N-terminal leader sequence and/or transmembrane domain have been deleted. Other preferred immunogenic portions may contain a small N- and/or C-terminal deletion (e.g., 1–30 amino acids, preferably 5–15 amino acids), relative to the mature protein.

Immunogenic portions may generally be identified using well known techniques, such as those summarized in Paul, *Fundamental Immunology,* 3rd ed., 243–247 (Raven Press, 1993) and references cited therein. Such techniques include screening polypeptides for the ability to react with antigen-specific antibodies, antisera and/or T-cell lines or clones. As used herein, antisera and antibodies are "antigen-specific" if they specifically bind to an antigen (i.e., they react with the protein in an ELISA or other immunoassay, and do not react detectably with unrelated proteins). Such antisera and antibodies may be prepared as described herein, and using well known techniques. An immunogenic portion of a native lung tumor protein is a portion that reacts with such antisera and/or T-cells at a level that is not substantially less than the reactivity of the full length polypeptide (e.g., in an ELISA and/or T-cell reactivity assay). Such immunogenic portions may react within such assays at a level that is similar to or greater than the reactivity of the full length polypeptide. Such screens may generally be performed using methods well known to those of ordinary skill in the art, such as those described in Harlow and Lane, *Antibodies: A Laboratory Manual,* Cold Spring Harbor Laboratory, 1988. For example, a polypeptide may be immobilized on a solid support and contacted with patient sera to allow binding of antibodies within the sera to the immobilized polypeptide. Unbound sera may then be removed and bound antibodies detected using, for example, $^{125}$I-labeled Protein A.

As noted above, a composition may comprise a variant of a native lung tumor protein. A polypeptide "variant," as used herein, is a polypeptide that differs from a native lung tumor protein in one or more substitutions, deletions, additions and/or insertions, such that the immunogenicity of the polypeptide is not substantially diminished. In other words, the ability of a variant to react with antigen-specific antisera may be enhanced or unchanged, relative to the native protein, or may be diminished by less than 50%, and preferably less than 20%, relative to the native protein. Such variants may generally be identified by modifying one of the above polypeptide sequences and evaluating the reactivity of the modified polypeptide with antigen-specific antibodies or antisera as described herein. Preferred variants include those in which one or more portions, such as an N-terminal leader sequence or transmembrane domain, have been removed. Other preferred variants include variants in which a small portion (e.g., 1–30 amino acids, preferably 5–15 amino acids) has been removed from the N- and/or C-terminal of the mature protein.

Polypeptide variants preferably exhibit at least about 70%, more preferably at least about 90% and most preferably at least about 95% identity (determined as described above) to the identified polypeptides.

Preferably, a variant contains conservative substitutions. A "conservative substitution" is one in which an amino acid is substituted for another amino acid that has similar properties, such that one skilled in the art of peptide chemistry would expect the secondary structure and hydropathic nature of the polypeptide to be substantially unchanged. Amino acid substitutions may generally be made on the basis of similarity in polarity, charge, solubility, hydrophobicity, hydrophilicity and/or the amphipathic nature of the residues. For example, negatively charged amino acids include aspartic acid and glutamic acid; positively charged amino acids include lysine and arginine, and amino acids with uncharged polar head groups having similar hydrophilicity values include leucine, isoleucine and valine; glycine and alanine; asparagine and glutamine; and serine, threonine, phenylalanine and tyrosine. Other groups of amino acids that may represent conservative changes include: (1) ala, pro, gly, glu, asp, gln, asn, ser, thr; (2) cys, ser, tyr, thr; (3) val, ile, leu, met, ala, phe; (4) lys, arg, his; and (5) phe, tyr, trp, his. A variant may also, or alternatively, contain nonconservative changes. In a preferred embodiment, variant polypeptides differ from a native sequence by substitution, deletion or addition of five amino acids or fewer. Variants may also (or alternatively) be modified by, for example, the deletion or addition of amino acids that have minimal influence on the immunogenicity, secondary structure and hydropathic nature of the polypeptide.

As noted above, polypeptides may comprise a signal (or leader) sequence at the N-terminal end of the protein which co-translationally or post-translationally directs transfer of the protein. The polypeptide may also be conjugated to a linker or other sequence for ease of synthesis, purification or identification of the polypeptide (e.g., poly-His), or to enhance binding of the polypeptide to a solid support. For example, a polypeptide may be conjugated to an immunoglobulin Fc region.

Polypeptides may be prepared using any of a variety of well known techniques. Recombinant polypeptides encoded by DNA sequences as described above may be readily prepared from the DNA sequences using any of a variety of expression vectors known to those of ordinary skill in the art. Expression may be achieved in any appropriate host cell that has been transformed or transfected with an expression vector containing a DNA molecule that encodes a recombinant polypeptide. Suitable host cells include prokaryotes, yeast, higher eukaryotic and plant cells. Preferably, the host cells employed are *E. coli,* yeast or a mammalian cell line such as COS or CHO. Supernatants from suitable host/vector systems which secrete recombinant protein or polypeptide into culture media may be first concentrated using a commercially available filter. Following concentration, the concentrate may be applied to a suitable purification matrix such as an affinity matrix or an ion exchange resin. Finally, one or more reverse phase HPLC steps can be employed to further purify a recombinant polypeptide.

Portions and other variants having fewer than about 100 amino acids, and generally fewer than about 50 amino acids, may also be generated by synthetic means, using techniques well known to those of ordinary skill in the art. For example, such polypeptides may be synthesized using any of the commercially available solid-phase techniques, such as the Merrifield solid-phase synthesis method, where amino acids are sequentially added to a growing amino acid chain. See Merrifield, *J. Am Chem. Soc.* 85:2149–2146, 1963. Equipment for automated synthesis of polypeptides is commercially available from suppliers such as Perkin Elmer/Applied BioSystems Division (Foster City, Calif.), and may be operated according to the manufacturer's instructions.

Within certain specific embodiments, a polypeptide may be a fusion protein that comprises multiple polypeptides as described herein, or that comprises at least one polypeptide as described herein and an unrelated sequence, such as a known tumor protein. A fusion partner may, for example, assist in providing T helper epitopes (an immunological fusion partner), preferably T helper epitopes recognized by humans, or may assist in expressing the protein (an expression enhancer) at higher yields than the native recombinant protein. Certain preferred fusion partners are both immunological and expression enhancing fusion partners. Other fusion partners may be selected so as to increase the solubility of the protein or to enable the protein to be targeted to desired intracellular compartments. Still further fusion partners include affinity tags, which facilitate purification of the protein.

Fusion proteins may generally be prepared using standard techniques, including chemical conjugation. Preferably, a fusion protein is expressed as a recombinant protein, allowing the production of increased levels, relative to a non-fused protein, in an expression system. Briefly, DNA sequences encoding the polypeptide components may be assembled separately, and ligated into an appropriate expression vector. The 3' end of the DNA sequence encoding one polypeptide component is ligated, with or without a peptide linker, to the 5' end of a DNA sequence encoding the second polypeptide component so that the reading frames of the sequences are in phase. This permits translation into a single fusion protein that retains the biological activity of both component polypeptides.

A peptide linker sequence may be employed to separate the first and the second polypeptide components by a distance sufficient to ensure that each polypeptide folds into its secondary and tertiary structures. Such a peptide linker sequence is incorporated into the fusion protein using standard techniques well known in the art. Suitable peptide linker sequences may be chosen based on the following factors: (1) their ability to adopt a flexible extended conformation; (2) their inability to adopt a secondary structure that could interact with functional epitopes on the first and second polypeptides; and (3) the lack of hydrophobic or charged residues that might react with the polypeptide functional epitopes. Preferred peptide linker sequences contain Gly, Asn and Ser residues. Other near neutral amino acids, such as Thr and Ala may also be used in the linker sequence. Amino acid sequences which may be usefully employed as linkers include those disclosed in Maratea et al., *Gene* 40:39–46, 1985; Murphy et al., *Proc. Natl. Acad. Sci. USA* 83:8258–8262, 1986; U.S. Pat. Nos. 4,935,233 and 4,751,180. The linker sequence may generally be from 1 to about 50 amino acids in length. Linker sequences are not required when the first and second polypeptides have non-essential N-terminal amino acid regions that car. be used to separate the functional domains and prevent steric interference.

The ligated DNA sequences are operably linked to suitable transcriptional or translational regulatory elements. The regulatory elements responsible for expression of DNA are located only 5' to the DNA sequence encoding the first polypeptides. Similarly, stop codons required to end translation and transcription termination signals are only present 3' to the DNA sequence encoding the second polypeptide.

Fusion proteins are also provided that comprise a polypeptide of the present invention together with an unrelated immunogenic protein. Preferably the immunogenic protein is capable of eliciting a recall response. Examples of such proteins include tetanus, tuberculosis and hepatitis proteins (see, for example, Stoute et al. *New Engl. J. Med.*, 336:86–91, 1997).

Within preferred embodiments, an immunological fusion partner is derived from protein D, a surface protein of the gram-negative bacterium Haemophilus influenza B (WO 91/18926). Preferably, a protein D derivative comprises approximately the first third of the protein (e.g., the first N-terminal 100–110 amino acids), and a protein D derivative may be lipidated. Within certain preferred embodiments, the first 109 residues of a Lipoprotein D fusion partner is included on the N-terminus to provide the polypeptide with additional exogenous T-cell epitopes and to increase the expression level in *E coli* (thus functioning as an expression enhancer). The lipid tail ensures optimal presentation of the antigen to antigen presenting cells. Other fusion partners include the non-structural protein from influenzae virus, NS1 (hemaglutinin). Typically, the N-terminal 81 amino acids are used, although different fragments that include T-helper epitopes may be used.

In another embodiment, the immunological fusion partner is the protein known as LYTA, or a portion thereof (preferably a C-terminal portion). LYTA is derived from *Streptococcus pneumoniae,* which synthesizes an N-acetyl-L-alanine amidase known as amidase LYTA (encoded by the LytA gene; *Gene* 43:265–292, 1986). LYTA is an autolysin that specifically degrades certain bonds in the peptidoglycan backbone. The C-terminal domain of the LYTA protein is responsible for the affinity to the choline or to some choline analogues such as DEAE. This property has been exploited for the development of *E. coli* C-LYTA expressing plasmids useful for expression of fusion proteins. Purification of hybrid proteins containing the C-LYTA fragment at the amino terminus has been described (see *Biotechnology* 10:795–798, 1992). Within a preferred embodiment, a repeat portion of LYTA may be incorporated into a fusion protein. A repeat portion is found in the C-terminal region starting at residue 178. A particularly preferred repeat portion incorporates residues 188–305.

In general, polypeptides (including fusion proteins) and polynucleotides as described herein are isolated. An "isolated" polypeptide or polynucleotide is one that is removed from its original environment. For example, a naturally-occurring protein is isolated if it is separated from some or all of the coexisting materials in the natural system. Preferably, such polypeptides are at least about 90% pure, more preferably at least about 95% pure and most preferably at least about 99% pure. A polynucleotide is considered to be isolated if, for example, it is cloned into a vector that is not a part of the natural environment.

Binding Agents

The present invention further provides agents, such as antibodies and antigen-binding fragments thereof, that specifically bind to a lung tumor protein. As used herein, an antibody, or antigen-binding fragment thereof, is said to "specifically bind" to a lung tumor protein if it reacts at a detectable level (within, for example, an ELISA) with a lung tumor protein, and does not react detectably with unrelated proteins under similar conditions. As used herein, "binding" refers to a noncovalent association between two separate molecules such that a complex is formed. The ability to bind may be evaluated by, for example, determining a binding constant for the formation of the complex. The binding constant is the value obtained when the concentration of the complex is divided by the product of the component concentrations. In general, two compounds are said to "bind," in the context of the present invention, when the binding constant for complex formation exceeds about $10^3$ L/mol.

The binding constant may be determined using methods well known in the art.

Binding agents may be further capable of differentiating between patients with and without a cancer, such as lung cancer, using the representative assays provided herein. In other words, antibodies or other binding agents that bind to a lung tumor protein will generate a signal indicating the presence of a cancer in at least about 20% of patients with the disease, and will generate a negative signal indicating the absence of the disease in at least about 90% of individuals without the cancer. To determine whether a binding agent satisfies this requirement, biological samples (e.g. blood, sera, sputum urine and/or tumor biopsies ) from patients with and without a cancer (as determined using standard clinical tests) may be assayed as described herein for the presence of polypeptides that bind to the binding agent. It will be apparent that a statistically significant number of samples with and without the disease should be assayed. Each binding agent should satisfy the above criteria; however, those of ordinary skill in the art will recognize that binding agents may be used in combination to improve sensitivity.

Any agent that satisfies the above requirements may be a binding agent For example, a binding agent may be a ribosome, with or without a peptide component, an RNA molecule or a polypeptide. In a preferred embodiment, a binding agent is an antibody or an antigen-binding fragment thereof. Antibodies may be prepared by any of a variety of techniques known to those of ordinary skill in the art. See, e.g., Harlow and Lane, *Antibodies: A Laboratory Manual,* Cold Spring Harbor Laboratory, 1988. In general, antibodies can be produced by cell culture techniques, including the generation of monoclonal antibodies as described herein, or via transfection of antibody genes into suitable bacterial or mammalian cell hosts, in order to allow for the production of recombinant antibodies. In one technique, an immunogen comprising the polypeptide is initially injected into any of a wide variety of mammals (e.g., mice, rats, rabbits, sheep or goats). In this step, the polypeptides of this invention may serve as the immunogen without modification. Alternatively, particularly for relatively short polypeptides, a superior immune response may be elicited if the polypeptide is joined to a carrier protein, such as bovine serum albumin or keyhole limpet hemocyanin. The immunogen is injected into the animal host, preferably according to a predetermined schedule incorporating one or more booster immunizations, and the animals are bled periodically. Polyclonal antibodies specific for the polypeptide may then be purified from such antisera by, for example, affinity chromatography using the polypeptide coupled to a suitable solid support.

Monoclonal antibodies specific for an antigenic polypeptide of interest may be prepared, for example, using the technique of Kohler and Milstein, *Eur. J. Immunol.* 6:511–519, 1976, and improvements thereto. Briefly, these methods involve the preparation of immortal cell lines capable of producing antibodies having the desired specificity (i.e., reactivity with the polypeptide of interest). Such cell lines may be produced, for example, from spleen cells obtained from an animal immunized as described above. The spleen cells are then immortalized by, for example, fusion with a myeloma cell fusion partner, preferably one that is syngeneic with the immunized animal. A variety of fusion techniques may be employed. For example, the spleen cells and myeloma cells may be combined with a nonionic detergent for a few minutes and then plated at low density on a selective medium that supports the growth of hybrid cells, but not myeloma cells. A preferred selection technique uses HAT (hypoxanthine, aminopterin, thymidine) selection. After a sufficient time, usually about 1 to 2 weeks, colonies of hybrids are observed. Single colonies are selected and their culture supernatants tested for binding activity against the polypeptide. Hybridomas having high reactivity and specificity are preferred.

Monoclonal antibodies may be isolated from the supernatants of growing hybridoma colonies. In addition, various techniques may be employed to enhance the yield, such as injection of the hybridoma cell line into the peritoneal cavity of a suitable vertebrate host, such as a mouse. Monoclonal antibodies may then be harvested from the ascites fluid or the blood. Contaminants may be removed from the antibodies by conventional techniques, such as chromatography, gel filtration, precipitation, and extraction. The polypeptides of this invention may be used in the purification process in, for example, an affinity chromatography step.

Within certain embodiments, the use of antigen-binding fragments of antibodies may be preferred. Such fragments include Fab fragments, which may be prepared using standard techniques. Briefly, immunoglobulins may be purified from rabbit serum by affinity chromatography on Protein A bead columns (Harlow and Lane, *Antibodies: A Laboratory Manual,* Cold Spring Harbor Laboratory, 1988) and digested by papain to yield Fab and Fc fragments. The Fab and Fc fragments may be separated by affinity chromatography on protein A bead columns.

Monoclonal antibodies of the present invention may be coupled to one or more therapeutic agents. Suitable agents in this regard include radionuclides, differentiation inducers, drugs, toxins, and derivatives thereof. Preferred radionuclides include $^{90}Y$, $^{123}I$, $^{125}I$, $^{131}I$, $^{186}Re$, $^{188}Re$, $^{211}At$, and $^{212}Bi$. Preferred drugs include methotrexate, and pyrimidine and purine analogs. Preferred differentiation inducers include phorbol esters and butyric acid. Preferred toxins include ricin, abrin, diptheria toxin,. cholera toxin, gelonin, *Pseudomonas exotoxin,* Shigella toxin, and pokeweed antiviral protein.

A therapeutic agent may be coupled (e.g., covalently bonded) to a suitable monoclonal antibody either directly or indirectly (e.g., via a linker group). A direct reaction between an agent and an antibody is possible when each possesses a substituent capable of reacting with the other. For example, a nucleophilic group, such as an amino or sulfhydryl group, on one may be capable of reacting with a carbonyl-containing group, such as an anhydride or an acid halide, or with an alkyl group containing a good leaving group (e.g., a halide) on the other.

Alternatively, it may be desirable to couple a therapeutic agent and an antibody via a linker group. A linker group can function as a spacer to distance an antibody from an agent in order to avoid interference with binding capabilities. A linker group can also serve to increase the chemical reactivity of a substituent on an agent or an antibody, and thus increase the coupling efficiency. An increase in chemical reactivity may also facilitate the use of agents, or functional groups on agents, which otherwise would not be possible.

It will be evident to those skilled in the art that a variety of bifunctional or polyfunctional reagents, both homo- and hetero-functional (such as those described in the catalog of the Pierce Chemical Co., Rockford, Ill.), may be employed as the linker group. Coupling may be effected, for example, through amino groups, carboxyl groups, sulfhydryl groups or oxidized carbohydrate residues. There are numerous references describing such methodology, e.g., U.S. Pat. No. 4,671,958, to Rodwell et al.

Where a therapeutic agent is more potent when free from the antibody portion of the immunoconjugates of the present invention, it may be desirable to use a linker group which is cleavable during or upon internalization into a cell. A number of different cleavable linker groups have been described. The mechanisms for the intracellular release of an agent from these linker groups include cleavage by reduction of a disulfide bond (e.g., U.S. Pat. No. 4,489,710, to Spitler), by irradiation of a photolabile bond (e.g., U.S. Pat. No. 4,625,014, to Senter et al.), by hydrolysis of derivatized amino acid side chains (e.g., U.S. Pat. No. 4,638,045, to Kohn et al.), by serum complement-mediated hydrolysis (e.g., U.S. Pat. No. 4,671,958, to Rodwell et al.), and acid-catalyzed hydrolysis (e.g., U.S. Pat. No. 4,569,789, to Blattler et al.).

It may be desirable to couple more than one agent to an antibody. In one embodiment, multiple molecules of an agent are coupled to one antibody molecule. In another embodiment, more than one type of agent may be coupled to one antibody. Regardless of the particular embodiment, immunoconjugates with more than one agent may be prepared in a variety of ways. For example, more than one agent may be coupled directly to an antibody molecule, or linkers which provide multiple sites for attachment can be used. Alternatively, a carrier can be used.

A carrier may bear the agents in a variety of ways, including covalent bonding either directly or via a linker group. Suitable carriers include proteins such as albumins (e.g., U.S. Pat. No. 4,507,234, to Kato et al.), peptides and polysaccharides such as aminodextran (e.g., U.S. Pat. No. 4,699,784, to Shih et al.). A carrier may also bear an agent by noncovalent bonding or by encapsulation, such as within a liposome vesicle (e.g., U.S. Pat. Nos. 4,429,008 and 4,873,088). Carriers specific for radionuclide agents include radiohalogenated small molecules and chelating compounds. For example, U.S. Pat. No. 4,735,792 discloses representative radiohalogenated small molecules and their synthesis. A radionuclide chelate may be formed from chelating compounds that include those containing nitrogen and sulfur atoms as the donor atoms for binding the metal, or metal oxide, radionuclide. For example, U.S. Pat. No. 4,673,562, to Davison et al. discloses representative chelating compounds and their synthesis.

A variety of routes of administration for the antibodies and immunoconjugates may be used. Typically, administration will be intravenous, intramuscular, subcutaneous or in the bed of a resected tumor. It will be evident that the precise dose of the antibody/immunoconjugate will vary depending upon the antibody used, the antigen density on the tumor, and the rate of clearance of the antibody.

T Cells

Immunotherapeutic compositions may also, or alternatively, comprise T cells specific for a lung tumor protein. Such cells may generally be prepared in vitro or ex vivo, using standard procedures. For example, T cells may be isolated from bone marrow, peripheral blood, or a fraction of bone marrow or peripheral blood of a patient, using a commercially available cell separation system, such as the Isolex™ System, available from Nexell Therapeutics, Inc. Irvine, Calif. (see also U.S. Pat. Nos. 5,240,856; 5,215,926; WO 89/06280; WO 91/16116 and WO 92/07243). Alternatively, T cells may be derived from related or unrelated humans, non-human mammals, cell lines or cultures.

T cells may be stimulated with a lung tumor polypeptide, polynucleotide encoding a lung tumor polypeptide and/or an antigen presenting cell (APC) that expresses such a polypeptide. Such stimulation is performed under conditions and for a time sufficient to permit the generation of T cells that are specific for the polypeptide. Preferably, a lung tumor polypeptide or polynucleotide is present within a delivery vehicle, such as a microsphere, to facilitate the generation of specific T cells.

T cells are considered to be specific for a lung tumor polypeptide if the T cells specifically proliferate, secrete cytokines or kill target cells coated with the polypeptide or expressing a gene encoding the polypeptide. T cell specificity may be evaluated using any of a variety of standard techniques. For example, within a chromium release assay or proliferation assay, a stimulation index of more than two fold increase in lysis and/or proliferation, compared to negative controls, indicates T cell specificity. Such assays may be performed, for example, as described in Chen et al., Cancer Res. 54:1065–1070, 1994. Alternatively, detection of the proliferation of T cells may be accomplished by a variety of known techniques. For example, T cell proliferation can be detected by measuring an increased rate of DNA synthesis (e.g., by pulse-labeling cultures of T cells with tritiated thymidine and measuring the amount of tritiated thymidine incorporated into DNA). Contact with a lung tumor polypeptide (100 ng/ml–100 µg/ml, preferably 200 ng/ml–25 µg/ml) for 3–7 days should result in at least a two fold increase in proliferation of the T cells. Contact as described above for 2–3 hours should result in activation of the T cells, as measured using standard cytokine assays in which a two fold increase in the level of cytokine release (e.g., TNF or IFN-γ) is indicative of T cell activation (see Coligan et al., Current Protocols in Immunology, vol. 1, Wiley Interscience (Greene 1998)). T cells that have been activated in response to a lung tumor polypeptide, polynucleotide or polypeptide-expressing APC may be CD4$^+$ and/or CD8$^+$. Lung tumor protein-specific T cells may be expanded using standard techniques. Within preferred embodiments. the T cells are derived from either a patient or a related, or unrelated, donor and are administered to the patient following stimulation and expansion.

For therapeutic purposes, CD4$^+$ or CD8$^+$ T cells that proliferate in response to a lung tumor polypeptide, polynucleotide or APC can be expanded in number either in vitro or in vivo. Proliferation of such T cells in vitro may be accomplished in a variety of ways. For example, the T cells can be re-exposed to a lung tumor polypeptide, or a short peptide corresponding to an immunogenic portion of such a polypeptide, with or without the addition of T cell growth factors, such as interleukin-2, and/or stimulator cells that synthesize a lung tumor polypeptide. Alternatively, one or more T cells that proliferate in the presence of a lung tumor protein can be expanded in number by cloning. Methods for cloning cells are well known in the art, and include limiting dilution.

Pharmaceutical Compositions and Vaccines

Within certain aspects, polypeptides, polynucleotides, T cells and/or binding agents disclosed herein may be incorporated into pharmaceutical compositions or immunogenic compositions (i. e., vaccines). Pharmaceutical compositions comprise one or more such compounds and a physiologically acceptable carrier. Vaccines may comprise one or more such compounds and an immunostimulant. An immunostimulant may be any substance that enhances or potentiates an immune response to an exogenous antigen. Examples of immunostimulants include adjuvants, biodegradable microspheres (e.g., polylactic galactide) and liposomes (into which the compound is incorporated; see e.g., Fullerton, U.S. Pat. No. 4,235,877). Vaccine preparation is generally described in, for example, M. F. Powell and M. J. Newman, eds., "Vaccine Design (the subunit and adjuvant approach)," Plenum Press (NY, 1995). Pharmaceutical compositions and vaccines within the scope of the present invention may also contain other compounds, which may be biologically active or inactive. For example, one or more immunogenic portions of other tumor antigens may be present, either incorporated into a fusion polypeptide or as a separate compound, within the composition or vaccine.

A pharmaceutical composition or vaccine may contain DNA encoding one or more of the polypeptides as described above, such that the polypeptide is generated in situ. As noted above, the DNA may be present within any of a variety of delivery systems known to those of ordinary skill in the art, including nucleic acid expression systems, bacteria and viral expression systems. Numerous gene delivery techniques are well known in the art, such as those described by Rolland, Crit. Rev. Therap. Drug Carrier Systems 15: 143–198, 1998, and references cited therein. Appropriate nucleic acid expression. systems contain the necessary DNA sequences for expression in the patient (such as a suitable promoter and terminating signal). Bacterial delivery systems involve the administration of a bacterium (such as Bacillus-Calmette-Guerrin) that expresses an immunogenic portion of the polypeptide on its cell surface or secretes such an epitope. In a preferred embodiment, the DNA may be introduced using a viral expression system (e.g., vaccinia or other pox virus, retrovirus, or adenovirus), which may involve the use of a non-pathogenic (defective), replication competent virus. Suitable systems are disclosed, for example, in Fisher-Hoch et al., Proc. Natl. Acad. Sci. USA 86:317–321, 1989; Flexner et al., Ann. N.Y. Acad. Sci. 569:86–103, 1989; Flexner et al., Vaccine 8:17–21, 1990; U.S. Pat. Nos. 4,603,112, 4,769,330, and 5,017,487; WO 89/01973; U.S. Pat. No. 4,777,127; GB2,200,651; EP 0,345, 242; WO 91/02805; Berkner, Biotechniques 6:616–627, 1988; Rosenfeld et al., Science 252:431–434, 1991; Kolls et al., Proc. Natl. Acad. Sci. USA 91:215–219, 1994; Kass-Eisler et al., Proc. Natl. Acad. Sci. USA 90:11498–11502, 1993; Guzman et al., Circulation 88:2838–2848, 1993; and Guzman et al., Cir. Res. 73:1202–1207, 1993. Techniques for incorporating DNA into such expression systems are well known to those of ordinary skill in the art. The DNA may also be "naked," as described, for example, in Ulmer et al., Science 259:1745–1749, 1993 and reviewed by Cohen, Science 259:1691–1692, 1993. The uptake of naked DNA may be increased by coating the DNA onto biodegradable beads, which are efficiently transported into the cells.

While any suitable carrier known to those of ordinary skill in the art may be employed in the pharmaceutical compositions of this invention, the type of carrier will vary depending on the mode of administration. Compositions of the present invention may be formulated for any appropriate manner of administration, including for example, topical, oral, nasal, intravenous, intracranial, intraperitoneal, subcutaneous or intramuscular administration. For parenteral administration, such as subcutaneous injection, the carrier preferably comprises water, saline, alcohol, a fat, a wax or a buffer. For oral administration, any of the above carriers or a solid carrier, such as mannitol, lactose, starch, magnesium stearate, sodium saccharine, talcum, cellulose, glucose, sucrose, and magnesium carbonate, may be employed. Biodegradable microspheres (e.g., polylactate polyglycolate) may also be employed as carriers for the pharmaceutical compositions of this invention. Suitable biodegradable microspheres are disclosed, for example, in U.S. Pat. Nos. 4,897,268 and 5,075,109.

Such compositions may also comprise buffers (e.g., neutral buffered saline or phosphate buffered saline), carbohydrates (e.g., glucose, maniose, sucrose or dextrans), mannitol, proteins, polypeptides or amino acids such as glycine, antioxidants, chelating agents such as EDTA or glutathione, adjuvants (e.g., aluminum hydroxide) and/or preservatives. Alternatively, compositions of the present invention may be formulated as a lyophilizate. Compounds may also be encapsulated within liposomes using well known technology.

Any of a variety of immunostimiiulants may be employed in the vaccines of this invention. For example, an adjuvant may be included. Most adjuvants contain a substance designed to protect the antigen from rapid catabolism, such as aluminum hydroxide or mineral oil, and a stimulator of immune responses, such as lipid A, Bortadella pertussis or Mycobacterium tuberculosis derived proteins. Suitable adjuvants are commercially available as, for example, Freund's Incomplete Adjuvant and Complete Adjuvant (Difco Laboratories, Detroit, Mich.); Merck Adjuvant 65 (Merck and Company, Inc., Rahway, N.J.); AS-2 (SmithKline Beecham, Philadelphia, Pa.); aluminum salts such as aluminum hydroxide gel (alum) or aluminum phosphate; salts of calcium, iron or zinc; an insoluble suspension of acylated tyrosine; acylated sugars; cationically or anionically derivatized polysaccharides; polyphosphazenes; biodegradable microspheres; monophosphoryl lipid A and quil A. Cytokines, such as GM-CSF or interleukin-2, -7, or -12, may also be used as adjuvants.

Within the vaccines provided herein, the adjuvant composition is preferably designed to induce an immune response predominantly of the Th1 type. High levels of Th1-type cytokines (e.g., IFN-γ, TNFα, IL-2 and IL-12) tend to favor the induction of cell mediated immune responses to an administered antigen. In contrast, high levels of Th2-type cytokines (e.g, IL-4, IL-5, IL-6 and IL-10) tend to favor the induction of humoral immune responses. Following application of a vaccine as provided herein, a patient will support an immune response that includes Th1- and Th2-type responses. Within a preferred embodiment, in which a response is predominantly Th1-type, the level of Th1-type cytokines will increase to a greater extent than the level of Th2-type cytokines. The levels of these cytokines may be readily assessed using standard assays. For a review of the families of cytokines, see Mosmann and Coffman, Ann. Rev. Immunol. 7:145–173, 1989.

Preferred adjuvants for use in eliciting a predominantly Th1-type response include, for example, a combination of monophosphoryl lipid A, preferably 3-de-O-acylated monophosphoryl lipid A (3D-MPL), together with an aluminum salt. MPL adjuvants are available from Ribi ImmunoChem Research Inc. (Hamilton, Mont.) (see U.S. Pat. Nos. 4,436, 727; 4,877,611; 4,866,034 and 4,912,094). CpG-containing oligonucleotides (in which the CpG dinucleotide is unmethylated) also induce a predominantly Th1 response. Such oligonucleotides are well known and are described, for example, in WO 96/02555 and WO 99/33488. Immunostimulatory DNA sequences are also described, for example, by Sato et al., Science 273:352, 1996. Another preferred adjuvant is a saponin, preferably QS21 (Aquila Biopharmaceuticals Inc., Framingham, Mass.), which may be used alone or in combination with other adjuvants. For example, an enhanced system involves the combination of a monophosphoryl lipid A and saponin derivative, such as the combination of QS21 and 3D-MPL as described in WO 94/00153, or a less reactogenic composition where the QS21 is quenched with cholesterol, as described in WO 96/33739. Other preferred formulations comprises an oil-in-water emulsion and tocopherol. A particularly potent adjuvant formulation involving QS21, 3D-MPL and tocopherol in an oil-in-water emulsion is described in WO 95/17210.

Other preferred adjuvants include Montanide ISA 720 (Seppic, France), SAF (Chiron, California, United States), ISCOMS (CSL), MF-59 (Chiron), the SBAS series of adjuvants (e.g., SBAS-2 or SBAS-4, available from SmithKline Beechamn, Rixensart, Belgium), Detox (Ribi ImmunoChem Research Inc., Hamilton, Mont.), RC-529 (Ribi ImmunoChem Research Inc., Hamilton, Mont.) and Aminoalkyl glucosaminide 4-phosphates (AGPs).

Any vaccine provided herein may be prepared using well known methods that result in a combination of antigen, immune response enhancer and a suitable carrier or excipient. The compositions described herein may be administered as part of a sustained release formulation (i.e., a formulation such as a capsule, sponge or gel (composed of polysaccharides, for example) that effects a slow release of compound following administration). Such formulations may generally be prepared using well known technology (see, e.g. Coombes et al., Vaccine 14:1429–1438, 1996) and administered by, for example, oral, rectal or subcutaneous implantation, or by implantation at the desired target site. Sustained-release formulations may contain a polypeptide, polynucleotide or antibody dispersed in a carrier matrix and/or contained within a reservoir surrounded by a rate controlling membrane.

Carriers for use within such formulations are biocompatible, and may also be biodegradable; preferably the formulation provides a relatively constant level of active component release. Such carriers include microparticles of poly(lactide-co-glycolide), as well as polyacrylate, latex, starch, cellulose and dextran. Other delayed-release carriers include supramolecular biovectors, which comprise a non-liquid hydrophilic core (e.g., a cross-linked polysaccharide or oligosaccharide) and, optionally, an external layer comprising an amphiphilic compound, such as a phospholipid (see e.g., U.S. Pat. No. 5,151,254 and PCT applications WO 94/20078, WO/94/23701 and WO 96/06638). The amount of active compound contained within a sustained release formulation depends upon the site of implantation, the rate and expected duration of release and the nature of the condition to be treated or prevented.

Any of a variety of delivery vehicles may be employed within pharmaceutical compositions and vaccines to facilitate production of an antigen-specific immune response that targets tumor cells. Delivery vehicles include antigen presenting cells (APCs), such as dendritic cells, macrophages, B cells, monocytes and other cells that may be engineered to be efficient APCs. Such cells may, but need not, be genetically modified to increase the capacity for presenting the antigen, to improve activation and/or maintenance of the T cell response, to have anti-tumor effects per se and/or to be immunologically compatible with the receiver (i.e., matched HLA haplotype). APCs may generally be isolated from any of a variety of biological fluids and organs, including tumor and peritumoral tissues, and may be autologous, allogeneic, syngeneic or xenogeneic cells.

Certain preferred embodiments of the present invention use dendritic cells or progenitors thereof as antigen-presenting cells. Dendritic cells are highly potent APCs (Banchereau and Steinman, Nature 392:245–251, 1998) and have been shown to be effective as a physiological adjuvant for eliciting prophylactic or therapeutic antitumor immunity (see Timmerman and Levy, Ann. Rev. Med. 50:507–529, 1999). In general, dendritic cells may be identified based on their typical shape (stellate in situ, with marked cytoplasmic processes (dendrites) visible in vitro), their ability to take up, process and present antigens with high efficiency, and their ability to activate naive T cell responses. Dendritic cells may, of course, be engineered to express specific cell-surface receptors or ligands that are not commonly found on dendritic cells in vivo or ex vivo, and such modified dendritic cells are contemplated by the present invention. As an alternative to dendritic cells, secreted vesicles antigen-loaded dendritic cells (called exosomes) may be used within a vaccine (see Zitvogel et al., Nature Med. 4:594–600, 1998).

Dendritic cells and progenitors may be obtained from peripheral blood, bone marrow, tumor-infiltrating cells, peri-tumoral tissues-infiltrating cells, lymph nodes, spleen, skin, umbilical cord blood or any other suitable tissue or fluid. For example, dendritic cells may be differentiated ex vivo by adding a combination of cytokines such as GM-CSF, IL-4, IL-13 and/or TNFα to cultures of monocytes harvested from peripheral blood. Alternatively, CD34 positive cells harvested from peripheral blood, umbilical cord blood or bone marrow may be differentiated into dendritic cells by adding to the culture medium combinations of GM-CSF, IL-3, TNFα, CD40 ligand, LPS, flt3 ligand and/or other compound(s) that induce differentiation, maturation and proliferation of dendritic cells.

Dendritic cells are conveniently categorized as "immature" and "mature" cells, which allows a simple way to discriminate between two well characterized phenotypes. However, this nomenclature should not be construed to exclude all possible intermediate stages of differentiation. Immature dendritic cells are characterized as APC with a high capacity for antigen uptake and processing, which correlates with the high expression of Fcγ receptor and mannose receptor. The mature phenotype is typically characterized by a lower expression of these markers, but a high expression of cell surface molecules responsible for T cell activation such as class I and class II MHC, adhesion molecules (e.g., CD54 and CD11) and costimulatory molecules (e.g., CD40, CD80, CD86 and 4-1BB).

APCs may generally be transfected with a polynucleotide encoding a lung tumor protein (or portion or other variant thereof) such that the lung tumor polypeptide, or an immunogenic portion thereof, is expressed on the cell surface. Such transfection may take place ex vivo, and a composition or vaccine comprising such transfected cells may then be used for therapeutic purposes, as described herein. Alternatively, a gene delivery vehicle that targets a dendritic or other antigen presenting cell may be administered to a patient, resulting in transfection that occurs in vivo. In vivo and ex vivo transfection of dendritic cells, for example, may generally be performed using any methods known in the art, such as those described in WO 97/24447, or the gene gun approach described by Mahvi et al., Immunology and cell Biology 75:456–460, 1997. Antigen loading of dendritic cells may be achieved by incubating dendritic cells or progenitor cells with the lung tumor polypeptide, DNA (naked or within a plasmid vector) or RNA; or with antigen-expressing recombinant bacterium or viruses (e.g., vaccinia, fowlpox, adenovirus or lentivirus vectors). Prior to loading, the polypeptide may be covalently conjugated to an immunological partner that provides T cell help (e.g., a carrier molecule). Alternatively, a dendritic cell may be pulsed with a non-conjugated immunological partner, separately or in the presence of the polypeptide.

Vaccines and pharmaceutical compositions may be presented in unit-dose or multi-dose containers, such as sealed ampoules or vials. Such containers are preferably hermetically sealed to preserve sterility of the formulation until use. In general, formulations may be stored as suspensions, solutions or emulsions in oily or aqueous vehicles.

Alternatively, a vaccine or pharmaceutical composition may be stored in a freeze-dried condition requiring only the addition of a sterile liquid carrier immediately prior to use.

Cancer Therapy

In further aspects of the present invention, the compositions described herein may be used for immunotherapy of cancer, such as lung cancer. Within such methods, pharmaceutical compositions and vaccines are typically administered to a patient. As used herein, a "patient" refers to any warm-blooded animal, preferably a human. A patient may or may not be afflicted with cancer. Accordingly, the above pharmaceutical compositions and vaccines may be used to prevent the development of a cancer or to treat a patient afflicted with a cancer. A cancer may be diagnosed using critria generally accepted in the art, including the presence of a malignant tumor. Pharmaceutical compositions and vaccines may be administered either prior to or following surgical removal of primary tumors and/or treatment such as administration of radiotherapy or conventional chemotherapeutic drugs.

Within certain embodiments, immunotherapy may be active immunotherapy, in which treatment relies on the in vivo stimulation of the endogenous host immune system to react against tumors with the administration of immune response-modifying agents (such as polypeptides and polynucleotides disclosed herein).

Within other embodiments, immunotherapy may be passive immunotherapy, in which treatment involves the delivery of agents with established tumor-immune reactivity (such as effector cells or antibodies) that can directly or indirectly mediate antitumor effects and does not necessarily depend on an intact host immune system. Examples of effector cells include T cells as discussed above, T lymphocytes (such as $CD8^+$ cytotoxic T lymphocytes and $CD4^+$ T-helper tumor-infiltrating lymphocytes), killer cells (such as Natural Killer cells and lymphokine-activated killer cells), B cells and antigen-presenting cells (such as dendritic cells and macrophages) expressing a polypeptide provided herein. T cell receptors and antibody receptors specific for the polypeptides recited herein may be cloned, expressed and transferred into other vectors or effector cells for adoptive immunotherapy. The polypeptides provided herein may also be used to generate antibodies or anti-idiotypic antibodies (as described above and in U.S. Pat. No. 4,918,164) for passive immunotherapy.

Effector cells may generally be obtained in sufficient quantities for adoptive immunotherapy by growth in vitro, as described herein. Culture conditions for expanding single antigen-specific effector cells to several billion in number with retention of antigen recognition in vivo are well known in the art. Such in vitro culture conditions typically use intermittent stimulation with antigen, often in the presence of cytokines (such as IL-2) and non-dividing feeder cells. As noted above, immunoreactive polypeptides as provided herein may be used to rapidly expand antigen-specific T cell cultures in order to generate a sufficient number of cells for immunotherapy. In particular, antigen-presenting cells, such as dendritic, macrophage, monocyte, fibroblast and/or B cells, may be pulsed with immunoreactive polypeptides or transfected with one or more polynucleotides using standard techniques well known in the art. For example, antigen-presenting cells can be transfected with a polynucleotide having a promoter appropriate for increasing expression in a recombinant virus or other expression system. Cultured effector cells for use in therapy must be able to grow and distribute widely, and to survive long term in vivo. Studies have shown that cultured effector cells can be induced to grow in vivo and to survive long term in substantial numbers by repeated stimulation with antigen supplemented with IL-2 (see, for example, Cheever et al., *Immunological Reviews* 157:177, 1997).

Alternatively, a vector expressing a polypeptide recited herein may be introduced into antigen presenting cells taken from a patient and clonally propagated ex vivo for transplant back into the same patient. Transfected cells may be reintroduced into the patient using any means known in the art, preferably in sterile form by intravenous, intracavitary, intraperitoneal or intratumor administration.

Routes and frequency of administration of the therapeutic compositions disclosed herein, as well as dosage, will vary from individual to individual, and may be readily established using standard techniques. In general, the pharmaceutical compositions and vaccines may be administered by injection (e.g., intracutaneous, intramuscular, intravenous or subcutaneous), intranasally (e.g., by aspiration) or orally. Preferably, between 1 and 10 doses may be administered over a 52 week period. Preferably, 6 doses are administered, at intervals of 1 month, and booster vaccinations may be given periodically thereafter. Alternate protocols may be appropriate for individual patients. A suitable dose is an amount of a compound that, when administered as described above, is capable of promoting an anti-tumor immune response, and is at least 10–50% above the basal (ie., untreated) level. Such response can be monitored by measuring the anti-tumor antibodies in a patient or by vaccine-dependent generation of cytolytic effector cells capable of killing the patient's tumor cells in vitro. Such vaccines should also be capable of causing an immune response that leads to an improved clinical outcome (e.g., more frequent remissions, complete or partial or longer disease-free survival) in vaccinated patients as compared to non-vaccinated patients. In general, for pharmaceutical compositions and vaccines comprising one or more polypeptides, the amount of each polypeptide present in a dose ranges from about 25 $\mu$g to 5 mg per kg of host. Suitable dose sizes will vary with the size of the patient, but will typically range from about 0.1 mL to about 5 mL.

In general, an appropriate dosage and treatment regimen provides the active compound(s) in an amount sufficient to provide therapeutic and/or prophylactic benefit. Such a response can be monitored by establishing an improved clinical outcome (e.g., more frequent remissions, complete or partial, or longer disease-free survival) in treated patients as compared to non-treated patients. Increases in preexisting immune responses to a lung tumor protein generally correlate with an improved clinical outcome. Such immune responses may generally be evaluated using standard proliferation, cytotoxicity or cytok-ne assays, which may be performed using samples obtained from a patient before and after treatment.

Methods for Detecting Cancer

In general, a cancer may be detected in a patient based on the presence of one or more lung tumor proteins and/or polynucleotides encoding such proteins in a biological sample (for example, blood, sera, sputum urine and/or tumor biopsies) obtained from the patient. In other words, such proteins may be used as markers to indicate the presence or absence of a cancer such as lung cancer. In addition, such proteins may be useful for the detection of other cancers. The binding agents provided herein generally permit detection of the level of antigen that binds to the agent in the biological sample. Polynucleotide primers and probes may be used to detect the level of mRNA encoding a tumor protein, which is also indicative of the presence or absence of a cancer. In general, a lung tumor sequence should be present at a level that is at least three fold higher in tumor tissue than in normal tissue.

There are a variety of assay formats known to those of ordinary skill in the art for using a binding agent to detect polypeptide markers in a sample. See, e.g, Harlow and Lane, *Antibodies: A Laboratory Manual,* Cold Spring Harbor Laboratory, 1988. In general, the presence or absence of a cancer in a patient may be determined by (a) contacting a biological sample obtained from a patient with a binding agent; (b) detecting in the sample a level of polypeptide that binds to the binding agent; and (c) comparing the level of polypeptide with a predetermined cut-off value.

In a preferred embodiment, the assay involves the use of binding agent immobilized on a solid support to bind to and remove the polypeptide from the remainder of the sample. The bound polypeptide may then be detected using a detection reagent that contains a reporter group and specifically binds to the binding agent/polypeptide complex. Such detection reagents may comprise, for example, a binding agent that specifically binds to the polypeptide or an antibody or other agent that specifically binds to the binding agent, such as an anti-immunoglobulin, protein G, protein A or a lectin. Alternatively, a competitive assay may be utilized, in which a polypeptide is labeled with a reporter group and allowed to bind to the immobilized binding agent after incubation of the binding agent with the sample. The extent to which components of the sample inhibit the binding of the labeled polypeptide to the binding agent is indicative of the reactivity of the sample with the immobilized binding agent. Suitable polypeptides for use within such assays include full length lung tumor proteins and portions thereof to which the binding agent binds, as described above.

The solid support may be any material known to those of ordinary skill in the art to which the tumor protein may be attached. For example, the solid support may be a test well in a microtiter plate or a nitrocellulose or other suitable membrane. Alternatively, the support may be a bead or disc, such as glass, fiberglass, latex or a plastic material such as polystyrene or polyvinylchloride. The support may also be a magnetic particle or a fiber optic sensor, such as those disclosed, for example, in U.S. Pat. No. 5,359,681. The binding agent may be immobilized on the solid support using a variety of techniques known to those of skill in the art, which are amply described in the patent and scientific literature. In the context of the present invention, the term "immobilization" refers to both noncovalent association, such as adsorption, and covalent attachment (which may be a direct linkage between the agent and functional groups on the support or may be a linkage by way of a cross-linking agent). Immobilization by adsorption to a well in a microtiter plate or to a membrane is preferred. In such cases, adsorption may be achieved by contacting the binding agent, in a suitable buffer, with the solid support for a suitable amount of time. The contact time varies with temperature, but is typically between about 1 hour and about 1 day. In general, contacting a well of a plastic microtiter plate (such as polystyrene or polyvinylchloride) with an amount of binding agent ranging from about 10 ng to about 10 µg, and preferably about 100 ng to about 1 µg, is sufficient to immobilize an adequate amount of binding agent.

Covalent attachment of binding agent to a solid support may generally be achieved by first reacting the support with a bifunctional reagent that will react with both the support and a functional group, such as a hydroxyl or amino group, on the binding agent. For example, the binding agent may be covalently attached to supports having an appropriate polymer coating using benzoquinone or by condensation of an aldehyde group on the support with an amine and an active hydrogen on the binding partner (see, e.g., Pierce Immunotechnology Catalog and Handbook., 1991, at A12–A13).

In certain embodiments, the assay is a two-antibody sandwich assay. This assay may be performed by first contacting an antibody that has been immobilized on a solid support, commonly the well of a microtiter plate, with the sample, such that polypeptides within the sample are allowed to bind to the immobilized antibody. Unbound sample is then removed from the immobilized polypeptide-antibody complexes and a detection reagent (preferably a second antibody capable of binding to a different site on the polypeptide) containing a reporter group is added. The amount of detection reagent that remains bound to the solid support is then determined using a method appropriate for the specific reporter group.

More specifically, once the antibody is immobilized on the support as described above, the remaining protein binding sites on the support are typically blocked. Any suitable blocking agent known to those of ordinary skill in the art, such as bovine serum albumin or Tween 20™ (Sigma Chemical Co., St. Louis, Mo.). The immobilized antibody is then incubated with the sample, and polypeptide is allowed to bind to the antibody. The sample may be diluted with a suitable diluent, such as phosphate-buffered saline (PBS) prior to incubation. In general, an appropriate contact time (i.e., incubation time) is a period of time that is sufficient to detect the presence of polypeptide within a sample obtained from an individual with lung cancer. Preferably, the contact time is sufficient to achieve a level of binding that is at least about 95% of that achieved at equilibrium between bound and unbound polypeptide. Those of ordinary skill in the art will recognize that the time necessary to achieve equilibrium may be readily determined by assaying the level of binding that occurs over a period of time. At room temperature, an incubation time of about 30 minutes is generally sufficient.

Unbound sample may then be removed by washing the solid support with an appropriate buffer, such as PBS containing 0.1% Tween 20™. The second antibody, which contains a reporter group, may then be added to the solid support. Preferred reporter groups include those groups recited above.

The detection reagent is then incubated with the immobilized antibody-polypeptide complex for an amount of time sufficient to detect the bound polypeptide. An appropriate amount of time may generally be determined by assaying the level of binding that occurs over a period of time. Unbound detection reagent is then removed and bound detection reagent is detected using the reporter group. The method employed for detecting the reporter group depends upon the nature of the reporter group. For radioactive groups, scintillation counting or autoradiographic methods are generally appropriate. Spectroscopic methods may be used to detect dyes, luminescent groups and fluorescent groups. Biotin may be detected using avidin, coupled to a different reporter group (commonly a radioactive or fluorescent group or an enzyme). Enzyme reporter groups may generally be detected by the addition of substrate (generally for a specific period of time), followed by spectroscopic or other analysis of the reaction products.

To determine the presence or absence of a cancer, such as lung cancer, the signal detected from the reporter group that remains bound to the solid support is generally compared to a signal that corresponds to a predetermined cut-off value. In one preferred embodiment, the cut-off value for the detection of a cancer is the average mean signal obtained when the immobilized antibody is incubated with samples from patients without the cancer. In general, a sample generating a signal that is three standard deviations above the predetermined cut-off value is considered positive for the cancer. In an alternate preferred embodiment, the cut-off value is determined using a Receiver Operator Curve, according to the method of Sackett et al., *Clinical Epidemiology: A Basic Science for Clinical Medicine,* Little Brown and Co., 1985, p. 106–7. Briefly, in this embodiment, the cut-off value may be determined from a plot of pairs of true positive rates (ie., sensitivity) and false positive razes (100%-specificity) that correspond to each possible cut-off value for the diagnostic test result. The cut-off value on the plot that is the closest to the upper left-hand corner (i.e., the value that encloses the largest area) is the most accurate cut-off value, and a sample generating a signal that is higher than the cut-off value determined by this method may be considered positive. Alternatively, the cut-off value may be shifted to the left along the plot, to minimize the false positive rate, or to the right, to minimize the false negative rate. In general, a sample generating a signal that is higher than the cut-off value determined by this method is considered positive for a cancer.

In a related embodiment, the assay is performed in a flow-through or strip test format, wherein the binding agent is immobilized on a membrane, such as nitrocellulose. In the flow-through test, polypeptides within the sample bind to the immobilized binding agent as the sample passes through the membrane. A second, labeled binding agent then binds to the binding agent-polypeptide complex as a solution containing the second binding agent flows through the membrane. The detection of bound second binding agent may then be performed as described above. In the strip test format, one end of the membrane to which binding agent is bound is immersed in a solution containing the sample. The sample migrates along the membrane through a region containing second binding agent and to the area of immobilized binding agent. Concentration of second binding agent at the area of immobilized antibody indicates the presence of a cancer. Typically, the concentration of second binding agent at that site generates a pattern, such as a line, that can be read visually. The absence of such a pattern indicates a negative result. In general, the amount of binding agent immobilized on the membrane is selected to generate a visually discernible pattern when the biological sample contains a level of polypeptide that would be sufficient to generate a positive signal in the two-antibody sandwich assay, in the format discussed above. Preferred binding agents for use in such assays are antibodies and antigen-binding fragments thereof Preferably, the amount of antibody immobilized on the membrane ranges from about 25 ng to about 1 $\mu$g, and more preferably from about 50 ng to about 500 ng. Such tests can typically be performed with a very small amount of biological sample.

Of course, numerous other assay protocols exist that are suitable for use with the tumor proteins or binding agents of the present invention. The above descriptions are intended to be exemplary only. For example, it will be apparent to those of ordinary skill in the art that the above protocols may be readily modified to use lung tumor polypeptides to detect antibodies that bind to such polypeptides in a biological sample. The detection of such lung tumor protein specific antibodies may correlate with the presence of a cancer.

A cancer may also, or alternatively, be detected based on the presence of T cells that specifically react with a lung tumor protein in a biological sample. Within certain methods, a biological sample comprising $CD4^+$ and/cr $CD8^+$ T cells isolated from a patient is incubated with a lung tumor polypeptide, a polynucleotide encoding such a polypeptide and/or an APC that expresses at least an immunogenic portion of such a polypeptide, and the presence or absence of specific activation of the T cells is detected. Suitable biological samples include, but are not limited to, isolated T cells. For example, T cells may be isolated from a patient by routine techniques (such as by Ficoll/Hypaque density gradient centrifugation of peripheral blood lymphocytes). T cells may be incubated in vitro for 2–9 days (typically 4 days) at 37° C. with polypeptide (e.g., 5–25 $\mu$g/ml). It may be desirable to incubate another aliquot of a T cell sample in the absence of lung tumor polypeptide to serve as a control. For $CD4^+$ T cells, activation is preferably detected by evaluating proliferation of the T cells. For $CD8^+$ T cells, activation is preferably detected by evaluating cytolytic activity. A level of proliferation that is at least two fold greater and/or a level of cytolytic activity that is at least 20% greater than in ts disease-free patients indicates the presence of a cancer in the patient.

As noted above, a cancer may also, or alternatively, be detected based on the level of mRNA encoding a lung tumor protein in a biological sample. For example, at least two oligonucleotide primers may be employed in a polymerase chain reaction (PCR) based assay to amplify a portion of a lung tumor cDNA derived from a biological sample, wherein at least one of the oligonucleotide primers is specific for (i.e., hybridizes to) a polynucleotide encoding the lung tumor protein. The amplified cDNA is then separated and detected using techniques well known in the art, such as gel electrophoresis. Similarly, oligonucleotide probes that specifically hybridize to a polynucleotide encoding a lung tumor protein may be used in a hybridization assay to detect the presence of polynucleotide encoding the tumor protein in a biological sample.

To permit hybridization under assay conditions, oligonucleotide primers and probes should comprise an oligonucleotide sequence that has at least about 60%, preferably at least about 75% and more preferably at least about 90%. identity to a portion of a polynucleotide encoding a lung tumor protein that is at least 10 nucleotides, and preferably at least 20 nucleotides, in length. Preferably, oligonucleotide primers and/or probes will hybridize to a polynucleotide encoding a polypeptide disclosed herein under moderately stringent conditions, as defined above. Oligonucleotide primers and/or probes which may be usefully employed in the diagnostic methods described herein preferably are at least 10–40 nucleotides in length. In a preferred embodiment, the oligonucleotide primers comprise at least 10 contiguous nucleotides, more preferably at least 15 contiguous nucleotides, of a DNA molecule having a sequence recited in SEQ ID NO: 1–109, 111, 113, 115–151, 153, 154, 157, 158, 160, 162–164, 167, 168, 171, 173, 175, 177–224, 255–337, 345, 347 and 349. Techniques for both PCR based assays and hybridization assays are well known in the art (see, for example, Mullis et al., *Cold Spring Harbor Symp. Quant. Biol.,* 51:263, 1987; Erlich ed., *PCR Technology,* Stockton Press, NY, 1989).

One preferred assay employs RT-PCR, in which PCR is applied in conjunction with reverse transcription. Typically, RNA is extracted from a biological sample, such as biopsy tissue, and is reverse transcribed to produce cDNA molecules. PCR amplification using at least one specific primer generates a cDNA molecule, which may be separated and visualized using, for example, gel electrophoresis. Amplification may be performed on biological samples taken from a test patient and from an individual who is not afflicted with a cancer. The amplification reaction may be performed on several dilutions of cDNA spanning two orders of magnitude. A two-fold or greater increase in expression in several dilutions of the test patient sample as compared to the same dilutions of the non-cancerous sample is typically considered positive.

In another embodiment, the disclosed compositions may be used as markers for the progression of cancer. In this embodiment, assays as described above for the diagnosis of a cancer may be performed over time, and the change in the level of reactive polypeptide(s) or polynucleotide evaluated. For example, the assays may be performed every 24–72 hours for a period of 6 months to 1 year, and thereafter performed as needed. In general, a cancer is progressing in those patients in whom the level of polypeptide or polynucleotide detected increases over time. In contrast, the cancer is not progressing when the level of reactive polypeptide or polynucleotide either remains constant or decreases with time.

Certain in vivo diagnostic assays may be performed directly on a tumor. One such assay involves contacting tumor cells with a binding agent. The bound binding agent may then be detected directly or indirectly via a reporter group. Such binding agents may also be used in histological applications. Alternatively, polynucleotide probes may be used within such applications.

As noted above, to improve sensitivity, multiple lung tumor protein markers may be assayed within a given sample. It will be apparent that binding agents specific for different proteins provided herein may be combined within a single assay. Further, multiple primers or probes may be used concurrently. The selection of tumor protein markers may be based on routine experiments to determine combinations that results in optimal sensitivity. In addition, or alternatively, assays for tumor proteins provided herein may be combined with assays for other known tumor antigens.

Diagnostic Kits

The present invention further provides kits for use within any of the above diagnostic methods. Such kits typically comprise two or more components necessary for performing a diagnostic assay. Components may be compounds, reagents, containers and/or equipment. For example, one container within a kit may contain a monoclonal antibody or fragment thereof that specifically binds to a lung tumor protein. Such antibodies or fragments may be provided attached to a support material, as described above. One or more additional containers may enclose elements, such as reagents or buffers, to be used in the assay. Such kits may also, or alternatively, contain a detection reagent as described above that contains a reporter group suitable for direct or indirect detection of antibody binding.

Alternatively, a kit may be designed to detect the level of mRNA encoding a lung tumor protein in a biological sample. Such kits generally comprise at least one oligonucleotide probe or primer, as described above, that hybridizes to a polynucleotide encoding a lung tumor protein. Such an oligonucleotide may be used, for example, within a PCR or hybridization assay. Additional components that may be present within such kits include a second oligonucleotide and/or a diagnostic reagent or container to facilitate the detection of a polynucleotide encoding a lung tumor protein.

The following Examples are offered by way of illustration and not by way of limitation.

EXAMPLE 1

Isolation and Characterization of cDNA Sequences Encoding Lung Tumor Polypeptides This example illustrates the isolation of cDNA molecules encoding lung tumor-specific polypeptides from lung tumor cDNA libraries.

A. Isolation of cDNA Sequences from a Lung Squamous Cell Carcinoma Library

A human lung squamous cell carcinoma cDNA expression library was constructed from poly $A^+$ RNA from a pool of two patient tissues using a Superscript Plasmid System for cDNA Synthesis and Plasmid Cloning kit (BRL Life Technologies, Gaithersburg, Md.) following the manufacturer's protocol. Specifically, lung carcinoma tissues were homogenized with polytron (Kinematica, Switzerland) and total RNA was extracted using Trizol reagent (BRL Life Technologies) as directed by the manufacturer. The poly $A^+$ RNA was then purified using an oligo dT cellulose column as described in Sambrook et al., *Molecular Cloning: A Laboratory Manual,* Cold Spring Harbor Laboratories, Cold Spring Harbor, N.Y., 1989. First-strand cDNA was synthesized using the NotI/Oligo-dT18 primer. Double-stranded cDNA was synthesized, ligated with BstXI/EcoRI adaptors (Invitrogen, San Diego, Calif.) and digested with NotI. Following size fractionation with cDNA size fractionation columns (BRL Life Technologies), the cDNA was ligated into the BstXI/NotI site of pcDNA3.1 (Invitrogen) and transformed into ElectroMax *E. coli* DH10B cells (BRL Life Technologies) by electroporation.

Using the same procedure, a normal human lung cDNA expression library was prepared from a pool of four tissue specimens. The cDNA libraries were characterized by determining the number of independent colonies, the percentage of clones that carried insert, the average insert size and by sequence analysis. The lung squamous cell carcinoma library contained $2.7 \times 10^6$ independent colonies, with 100% of clones having an insert and the average insert size being 2100 base pairs. The normal lung cDNA library contained $1.4 \times 10^6$ independent colonies, with 90% of clones having inserts and the average insert size being 1800 base pairs. For both libraries, sequence analysis showed that the majority of clones had a full length cDNA sequence and were synthesized from mRNA.

cDNA library subtraction was performed using the above lung squamous cell carcinoma and normal lung cDNA libraries, as described by Hara et al. (*Blood,* 84:189–199, 1994) with some modifications. Specifically, a lung squamous cell carcinoma-specific subtracted cDNA library was generated as follows. Normal tissue cDNA library (80 µg) was digested with BamHI and XhoI, followed by a filling-in reaction with DNA polymerase Klenow fragment. After phenol-chloroform extraction and ethanol precipitation, the DNA was dissolved in 133 µl of $H_2O$, heat-denatured and mixed with 133 µl (133 µg) of Photoprobe biotin (Vector Laboratories, Burlingame, Calif.). As recommended by the manufacturer, the resulting mixture was irradiated with a 270 W sunlamp on ice for 20 minutes. Additional Photoprobe biotin (67 µl) was added and the biotinylation reaction was repeated. After extraction with butanol five times, the DNA was ethanol-precipitated and dissolved in 23 µl $H_2O$ to form the driver DNA.

To form the tracer DNA, 10 µg lung squamous cell carcinoma cDNA library was digested with NotI and SpeI, phenol chloroform extracted and passed through Chroma spin-400 columns (Clontech, Palo Alto, Calif.). Typically, 5 µg of cDNA was recovered after the sizing column. Following ethanol precipitation, the tracer DNA was dissolved in 5 µl $H_2O$. Tracer DNA was mixed with 15 µl driver DNA and 20 µl of 2×hybridization buffer (1.5 M NaCl/10 mM EDTA/50 mM HEPES pH 7.5/0.2% sodium dodecyl sulfate), overlaid with mineral oil, and heat-denatured completely. The sample was immediately transferred into a 68° C. water bath and incubated for 20 hours (long hybridization

[LH]). The reaction mixture was then subjected to a streptavidin treatment followed by phenol/chloroform extraction. This process was repeated three more times. Subtracted DNA was precipitated, dissolved in 12 μl H$_2$O, mixed with 8 μl driver DNA and 20 μl of 2×hybridization buffer, and subjected to a hybridization at 68° C. for 2 hours (short hybridization [SH]). After removal of biotinylated double-stranded DNA, subtracted cDNA was ligated into NotI/SpeI site of chloramphenlicol resistant pBCSK$^+$ (Stratagene, La Jolla, Calif.) and transformed into ElectroMax *E. coli* DH10B cells by electroporation to generate a lung squamous cell carcinoma specific subtracted cDNA library (herein after referred to as "lung subtraction I").

A second lung squamous cell carcinoma specific subtracted cDNA library (referred to as "lung subtraction II") was generated in a similar way to the lung subtraction library I, except that eight frequently recovered genes from lung subtraction I were included in the driver DNA, and 24,000 independent clones were recovered.

To analyze the subtracted cDNA libraries, plasmid DNA was prepared from 320 independent clones, randomly picked from the subtracted lung squamous cell carcinoma specific libraries. Representative cDNA clones were further characterized by DNA sequencing with a Perkin Elmer/Applied Biosystems Division Automated Sequencer Model 373A and/or Model 377 (Foster City, Calif.). The cDNA sequences for sixty isolated clones are provided in SEQ ID NO: 1–60. These sequences were compared to known sequences in the gene bank using the EMBL and GenBank databases (release 96). No significant homologies were found to the sequences provided in SEQ ID NO: 2, 3, 19, 38 and 46. The sequences of SEQ ID NO: 1, 6–8, 10–13, 15, 17, 18, 20–27, 29, 30, 32, 34–37, 39–45, 47–49, 51, 52, 54, 55 and 57–59 show some homology to previously identified expressed sequence tags (ESTs). The sequences of SEQ ID NO: 9, 28, 31 and 33 were found to show some homology to previously identified non-human gene sequences and the sequences of SEQ ID NO: 4, 5, 14, 50, 53, 56 and 60 were found to show some homology to gene sequences previously identified in humans.

The subtraction procedure described above was repeated using the above lung squamous cell carcinoma cDNA library as the tracer DNA, and the above normal lung tissue cDNA library and a cDNA library from normal liver and heart (constructed from a pool of one sample of each tissue as described above), plus twenty other cDNA clones that were frequently recovered in lung subtractions I and II, as the driver DNA (lung subtraction III). The normal liver and heart cDNA library contained 1.76×10$^6$ independent colonies, with 100% of clones having inserts and the average insert size being 1600 base pairs. Ten additional clones were isolated (SEQ ID NO: 61–70). Comparison of these cDNA sequences with those in the gene bank as described above, revealed no significant homologies to the sequences provided in SEQ ID NO: 62 and 67. The sequences of SEQ ID NO: 61, 63–66, 68 and 69 were found to show some homology to previously isolated ESTs and the sequence provided in SEQ ID NO: 70 was found to show some homology to a previously identified rat gene.

In further studies, the subtraction procedure described above was repeated using the above lung squamous cell carcinoma cDNA library as the tracer DNA, and a cDNA library from a pool of normal lung, kidney, colon, pancreas, brain, resting PBMC, heart, skin and esophagus as the driver DNA, with esophagus cDNAs making up one third of the driver material. Since esophagus is enriched in normal epithelial cells, including differentiated squamous cells, this procedure is likely to enrich genes that are tumor specific rather than tissues specific. The cDNA sequences of 48 clones determined in this subtraction are provided in SEQ ID NO: 177–224. The sequences of SEQ ID NO: 177, 178, 180, 181, 183, 187, 192, 195–197, 208, 211, 212, 215, 216, 218 and 219 showed some homology to previously identified genes. The sequences of SEQ ID NO: 179, 182, 184–186, 188–191, 193, 194, 198–207, 209 210, 213, 214, 217, 220 and 224 showed some homology to previously determined ESTs. The sequence of SEQ ID NO: 221–223 showed no homology to any previously determined sequence.

B. Isolation of cDNA Sequences from a Lung Adenocarcinoma Library

A human lung adenocarcinoma cDNA expression library was constructed as described above. The library contained 3.2×10$^6$ independent colonies, with 100% of clones having an insert and the average insert size being 1500 base pairs. Library subtraction was performed as described above using the normal lung and normal liver and heart cDNA expression libraries described above as the driver DNA. Twenty-six hundred independent clones were recovered.

Initial cDNA sequence analysis from 100 independent clones revealed many ribosomal protein genes. The cDNA sequences for fifteen clones isolated in this subtraction are provided in SEQ ID NO: 71–86. Comparison of these sequences with those in the gene bank as described above revealed no significant homologies to the sequence provided in SEQ ID NO: 84. The sequences of SEQ ID NO: 71, 73, 74, 77, 78 and 80–82 were found to show some homology to previously isolated ESTs, and the sequences of SEQ ID NO: 72, 75, 76, 79, 83 and 85 were found to show some homology to previously identified human genes.

In further studies, a cDNA library (referred to as mets3616A) was constructed from a metastatic lung adenocarcinoma. The determined cDNA sequences of 25 clones sequenced at random from this library are provided in SEQ ID NO: 255–279. The mets3616A cDNA library was subtracted against a cDNA library prepared from a pool of normal lung, liver, pancreas, skin, kidney, brain and resting PBMC. To increase the specificity of the subtraction, the driver was spiked with genes that were determined to be most abundant in the mets3616A cDNA library, such as EF1-alpha, integrin-beta and anticoagulant protein PP4, as well as with cDNAs that were previously found to be differentially expressed in subtracted lung adenocarcinoma cDNA libraries. The determined cDNA sequences of 51 clones isolated from the subtracted library (referred to as mets3616A-S1) are provided in SEQ ID NO: 280–330.

Comparison of the sequences of SEQ ID NO: 255–330 with those in the public databases revealed no significant homologies to the sequences of SEQ ID NO: 255–258, 260, 262–264, 270, 272, 275, 276, 279, 281, 287, 291, 296, 300 and 310. The sequences of SEQ ID NO: 259, 261, 265–269, 271, 273, 274, 277, 278, 282–285, 288–290, 292, 294, 297–299, 301, 303–309, 313, 314, 316, 320–324 and 326–330 showed some homology to previously identified gene sequences, while the sequences of SEQ ID NO: 280, 286, 293, 302, 310, 312, 315, 317–319 and 325 showed some homology to previously isolated expressed sequence tags (ESTs).

EXAMPLE 2

Determination of Tissue Specificity of Lung Tumor Polypeptides

Using gene specific primers, mRNA expression levels for seven representative lung tumor polypeptides described in Example 1 were examined in a variety of normal and tumor tissues using RT-PCR.

Briefly, total RNA was extracted from a variety of normal and tumor tissues using Trizol reagent as described above. First strand synthesis was carried out using 2 μg of total RNA with SuperScript II reverse transcriptase (BRL Life Technologies) at 42° C. for one hour. The cDNA was then amplified by PCR with gene-specific primers. To ensure the semi-quantitative nature of the RT-PCR, β-actin was used as an internal control for each of the tissues examined. 1 μl of 1:30 dilution of cDNA was employed to enable the linear range amplification of the β-actin template and was sensitive enough to reflect the differences in the initial copy numbers. Using these conditions, the β-actin levels were determined for each reverse transcription reaction from each tissue. DNA contamination was minimized by DNase treatment and by assuring a negative PCR result when using first strand cDNA that was prepared without adding reverse transcriptase.

mRNA Expression levels were examined in five different types of tumor tissue (lung squamous cell carcinoma from 3 patients, lung adenocarcinoma, colon tumor from 2 patients, breast tumor and prostate tumor), and thirteen different normal tissues (lung from 4 donors, prostate, brain, kidney, liver, ovary, skeletal muscle, skin, small intestine, stomach, myocardium, retina and testes). Using a 10-fold amount of cDNA, the antigen LST-S-1-90 (SEQ ID NO: 3) was found to be expressed at high levels in lung squamous cell carcinoma and in breast tumor, and at low to undetectable levels in the other tissues examined.

The antigen LST-S-2-68 (SEQ ID NO: 15) appears to be specific to lung and breast tumor, however, expression was also detected in normal kidney. Antigens LST-S-1-169 (SEQ ID NO: 6) and LST-S-1-133 (SEQ ID NO: 5) appear to be very abundant in lung tissues (both normal and tumor), with the expression of these two genes being decreased in most of the normal tissues tested. Both LST-S-1-169 and LST-S-1-133 were also expressed in breast and colon tumors. Antigens LST-S-1-6 (SEQ ID NO. 7) and LST-S-2-12-5F (SEQ ID NO: 47) did not show tumor or tissue specific expression, with the expression of LST-S-1-28 being rare and only detectable in a few tissues. The antigen LST-S-3-7 (SEQ ID NO: 63) showed lung and breast tumor specific expression, with its message only being detected in normal testes when the PCR was performed for 30 cycles. Lower level expression was detected in some normal tissues when the cycle number was increased to 35. Antigen LST-S-3-13 (SEQ ID NO: 66) was found to be expressed in 3 out of 4 lung tumors, one breast tumor and both colon tumor samples. Its expression in normal tissues was lower compared to tumors, and was only detected in 1 out of 4 normal lung tissues and in normal tissues from kidney, ovary and retina. Expression of antigens LST-S-3-4 (SEQ ID NO: 62) and LST-S-3-14 (SEQ ID NO: 67) was rare and did not show any tissue or tumor specificity. Consistent with Northern blot analyses, the RT-PCT results on antigen LAT-S1-A-10A (SEQ ID NO: 78) suggested that its expression is high in lung, colon, stomach and small intestine tissues, including lung and colon tumors, whereas its expression was low or undetectable in other tissues.

A total of 2002 cDNA fragments isolated in lung subtractions I, II and III, described above, were colony PCR amplified and their mRNA expression levels in lung tumor, normal lung, and various other normal and tumor tissues were determined using microarray technology (Synteni, Palo Alto, Calif.). Briefly, the PCR amplification products were dotted onto slides in an array format, with each product occupying a unique location in the array. mRNA was extracted from the tissue sample to be tested, reverse transcribed, and fluorescent-labeled cDNA probes were generated. The microarrays were probed with the labeled cDNA probes, the slides scanned and fluorescence intensity was measured. This intensity correlates with the hybridization intensity. Seventeen non-redundant cDNA clones showed over-expression in lung squamous tumors, with expression in normal tissues tested (lung, skin, lymph node, colon, liver, pancreas, breast, heart, bone marrow, large intestine, kidney, stomach, brain, small intestine, bladder and salivary gland) being either undetectable, or 10-fold less compared to lung squamous tumors. The determined partial cDNA sequences for the clone L513S are provided in SEQ ID NO: 87 and 88; those for L514S are provided in SEQ ID NO: 89 and 90; those for L516S in SEQ ID NO: 91 and 92; that for L517S in SEQ ID NO: 93; that. for L519S in SEQ ID NO: 94; those for L520S in SEQ ID NO: 95 and 96; those for L521S in SEQ ID NO: 97 and 98; that for L522S in SEQ ID NO: 99; that for L523S in SEQ ID NO: 100; that for L524S in SEQ ID NO: 101; that for L525S in SEQ ID NO: 102; that for L526S in SEQ ID NO: 103; that for L527S in SEQ ID NO: 104; that for L528S in SEQ ID NO: 105; that for L529S in SEQ ID NO: 106; and those for L530S in SEQ ID NO: 107 and 108. Additionally, the full-length cDNA sequence for L530S is provided in SEQ ID NO: 151, with the corresponding predicted amino acid sequence being provided in SEQ ID NO: 152. L530S shows homology to a splice variant of a p53 tumor suppressor homologue, p63. The cDNA sequences of 7 known isoforms of p63 are provided in SEQ ID NO: 331–337, with the corresponding predicted amino acid sequences being provided in SEQ ID NO: 338–344, respectively.

Due to polymorphisms, the clone L531S appears to have two forms. A first determined full-length cDNA sequence for L531S is provided in SEQ ID NO: 109, with the corresponding predicted amino acid sequence being provided in SEQ ID NO: 110. A second determined full-length cDNA sequence for L531S is provided in SEQ ID NO: 111, with the corresponding predicted amino acid sequence being provided in SEQ ID NO: 112. The sequence of SEQ ID NO: 111 is identical to that of SEQ ID NO: 109, except that it contains a 27 bp insertion. Similarly, L514S also has two alternatively spliced forms; the first variant cDNA is listed as SEQ ID NO: 153, with the corresponding amino acid sequence being provided in SEQ ID NO: 155. The second variant form of L514S full-length cDNA is provided in SEQ ID NO: 154, with its corresponding amino acid sequence being provided in SEQ ID NO: 156.

Full length cloning for L524S (SEQ ID NO: 101) yielded two variants (SEQ ID NO: 163 and 164) with the corresponding predicted amino acid sequences of SEQ ID NO: 165 and 166, respectively. Both variants have been shown to encode parathyroid hormone-related peptide.

Attempts to isolate the full-length cDNA for L519S, resulted in the isolation of the extended cDNA sequence provided in SEQ ID NO: 173, which contains a potential open reading frame. The predicted amino acid sequence encoded by the sequence of SEQ ID NO: 173 is provided in SEQ ID NO: 174. Additionally, the full-length cDNA sequence for the clone of SEQ ID NO: 100 (known as L523S), a known gene, is provided in SEQ ID NO: 175, with the corresponding predicted amino acid sequence provided in SEQ ID NO: 176. In further studies, a full-length cDNA sequence for L523S was isolated from a L523S-positive tumor cDNA library by PCR amplification using gene specific primers designed from the sequence of SEQ ID NO:

175. The determined cDNA sequence is provided in SEQ ID NO: . The amino acid sequence encoded by this sequence is provided in SEQ ID NO: . This protein sequence differs from the previously published protein sequence at two amino acid positions, namely at positions 158 and 410.

Comparison of the sequences of L514S and L531S (SEQ ID NO: 87 and 88, 89 and 90, and 109, respectively) with those in the gene bank, as described above, revealed no significant homologies to known sequences. The sequences of L5113S, L516S, L517S, L519S, L520S and L530S (SEQ ID NO: 87 and 88, 91 and 92, 93, 94, 95 and 96, 107 and 108, respectively) were found to show some homology to previously identified ESTs. The sequences of L521S, L522S, L523S, L524S, L525S, L526S, L527S, L528S and L529S (SEQ ID NO: 97 and 98, 99, 99, 101, 102, 103, 104, 105, and 106, respectively) were found to represent known genes. The determined full-length cDNA sequences for L520S is provided in SEQ ID NO: 113, with the corresponding predicted amino acid sequence being provided in SEQ ID NO: 114. Subsequent microarray analysis has shown L520S to be overexpressed in breast tumors in addition to lung squamous tumors.

Further analysis has demonstrated that L529S (SEQ ID NO: 106 and 115), L525S (SEQ ID NO: 102 and 120) and L527S (SEQ ID NO: 104) are cytoskeletal components and potentially squamous cell specific proteins. L529S is connexin 26, a gap junction protein. It is highly expressed in lung squamous tumor 9688T, and moderately over-expressed in two others. However, lower level expression of connexin 26 is also detectable in normal skin, colon, liver and stomach. The over-expression of connexin 26 in some breast tumors has been reported and a mutated form of L529S may result in over-expression in lung tumors. L525S is plakophilin 1, a desmosomal protein found in plaque-bearing adhering junctions of the skin. Expression levels for L525S mRNA is highly elevated in three out of four lung squamous tumors tested, and in normal skin. L527S has been identified as keratin 6 isoform, type II 58 Kd keratin, and cytokeratin 13 and shows over-expression in squamous tumors and low expression in normal skin, breast and colon tissues. Notably, keratin and keratin-related genes have been extensively documented as potential markers for lung cancer including CYFRA2.1 (Pastor, A., et al, *Eur. Respir. J.*, 10:603–609, 1997). L513S (SEQ ID NO: 87 and 88) shows moderate over-expression in several tumor tissues tested, and encodes a protein that was first isolated as a pemphigus vulgaris antigen.

L520S (SEQ ID NO: 95 and 96) and L521S (SEQ ID NO: 97 and 98) are highly expressed in lung squamous tumors, and L520S is up-regulated in normal salivary gland and L521S is over-expressed in normal skin. Both belong to a family of small proline rich proteins and represent markers for fully differentiated squamous cells. L521S has been described as a specific marker for lung squamous tumor (Hu, R., et al, *Lung Cancer*, 20:25–30, 1998). L515S (SEQ ID NO: 162) encodes IGF-β2 and L516S is an aldose reductase homologue and both are moderately expressed in lung squamous tumors and in normal colon. Notably, L516S (SEQ ID NO: 91 and 92) is up-regulated in metastatic tumors but not primary lung adenocarcinoma, an indication of its potential role in metastasis and a potential prognostic marker. L522S (SEQ ID NO: 99) is moderately over-expressed in lung squamous tumors with minimum expression in normal tissues. L522S has been shown to belong to a class IV alcohol dehydrogenase, ADH7, and its expression profile suggests it is a squamous cell specific antigen. L523S (SEQ ID NO: 100) is moderately over-expressed in lung squamous tumor, human pancreatic cancer cell lines and pancreatic cancer tissues, suggesting this gene may be a shared antigen between pancreatic and lung squamous cell cancer.

L524S (SEQ ID NO: 101) is over-expressed in the majority of squamous tumors tested and is homologous with parathyroid hormone-related peptide (PTHrP), which is best known to cause humoral hypercalcaemia associated with malignant tumors such as leukemia, prostate and breast cancer. It is also believed that PTHrP is most commonly associated with squamous carcinoma of lung and rarely with lung adenocarcinoma (Davidson, L. A., et al, *J. Pathol.*, 178: 398–401, 1996). L528S (SEQ ID NO: 105) is highly over-expressed in two lung squamous tumors with moderate expression in two other squamous tumors, one lung adenocarcinoma and some normal tissues, including skin, lymph nodes, heart, stomach and lung. It encodes the NMB gene that is similar to the precursor of melanocyte specific gene Pmel 17, which is reported to be preferentially expressed in low-metastatic potential melanoma cell lines. This suggests that L528S may be a shared antigen in both melanoma and lung squamous cell carcinoma. L526S (SEQ ID NO: 103) is overexpressed in all lung squamous cell tumor tissues tested and has been shown to share homology with a gene (ATM) in which a mutation causes ataxia telangiectasia, a genetic disorder in humans causing a predisposition to cancer, among other symptoms. ATM encodes a protein that activates p53 mediated cell-cycle checkpoint through direct binding and phosphorylation of the p53 molecule. Approximately 40% of lung cancer is associated with p53 mutations, and it is speculated that over-expression of ATM is a result of compensation for loss of p53 function, but it is unknown whether over-expression is the cause of result of lung squamous cell carcinoma. Additionally, expression of L526S (ATM) is also detected in a metastatic but not lung adenocarcinoma, suggesting a role in metastasis.

Expression of L523S (SEQ ID NO: 175), was also examined by real time RT-PCR as described above. In a first study using a panel of lung squamous tumors, L523S was found to be expressed in 4/7 lung squamous tumors, 2/3 head and neck squamous tumors and 2/2 lung adenocarcinomas, with low level expression being observed in skeletal muscle, soft palate and tonsil. In a second study using a lung adenocarcinoma panel, expression of L523S was observed in 4/9 primary adenocarcinomas, 2/2 lung pleural effusions, 1/1 metastatic lung adenocarcinomas and 2/2 lung squamous tumors, with little expression being observed in normal tissues.

Expression of L523S in lung tumors and various normal tissues was also examined by Northern blot analysis, using standard techniques. In a first study, L523S was found to be expressed in a number of lung adenocarcinomas and squamous cell carcinomas, as well as normal tonsil. No expression was observed in normal lung. In a second study using a normal tissue blot (HB-12) from Clontech, no expression was observed in brain, skeletal muscle, colon, thymus, spleen, kidney, liver, small intestine, lung or PBMC, although there was strong expression in placenta.

EXAMPLE 3

Isolation and Characterization of Lung Tumor Polypeptides by PCR-Based Subtraction Eight hundred and fifty seven clones from a cDNA subtraction library, containing cDNA from a pool of two human lung squamous tumors subtracted against eight normal human tissue cDNAs including lung, PBMC, brain, heart, kidney, liver, pancreas, and skin, (Clontech, Palo Alto, Calif.) were derived and submitted to a first round of PCR amplification. This library was subjected to a second round of PCR amplification, following the manufacturer's protocol. The resulting cDNA fragments were subcloned into the vector P7-Adv vector (Clontech, Palo Alto, Calif.) and transformed into DH5α E. coli (Gibco, BRL). DNA was isolated from independent clones and sequenced using a Perkin Elmer/Applied Biosystems Division Automated Sequencer Model 373A.

One hundred and sixty two positive clones were sequenced. Comparison of the DNA sequences of these clones with those in the the EMBL and GenBank databases, as described above, revealed no significant homologies to 13 of these clones, hereinafter referred to as Contigs 13, 16, 17, 19, 22, 24, 29, 47, 49, 56–59. The determined cDNA sequences for these clones are provided in SEQ ID NO: 125, 127–129, 131–133, 142, 144, 148–150, and 157, respectively. Contigs 1, 3–5, 7–10, 12, 11, 15, 20, 31, 33, 38, 39, 41, 43, 44, 45, 48, 50, 53, 54 (SEQ ID NO: 115–124, 126, 130, 134–141, 143, 145–147, respectively) were found to show some degree of homology to previously identified DNA sequences. Contig 57 (SEQ ID NO: 149) was found to represent the clone L519S (SEQ ID NO: 94) disclosed in U.S. patent application Ser. No. 09/123,912, filed Jul. 27, 1998. To the best of the inventors' knowledge, none of these sequences have been previously shown to be differentially over-expressed in lung tumors.

mRNA expression levels for representative clones in lung tumor tissues, normal lung tissues (n=4), resting PBMC, salivary gland, heart, stomach, lymph nodes, skeletal muscle, soft palate, small intestine, large intestine, bronchial, bladder, tonsil, kidney, esophagus, bone marrow, colon, adrenal gland, pancreas, and skin, (all derived from human) were determined by RT-PCR as described above. Expression levels using microarray technology, as described above, were examined in one sample of each tissue type unless otherwise indicated.

Contig 3 (SEQ ID NO: 116) was found to be highly expressed in all head and neck squamous cell tumors tested (17/17), and expressed in the majority (8/12) of lung squamous tumors, (high expression in 7/12, moderate in 2/12, and low in 2/12), while showing negative expression for 2/4 normal lung tissues and low expression in the remaining two samples. Contig 3 showed moderate expression in skin and soft palate, and lowered expression levels in resting PBMC, large intestine, salivary gland, tonsil, pancreas, esophagus, and colon. Contig 11 (SEQ ID NO: 124) was found to be expressed in all head and neck squamous cell tumors tested (17/17): highly expressed in 14/17, and moderately expressed in 3/17. Additionally, expression in lung squamous tumors showed high expression in 3/12 and moderate in 4/12. Contig 11 was negative for 3/4 normal lung samples, with the remaining sample having only low expression. Contig 11 showed low to moderate reactivity to salivary gland, soft palate, bladder, tonsil, skin, esophagus, and large intestine. Contig 13 (SEQ ID NO: 125) was found to be expressed in all head and neck squamous cell tumors tested (17/17): highly expressed in 12/17, and moderately expressed in 5/17. Contig 13 was expressed in 7/12 lung squamous tumors, with high expression in 4/12 and moderate expression in three samples. Analysis of normal lung samples showed negative expression for 2/4 and low to moderate expression in the remaining two samples. Contig 13 did show low to moderate reactivity to resting PBMC, salivary gland, bladder, pancreas, tonsil, skin, esophagus, and large intestine, as well as high expression in soft palate. Contig 16 (SEQ ID NO: 127) was found to be moderately expressed in some head and neck squamous cell tumors (6/17) and one lung squamous tumor; while showing no expression in any normal lung samples tested. Contig 16 did show low reactivity to resting PBMC, large intestine, skin, salivary gland, and soft palate. Contig 17 (SEQ ID NO: 128) was shown to be expressed in all head and neck squamous cell tumors tested (17/17): highly expressed in 5/17, and moderately expressed in 12/17. Expression levels in lung squamous tumors showed one tumor sample with high expression and 3/12 with moderate levels. Contig 17 was negative for 2/4 normal lung samples, with the remaining samples having only low expression. Additionally, low level expression was found in esophagus and soft palate. Contig 19 (SEQ ID NO: 129) was found to be expressed in most head and neck squamous cell tumors tested (11/17); with two samples having high levels, 6/17 showing moderate expression, and low expression being found in 3/17. Testing in lung squamous tumors revealed only moderate expression in 3/12 samples. Expression levels in 2/4 of normal lung samples were negative, the two other samples having only low expression. Contig 19 showed low expression levels in esophagus, resting PBMC, salivary gland, bladder, soft palate and pancreas.

Contig 22 (SEQ ID NO: 131), was shown to be expressed in most head and neck squamous cell tumors tested (13/17) with high expression in four of these samples, moderate expression in 6/17, and low expression in 3/17. Expression levels in lung squamous tumors were found to be moderate to high for 3/12 tissues tested, with negative expression in two normal lung samples and low expression in two other samples (n=4). Contig 22 showed low expression in skin, salivary gland and soft palate. Similarly, Contig 24 (SEQ ID NO: 132) was found to be expressed in most head and neck squamous cell tumors tested (13/17) with high expression in three of these samples, moderate expression in 6/17, and low expression in 4/17. Expression levels in lung squamous tumors were found to be moderate to high for 3/12 tissues tested, with negative expression for three normal lung samples and low expression in one sample (n=4). Contig 24 showed low expression in skin, salivary gland and soft palate. Contig 29 (SEQ ID NO: 133) was expresed in nearly all head and neck squamous cell tumors tested (16/17): highly expressed in 4/17, moderately expressed in 11/17, with low expression in one sample. Also, it was moderately expressed in 3/12 lung squamous tumors, while being negative for 2/4 normal lung samples. Contig 29 showed low to moderate expression in large intestine, skin, salivary gland, pancreas, tonsil, heart and soft palate. Contig 47 (SEQ ID NO: 142) was expressed in most head and neck squamous cell tumors tested (12/17): moderate expression in 10/17, and low expression in two samples. In lung squamous tumors, it was highly expressed in one sample and moderately expressed in two others (n=13). Contig 47 was negative for 2/4 normal lung samples, with the remaining two samples having moderate expression. Also, Contig 47 showed moderate expression in large intestine, and pancreas, and low expression in skin, salivary gland. soft palate, stomach, bladder, resting PBMC, and tonsil.

Contig 48 (SEQ ID NO: 143) was expressed in all head and neck squamous cell tumors tested (17/17): highly expressed in 3/17 and moderately expressed in 7/17, with low expression in two samples. Expression levels in lung squamous tumors were high to moderate in three samples (n=13). Contig 48 was negative for one out of four normal lung samples, the remaining showing low or moderate expression. Contig 48 showed moderate expression in soft palate, large intestine, pancreas, and bladder, and low expression in esophagus, salivary gland, resting PBMC, and heart Contig 49 (SEQ ID NO: 144) was expressed at low to moderate levels in 6/17 head and neck squamous cell tumors tested. Expression levels in lung squamous tumors were moderate in three samples (n=13). Contig 49 was negative for 2/4 normal lung samples, the remaining samples showing low expression. Moderate expression levels in skin, salivary gland, large intestine, pancreas, bladder and resting PBMC were shown, as well as low expression in soft palate, lymph nodes, and tonsil. Contig 56 (SEQ ID NO: 148) was expressed in low to moderate levels in 3/17 head and neck squamous cell tumors tested, and in lung squamous tumors, showing low to moderate levels in three out of thirteen samples. Notably, low expression levels were detected in one adenocarcinoma lung tumor sample (n=2). Contig 56 was negative for 3/4 normal lung samples, and showed moderate expression levels in only large intestine, and low expression in salivary gland, soft palate, pancreas, bladder, and resting PBMC. Contig 58, also known as L769P, (SEQ ID NO: 150) was expressed at moderate levels in 11/17 head and neck squamous cell tumors tested and low expression in one additional sample. Expression in lung squamous tumors showed low to moderate levels in three out of thirteen samples. Contig 58 was negative for 3/4 normal lung samples, with one sample having low expression. Moderate expression levels in skin, large intestine, and resting PBMC were demonstrated, as well as low expression in salivary gland, soft palate, pancreas, and bladder. Contig 59 (SEQ ID NO: 157) was expressed in some head, neck, and lung squamous tumors. Low level expression of Contig 59 was also detected in salivary gland and large intestine.

The full-length cDNA sequence for Contig 22, also referred to as L763P, is provided in SEQ ID NO: 158, with the corresponding predicted amino acid sequence being provided in SEQ ID NO: 159. Real-time RT-PCR analysis of L763P revealed that it is highly expressed in 3/4 lung squamous tumors as well as 4/4 head and neck squamous tumors, with low level expression being observed in normal brain, skin, soft pallet and trachea. Subsequent database searches revealed that the sequence of SEQ ID NO: 158 contains a mutation,. resulting in a frameshift in the corresponding protein sequence. A second cDNA sequence for L763P is provided in SEQ ID NO: 345, with the corresponding amino acid sequence being provided in SEQ ID NO: 346. The sequences of SEQ ID NO: 159 and 346 are identical with the exception of the C-terminal 33 amino acids of SEQ ID NO: 159.

The full-length cDNA sequence incorporating Contigs 17, 19, and 24, referred to as L762P, is provided in SEQ ID NO: 160, with the corresponding predicted amino acid sequence being provided in SEQ ID NO: 161. Further analysis of L762P has determined it to be a type I membrane protein and two additional variants have been sequenced. Variant 1 (SEQ ID NO: 167, with the corresponding amino acid sequence in SEQ ID NO: 169) is an alternatively spliced form of SEQ ID NO: 160 resulting in deletion of 503 nucleotides, as well as deletion of a short segment of the expressed protein. Variant 2 (SEQ ID NO: 168, with the corresponding amino acid sequence in SEQ ID NO: 170) has a two nucleotide deletion at the 3' coding region in comparison to SEQ ID NO: 160, resulting in a secreted form of the expressed protein. Real-time RT-PCR analysis of L762P revealed that is over-expressed in 3/4 lung squamous tumors and 4/4 head & neck tumors, with low level expression being observed in normal skin, soft pallet and trachea.

The full-length cDNA sequence for contig 56 (SEQ ID NO: 148), also referred to as L773P, is provided in SEQ ID NO: 171, with the predicted amino acid sequence in SEQ ID NO: 172. L773P was found to be identical to dihydroxyl dehydrogenase at the 3' portion of the gene, with divergent 5' sequence. As a result, the 69 N-terminal amino acids are unique. The cDNA sequence encoding the 69 N-terminal amino acids is provided in SEQ ID NO: 349, with the N-terminal amino acid sequence being provided in SEQ ID NO: 350. Real-time PCR revealed that L773P is highly expressed in lung squamous tumor and lung adenocarcinoma, with no detectable expression in normal tissues. Subsequent Northern blot analysis of L773P demonstrated that this transcript is differentially over-expressed in squamous tumors and detected at approximately 1.6 Kb in primary lung tumor tissue and approximately 1.3 Kb in primary head and neck tumor tissue.

Subsequent microarray analysis has shown Contig 58, also referred to as L769S (SEQ ID NO: 150), to be over-expressed in breast tumors in addition to lung squamous tumors.

EXAMPLE 4

Synthesis of Polypeptides

Polypeptides may be synthesized on a Perkin Elmer/Applied Biosystems Division 430A peptide synthesizer using FMOC chemistry with HPTU (O-Benzotriazole-N,N,N',N'-tetramethyluronium hexafluorophosphate) activation. A Gly-Cys-Gly sequence may be attached to the amino terminus of the peptide to provide a method of conjugation, binding to an immobilized surface, or labeling of the peptide. Cleavage of the peptides from the solid support may be carried out using the following cleavage mixture: trifluoroacetic acid:ethanedithiol:thioanisole:water:phenol (40:1:2:2:3). After cleaving for 2 hours, the peptides may be precipitated in cold methyl-t-butyl-ether. The peptide pellets may then be dissolved in water containing 0.1% trifluoroacetic acid (TFA) and lyophilized prior to purification by C18 reverse phase HPLC. A gradient of 0%–60% acetonitrile (containing 0.1% TFA) in water (containing 0.1% TFA) may be used to elute the peptides. Following lypphihization of the pure fractions, the peptides may be characterized using electrospray or other types of mass spectrometry and by amino acid analysis.

EXAMPLE 5

Preperation of Antibodies Against Lung Cancer Antigens

Polyclonal antibodies against the lung cancer antigens L514S, L528S and L531S (SEQ ID NO: 155, 225 and 112, respectively) were prepared as follows.

Rabbits were immunized with recombinant protein expressed in and purified from E. coli as described above. For the initial immunization, 400 μg of antigen combined with muramyl dipeptide (MDP) was injected subcutaneously (S.C.). Animals were boosted S.C. 4 weeks later with 200 μg of antigen mixed with incomplete Freund's Adjuvant (IFA). Subsequent boosts of 100 μg of antigen mixed with IFA were injected S.C. as necessary to induce high antibody titer responses. Serum bleeds from immunized rabbits were tested for antigen-specific reactivity using ELISA assays with purified protein. Polyclonal antibodies against L514S, L528S and L531S were affinity purified from high titer polyclonal sera using purified protein attached to a solid support.

Immunohistochemical analysis using polyclonal antibodies against L514S was performed on a panel of 5 lung tumor samples, 5 normal lung tissue samples and normal colon, kidney, liver, brain and bone marrow. Specifically, tissue samples were fixed in formalid solution for 24 hours and embedded in paraffin before being sliced into 10 micron sections. Tissue sections were permeabilized and incubated with antibody for 1 hr. HRP-labeled anti-mouse followed by incubation with DAB chromogen was used to visualize L514S inmmunoreactivity. L514S was found to be highly expressed in lung tumor tissue with little or no expression being observed in normal lung, brain or bone marrow. Light staining was observed in colon and kidney. Staining was seen in normal liver but no mRNA has been detected in this tissue making this result suspect.

EXAMPLE 6

Peptide Priming of Mice and Propagation of CTL Lines

Immunogenic peptides from the lung cancer antigen L762P (SEQ ID NO: 161) for HLA-A2/$K^b$-restricted CD8+ T cells were identified as follows.

The location of HLA-A2 binding peptides within the lung cancer antigen L762P (SEQ ID NO: 161) was predicted using a computer program which predicts peptides sequences likely to being to HLA-A*0201 by fitting to the known peptide binding motif for HLA-A*0201 (Rupert et al. (1993) Cell 74:929; Rammensee et al. (1995) Immunogenetics 41:178–228). A series of 19 synthetic peptides corresponding to a selected subset of the predicted HLA-A*0201 binding peptides was prepared as described above.

Mice expressing the transgene for human HLA A2/$K^b$ (provided by Dr L. Sherman, The Scripps Research Institute. La Jolla, Calif.) were immunized with the synthetic peptides, as described by Theobald et al., Proc. Natl. Acad. Sci. USA 92:11993–11997, 1995 with the following modifications. Mice were immunized with 50 μg of L726P peptide and 120 μg of an I-$A^b$ binding peptide derived from hepatitis B Virus protein emulsified in incomplete Freund's adjuvant. Three weeks later these mice were sacrificed and single cell suspensions prepared. Cells were then resuspended at 7×$10^6$ cells/ml in complete media (RPMI-1640; Gibco BRL, Gaithersburg, Md.) containing 10% FCS, 2 mM Glutamine (Gibco BRL), sodium pyruvate (Gibco BRL), non-essential amino acids (Gibco BRL), 2×$10^{-5}$ M 2-mercaptoethanol, 50 U/ml penicillin and streptomycin, and cultured in the presence of irradiated (3000 rads) L762P peptide-(5 μg/ml) and 10 mg/ml $B_2$-microglobulin-(3 μg/ml) LPS blasts (A2 transgenic spleens cells cultured in the presence of 7 μg/ml dextran sulfate and 25 μg/ml LPS for 3 days). After six days, cells (5×$10^5$/ml) were restimulated with 2.5×$10^6$/ml peptide pulsed irradiated (20,000 rads) EL4A2Kb cells (Sherman et al, Science 258:815–818, 1992) and 5×$10^6$/ml irradiated (3000 rads) A2/$K^b$-transgenic spleen feeder cells. Cells were cultured in the presence of 10U/ml IL-2. Cells were restimulated on a weekly basis as described, in preparation for cloning the line.

Peptide-specific cell lines were cloned by limiting dilution analysis with irradiated (20,000 rads) L762P peptide-pulsed EL4 A2Kb tumor cells (1×$10^4$ cells/well) as stimulators and irradiated (3000 rads) A2/$K^b$-transgenic spleen cells as feeders (5×$10^5$ cells/well) grown in the presence of 10 U/ml IL-2. On day 7, cells were restimulated as before. On day 14, clones that were growing were isolated and maintained in culture.

Cell lines specific for L762P-87 (SEQ ID NO: 226; corresponding to amino acids 87–95 of SEQ ID NO: 161), L726P-145 (SEQ ID NO: 227; corresponding to amino acids 145–153 of SEQ ID NO: 161), L726P-585 (SEQ ID NO: 228; corresponding to amino acids 585–593 of SEQ ID NO: 161), L762P-425 (SEQ ID NO: 229; corresponding to amino acids 425–433 of SEQ ID NO: 161), L762P(10)-424 (SEQ ID NO: 230; corresponding to amino acids 424–433 of SEQ ID NO: 161) and L762P(10)-458 (SEQ ID NO: 231; corresponding to amino acids 458–467 of SEQ ID NO: 161) demonstrated significantly higher reactivity (as measured by percent specific lysis) against L762P peptide-pulsed EL4-A2/$K^b$ tumor target cells than control peptide-pulsed EL4-A2/$K^b$ tumor target cells.

EXAMPLE 7

Identification of CD4 Immunogenic T Cell Epitopes Derived from the Lung Cancer Antigen L762P CD4 T cell lines specific for the antigen L762P (SEQ ID NO: 161) were generated as follows.

A series of 28 overlapping peptides were synthesized that spanned approximately 50% of the L762P sequence. For priming, peptides were combined into pools of 4–5 peptides, pulsed at 20 micrograms/ml into dendritic cells for 24 hours. Ihe dendritic cells were then washed and mixed with positively selected CD4+ T cells in 96 well U-bottomed plates. Forty cultures were generated for each peptide pool. Cultures were restimulated weekly with fresh dendritic cells loaded with peptide pools. Following a total of 3 stimulation cycles, cells were rested for an additional week and tested for specificity to antigen presenting cells (APC) pulsed with peptide pools using interferon-gamma ELISA and proliferation assays. For these assays, adherent monocytes loaded with either the relevant peptide pool or an irrelevant peptide were used as APC. T cell lines that appeared to specifically recognize L762P peptide pools both by cytokine release and proliferation were identified for each pool. Emphasis was placed on identifying T cells with proliferative responses. T cell lines that demonstrated either both L762P-specific cytokine secretion and proliferation, or strong proliferation alone were further expanded to be tested for recognition of individual peptides from the pools, as well as for recognition of recombinant L762P. The source of recombinant L762P was E. coli, and the material was partially purified and endotoxin positive. These studies employed 10 micrograms of individual peptides, 10 or 2 micrograms of an irrelevant peptide, and 2 or 0.5 micrograms of either L762P protein or an irrelevant, equally impure, E. coli generated recombinant protein. Significant interferon-gamma production and CD4 T cell proliferation was induced by a number of L762P-derived peptides in each pool. The amino acid sequences for these peptides are provided in SEQ ID NO: 232–251. These peptides correspond to amino acids 661–680, 676–696, 526–545, 874–893, 811–830, 871–891, 856–875, 826–845, 795–815, 736–755, 706–725, 706–725, 691–710, 601–620, 571–590, 556–575, 616–635, 646–665, 631–650, 541–560 and 586–605, respectively, of SEQ ID NO: 161.

CD4 T cell lines that demonstrated specificity for individual L762P-derived peptides were further expanded by stimulation with the relevant peptide at 10 micrograms/ml. Two weeks post-stimulation, T cell lines were tested using both proliferation and IFN-gamma ELISA assays for recognition of the specific peptide. A number of previously identified T cells continued to demonstrate L762P-peptide specific activity. Each of these lines was further expanded on the relevant peptide and, following two weeks of expansion, tested for specific recognition of the L762P-peptide in titration experiments, as well as for recognition of recombinant *E. coli*-derived L762P protein. For these experiments, autologous adherent monocytes were pulsed with either the relevant L762P-derived peptide, an irrelevant mammaglobin-derived peptide, recombinant *E. coli*-derived L762P (approx. 50% pure), or an irrelevant *E. coli*-derived protein. The majority of T cell lines were found to show low affinity for the relevant peptide, since specific proliferation and IFN-gamma ratios dramatically decreased as L762P peptide was diluted. IHowever, four lines were identified that demonstrated significant activity even at 0.1 micrograms/ml peptide. Each of these lines (referred to as A/D5, D/F5, E/A7 and E/B6) also appeared to specifically proliferate in response to the *E. coli*-derived L762P protein preparation, but not in response to the irrelevant protein preparation. The amino acid sequences of the L762P-derived peptides recognized by these lines are provided in SEQ ID NO: 234, 249, 236 and 245, respectively. No protein specific IFN-gamma was detected for any of the lines. Lines A/D5, E/A7 and E/B6 were cloned on autologous adherent monocytes pulsed with the relevant peptide at 0.1 (A/D5 and E/A7) or 1 (D/F5) micro gram/ml. Following growth, clones were tested for specificity for the relevant peptide. Numerous clones specific for the relevant peptide were identified for lines A/D5 and E/A7.

EXAMPLE 8

Protein Expression of Lung Tumor-Specific Antigens a) Expression of L514S in *E. coli*

The lung tumor antigen L514S (SEQ ID NO: 89) was subcloned into the expression vector pE32b at NcoI and NotI sites, and transformed into *E. coli* using standard techniques. The protein was expressed from residues 3–153 of SEQ ID NO: 89. The expressed amino acid sequence and the corresponding DNA sequence are provided in SEQ ID NO: 252 and 253, respectively.

b) Expression of L762P

Amino acids 32–944 of the lung tumor antigen L762P (SEQ ID NO: 161), with a 6× His Tag, were subcloned into a modified pET28 expression vector, using kanamycin resistance, and transformed into BL21 CodonPlus using standard techniques. Low to moderate levels of expression were observed. The determined DNA sequence of the L762P expression construct is provided in SEQ ID NO: 254.

From the foregoing it will be appreciated that, although specific embodiments of the invention have been described herein for purposes of illustration, various modifications may be made without deviating from the spirit and scope of the invention. Accordingly, the invention is not limited except as by the appended claims.

We claim:

1. An isolated polynucleotide comprising SEQ ID NO: 347.

2. An isolated polynucleotide complementary to a polynucleotide according to claim 1.

3. An expression vector, comprising a polynucleotide according to claim 1.

4. A host cell transformed or transfected with an expression vector according to claim 3.

5. An isolated polynucleotide encoding a fusion protein, wherein said fusion protein is encoded by a polynucleotide comprising SEQ ID No. 347.

6. A composition comprising a physiologically acceptable carrier and at least one component selected from the group consisting of:

(a) a polynucleotide according to claim 1; or (b) a polynucleotide according to claim 5.

7. A composition comprising an immunostimulant and at least one component selected from the group consisting of:

(a) a polynucleotide according to claim 1; or (b) a polynucleotide according to claim 5.

8. A composition according to claim 7, wherein the immunostimulant is an adjuvant.

9. A composition according to claim 7, wherein the immunostimulant induces a predominantly Type I response.

* * * * *

SEQUENCE LISTING

```
<160> NUMBER OF SEQ ID NOS: 350

<210> SEQ ID NO 1
<211> LENGTH: 315
<212> TYPE: DNA
<213> ORGANISM: Homo sapien
<220> FEATURE:
<221> NAME/KEY: misc_feature
<222> LOCATION: (1)...(315)
<223> OTHER INFORMATION: n = A,T,C or G

<400> SEQUENCE: 1
gcagagacag actggtggtt gaacctggag gtgccaaaaa agccagctgc gggcccagga      60
cagctgccgt gagactcccg atgtcacagg cagtctgtgt ggttacagcg cccctcagtg     120
ttcatctcca gcagagacaa cggaggaggc tcccaccagg acggttctca ttatttatat     180
gttaatatgt ttgtaaactc atgtacagtt tttttggggg gggaagcaat gggaanggta     240
naaattacaa atagaatcat ttgctgtaat ccttaaatgg caaacggtca ggccacgtga     300
aaaaaaaaaa aaaaa                                                      315

<210> SEQ ID NO 2
<211> LENGTH: 380
<212> TYPE: DNA
<213> ORGANISM: Homo sapien

<400> SEQUENCE: 2
atttaggctt aagattttgt ttaccctttgt tactaaggag caaattagta ttaaagtata     60
atatatataa acaaatacaa aaagtttga gtggttcagc tttttttattt tttttaatgg     120 cataacttttt aacaacactg ctctgtaatg ggttgaactg tggtactcag actgagataa    180
ctgaaatgag tggatgtata gtgttattgc ataattatcc cactatgaag caaagggact     240
```

| | |
|---|---|
| ggataaattc ccagtctaga ttattagcct tgttaacca tcaagcacct agaagaagaa | 300 |
| ttattggaaa ttttgtcctc tgtaactggc actttgggt gtgacttatc ttttgccttt | 360 |
| gtaaaaaaaa aaaaaaaaaa | 380 |

<210> SEQ ID NO 3
<211> LENGTH: 346
<212> TYPE: DNA
<213> ORGANISM: Homo sapien
<220> FEATURE:
<221> NAME/KEY: misc_feature
<222> LOCATION: (1)...(346)
<223> OTHER INFORMATION: n = A,T,C or G

<400> SEQUENCE: 3

| | |
|---|---|
| ttgtaagtat acaattttag aaaggattaa atgttattga tcatttact gaatactgca | 60 |
| catcctcacc atacaccatc cactttccaa taacatttaa tcctttctaa aattgtaagt | 120 |
| atacaattgt actttctttg gattttcata acaaatatac catagactgt taattttatt | 180 |
| gaagtttcct taatggaatg agtcattttt gtcttgtgct tttgaggtta ccttgcttt | 240 |
| gacttccaac aatttgatca tatagtgttg agctgtgaa atctttaagt ttattctata | 300 |
| gcaataattt ctattnnnag anncngggnn naaaannann annaaa | 346 |

<210> SEQ ID NO 4
<211> LENGTH: 372
<212> TYPE: DNA
<213> ORGANISM: Homo sapien
<220> FEATURE:
<221> NAME/KEY: misc_feature
<222> LOCATION: (1)...(372)
<223> OTHER INFORMATION: n = A,T,C or G

<400> SEQUENCE: 4

| | |
|---|---|
| actagtctca ttactccaga attatgctct tgtacctgtg tggctgggtt tcttagtcgt | 60 |
| tggtttggtt tggttttttg aactggtatg tagggtggtt cacagttcta atgtaagcac | 120 |
| tctcttctcc aagttgtgct ttgtggggac aatcattctt tgaacattag agaggaaggc | 180 |
| agttcaagct gttgaaaaga ctattgctta tttttgtttt taaagaccta cttgacgtca | 240 |
| tgtggacagt gcacgtgcct tacgctacat cttgttttct aggaagaagg ggatgcnggg | 300 |
| aaggantggg tgctttgtga tggataaaac gnctaaataa cacacctta cattttgaaa | 360 |
| aaaacaaaac aa | 372 |

<210> SEQ ID NO 5
<211> LENGTH: 698
<212> TYPE: DNA
<213> ORGANISM: Homo sapien
<220> FEATURE:
<221> NAME/KEY: misc_feature
<222> LOCATION: (1)...(698)
<223> OTHER INFORMATION: n = A,T,C or G

<400> SEQUENCE: 5

| | |
|---|---|
| actagtanga tagaaacact gtgtcccgag agtaaggaga gaagctacta ttgattagag | 60 |
| cctaacccag gttaactgca agaagaggcg ggatactttc agctttccat gtaactgtat | 120 |
| gcataaagcc aatgtagtcc agtttctaag atcatgttcc aagctaactg aatcccactt | 180 |
| caatacacac tcatgaactc ctgatggaac aataacaggc ccaagccgt ggtatgatgt | 240 |
| gcacacttgc tagactcaga aaaaatacta ctctcataaa tgggtgggag tattttgggt | 300 |
| gacaacctac tttgcttggc tgagtgaagg aatgatattc atatnttcat ttattccatg | 360 |

| | |
|---|---|
| gacatttagt tagtgctttt tatataccag gcatgatgct gagtgacact cttgtgtata | 420 |
| tntccaaatn ttngtncngt cgctgcacat atctgaaatc ctatattaag antttcccaa | 480 |
| natgangtcc ctggtttttc cacgccactt gatcngtcaa ngatctcacc tctgtntgtc | 540 |
| ctaaaaccnt ctnctnnang gttagacngg acctctcttc tcccttcccg aanaatnaag | 600 |
| tgtgngaaga nanccncncn cccccctncn tncnncctng ccngctnnnc cncntgtngg | 660 |
| gggngccgcc cccgcggggg gaccccccccn ttttcccc | 698 |

<210> SEQ ID NO 6
<211> LENGTH: 740
<212> TYPE: DNA
<213> ORGANISM: Homo sapien
<220> FEATURE:
<221> NAME/KEY: misc_feature
<222> LOCATION: (1)...(740)
<223> OTHER INFORMATION: n = A,T,C or G

<400> SEQUENCE: 6

| | |
|---|---|
| actagtcaaa aatgctaaaa taatttggga gaaaatattt tttaagtagt gttatagttt | 60 |
| catgtttatc ttttattatg tnttgtgaag ttgtgtcttt tcactaatta cctatactat | 120 |
| gccaatattt cctatatct atccataaca tttatactac atttgtaaga gaatatgcac | 180 |
| gtgaaactta acactttata aggtaaaaat gaggtttcca agatttaata atctgatcaa | 240 |
| gttcttgtta tttccaaata gaatggactt ggtctgttaa ggggctaagg gagaagaaga | 300 |
| agataaggtt aaaagttgtt aatgaccaaa cattctaaaa gaaatgcaaa aaaaaattta | 360 |
| ttttcaagcc ttcgaactat ttaaggaaag caaaatcatt tcctanatgc atatcatttg | 420 |
| tgagantttc tcantaatat cctgaatcat tcatttcagc tnaggcttca tgttgactcg | 480 |
| atatgtcatc tagggaaagt ctatttcatg gtccaaacct gttgccatag ttggtnaggc | 540 |
| tttcctttaa ntgtgaanta ttnacangaa attttctctt tnanagttct tnatagggtt | 600 |
| aggggtgtgg gaaaagcttc taacaatctg tagtgttncg tgttatctgt ncagaaccan | 660 |
| aatnacggat cgnangaagg actgggtcta tttacangaa cgaatnatct ngttnnntgt | 720 |
| gtnnncaact ccngggagcc | 740 |

<210> SEQ ID NO 7
<211> LENGTH: 670
<212> TYPE: DNA
<213> ORGANISM: Homo sapien
<220> FEATURE:
<221> NAME/KEY: misc_feature
<222> LOCATION: (1)...(670)
<223> OTHER INFORMATION: n = A,T,C or G

<400> SEQUENCE: 7

| | |
|---|---|
| gctggggagc tcggcatggc ggtccccgct gcagccatgg ggccctcggc gttgggccag | 60 |
| agcggccccg gctcgatggc cccgtggtgc tcagtgagca gcggcccgtc gcgctacgtg | 120 |
| cttgggatgc aggagctgtt ccggggccac agcaagaccg cgagttcctg cgcacagcg | 180 |
| ccaaggtgca ctcggtggcc tggagttgcg acgggcgtcg cctacctcgg ggtcttcgac | 240 |
| aagacgccac gtcttcttgc tgganaanga ccgttggtca aagaaaacaa ttatcgggga | 300 |
| catggggata gtgtggacca ctttgttggc atccaagtaa tcctgaccta tttgttacgg | 360 |
| cgtctggaga taaaaccatt cgcatctggg atgtgaggac tacaaaatgc attgccactg | 420 |
| tgaacactaa aggggagaac attaatatct gctggantcc tgatgggcan accattgctg | 480 |

-continued

| | |
|---|---|
| tagcnacaag gatgatgtgg tgactttatt gatgccaaga aacccgttc caaagcaaaa | 540 |
| aaacanttcc aanttcgaag tcaccnaaat ctcctggaac aatgaacatn aatatnttct | 600 |
| tcctgacaat ggnccttggg tgtntcacat cctcagctnc cccaaaactg aancctgtnc | 660 |
| natccacccc | 670 |

<210> SEQ ID NO 8
<211> LENGTH: 689
<212> TYPE: DNA
<213> ORGANISM: Homo sapien
<220> FEATURE:
<221> NAME/KEY: misc_feature
<222> LOCATION: (1)...(689)
<223> OTHER INFORMATION: n = A,T,C or G

<400> SEQUENCE: 8

| | |
|---|---|
| actagtatct aggaatgaac agtaaaagag gagcagttgg ctacttgatt acaacagagt | 60 |
| aaatgaagta ctggatttgg gaaaacctgg ttttattaga acatatggaa tgaaagccta | 120 |
| cacctagcat tgcctactta gcccctgaa ttaacagagc ccaattgaga caaaccctg | 180 |
| gcaacaggaa attcaaggga gaaaagtaa gcaacttggg ctaggatgag ctgactccct | 240 |
| tagagcaaag ganagacagc ccccattacc aaataccatt tttgcctggg gcttgtgcag | 300 |
| ctggcagtgt tcctgcccca gcatggcacc ttatngtttt gatagcaact tcgttgaatt | 360 |
| ttaccaact tattacttga aattataata tagcctgtcc gtttgctgtn tccaggctgt | 420 |
| gatatatntt cctagtggtt tgactttnaa aataaatnag gtttantttt ctcccccnn | 480 |
| cnntnctncc nntcnctcnn cnntccccc cnctcngtcc tccnnnnttn gggggggccn | 540 |
| ccccncggn ggacccccct ttggtccctt agtggaggtt natggcccct ggnnttatcc | 600 |
| nggccntann tttccccgtn nnaaatgntt cccctccca ntcccnccac ctcaanccgg | 660 |
| aagcctaagt ttntaccctg ggggtcccc | 689 |

<210> SEQ ID NO 9
<211> LENGTH: 674
<212> TYPE: DNA
<213> ORGANISM: Homo sapien
<220> FEATURE:
<221> NAME/KEY: misc_feature
<222> LOCATION: (1)...(674)
<223> OTHER INFORMATION: n = A,T,C or G

<400> SEQUENCE: 9

| | |
|---|---|
| gtccactctc ctttgagtgt actgtcttac tgtgcactct gttttcaac tttctagata | 60 |
| taaaaatgc ttgttctata gtggagtaag agctcacaca cccaaggcag caagataact | 120 |
| gaaaaagcg aggcttttt gccaccttgg taaaggccag ttcactgcta tagaactgct | 180 |
| ataagcctga agggaagtag ctatgagact ttccattttt cttagttctc ccaataggct | 240 |
| ccttcatgga aaaaggcttc ctgtaataat tttcacctaa tgaattagca gtgtgattat | 300 |
| ttctgaaata agagacaaat tgggccgcag agtcttcctg tgatttaaaa taaacaaccc | 360 |
| aaagttttgt ttggtcttca ccaaaggaca tactctaggg ggtatgttgt tgaagacatt | 420 |
| caaaaacatt agctgttctg tctttcaatt tcaagttatt ttggagactg cctccatgtg | 480 |
| agttaattac tttgctctgg aactagcatt attgtcatta tcatcacatt ctgtcatcat | 540 |
| catctgaata atattgtgga tttcccccctc tgcttgcatc ttcttttgac tcctctggga | 600 |
| anaaatgtca aaaaaaagg tcgatctact cngcaaggnc catctaatca ctgcgctgga | 660 |
| aggacccnct gccc | 674 |

<210> SEQ ID NO 10
<211> LENGTH: 346
<212> TYPE: DNA
<213> ORGANISM: Homo sapien
<220> FEATURE:
<221> NAME/KEY: misc_feature
<222> LOCATION: (1)...(346)
<223> OTHER INFORMATION: n = A,T,C or G

<400> SEQUENCE: 10

```
actagtctgc tgatagaaag cactatacat cctattgttt ctttctttcc aaaatcagcc      60
ttctgtctgt aacaaaaatg tactttatag agatggagga aaaggtctaa tactacatag     120
ccttaagtgt ttctgtcatt gttcaagtgt attttctgta acagaaacat atttggaatg     180
tttttctttt ccccttataa attgtaattc ctgaaatact gctgctttaa aaagtcccac     240
tgtcagatta tattatctaa caattgaata ttgtaaatat acttgtctta cctctcaata     300
aaagggtact tttctattan nnagnngnnn gnnnnataaa anaaaa                    346
```

<210> SEQ ID NO 11
<211> LENGTH: 602
<212> TYPE: DNA
<213> ORGANISM: Homo sapien

<400> SEQUENCE: 11

```
actagtaaaa agcagcattg ccaataatc cctaattttc cactaaaaat ataatgaaat      60
gatgttaagc tttttgaaaa gtttaggtta aacctactgt tgttagatta atgtatttgt     120
tgcttccctt tatctggaat gtggcattag ctttttatt ttaaccctct ttaattctta     180
ttcaattcca tgacttaagg ttggagagct aaacactggg attttggat aacagactga     240
cagttttgca taattataat cggcattgta catagaaagg atatggctac cttttgttaa     300
atctgcactt tctaaatatc aaaaaggga aatgaagtta taaatcaatt tttgtataat     360
ctgtttgaaa catgagtttt atttgcttaa tattagggct ttgccccttt tctgtaagtc     420
tcttgggatc ctgtgtagaa ctgttctcat taaacaccaa acagttaagt ccattctctg     480
gtactagcta caaattcggt ttcatattct acttaacaat ttaaataaac tgaaatattt     540
ctagatggtc tacttctgtt catataaaaa caaaacttga tttccaaaaa aaaaaaaaaa     600
aa                                                                    602
```

<210> SEQ ID NO 12
<211> LENGTH: 685
<212> TYPE: DNA
<213> ORGANISM: Homo sapien
<220> FEATURE:
<221> NAME/KEY: misc_feature
<222> LOCATION: (1)...(685)
<223> OTHER INFORMATION: n = A,T,C or G

<400> SEQUENCE: 12

```
actagtcctg tgaaagtaca actgaaggca gaaagtgtta ggattttgca tctaatgttc      60
attatcatgg tattgatgga cctaagaaaa taaaattag actaagcccc caaataagct     120
gcatgcattt gtaacatgat tagtagattt gaatatatag atgtagtatn ttgggtatct     180
aggtgtttta tcattatgta aaggaattaa agtaaaggac tttgtagttg tttttattaa     240
atatgcatat agtagagtgc aaaaatatag caaaaatana aactaaaggt agaaaagcat     300
tttagatatg ccttaatnta nnaactgtgc caggtggccc tcggaataga tgccaggcag     360
```

| | |
|---|---:|
| agaccagtgc ctgggtggtg cctcccttg tctgcccccc tgaagaactt ccctcacgtg | 420 |
| angtagtgcc ctcgtaggtg tcacgtggan tantgggane aggccgnnen gtnanaagaa | 480 |
| ancanngtga nagtttcncc gtngangcng aactgtccct gngccnnnac gctcccanaa | 540 |
| cntntccaat ngacaatcga gtttccnnnc tccngnaacc tngccgnnnn cnngcccnnc | 600 |
| cantntgnta acccegegee cggategete tennntegtt ctencnenaa ngggntttcn | 660 |
| cnnccgccgt cncnncccg cnncc | 685 |

<210> SEQ ID NO 13
<211> LENGTH: 694
<212> TYPE: DNA
<213> ORGANISM: Homo sapien
<220> FEATURE:
<221> NAME/KEY: misc_feature
<222> LOCATION: (1)...(694)
<223> OTHER INFORMATION: n = A,T,C or G

<400> SEQUENCE: 13

| | |
|---|---:|
| cactagtcac tcattagcgt tttcaatagg gctcttaagt ccagtagatt acgggtagtc | 60 |
| agttgacgaa gatctggttt acaagaacta attaaatgtt tcattgcatt tttgtaagaa | 120 |
| cagaataatt ttataaaatg tttgtagttt ataattgccg aaaataattt aaagacactt | 180 |
| tttctctgtg tgtgcaaatg tgtgtttgtg atccattttt tttttttttt taggacacct | 240 |
| gtttactagc tagctttaca atatgccaaa aaggatttc tccctgaccc catccgtggt | 300 |
| tcaccctctt ttcccccat gcttttgcc ctagtttata acaaaggaat gatgatgatt | 360 |
| taaaaagtag ttctgtatct tcagtatctt ggtcttccag aaccctctgg ttgggaaggg | 420 |
| gatcattttt tactggtcat ttcccttttgg agtgtactac tttaacagat ggaaagaact | 480 |
| cattggccat ggaaacagcc gangtgttgg gagccagcag tgcatggcac cgtccggcat | 540 |
| ctggcntgat tggtctggct gccgtcattg tcagcacagt gccatgggac atggggaana | 600 |
| ctgactgcac ngccaatggt tttcatgaag aatacngcat ncncngtgat cacgtnancc | 660 |
| angacgctat gggggncana gggccanttg cttc | 694 |

<210> SEQ ID NO 14
<211> LENGTH: 679
<212> TYPE: DNA
<213> ORGANISM: Homo sapien
<220> FEATURE:
<221> NAME/KEY: misc_feature
<222> LOCATION: (1)...(679)
<223> OTHER INFORMATION: n = A,T,C or G

<400> SEQUENCE: 14

| | |
|---|---:|
| cagccgcctg catctgtatc cagcgccang tcccgccagt cccagctgcg cgcgcccccc | 60 |
| agtcccgnac ccgttcggcc cangctnagt tagncctcac catnccggtc aaaggangca | 120 |
| ccaagtgcat caaatacctg cngtncggat ntaaattcat cttctggctt gccgggattg | 180 |
| ctgtccntgc cattggacta nggctccgat ncgactctca gaccanganc atcttcganc | 240 |
| naganactaa tnatnattnt tccagcttct acacaggagt ctatattctg atcggatccg | 300 |
| gcnccctcnt gatgctggtg ggcttcctga gctgctgcgg ggctgtgcaa gagtcccant | 360 |
| gcatgctggg actgttcttc ggcttcntct tggtgatatn cgccattgaa atacctgcgg | 420 |
| ccatctgggg atattccact ncgatnatgt gattaaggaa ntccacgag ttttacaagg | 480 |
| acacgtacaa cnacctgaaa accnnggatg anccccaccg ggaancnctg aangccatcc | 540 |
| actatgcgtt gaactgcaat ggtttggctg gggncctga acaatttaat cncatacatc | 600 |

```
tggccccann aaaggacntn ctcganncct tcnccgtgna attcngttct gatnccatca    660
cagaagtctc gaacaatcc                                                679

<210> SEQ ID NO 15
<211> LENGTH: 695
<212> TYPE: DNA
<213> ORGANISM: Homo sapien
<220> FEATURE:
<221> NAME/KEY: misc_feature
<222> LOCATION: (1)...(695)
<223> OTHER INFORMATION: n = A,T,C or G

<400> SEQUENCE: 15
actagtggat aaaggccagg gatgctgctc aacctcctac catgtacagg gacgtctccc     60
cattacaact acccaatccg aagtgtcaac tgtgtcagga ctaanaaacc ctggttttga    120
ttaaaaaagg gcctgaaaaa aggggagcca caaatctgtc tgcttcctca cnttantcnt    180
tggcaaatna gcattctgtc tcnttggctg cngcctcanc ncaaaaaanc ngaactcnat    240
cnggcccagg aatacatctc ncaatnaacn aaattganca aggcnntggg aaatgccnga    300
tgggattatc ntccgcttgt tganctctca agtttcnttc ccttcattcn accctgccag    360
ccnagttctg ttagaaaaat gccngaattc naacnccggt tttcntactc ngaatttaga    420
tctncanaaa cttcctggcc acnattcnaa ttnanggnca cgnacanatn ccttccatna    480
ancncacccc acntttgana gccangacaa tgactgctn aantgaaggc ntgaaggaan    540
aactttgaaa ggaaaaaaaa ctttgtttcc ggccccttcc aacncttctg tgttnancac    600
tgccttctng naaccctgga agcccngnga cagtgttaca tgttgttcta nnaaacngac    660
ncttnaatnt cnatcttccc nanaacgatt ncncc                              695

<210> SEQ ID NO 16
<211> LENGTH: 669
<212> TYPE: DNA
<213> ORGANISM: Homo sapien
<220> FEATURE:
<221> NAME/KEY: misc_feature
<222> LOCATION: (1)...(669)
<223> OTHER INFORMATION: n = A,T,C or G

<400> SEQUENCE: 16
cgccgaagca gcagcgcagg ttgtccccgt ttccctccc ccttcccttc tccggttgcc     60
ttcccgggcc ccttacactc cacagtcccg gtcccgccat gtcccagaaa caagaagaag    120
agaaccctgc ggaggagacc ggcgaggaga agcaggacac gcaggagaaa gaaggtattc    180
tgcctgagag agctgaagag gcaaagctaa aggccaaata cccaagccta ggacaaaagc    240
ctggaggctc cgacttcctc atgaagagac tccagaaagg gcaaaagtac tttgactcng    300
gagactacaa catggccaaa gccaacatga agaataagca gctgccaagt gcangaccag    360
acaagaacct ggtgactggt gatcacatcc caccccaca ggatctgccc agagaaagtc    420
ctcgctcgtc accagcaagc ttgcgggtgg ccaagttgaa tgatgctgcc ggggctctgc    480
canatctgag acgcttccct ccctgcccca cccgggtcct gtgctggctc ctgcccttcc    540
tgcttttgca gccangggtc aggaagtggc ncnggtngtg gctggaaagc aaaacccttt    600
cctgttggtg tcccacccat ggagccctg gggcgagccc angaacttga nccttttgt    660 tntcttncc                                                          669

<210> SEQ ID NO 17
```

<211> LENGTH: 697
<212> TYPE: DNA
<213> ORGANISM: Homo sapien
<220> FEATURE:
<221> NAME/KEY: misc_feature
<222> LOCATION: (1)...(697)
<223> OTHER INFORMATION: n = A,T,C or G

<400> SEQUENCE: 17

| | | | | | |
|---|---|---|---|---|---|
| gcaagatatg | gacaactaag | tgagaaggta | atnctctact | gctctagntn | ctccnggcnn | 60 |
| gacgcgctga | ggagannnac | gctggcccan | ctgccggcca | cacacgggga | tcntggtnat | 120 |
| gcctgcccan | gggancccca | ncnctcggan | cccatntcac | acccgnnccn | tncgcccacn | 180 |
| ncctggctcn | cncngcccng | nccagctcnc | gnccccctcc | gccnnnctcn | ttnncntctc | 240 |
| cncnccctcc | ncnacnacct | cctaccncg | gctccctccc | cagcccccc | ccgcaanect | 300 |
| ccacnacncc | ntcnncncga | ancnccnctc | gcnctcngcc | ccngcccct | gcccccgcc | 360 |
| cncnacnncg | cgntcccccg | cgcncgcngc | ctcnccccct | cccacacag | ncncacccgc | 420 |
| agncacgcnc | tccgcccnct | gacgccccnn | cccgccgcgc | tcaccttcat | ggnccnacng | 480 |
| cccgctcnc | ncnctgcnc | gccgncnngg | cgccccgccc | cnnccgngtn | ccncncgnng | 540 |
| cccngcngn | angcngtgcg | cnncangncc | gngccgnncn | nacccctccg | nccnccgccc | 600 |
| cgcccgctgg | gggctcccgc | cncgcggntc | antccccncc | cntncgccca | ctntccgntc | 660 |
| cnncnctcnc | gctcngcgcn | cgcccnccnc | ccccccc | | | 697 |

<210> SEQ ID NO 18
<211> LENGTH: 670
<212> TYPE: DNA
<213> ORGANISM: Homo sapien
<220> FEATURE:
<221> NAME/KEY: misc_feature
<222> LOCATION: (1)...(670)
<223> OTHER INFORMATION: n = A,T,C or G

<400> SEQUENCE: 18

| | | | | | |
|---|---|---|---|---|---|
| ctcgtgtgaa | gggtgcagta | cctaagccgg | agcggggtag | aggcgggccg | gcacccctt | 60 |
| ctgacctcca | gtgccgccgg | cctcaagatc | agacatggcc | cagaacttga | acgacttggc | 120 |
| gggacggctg | cccgccgggc | ccggggcat | ggcacggcc | ctgaagctgt | tgctgggggc | 180 |
| cggcgccgtg | gcctacggtg | tgcgcgaatc | tgtgttcacc | gtggaaggcg | ggcncagagc | 240 |
| catcttcttc | aatcggatcg | gtggagtgca | caggacacta | tcctgggccg | anggccttca | 300 |
| cttcaggatc | cttggttcca | gtaccccanc | atctatgaca | ttcgggccag | acctcgaaaa | 360 |
| aatctcctcc | ctacaggctc | caaagaccta | cagatggtga | atatctccct | gcgagtgttg | 420 |
| tctcgaccaa | tgctcangaa | cttcctaaca | tgttccancg | cctaagggct | ggactacnaa | 480 |
| gaacgantgt | tgccgtccat | tgtcacgaag | tgctcaagaa | tttnggtggc | caagttcaat | 540 |
| gncctcacnn | ctgatcnccc | agcggggcca | agttanccct | ggttgatccc | cggggganctg | 600 |
| acnnaaaagg | gccaaggact | tcccctcatc | ctggataatg | tggccntcac | aaagctcaac | 660 |
| tttanccacc | | | | | | 670 |

<210> SEQ ID NO 19
<211> LENGTH: 606
<212> TYPE: DNA
<213> ORGANISM: Homo sapien
<220> FEATURE:
<221> NAME/KEY: misc_feature
<222> LOCATION: (1)...(606)
<223> OTHER INFORMATION: n = A,T,C or G

```
<400> SEQUENCE: 19
actagtgcca acctcagctc ccaggccagt tctctgaatg tcgaggagtt ccaggatctc    60
tggcctcagt tgtccttggt tattgatggg ggacaaattg gggatggcca gagccccgag   120
tgtcgccttg gctcaactgt ggttgatttg tctgtgcccg gaaagtttgg catcattcgt   180
ccaggctgtg ccctggaaag tactacagcc atcctccaac agaagtacgg actgctcccc   240
tcacatgcgt cctacctgtg aaactctggg aagcaggaag gcccaagacc tggtgctgga   300
tactatgtgt ctgtccactg acgactgtca aggcctcatt tgcagaggcc accggagcta   360
gggcactagc ctgactttta aggcagtgtg tctttctgag cactgtagac caagcccttg   420
gagctgctgt tttagcctg cacctgggga aaggatgtat ttatttgtat tttcatatat   480
cagccaaaag ctgaatggaa aagttnagaa cattcctagg tggccttatt ctaataagtt   540
tcttctgtct gttttgtttt tcaattgaaa agttattaaa aacagatttt agaatctagt   600
gagacc                                                              606

<210> SEQ ID NO 20
<211> LENGTH: 449
<212> TYPE: DNA
<213> ORGANISM: Homo sapien

<400> SEQUENCE: 20
actagtaaac aacagcagca gaaacatcag tatcagcagc gtcgccagca ggagaatatg    60
cagcgccaga gccgaggaga accccgctcc cctgaggagg acctgtccaa actcttcaaa   120
ccaccacagc cgcctgccag gatggactcg ctgctcattg caggccagat aaacacttac   180
tgccagaaca tcaaggagtt cactgcccaa aacttaggca agctcttcat ggcccaggct   240
cttcaagaat acaacaacta agaaaaggaa gtttccagaa aagaagttaa catgaactct   300
tgaagtcaca ccagggcaac tcttggaaga atatatttg catattgaaa agcacagagg   360
atttcttag tgtcattgcc gattttggct ataacagtgt cttctagcc ataataaaat   420
aaaacaaaat cttgactgct tgctcaaaa                                    449

<210> SEQ ID NO 21
<211> LENGTH: 409
<212> TYPE: DNA
<213> ORGANISM: Homo sapien

<400> SEQUENCE: 21
tatcaatcaa ctggtgaata attaaacaat gtgtggtgtg atcatacaaa gggtaccact    60
caatgataaa aggaacaagc tgcctatatg tggaacaaca tggatgcatt tcagaaactt   120
tatgttgagt gaaagaacaa acacggagaa catactatgt ggttctcttt atgtaacatt   180
acagaaataa aaacagaggc aaccaccttt gaggcagtat ggagtgagat agactggaaa   240
aaggaaggaa ggaaactcta cgctgatgga aatgtctgtg tcttcattgg gtggtagtta   300
tgtggggata tacatttgtc aaaatttatt gaactatata ctaaagaact ctgcatttta   360
ttgggatgta aataataaccct caattaaaaa gacaaaaaaa aaaaaaaaa             409

<210> SEQ ID NO 22
<211> LENGTH: 649
<212> TYPE: DNA
<213> ORGANISM: Homo sapien
<220> FEATURE:
<221> NAME/KEY: misc_feature
<222> LOCATION: (1)...(649)
```

<223> OTHER INFORMATION: n = A,T,C or G

<400> SEQUENCE: 22

```
acaattttca ttatcttaag cacattgtac atttctacag aacctgtgat tattctcgca    60
tgataaggat ggtacttgca tatggtgaat tactactgtt gacagtttcc gcagaaatcc   120
tatttcagtg gaccaacatt gtggcatggc agcaaatgcc aacattttgt ggaatagcag   180
caaatctaca agagaccctg gttggttttt cgttttgttt tctttgtttt ttccccttc    240
tcctgaatca gcagggatgg aagagggta gggaagttat gaattactcc ttccagtagt    300
agctctgaag tgtcacattt aatatcagtt tttttaaac atgattctag ttnaatgtag    360
aagagagaag aaagaggaag tgttcacttt tttaatacac tgatttagaa atttgatgtc   420
ttatatcagt agttctgagg tattgatagc ttgctttatt tctgccttta cgttgacagt   480
gttgaagcag ggtgaataac tagggcata tatatttttt tttttgtaa gctgtttcat    540
gatgttttct ttggaatttc cggataagtt caggaaaaca tctgcatgtt gttatctagt   600
ctgaagttcn tatccatctc attacaacaa aaacncccag aacggnttg              649
```

<210> SEQ ID NO 23
<211> LENGTH: 669
<212> TYPE: DNA
<213> ORGANISM: Homo sapien
<220> FEATURE:
<221> NAME/KEY: misc_feature
<222> LOCATION: (1)...(669)
<223> OTHER INFORMATION: n = A,T,C or G

<400> SEQUENCE: 23

```
actagtgccg tactggctga atccctgca ggaccaggaa gagaaccagt tcagactttg     60
tactctcagt caccagctct ggaattagat aaattccttg aagatgtcag gaatgggatc   120
tatcctctga cagcctttgg gctgcctcgg ccccagcagc cacagcagga ggaggtgaca   180
tcacctgtcg tgccccctc tgtcaagact ccgacacctg aaccagctga ggtggagact   240
cgcaaggtgg tgctgatgca gtgcaacatt gagtcggtgg aggagggagt caaacaccac   300
ctgacacttc tgctgaagtt ggaggacaaa ctgaaccggc acctgagctg tgacctgatg   360
ccaaatgaga atatccccga gttggcggct gagctggtgc agctgggctt cattagtgag   420
gctgaccaga gccggttgac ttctctgcta aagagactt gaacaagttc aattttgcca   480
ggaacagtac cctcaactca gccgctgtca ccgtctcctc ttagagctca ctcgggccag   540
gccctgatct gcgctgtggc tgtcctggac gtgctgcacc ctctgtcctt ccccccagtc   600
agtattacct gtgaagccct tccctccttt attattcagg anggctgggg gggctccttg   660
nttctaacc                                                          669
```

<210> SEQ ID NO 24
<211> LENGTH: 442
<212> TYPE: DNA
<213> ORGANISM: Homo sapien

<400> SEQUENCE: 24

```
actagtacca tcttgacaga ggatacatgc tcccaaaacg tttgttacca cacttaaaaa    60
tcactgccat cattaagcat cagtttcaaa attatagcca ttcatgattt acttttttcca  120
gatgactatc attattctag tcctttgaat ttgtaagggg aaaaaaaaca aaacaaaaa    180
cttacgatgc acttttctcc agcacatcag atttcaaatt gaaaattaaa gacatgctat   240
ggtaatgcac ttgctagtac tacacacttt ggtacaacaa aaaacagagg caagaaacaa   300
```

```
cggaaagaga aaagccttcc tttgttggcc cttaaactga gtcaagatct gaaatgtaga    360
gatgatctct gacgatacct gtatgttctt attgtgtaaa taaaattgct ggtatgaaat    420
gacctaaaaa aaaaaaaga aa                                              442
```

<210> SEQ ID NO 25
<211> LENGTH: 656
<212> TYPE: DNA
<213> ORGANISM: Homo sapien
<220> FEATURE:
<221> NAME/KEY: misc_feature
<222> LOCATION: (1)...(656)
<223> OTHER INFORMATION: n = A,T,C or G

<400> SEQUENCE: 25

```
tgcaagtacc acacactgtt tgaattttgc acaaaaagtg actgtaggat caggtgatag     60
ccccggaatg tacagtgtct tggtgcacca agatgccttc taaaggctga catacctttgg   120 accctaatgg ggcagagagt atagccctag cccagtggtg acatgaccac tcccttggg    180 aggcctgagg tagaggggag tggtatgtgt tttctcagtg gaagcagcac atgagtgggt   240
gacaggatgt tagataaagg ctctagttag ggtgtcattg tcatttgaga gactgacaca   300
ctcctagcag ctggtaaagg ggtgctggan gccatggagg anctctagaa acattagcat   360
gggctgatct gattacttcc tggcatcccg ctcactttta tgggaagtct tattagangg   420
atgggacagt tttccatatc cttgctgtgg agctctggaa cactctctaa atttccctct   480
attaaaaatc actgccctaa ctacacttcc tccttgaagg aatagaaatg gaactttctc   540
tgacatantt cttggcatgg ggagccagcc acaaatgana atctgaacgt gtccaggttt   600
ctcctganac tcatctacat agaattggtt aaaccctccc ttggaataag gaaaaa       656
```

<210> SEQ ID NO 26
<211> LENGTH: 434
<212> TYPE: DNA
<213> ORGANISM: Homo sapien
<220> FEATURE:
<221> NAME/KEY: misc_feature
<222> LOCATION: (1)...(434)
<223> OTHER INFORMATION: n = A,T,C or G

<400> SEQUENCE: 26

```
actagttcag actgccacgc caaccccaga aaatacccca catgccagaa aagtgaagtc     60
ctaggtgttt ccatctatgt ttcaatctgt ccatctacca ggcctcgcga taaaaacaaa   120
acaaaaaaac gctgccaggt tttagaagca gttctggtct caaaaccatc aggatcctgc   180
caccagggtt cttttgaaat agtaccacat gtaaagggga atttggcttt cacttcatct   240
aataactgaa ttgtcaggct ttgattgata attgtagaaa taagtagcct tctgttgtgg   300
gaataagtta taatcagtat tcatctcttt gttttttgtc actcttttct ctctaattgt   360
gtcatttgta ctgtttgaaa aatatttctt ctatnaaatt aaactaacct gccttaaaaa   420
aaaaaaaaaa aaaa                                                      434
```

<210> SEQ ID NO 27
<211> LENGTH: 654
<212> TYPE: DNA
<213> ORGANISM: Homo sapien
<220> FEATURE:
<221> NAME/KEY: misc_feature
<222> LOCATION: (1)...(654)
<223> OTHER INFORMATION: n = A,T,C or G

<400> SEQUENCE: 27

```
actagtccaa cacagtcaga aacattgttt tgaatcctct gtaaaccaag gcattaatct      60
taataaacca ggatccattt aggtaccact tgatataaaa aggatatcca taatgaatat     120
tttatactgc atcctttaca ttagccacta aatacgttat tgcttgatga agacctttca     180
cagaatccta tggattgcag catttcactt ggctacttca tacccatgcc ttaaagaggg     240
gcagtttctc aaaagcagaa acatgccgcc agttctcaag ttttcctcct aactccattt     300
gaatgtaagg gcagctggcc cccaatgtgg ggaggtccga acattttctg aattcccatt     360
ttcttgttcg cggctaaatg acagtttctg tcattactta gattccgatc tttcccaaag     420
gtgttgattt acaaagaggc cagctaatag cagaaatcat gaccctgaaa gagagatgaa     480
attcaagctg tgagccaggc agganctcag tatggcaaag gtcttgagaa tcngccattt     540
ggtacaaaaa aaattttaaa gcntttatgt tataccatgg aaccatagaa anggcaaggg     600
aattgttaag aanaatttta agtgtccaga cccanaanga aaaaaaaaaa aaaa           654
```

<210> SEQ ID NO 28
<211> LENGTH: 670
<212> TYPE: DNA
<213> ORGANISM: Homo sapien
<220> FEATURE:
<221> NAME/KEY: misc_feature
<222> LOCATION: (1)...(670)
<223> OTHER INFORMATION: n = A,T,C or G

<400> SEQUENCE: 28

```
cgtgtgcaca tactgggagg atttccacag ctgcacggtc acagcccttta cggattgcca      60
ggaaggggcg aaagatatgt gggataaact gagaaaagaa nccaaaaacc tcaacatcca     120
aggcagctta ttcgaactct gcggcagcgg caacggggcg gcggggtccc tgctcccggc     180
gttcccggtg ctcctggtgt ctctctcggc agctttagcg acctgncttt ccttctgagc     240
gtggggccag ctcccccgc ggcgcccacc cacnctcact ccatgctccc ggaaatcgag     300
aggaagatca ttagttcttt ggggacgttn gtgattctct gtgatgctga aaacactca     360
tatagggaat gtgggaaatc ctganctctt tnttatntcg tntgatttct tgtgttttat     420
ttgccaaaat gttaccaatc agtgaccaac cnagcacagc caaaaatcgg acntcngctt     480
tagtccgtct tcacacacag aataagaaaa cggcaaaccc accccacttt tnantttnat     540
tattactaan tttttctgt tgggcaaaag aatctcagga acngccctgg ggccnccgta     600
ctanagttaa ccnagctagt tncatgaaaa atgatgggct ccnnctcaat gggaaagcca     660
agaaaaagnc                                                              670
```

<210> SEQ ID NO 29
<211> LENGTH: 551
<212> TYPE: DNA
<213> ORGANISM: Homo sapien
<220> FEATURE:
<221> NAME/KEY: misc_feature
<222> LOCATION: (1)...(551)
<223> OTHER INFORMATION: n = A,T,C or G

<400> SEQUENCE: 29

```
actagtcctc cacagcctgt gaatcccct agacctttca agcatagtga gcggagaaga      60
agatctcagc gtttagccac cttacccatg cctgatgatt ctgtagaaaa ggtttcttct     120
ccctctccag ccactgatgg gaaagtattc tccatcagtt ctcaaaatca gcaagaatct     180
tcagtaccag aggtgcctga tgttgcacat ttgccacttg agaagctggg accctgtctc     240
```

-continued

```
cctcttgact taagtcgtgg ttcagaagtt acagcaccgg tagcctcaga ttcctcttac    300
cgtaatgaat gtcccagggc agaaaaagag gatacncaga tgcttccaaa tccttcttcc    360
aaagcaatag ctgatgggaa gaggagctcc agcagcagca ggaatatcga aaacagaaaa    420
aaaagtgaaa ttgggaagac aaaagctcaa cagcatttgg taaggagaaa aganaagatg    480
aggaaggaag agagaagaga gacnaagatc nctacggacc gnnncggaag aagaagaagn    540
aaaaaanaaa a                                                        551
```

<210> SEQ ID NO 30
<211> LENGTH: 684
<212> TYPE: DNA
<213> ORGANISM: Homo sapien
<220> FEATURE:
<221> NAME/KEY: misc_feature
<222> LOCATION: (1)...(684)
<223> OTHER INFORMATION: n = A,T,C or G

<400> SEQUENCE: 30

```
actagttcta tctggaaaaa gcccggggttg gaagaagctg tggagagtgc gtgtgcaatg     60
cgagactcat ttcttggaag catccctggc aaaaatgcag ctgagtacaa ggttatcact    120
gtgatagaac ctggactgct ttttgagata atagagatgc tgcagtctga agagacttcc    180
agcacctctc agttgaatga attaatgatg gcttctgagt caactttact ggctcaggaa    240
ccacgagaga tgactgcaga tgtaatcgag cttaaaggga aattcctcat caacttagaa    300
ggtggtgata ttcgtgaaga gtcttcctat aaagtaattg tcatgccgac tacgaaagaa    360
aaatgccccc gttgttggaa gtatacagcg ggagtcttca gatacactgt gtcctcgatg    420
tgcagaagtt gtcagtggga aaatagtatt aacagctcac tcgagcaaga accctcctga    480
cagtactggg ctagaagttt ggatggatta tttacaatat aggaaagaaa gccaagaatt    540
aggtnatgag tggatgagta aatggtggan gatggggaat tcaaatcaga attatggaag    600
aagttnttcc tgttactata gaaggaatt atgtttattt acatgcagaa aatatanatg    660
tgtggtgtgt accgtggatg gaan                                          684
```

<210> SEQ ID NO 31
<211> LENGTH: 654
<212> TYPE: DNA
<213> ORGANISM: Homo sapien
<220> FEATURE:
<221> NAME/KEY: misc_feature
<222> LOCATION: (1)...(654)
<223> OTHER INFORMATION: n = A,T,C or G

<400> SEQUENCE: 31

```
gcgcagaaaa ggaaccaata tttcagaaac aagcttaata ggaacagctg cctgtacatc     60
aacatcttct cagaatgacc cagaagttat catcgtggga gctggcgtgc ttggctctgc    120
tttggcagct gtgctttcca gagatggaag aaaggtgaca gtcattgaga gagacttaaa    180
agagcctgac agaatagttg gagaattcct gcagccgggt ggttatcatg ttctcaaaga    240
ccttggtctt ggagatacag tggaaggtct tgatgcccag gttgtaaatg gttacatgat    300
tcatgatcag ggaaagcaaa tcagangttc agattcctta ccctctgtca gaaaacaatc    360
aagtgcagag tggaagagct tccatcacg gaagattcat catgagtctc cggaaagcag    420
ctatggcaga gcccaatgca aagtttattg aaggtgttgt gttacagtta ttagaggaag    480
atgatgttgt gatgggagtt cagtacaagg ataaagagac tgggagatat caaggaactc    540
```

| | |
|---|---|
| catgctccac tgactgttgt tgcagatggg cttttctcca anttcaggaa aagcctggtc | 600 |
| tcaataaagt ttctgtatca ctcatttggt tggcttctta tgaagaatgc nccc | 654 |

<210> SEQ ID NO 32
<211> LENGTH: 673
<212> TYPE: DNA
<213> ORGANISM: Homo sapien
<220> FEATURE:
<221> NAME/KEY: misc_feature
<222> LOCATION: (1)...(673)
<223> OTHER INFORMATION: n = A,T,C or G

<400> SEQUENCE: 32

| | |
|---|---|
| actagtgaag aaaagaaat tctgatacgg acaaaaatg ctcttcaaaa catcattctt | 60 |
| tatcacctga caccaggagt tttcattgga aaggatttg aacctggtgt tactaacatt | 120 |
| ttaaagacca cacaaggaag caaaatcttt ctgaaagaag taaatgatac acttctggtg | 180 |
| aatgaattga atcaaaaga atctgacatc atgcaacaa atggtgtaat tcatgttgta | 240 |
| gataaactcc tctatccagc agacacacct gttggaaatg atcaactgct ggaaatactt | 300 |
| aataaattaa tcaaatacat ccaaattaag tttgttcgtg gtagcacctt caaagaaatc | 360 |
| cccgtgactg tctatnagcc aattattaaa aaatacacca aaatcattga tgggagtgcc | 420 |
| tgtgggaaat aactgaaaaa gagaccgaga agaacgaatc attacaggtc ctgaaataaa | 480 |
| atacctagga tttctactgg aggtggagaa acagaagaac tctgaagaaa ttgttacaag | 540 |
| aagangtccc aaggtcacca aattcattga aggtggtgat ggtctttatt tgaagatgaa | 600 |
| gaaattaaaa gacgcttcag ggagacnccc catgaaggaa ttgccagcca caaaaaatt | 660 |
| cagggattag aaa | 673 |

<210> SEQ ID NO 33
<211> LENGTH: 673
<212> TYPE: DNA
<213> ORGANISM: Homo sapien
<220> FEATURE:
<221> NAME/KEY: misc_feature
<222> LOCATION: (1)...(673)
<223> OTHER INFORMATION: n = A,T,C or G

<400> SEQUENCE: 33

| | |
|---|---|
| actagttatt tactttcctc cgcttcagaa ggttttcag actgagagcc taagcatact | 60 |
| ggatctgttg tttcttttgg gtctcacctc atcagtgtgc atagtggcag aaattataaa | 120 |
| gaaggttgaa aggagcaggg aaaagatcca gaagcatgtt agttcgacat catcatcttt | 180 |
| tcttgaagta tgatgcatat tgcattattt tatttgcaaa ctaggaattg cagtctgagg | 240 |
| atcatttaga agggcaagtt caagaggata tgaagatttg agaactttt aactattcat | 300 |
| tgactaaaaa tgaacattaa tgttnaagac ttaagacttt aacctgctgg cagtcccaaa | 360 |
| tgaaattatg caactttgat atcatattcc ttgatttaaa ttgggctttt gtgattgant | 420 |
| gaaactttat aaagcatatg gtcagttatt tnattaaaaa ggcaaaacct gaaccacctt | 480 |
| ctgcacttaa agaagtctaa cagtacaaat acctatctat cttagatgga tntatttntt | 540 |
| tntatttta aatattgtac tatttatggt nggtggggct ttcttactaa tacacaaatn | 600 |
| aatttatcat ttcaanggca ttctatttgg gtttagaagt tgattccaag nantgcatat | 660 |
| ttcgctactg tnt | 673 |

<210> SEQ ID NO 34
<211> LENGTH: 684

<212> TYPE: DNA
<213> ORGANISM: Homo sapien
<220> FEATURE:
<221> NAME/KEY: misc_feature
<222> LOCATION: (1)...(684)
<223> OTHER INFORMATION: n = A,T,C or G

<400> SEQUENCE: 34

| | | | | | |
|---|---|---|---|---|---|
| actagtttat | tcaagaaaag | aacttactga | ttcctctgtt | cctaaagcaa | gagtggcagg | 60
| tgatcagggc | tggtgtagca | tccggttcct | ttagtgcagc | taactgcatt | tgtcactgat | 120
| gaccaaggag | gaaatcacta | agacatttga | gaagcagtgg | tatgaacgtt | cttggacaag | 180
| ccacagttct | gagccttaac | cctgtagttt | gcacacaaga | acgagctcca | cctcccttc | 240
| ttcaggagga | atctgtgcgg | atagattggc | tggactttc | aatggttctg | ggttgcaagt | 300
| gggcactgtt | atggctgggt | atggagcgga | cagccccagg | aatcagagcc | tcagcccggc | 360
| tgcctggttg | gaaggtacag | gtgttcagca | ccttcggaaa | aagggcataa | agtngtgggg | 420
| gacaattctc | agtccaagaa | gaatgcattg | accattgctg | gctatttgct | tncctagtan | 480
| gaattggatn | cattttgac | cangatnntt | ctnctatgct | ttnttgcaat | gaaatcaaat | 540
| cccgcattat | ctacaagtgg | tatgaagtcc | tgcnnccccc | agagaggctg | ttcaggcnat | 600
| gtcttccaag | ggcagggtgg | gttacaccat | tttacctccc | ctctccccc | agattatgna | 660
| cncagaagga | atttntttcc | tccc | | | 684

<210> SEQ ID NO 35
<211> LENGTH: 614
<212> TYPE: DNA
<213> ORGANISM: Homo sapien
<220> FEATURE:
<221> NAME/KEY: misc_feature
<222> LOCATION: (1)...(614)
<223> OTHER INFORMATION: n = A,T,C or G

<400> SEQUENCE: 35

| | | | | | |
|---|---|---|---|---|---|
| actagtccaa | cgcgttngcn | aatattcccc | tggtagccta | cttccttacc | cccgaatatt | 60
| ggtaagatcg | agcaatggct | tcaggacatg | ggttctcttc | tcctgtgatc | attcaagtgc | 120
| tcactgcatg | aagactggct | tgtctcagtg | tntcaacctc | accagggctg | tctcttggtc | 180
| cacacctcgc | tccctgttag | tgccgtatga | cagccccat | canatgacct | tggccaagtc | 240
| acggtttctc | tgtggtcaat | gttggtnggc | tgattggtgg | aaagtanggt | ggaccaaagg | 300
| aagncncgtg | agcagncanc | nccagttctg | caccagcagc | gcctccgtcc | tactngggtg | 360
| ttccngtttc | tcctggccct | gngtgggcta | nggcctgatt | cgggaanatg | cctttgcang | 420
| gaaggganga | taantgggat | ctaccaattg | attctggcaa | aacnatntct | aagattnttn | 480
| tgctttatgt | gggancana | tctanctctc | atttnntgct | gnanatnaca | ccctactcgt | 540
| gntcgancnc | gtcttcgatt | ttcgganaca | cnccantnaa | tactggcgtt | ctgttgttaa | 600
| aaaaaaaaaa | aaaa | | | | 614

<210> SEQ ID NO 36
<211> LENGTH: 686
<212> TYPE: DNA
<213> ORGANISM: Homo sapien
<220> FEATURE:
<221> NAME/KEY: misc_feature
<222> LOCATION: (1)...(686)
<223> OTHER INFORMATION: n = A,T,C or G

<400> SEQUENCE: 36

-continued

```
gtggctggcc cggttctccg cttctcccca tccctactt tcctccctcc ctcccttcc       60 ctccctcgtc gactgttgct tgctggtcgc agactccctg accctccct cacccctccc     120 taacctcggt gccaccggat tgccttctt ttcctgttgc ccagcccagc cctagtgtca     180 gggcggggc ctggagcagc ccgaggcact gcagcagaag ananaaaaga cacgacnaac     240
ctcagctcgc cagtccggtc gctngcttcc cgccgcatgg caatnagaca dacgccgctc    300
acctgctctg ggcacacgcg acccgtggtt gatttggcct tcagtggcat caccctatg    360 ggtatttctt aatcagcgct tgcaaagatg gttaacctat gctacgccag ggagatacag    420
gagactggat tggaacattt ttggggtcta aaggtctgtt tggggtgcaa cactgaataa    480
ggatgccacc aaagcagcta cagcagctgc agatttcaca gcccaagtgt gggatgctgt    540
ctcagganat naattgataa cctggctcat aacacattgt caagaatgtg gatttcccca    600
ggatattatt atttgtttac cggggganag gataactgtt tcncntattt taattgaaca    660
aactnaaaca aaanctaagg aaatcc                                         686
```

<210> SEQ ID NO 37
<211> LENGTH: 681
<212> TYPE: DNA
<213> ORGANISM: Homo sapien
<220> FEATURE:
<221> NAME/KEY: misc_feature
<222> LOCATION: (1)...(681)
<223> OTHER INFORMATION: n = A,T,C or G

<400> SEQUENCE: 37

```
gagacanacn naacgtcang agaanaaaag angcatggaa cacaanccag gcncgatggc      60
caccttccca ccagcancca gcgcccccca gcngccccca ngccggang accangactc     120 canccctgnat caatctganc tctattcctg gcccatncct acctcggagg tggangccgn    180
aaaggtcgca cnnncagaga agctgctgcc ancaccancc gccccnncc tgncgggctn    240 nataggaaac tggtgaccnn gctgcanaat tcatacagga gcacgcgang ggcacnnnct    300
cacactgagt tnnngatgan gcctnaccan ggacctnccc cagcnnattg annacnggac    360
tgcggaggaa ggaagacccc gnacnggatc ctggccggcn tgccaccccc ccaccctag    420 gattatnccc cttgactgag tctctgaggg gctacccgaa cccgcctcca ttccctacca    480
natnntgctc natcgggact dacangctgg ggatnggagg gctatcccc cancatcccc    540 tnanaccaac agcnacngan natngggct cccngggtc gggncaacnc tcctncaccc    600
cggcgcnggc cttcggtgnt gtcctccntc aacnaattcc naaanggcgg gcccccngt    660 ggactcctcn ttgttccctc c                                              681
```

<210> SEQ ID NO 38
<211> LENGTH: 687
<212> TYPE: DNA
<213> ORGANISM: Homo sapien
<220> FEATURE:
<221> NAME/KEY: misc_feature
<222> LOCATION: (1)...(687)
<223> OTHER INFORMATION: n = A,T,C or G

<400> SEQUENCE: 38

```
canaaaaaaa aaaacatggc cgaaaccagn aagctgcgcg atggcgccac ggcccctctt      60
ctcccggcct gtgtcggaa ggtttccctc cgaggcgccc cggctcccgc aagcggagga    120
gagggcggga cntgccgggg ccggagctca naggccctgg ggccgtctg ctctcccgcc    180 atcgcaaggg cggcgctaac ctnaggcctc cccgcaaagg tccccnangc ggnggcggcg    240
```

-continued

```
ggggctgtg anaaccgcaa aaanaacgct gggcgcgcng cgaacccgtc caccccccgcg      300 aaggananac ttccacagan gcagcgtttc cacagcccan agccacnttt ctagggtgat      360
gcaccccagt aagttcctgn cggggaagct caccgctgtc aaaaaanctc ttcgctccac      420
cggcgcacna aggggangan ggcangangc tgccgcccgc acaggtcatc tgatcacgtc      480
gcccgcccta ntctgctttt gtgaatctcc actttgttca accccacccg ccgttctctc      540
ctccttgcgc cttcctctna ccttaanaac cagcttcctc tacccnatng tanttnctct      600
gcncnngtng aaattaattc ggtccnccgg aacctcttnc ctgtggcaac tgctnaaaga      660
aactgctgtt ctgnttactg cngtccc                                          687
```

<210> SEQ ID NO 39
<211> LENGTH: 695
<212> TYPE: DNA
<213> ORGANISM: Homo sapien
<220> FEATURE:
<221> NAME/KEY: misc_feature
<222> LOCATION: (1)...(695)
<223> OTHER INFORMATION: n = A,T,C or G

<400> SEQUENCE: 39

```
actagtctgg cctacaatag tgtgattcat gtaggacttc tttcatcaat tcaaaacccc      60
tagaaaaacg tatacagatt atataagtag ggataagatt tctaacatttt ctgggctctc    120 tgaccctgc gctagactgt ggaaagggag tattattata gtatacaaca ctgctgttgc      180
cttattagtt ataacatgat aggtgctgaa ttgtgattca caatttaaaa acactgtaat     240
ccaaactttt tttttttaact gtagatcatg catgtgaatg ttaatgttaa tttgttcaan    300
gttgttatgg gtagaaaaaa ccacatgcct taaaatttta aaaagcaggg cccaaactta    360
ttagtttaaa attaggggta tgtttccagt ttgttattaa ntggttatag ctctgtttag    420
aanaaatcna ngaacangat ttngaaantt aagntgacat tatttnccag tgacttgtta    480
atttgaaatc anacacggca ccttccgttt tggtncatt ggnntttgaa tccaancngg     540
ntccaaatct tnttggaaac ngtccnttta acttttttac nanatcttat tttttattt     600 tggaatggcc ctatttaang ttaaaagggg ggggnnccac naccattcnt gaataaaact    660
naatatatat ccttggtccc ccaaaattta aggng                                695
```

<210> SEQ ID NO 40
<211> LENGTH: 674
<212> TYPE: DNA
<213> ORGANISM: Homo sapien
<220> FEATURE:
<221> NAME/KEY: misc_feature
<222> LOCATION: (1)...(674)
<223> OTHER INFORMATION: n = A,T,C or G

<400> SEQUENCE: 40

```
actagtagtc agttgggagt ggttgctata ccttgacttc atttatatga atttccactt      60
tattaaataa tagaaaagaa atcccggtg cttgcagtag agttataggaa cattctatgc    120 ttacagaaaa tatagccatg attgaaatca aatagtaaag gctgttctgg cttttatct    180 tcttagctca tcttaaataa gtagtacact tgggatgcag tgcgtctgaa gtgctaatca    240
gttgtaacaa tagcacaaat cgaacttagg atgtgtttct tctcttctgt gtttcgattt    300
tgatcaattc tttaattttg ggaacctata atacagtttt cctattcttg gagataaaaa    360
ttaaatggat cactgatatt taagtcattc tgcttctcat ctnaatattc catattctgt    420
```

| | |
|---|---|
| attagganaa antacctccc agcacagccc cctctcaaac cccacccaaa accaagcatt | 480 |
| tggaatgagt ctcctttatt tccgaantgt ggatggtata acccatatcn ctccaatttc | 540 |
| tgnttgggtt gggtattaat ttgaactgtg catgaaaagn ggnaatcttt nctttgggtc | 600 |
| aaantttncc ggttaatttg nctngncaaa tccaatttnc tttaagggtg tctttataaa | 660 |
| atttgctatt cngg | 674 |

<210> SEQ ID NO 41
<211> LENGTH: 657
<212> TYPE: DNA
<213> ORGANISM: Homo sapien
<220> FEATURE:
<221> NAME/KEY: misc_feature
<222> LOCATION: (1)...(657)
<223> OTHER INFORMATION: n = A,T,C or G

<400> SEQUENCE: 41

| | |
|---|---|
| gaaacatgca agtaccacac actgtttgaa ttttgcacaa aaagtgactg tagggatcag | 60 |
| gtgatagccc cggaatgtac agtgtcttgg tgcaccaaga tgccttctaa aggctgacat | 120 |
| accttgggac cctaatgggg cagagagtat agccctagcc cagtggtgac atgaccactc | 180 |
| cctttgggag gctgaagtta aagggaatgg tatgtgtttt ctcatggaag cagcacatga | 240 |
| atnggtnaca ngatgttaaa ntaaggntct antttgggtg tcttgtcatt tgaaaaantg | 300 |
| acacactcct ancanctggt aaaggggtgc tggaagccat ggaagaactc taaaaacatt | 360 |
| agcatgggct gatctgatta cttcctggca tcccgctcac ttttatggga agtcttatta | 420 |
| naaggatggg anantttttcc atatccttgc tgttggaact ctggaacact ctctaaattt | 480 |
| ccctctatta aaaatcactg nccttactac acttcctcct tgangggaata gaaatggacc | 540 |
| tttctctgac ttagttcttg gcatgggganc cagcccaaat taaaatctga cttntccggt | 600 |
| ttctccngaa ctcacctact tgaattggta aaacctcctt tggaattagn aaaaacc | 657 |

<210> SEQ ID NO 42
<211> LENGTH: 389
<212> TYPE: DNA
<213> ORGANISM: Homo sapien
<220> FEATURE:
<221> NAME/KEY: misc_feature
<222> LOCATION: (1)...(389)
<223> OTHER INFORMATION: n = A,T,C or G

<400> SEQUENCE: 42

| | |
|---|---|
| actagtgctg aggaatgtaa acaagtttgc tgggccttgc gagacttcac caggttgttt | 60 |
| cgatagctca cactcctgca ctgtgcctgt cacccaggaa tgtctttttt aattagaaga | 120 |
| caggaagaaa acaaaaacca gactgtgtcc cacaatcaga aacctccgtt gtggcagang | 180 |
| ggccttcacc gccaccaggg tgtcccgcca gacaggaga gactccagcc ttctgaggcc | 240 |
| atcctgaaga attcctgttt ggggttgtg aaggaaaatc acccggattt aaaaagatgc | 300 |
| tgttgcctgc ccgcgtngtn gggaagggac tggtttcctg gtgaatttct taaaagaaaa | 360 |
| atattttaag ttaagaaaaa aaaaaaaaa | 389 |

<210> SEQ ID NO 43
<211> LENGTH: 279
<212> TYPE: DNA
<213> ORGANISM: Homo sapien

<400> SEQUENCE: 43

| | |
|---|---|
| actagtgaca agctcctggt cttgagatgt cttctcgtta aggagatggg ccttttggag | 60 |

```
gtaaaggata aaatgaatga gttctgtcat gattcactat tctagaactt gcatgacctt      120
tactgtgtta gctctttgaa tgttcttgaa attttagact ttctttgtaa acaaataata      180
tgtccttatc attgtataaa agctgttatg tgcaacagtg tggagatcct tgtctgattt      240
aataaaatac ttaaacactg aaaaaaaaaa aaaaaaaa                              279
```

<210> SEQ ID NO 44
<211> LENGTH: 449
<212> TYPE: DNA
<213> ORGANISM: Homo sapien
<220> FEATURE:
<221> NAME/KEY: misc_feature
<222> LOCATION: (1)...(449)
<223> OTHER INFORMATION: n = A,T,C or G

<400> SEQUENCE: 44

```
actagtagca tcttttctac aacgttaaaa ttgcagaagt agcttatcat taaaaaacaa       60
caacaacaac aataacaata aatcctaagt gtaaatcagt tattctaccc cctaccaagg      120
atatcagcct gttttttccc tttttctcc tgggaataat tgtgggcttc ttcccaaatt      180
tctacagcct ctttcctctt ctcatgcttg agcttccctg tttgcacgca tgcgttgtgc      240
aagantgggc tgtttngctt ggantncggt ccnagtggaa ncatgctttc ccttgttact      300
gttggaagaa actcaaacct tcnacccta ggtgttncca ttttgtcaag tcatcactgt      360 attttttgtac tggcattaac aaaaaagaa atnaaatatt gttccattaa actttaataa      420
aactttaaaa gggaaaaaaa aaaaaaaa                                         449
```

<210> SEQ ID NO 45
<211> LENGTH: 559
<212> TYPE: DNA
<213> ORGANISM: Homo sapien
<220> FEATURE:
<221> NAME/KEY: misc_feature
<222> LOCATION: (1)...(559)
<223> OTHER INFORMATION: n = A,T,C or G

<400> SEQUENCE: 45

```
actagtgtgg gggaatcacg gacacttaaa gtcaatctgc gaaataattc ttttattaca       60
cactcactga agtttttgag tcccagagag ccattctatg tcaaacattc caagtactct      120
ttgagagccc agcattacat caacatgccc gtgcagttca aaccgaagtc cgcaggcaaa      180
tttgaagctt tgcttgtcat tcaaacagat gaaggcaaga gtattgctat tcgactaatt      240
ggtgaagctc ttggaaaaaa ttnactagaa tacttttttgt gttaagttaa ttacataagt      300
tgtattttgt taactttatc tttctacact acaattatgc ttttgtatat atattttgta      360
tgatggatat ctataattgt agattttgtt tttacaagct aatactgaag actcgactga      420
aatattatgt atctagccca tagtattgta cttaactttt acagggtgaa aaaaaaattc      480
tgtgtttgca ttgattatga tattctgaat aaatatggga atatattta atgtgggtaa      540 aaaaaaaaaa aaaaggaa                                                    559
```

<210> SEQ ID NO 46
<211> LENGTH: 731
<212> TYPE: DNA
<213> ORGANISM: Homo sapien
<220> FEATURE:
<221> NAME/KEY: misc_feature
<222> LOCATION: (1)...(731)
<223> OTHER INFORMATION: n = A,T,C or G

<400> SEQUENCE: 46

```
actagttcta gtaccatggc tgtcatagat gcaaccatta tattccattt agtttcttcc    60
tcaggttccc taacaattgt tgaaactga atatatatgt ttatgtatgt gtgtgtgttc    120
actgtcatgt atatggtgta tatgggatgt gtgcagtttt cagttatata tatattcata   180
tatacatatg catatatatg taaatatac atatatacat gcatacactt gtataatata   240
catatatata cacatatatg cacacatatn atcactgagt tccaaagtga gtctttattt   300
ggggcaattg tattctctcc ctctgtctgc tcactgggcc tttgcaagac atagcaattg   360
cttgatttcc tttggataag agtcttatct tcggcactct tgactctagc cttaacttta   420
gatttctatt ccagaatacc tctcatatct atcttaaaac ctaaganggg taaagangtc   480
ataagattgt agtatgaaag antttgctta gttaaattat atctcaggaa actcattcat   540
ctacaaatta aattgtaaaa tgatggtttg ttgtatctga aaaaatgttt agaacaagaa   600
atgtaactgg gtacctgtta tatcaaagaa cctcnattta ttaagtctcc tcatagccan   660
atccttatat ngccctctct gacctgantt aatananact tgaataatga atagttaatt   720
taggnttggg c                                                        731
```

<210> SEQ ID NO 47
<211> LENGTH: 640
<212> TYPE: DNA
<213> ORGANISM: Homo sapien
<220> FEATURE:
<221> NAME/KEY: misc_feature
<222> LOCATION: (1)...(640)
<223> OTHER INFORMATION: n = A,T,C or G

<400> SEQUENCE: 47

```
tgcgngccgg tttggcccctt ctttgtanga cactttcatc cgccctgaaa tcttcccgat    60
cgttaataac tcctcaggtc cctgcctgca cagggttttt tcttantttg ttgcctaaca   120
gtacaccaaa tgtgacatcc tttcaccaat atngattnct tcataccaca tcntcnatgg   180
anacgactnc aacaattttt tgatnacccn aaanactggg ggctnnaana agtcacantct   240
ggagcagcat ggacctgtcn gcnactaang gaacaanagt nntgaacatt tacacaacct   300
ttggtatgtc ttactgaaag anagaaacat gcttctnncc ctagaccacg aggncaaccg   360
caganattgc caatgccaag tccgagcggt tagatcaggt aatacattcc atggatgcat   420
tacatacntt gtccccgaaa nanaagatgc cctaanggct tcttcanact ggtccngaaa   480
acanctacac ctggtgcttg ganaacanac tctttggaag atcatctggc acaagttccc   540
cccagtgggt tttnccttgg cacctancttt accanatcna ttcggaancc attctttgcc   600
ntggcnttnt nttgggacca ntcttctcac aactgnaccc                         640
```

<210> SEQ ID NO 48
<211> LENGTH: 257
<212> TYPE: DNA
<213> ORGANISM: Homo sapien

<400> SEQUENCE: 48

```
actagtatat gaaaatgtaa atatcacttg tgtactcaaa caaaagttgg tcttaagctt    60
ccaccttgag cagccttgga aacctaacct gcctcttta gcataatcac attttctaaa   120
tgattttctt tgttcctgaa aaagtgattt gtattagttt tacatttgtt ttttggaaga   180
ttatatttgt atatgtatca tcataaaata tttaaataaa agtatctttt agagtgaaaa   240
aaaaaaaaaa aaaaaaa                                                  257
```

<210> SEQ ID NO 49
<211> LENGTH: 652
<212> TYPE: DNA
<213> ORGANISM: Homo sapien
<220> FEATURE:
<221> NAME/KEY: misc_feature
<222> LOCATION: (1)...(652)
<223> OTHER INFORMATION: n = A,T,C or G

<400> SEQUENCE: 49

```
actagttcag atgagtggct gctgaagggg ccccttgtc attttcatta taacccaatt      60
tccacttatt tgaactctta agtcataaat gtataatgac ttatgaatta gcacagttaa    120
gttgacacta gaaactgccc atttctgtat tacactatca aataggaaac attggaaaga    180
tggggaaaaa aatcttattt taaaatggct tagaaagttt tcagattact ttgaaaattc    240
taaacttctt tctgtttcca aaacttgaaa atatgtagat ggactcatgc attaagactg    300
ttttcaaagc tttcctcaca tttttaaagt gtgattttcc ttttaatata catatttatt    360
ttctttaaag cagctatatc ccaacccatg actttggaga tataccctatn aaaccaatat    420
aacagcangg ttattgaagc agctttctca aatgttgctt cagatgtgca agttgcaaat    480
tttattgtat ttgtanaata caattttttgt tttaaactgt atttcaatct atttctccaa    540
gatgcttttc atatagagtg aaatatccca ngataactgc ttctgtgtcg tcgcatttga    600
cgcataactg cacaaatgaa cagtgtatac ctcttggttg tgcattnacc cc             652
```

<210> SEQ ID NO 50
<211> LENGTH: 650
<212> TYPE: DNA
<213> ORGANISM: Homo sapien
<220> FEATURE:
<221> NAME/KEY: misc_feature
<222> LOCATION: (1)...(650)
<223> OTHER INFORMATION: n = A,T,C or G

<400> SEQUENCE: 50

```
ttgcgctttg attttttag ggcttgtgcc ctgtttcact tatagggtct agaatgcttg      60
tgttgagtaa aaaggagatg cccaatattc aaagctgcta atgttctctc ttgcccataaa   120
gactccgtgt aactgtgtga acacttggga tttttctcct ctgtcccgag gtcgtcgtct    180
gctttctttt ttgggttctt tctagaagat tgagaaatgc atatgacagg ctgagancac    240
ctccccaaac acacaagctc tcagccacan gcagcttctc cacagcccca gcttcgcaca    300
ggctcctgga nggctgcctg ggggaggcag acatgggagt gccaaggtgg ccagatggtt    360
ccaggactac aatgtctttta ttttttaactg tttgccactg ctgccctcac ccctgcccgg    420
ctctggagta ccgtctgccc canacaagtg ggantgaaat ggggggtgggg gggaacactg    480
attcccantt aggggggtgcc taactgaaca gtagggatan aaggtgtgaa cctgngaant    540
gcttttataa attatnttcc ttgttanatt tattttttaa tttaatctct gttnaactgc    600
ccngggaaaa gggaaaaaa aaaaaaaat tctntttaaa cacatgaaca                 650
```

<210> SEQ ID NO 51
<211> LENGTH: 545
<212> TYPE: DNA
<213> ORGANISM: Homo sapien
<220> FEATURE:
<221> NAME/KEY: misc_feature
<222> LOCATION: (1)...(545)
<223> OTHER INFORMATION: n = A,T,C or G

```
<400> SEQUENCE: 51
tggcgtgcaa ccagggtagc tgaagtttgg gtctgggact ggagattggc cattaggcct      60
cctganattc cagctcccct tccaccaagcc cagtcttgct acgtggcaca gggcaaacct    120
gactcccttt gggcctcagt ttcccctccc cttcatgana tgaaagaat actacttttt     180
cttgttggtc taacnttgct ggacncaaag tgtngtcatt attgttgtat tgggtgatgt    240
gtncaaaact gcagaagctc actgcctatg agaggaanta agagagatag tggatganag    300
ggacanaagg agtcattatt tggtatagat ccacccntcc caacctttct ctcctcagtc    360
cctgcnctc atgtntctgg tntggtgagt cctttgtgcc accanccatc atgctttgca    420
ttgctgccat cctgggaagg gggtgnatcg tctcacaact tgttgtcatc gtttganatg    480
catgctttct tnatnaaaca aanaaannaa tgtttgacag ngtttaaaat aaaaaanaaa    540
caaaa                                                                545

<210> SEQ ID NO 52
<211> LENGTH: 678
<212> TYPE: DNA
<213> ORGANISM: Homo sapien
<220> FEATURE:
<221> NAME/KEY: misc_feature
<222> LOCATION: (1)...(678)
<223> OTHER INFORMATION: n = A,T,C or G

<400> SEQUENCE: 52
actagtagaa gaactttgcc gcttttgtgc ctctcacagg cgcctaaagt cattgccatg      60
ggaggaagac gatttggggg gggagggggg gggggcangg tccgtggggc tttccctant    120
ntatctccat ntccantgnn cnntgtcgcc tcttccctcg tcncattnga anttantccc    180
tggnccccnn nccctctccn nctncncct cccccctccg ncncctccnn cttttntan      240
ncttccccat ctccntcccc cctnanngtc ccaacnccgn cagcaatnnc ncacttnctc    300
nctccncncc tccnnccgtt cttctnttct cnacntntnc ncnnntncn tgccnntnaa     360
annctctccc cnctgcaanc gattctctcc ctccncnnan ctntccactc cntncttctc    420
ncncgctcct nttcntcnnc ccacctctcn ccttcgnccc cantacnctc nccnccttn     480
cgnntcnttn nnntcctcnn accnccccncc tcccttcncc cctcttctcc ccggtntntc   540
tctctcccnc nncncnnct cnnccntcc nngcgnccnt ttccgccccn cnccncntt      600
ccttcntcnc cantccatcn cntntnccat nctcctncc nctcacnccc gctnccccn     660
ntctctttca cacngtcc                                                  678

<210> SEQ ID NO 53
<211> LENGTH: 502
<212> TYPE: DNA
<213> ORGANISM: Homo sapien
<220> FEATURE:
<221> NAME/KEY: misc_feature
<222> LOCATION: (1)...(502)
<223> OTHER INFORMATION: n = A,T,C or G

<400> SEQUENCE: 53
tgaagatcct ggtgtcgcca tgggccgccg ccccgcccgt tgttaccggt attgtaagaa      60
caagccgtac ccaaagtctc gcttctgccg aggtgtccct gatgccaaaa ttcgcatttt    120
tgacctgggg cggaaaaaang caaaantgga tgagtctccg ctttgtggcc acatggtgtc   180
agatcaatat gagcagctgt cctctgaagc cctgnangct gcccgaattt gtgccaataa    240
gtacatggta aaaagtngtg gcnaagatgc ttccatatcc gggtgcggnt ccaccccttc    300
```

```
cacgtcatcc gcatcaacaa gatgttgtcc tgtgctgggg ctgacaggct cccaacaggc      360
atgcgaagtg cctttggaaa acccanggca ctgtggccag ggttcacatt gggccaattn      420
atcatgttca tccgcaccaa ctgcagaaca angaacntgt naattnaagc cctgcccagg      480
gncaanttca aatttcccgg cc                                                502

<210> SEQ ID NO 54
<211> LENGTH: 494
<212> TYPE: DNA
<213> ORGANISM: Homo sapien
<220> FEATURE:
<221> NAME/KEY: misc_feature
<222> LOCATION: (1)...(494)
<223> OTHER INFORMATION: n = A,T,C or G

<400> SEQUENCE: 54
actagtccaa gaaaaatatg cttaatgtat attacaaagg ctttgtatat gttaacctgt       60
tttaatgcca aaagtttgct ttgtccacaa tttccttaag acctcttcag aaagggattt      120
gtttgcctta atgaatactg ttgggaaaaa acacagtata atgagtgaaa agggcagaag      180
caagaaattt ctacatctta gcgactccaa gaagaatgag tatccacatt tagatggcac      240
attatgagga ctttaatctt tccttaaaca caataatgtt ttcttttttc ttttattcac      300
atgatttcta agtatatttt tcatgcagga cagttttca accttgatgt acagtgactg       360
tgttaaattt ttctttcagt ggcaacctct ataatcttta aaatatggtg agcatcttgt      420
ctgttttgaa ngggatatga cnatnaatct atcagatggg aaatcctgtt tccaagttag      480
aaaaaaaaaa aaaa                                                        494

<210> SEQ ID NO 55
<211> LENGTH: 606
<212> TYPE: DNA
<213> ORGANISM: Homo sapien
<220> FEATURE:
<221> NAME/KEY: misc_feature
<222> LOCATION: (1)...(606)
<223> OTHER INFORMATION: n = A,T,C or G

<400> SEQUENCE: 55
actagtaaaa agcagcattg ccaaataatc cctaattttc cactaaaaat ataatgaaat       60
gatgttaagc ttttgaaaa gtttaggtta aacctactgt tgttagatta atgtatttgt      120
tgcttcccct tatctggaat gtggcattag cttttttatt ttaaccctct ttaattctta      180
ttcaattcca tgacttaagg ttggagagct aaacactggg attttttggat aacagactga      240 cagttttgca taattataat cggcattgta catagaaagg atatggctac cttttgttaa      300
atctgcactt tctaaatatc aaaaaaggga aatgaagtat aaatcaattt ttgtataatc      360
tgtttgaaac atgantttta tttgcttaat attanggctt tgcccttttc tgttagtctc      420
ttgggatcct gtgtaaaact gttctcatta aacaccaaac agttaagtcc attctctggt      480
actagctaca aattccgttt catattctac ntaacaattt aaattaactg aaatatttct      540
anatggtcta cttctgtcnt ataaaaacna aacttgantt nccaaaaaaa aaaaaaaaaa      600
aaaaaa                                                                606

<210> SEQ ID NO 56
<211> LENGTH: 183
<212> TYPE: DNA
<213> ORGANISM: Homo sapien
```

<400> SEQUENCE: 56

| actagtatat | ttaaacttac | aggcttattt | gtaatgtaaa | ccaccattttt | aatgtactgt | 60 |
| aattaacatg | gttataatac | gtacaatcct | tccctcatcc | catcacacaa | ctttttttgt | 120 |
| gtgtgataaa | ctgattttgg | tttgcaataa | aaccttgaaa | aataaaaaaa | aaaaaaaaaa | 180 |
| aaa | | | | | | 183 |

<210> SEQ ID NO 57
<211> LENGTH: 622
<212> TYPE: DNA
<213> ORGANISM: Homo sapien
<220> FEATURE:
<221> NAME/KEY: misc_feature
<222> LOCATION: (1)...(622)
<223> OTHER INFORMATION: n = A,T,C or G

<400> SEQUENCE: 57

| actagtcact | actgtcttct | ccttgtagct | aatcaatcaa | tattcttccc | ttgcctgtgg | 60 |
| gcagtggaga | gtgctgctgg | gtgtacgctg | cacctgccca | ctgagttggg | gaaagaggat | 120 |
| aatcagtgag | cactgttctg | ctcagagctc | ctgatctacc | ccacccccta | ggatccagga | 180 |
| ctgggtcaaa | gctgcatgaa | accaggccct | ggcagcaacc | tgggaatggc | tggaggtggg | 240 |
| agagaacctg | acttctcttt | ccctctccct | cctccaacat | tactggaact | ctatcctgtt | 300 |
| agggatcttc | tgagcttgtt | tccctgctgg | gtgggacaga | agacaaagga | gaagggaggg | 360 |
| tctacaanaa | gcagcccttc | tttgtcctct | ggggttaatg | agcttgacct | ananttcatg | 420 |
| gaganaccan | aagcctctga | tttttaattt | ccntnaaatg | tttgaagtnt | atatntacat | 480 |
| atatatattt | ctttnaatnt | ttgagtcttt | gatatgtctt | aaaatccant | ccctctgccn | 540 |
| gaaacctgaa | ttaaaaccat | gaanaaaaat | gtttnccta | aagatgttan | taattaattg | 600 |
| aaacttgaaa | aaaaaaaaaa | aa | | | | 622 |

<210> SEQ ID NO 58
<211> LENGTH: 433
<212> TYPE: DNA
<213> ORGANISM: Homo sapien

<400> SEQUENCE: 58

| gaacaaattc | tgattggtta | tgtaccgtca | aaagacttga | agaaatttca | tgattttgca | 60 |
| gtgtggaagc | gttgaaaatt | gaaagttact | gcttttccac | ttgctcatat | agtaaaggga | 120 |
| tcctttcagc | tgccagtgtt | gaataatgta | tcatccagag | tgatgttatc | tgtgacagtc | 180 |
| accagcttta | agctgaacca | ttttatgaat | accaaataaa | tagacctctt | gtactgaaaa | 240 |
| catatttgtg | actttaatcg | tgctgcttgg | atagaaatat | ttttactggt | tcttctgaat | 300 |
| tgacagtaaa | cctgtccatt | atgaatggcc | tactgttcta | ttatttgttt | tgacttgaat | 360 |
| ttatccacca | aagacttcat | ttgtgtatca | tcaataaagt | tgtatgtttc | aactgaaaaa | 420 |
| aaaaaaaaaa | aaa | | | | | 433 |

<210> SEQ ID NO 59
<211> LENGTH: 649
<212> TYPE: DNA
<213> ORGANISM: Homo sapien
<220> FEATURE:
<221> NAME/KEY: misc_feature
<222> LOCATION: (1)...(649)
<223> OTHER INFORMATION: n = A,T,C or G

<400> SEQUENCE: 59

```
actagttatt atctgacttt cnggttataa tcattctaat gagtgtgaag tagcctctgg    60
tgtcatttgg atttgcattt ctctgatgag tgatgctatc aagcaccttt gctggtgctg   120
ttggccatat gtgtatgttc cctggagaag tgtctgtgct gagccttggc ccactttta   180 attaggcgtn tgtcttttta ttactgagtt gtaaganttc tttatatatt ctggattcta   240
gacccttatc agatacatgg tttgcaaata ttttctccca ttctgtgggt tgtgttttca   300
ctttatcgat aatgtcctta gacatataat aaatttgtat tttaaaagtg acttgatttg   360
ggctgtgcaa ggtgggctca cgcttgtaat cccagcactt tgggagactg aggtgggtgg   420
atcatatgan gangctagga gttcgaggtc agcctggcca gcatagcgaa aacttgtctc   480
tacnaaaaat acaaaaatta gtcaggcatg gtggtgcacg tctgtaatac cagcttctca   540
ggangctgan gcacaaggat cacttgaacc ccagaangaa gangttgcag tganctgaag   600
atcatgccag gcaacaaaa atgagaactt gtttaaaaaa aaaaaaaa                 649

<210> SEQ ID NO 60
<211> LENGTH: 423
<212> TYPE: DNA
<213> ORGANISM: Homo sapien
<220> FEATURE:
<221> NAME/KEY: misc_feature
<222> LOCATION: (1)...(423)
<223> OTHER INFORMATION: n = A,T,C or G

<400> SEQUENCE: 60
actagttcag gccttccagt tcactgacaa acatggggaa gtgtgcccag ctggctggaa    60
acctggcagt gataccatca agcctgatgt ccaaaagagc aaagaatatt tctccaagca   120
gaagtgagcg ctgggctgtt tagtgccag gctgcggtgg gcagccatga gaacaaaacc   180
tcttctgtat ttttttttc cattagtana acacaagact cngattcagc cgaattgtgg   240
tgtcttacaa ggcagggctt tcctacaggg ggtgganaaa acagccttc ttccttggt    300 aggaatggcc tgagttggcg ttgtgggcag gctactggtt tgtatgatgt attagtagag   360
caacccatta atcttttgta gtttgtatna aacttganct gagaccttaa acaaaaaaaa   420
aaa                                                                 423

<210> SEQ ID NO 61
<211> LENGTH: 423
<212> TYPE: DNA
<213> ORGANISM: Homo sapien
<220> FEATURE:
<221> NAME/KEY: misc_feature
<222> LOCATION: (1)...(423)
<223> OTHER INFORMATION: n = A,T,C or G

<400> SEQUENCE: 61
cgggactgga atgtaaagtg aagttcggag ctctgagcac gggctcttcc cgccgggtcc    60
tccctcccca gaccccagag ggagaggccc acccgccca gccccgcccc agcccctgct   120
caggtctgag tatggctggg agtcgggggc acaggcctc tagctgtgct gctcaagaag   180
actggatcag ggtanctaca agtggccggg ccttgccttt gggattctac cctgttccta   240
atttggtgtt ggggtgcggg gtccctggcc cccttttcca cactncctcc ctccngacag   300
caacctccct tgggcaatt gggcctggnt ctccncccgn tgttgcacc ctttgttggt    360 ttaaggncctt taaaaatgtt annttttccc ntgccngggt taaaaaagga aaaaactnaa   420
aaa                                                                 423
```

<210> SEQ ID NO 62
<211> LENGTH: 683
<212> TYPE: DNA
<213> ORGANISM: Homo sapien
<220> FEATURE:
<221> NAME/KEY: misc_feature
<222> LOCATION: (1)...(683)
<223> OTHER INFORMATION: n = A,T,C or G

<400> SEQUENCE: 62

| | | | | | |
|---|---|---|---|---|---|
| gctggagagg | ggtacggact | ttcttggagt | tgtcccaggt | tggaatgaga | ctgaactcaa | 60 |
| gaagagaccc | taagagactg | gggaatggtt | cctgccttca | ggaaagtgaa | agacgcttag | 120 |
| gctgtcaaca | cttaaaggaa | gtccccttga | agcccagagt | ggacagacta | gacccattga | 180 |
| tggggccact | ggccatggtc | cgtggacaag | acattccngt | gggccatggc | acaccggggg | 240 |
| ggatcaaaat | gtgtacttgt | ggggtctcgc | cccttgccaa | aaccaaacca | ntcccactcc | 300 |
| tgtcnttgga | ctttcttccc | attccctcct | ccccaaatgc | acttcccctc | ctccctctgc | 360 |
| ccctcctgtg | tttttggaat | tctgtttccc | tcaaaattgt | taattttta | nttttngacc | 420 |
| atgaacttat | gtttggggtc | nangttcccc | ttnccaatgc | atactaatat | attaatggtt | 480 |
| atttatttt | gaatatttt | ttaatgaact | tggaaaaaat | tnntggaatt | tccttncttc | 540 |
| cntttntttt | ggggggggtg | ggggntggg | ttaaaattt | tttggaancc | cnatnggaaa | 600 |
| ttnttacttg | gggccccct | naaaaaantn | anttccaatt | cttnnatngc | ccctnttccn | 660 |
| ctaaaaaaaa | ananannaaa | aan | | | | 683 |

<210> SEQ ID NO 63
<211> LENGTH: 731
<212> TYPE: DNA
<213> ORGANISM: Homo sapien
<220> FEATURE:
<221> NAME/KEY: misc_feature
<222> LOCATION: (1)...(731)
<223> OTHER INFORMATION: n = A,T,C or G

<400> SEQUENCE: 63

| | | | | | |
|---|---|---|---|---|---|
| actagtcata | aagggtgtgc | gcgtcttcga | cgtggcggtc | ttggcgccac | tgctgcgaga | 60 |
| cccggccctg | gacctcaagg | tcatccactt | ggtgcgtgat | ccccgcgcgg | tggcgagttc | 120 |
| acggatccgc | tcgcgccacg | gcctcatccg | tgagagccta | caggtggtgc | gcagccgaga | 180 |
| ccgcgagctc | accgcatgcc | cttcttggag | gccgcgggcc | acaagcttgg | cgcccanaaa | 240 |
| gaaggcgtng | ggggcccgca | aantaccacg | ctctgggcgc | tatggaangt | cctcttgcaa | 300 |
| taatattggt | tnaaaanctg | canaanagcc | cctgcanccc | cctgaactgg | gntgcagggc | 360 |
| cncttacctn | gtttggntgc | ggttacaaag | aacctgtttn | ggaaaccct | nccnaaaacc | 420 |
| ttccgggaaa | attntncaaa | tttttnttgg | ggaattnttg | ggtaaacccc | ccnaaaatgg | 480 |
| gaaacnttt | tgccctnnaa | antaaaccat | tnggttccgg | gggcccccc | ncaaaaccct | 540 |
| tttttntttt | tttntgcccc | cantnncccc | ccggggcccc | ttttttttgg | ggaaaanccc | 600 |
| cccccctncc | nananttta | aaagggnggg | anaatttttn | nttnccccc | gggnccccn | 660 |
| ggngntaaaa | nggtttcncc | ccccgaggg | gngggnnnc | ctcnnaaacc | cntntcnnna | 720 |
| ccncnttttn | n | | | | | 731 |

<210> SEQ ID NO 64
<211> LENGTH: 313
<212> TYPE: DNA
<213> ORGANISM: Homo sapien
<220> FEATURE:
<221> NAME/KEY: misc_feature
<222> LOCATION: (1)...(313)
<223> OTHER INFORMATION: n = A,T,C or G

<400> SEQUENCE: 64

| | | | | | |
|---|---|---|---|---|---|
| actagttgtg | caaaccacga | ctgaagaaag | acgaaaagtg | ggaaataact | tgcaacgtct | 60 |
| gttagagatg | gttgctacac | atgttgggtc | tgtagagaaa | catcttgagg | agcagattgc | 120 |
| taaagttgat | agagaatatg | aagaatgcat | gtcagaagat | ctctcggaaa | atattaaaga | 180 |
| gattagagat | aagtatgaga | agaaagctac | tctaattaag | tcttctgaag | aatgaagatn | 240 |
| aaatgttgat | catgtatata | tatccatagt | gaataaaatt | gtctcagtaa | agttgtaaaa | 300 |
| aaaaaaaaaa | aaa | | | | | 313 |

<210> SEQ ID NO 65
<211> LENGTH: 420
<212> TYPE: DNA
<213> ORGANISM: Homo sapien
<220> FEATURE:
<221> NAME/KEY: misc_feature
<222> LOCATION: (1)...(420)
<223> OTHER INFORMATION: n = A,T,C or G

<400> SEQUENCE: 65

| | | | | | |
|---|---|---|---|---|---|
| actagttccc | tggcaggcaa | gggcttccaa | ctgaggcagt | gcatgtgtgg | cagagagagg | 60 |
| caggaagctg | gcagtggcag | cttctgtgtc | tagggagggg | tgtggctccc | tccttccctg | 120 |
| tctgggaggt | tggagggaag | aatctaggcc | ttagcttgcc | ctcctgccac | ccttcccctt | 180 |
| gtagatactg | ccttaacact | ccctcctctc | tcagctgtgg | ctgccaccca | agccaggttt | 240 |
| ctccgtgctc | actaatttat | ttccaggaaa | ggtgtgtgga | agacatgagc | cgtgtataat | 300 |
| atttgtttta | acattttcat | tgcaagtatt | gaccatcatc | cttggttgtg | tatcgttgta | 360 |
| acacaaatta | atgatattaa | aaagcatcca | aacaaagccn | annnnnaana | nnannngaaa | 420 |

<210> SEQ ID NO 66
<211> LENGTH: 676
<212> TYPE: DNA
<213> ORGANISM: Homo sapien
<220> FEATURE:
<221> NAME/KEY: misc_feature
<222> LOCATION: (1)...(676)
<223> OTHER INFORMATION: n = A,T,C or G

<400> SEQUENCE: 66

| | | | | | |
|---|---|---|---|---|---|
| actagtttcc | tatgatcatt | aaactcattc | tcagggttaa | gaaaggaatg | taaatttctg | 60 |
| cctcaatttg | tacttcatca | ataagttttt | gaagagtgca | gattttagt | caggtcttaa | 120 |
| aaataaactc | acaaatctgg | atgcatttct | aaattctgca | aatgtttcct | ggggtgactt | 180 |
| aacaaggaat | aatcccacaa | tatacctagc | tacctaaatac | atggagctgg | ggctcaaccc | 240 |
| actgttttta | aggatttgcg | cttacttgtg | gctgaggaaa | ataagtagt | tccgagggaa | 300 |
| gtagttttta | aatgtgagct | tatagatngg | aaacagaata | tcaacttaat | tatggaaatt | 360 |
| gttagaaacc | tgttctcttg | ttatctgaat | cttgattgca | attactattg | tactggatag | 420 |
| actccagccc | attgcaaagt | ctcagatatc | ttanctgtgt | agttgaattc | cttgaaaatt | 480 |
| cttttttaaga | aaaattgga | gtttnaaaga | aataaacccc | tttgttaaat | gaagcttggc | 540 |
| tttttggtga | aaaanaatca | tcccgcaggg | cttattgttt | aaaaanggaa | ttttaagcct | 600 |
| ccctggaaaa | anttgttaat | taaatgggga | aaatgntggg | naaaaattat | ccgttagggt | 660 |

```
ttaaagggaa aactta                                                    676

<210> SEQ ID NO 67
<211> LENGTH: 620
<212> TYPE: DNA
<213> ORGANISM: Homo sapien
<220> FEATURE:
<221> NAME/KEY: misc_feature
<222> LOCATION: (1)...(620)
<223> OTHER INFORMATION: n = A,T,C or G

<400> SEQUENCE: 67
caccattaaa gctgcttacc aagaacttcc ccagcatttt gacttccttg tttgatagct    60
gaattgtgag caggtgatag aagagccttt ctagttgaac atacagataa tttgctgaat   120
acattccatt taatgaaggg gttacatctg ttacgaagct actaagaagg agcaagagca   180
tagggaaaaa aaatctgatc agaacgcatc aaactcacat gtgccccctc tactacaaac   240
agattgtagt gctgtggtgg tttattccgt tgtgcagaac ttgcaagctg agtcactaaa   300
cccaaagaga ggaaattata ggttagttaa acattgtaat cccaggaact aagtttaatt   360 cactttttgaa gtgttttgtt ttttatttt ggtttgtctg atttactttg ggggaaaang   420
ctaaaaaaaa agggatatca atctctaatt cagtgcccac taaaagttgt ccctaaaaag   480
tctttactgg aanttatggg acttttttaag ctccaggtnt tttggtcctc caaattaacc   540
ttgcatgggc cccttaaaat tgttgaangg cattcctgcc tctaagtttg gggaaaattc   600 ccccntttn aaaatttgga                                                620

<210> SEQ ID NO 68
<211> LENGTH: 551
<212> TYPE: DNA
<213> ORGANISM: Homo sapien
<220> FEATURE:
<221> NAME/KEY: misc_feature
<222> LOCATION: (1)...(551)
<223> OTHER INFORMATION: n = A,T,C or G

<400> SEQUENCE: 68
actagtagct ggtacataat cactgaggag ctatttctta acatgctttt atagaccatg    60
ctaatgctag accagtattt aagggctaat ctcacacctc cttagctgta agagtctggc   120
ttagaacaga cctctctgtg caataacttg tggccactgg aaatccctgg gccggcatttt   180 gtattgggt tgcaatgact cccaagggcc aaaagagtta aagcacgac tgggatttct     240 tctgagactg tggtgaaact ccttccaagg ctgaggggt cagtangtgc tctgggaggg    300
actcggcacc actttgatat tcaacaagcc acttgaagcc caattataaa attgttattt    360
tacagctgat ggaactcaat ttgaaccttc aaaactttgt tagtttatcc tattatattg    420
ttaaacctaa ttcatttgt ctagcattgg atttggttcc tgtngcatat gtttttttcn    480
cctatgtgct cccctccccc nnatcttaat ttaaaccnca attttgcnat tcnccnnnnn   540
nannnannna a                                                        551

<210> SEQ ID NO 69
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 69
```

```
cagaaatgga aagcagagtt ttcatttctg tttataaacg tctccaaaca aaaatggaaa    60
gcagagtttt cattaaatcc ttttacctttt ttttttttctt ggtaatcccc tcaaataaca   120
gtatgtggga tattgaatgt taaagggata ttttttttcta ttattttat aattgtacaa    180 aattaagcaa atgttaaaag ttttatatgc tttattaatg ttttcaaaag gtatnataca    240
tgtgatacat tttttaagct tcagttgctt gtcttctggt actttctgtt atgggctttt    300
ggggagccan aaaccaatct acnatctctt tttgtttgcc aggacatgca ataaaattta    360
aaaaataaat aaaaactatt nagaaattga aaaaa                                396
```

<210> SEQ ID NO 70
<211> LENGTH: 536
<212> TYPE: DNA
<213> ORGANISM: Homo sapien
<220> FEATURE:
<221> NAME/KEY: misc_feature
<222> LOCATION: (1)...(536)
<223> OTHER INFORMATION: n = A,T,C or G

<400> SEQUENCE: 70

```
actagtgcaa aagcaaatat aaacatcgaa aaggcgttcc tcacgttagc tgaagatatc    60
cttcgaaaga cccctgtaaa agagcccaac agtgaaaatg tagatatcag cagtggagga   120
ggcgtgacag gctggaagag caaatgctgc tgagcattct cctgttccat cagttgccat   180
ccactacccc gttttctctt cttgctgcaa ataaaccac tctgtccatt tttaactcta    240
aacagatatt tttgtttctc atcttaacta tccaagccac ctatttatt tgttctttca    300 tctgtgactg cttgctgact ttatcataat tttcttcaaa caaaaaaatg tatagaaaaa   360
tcatgtctgt gacttcattt ttaaatgnta cttgctcagc tcaactgcat ttcagttgtt    420
ttatagtcca gttcttatca acattnaaac ctatngcaat catttcaaat ctattctgca    480
aattgtataa gaataaaagt tagaatttaa caattaaaaa aaaaaaaaaa aaaaaa       536
```

<210> SEQ ID NO 71
<211> LENGTH: 865
<212> TYPE: DNA
<213> ORGANISM: Homo sapien
<220> FEATURE:
<221> NAME/KEY: misc_feature
<222> LOCATION: (1)...(865)
<223> OTHER INFORMATION: n = A,T,C or G

<400> SEQUENCE: 71

```
gacaaagcgt taggagaaga anagaggcag ggaanactnc ccaggcacga tggccncctt    60
cccaccagca accagcgccc cccaccagcc cccaggcccg gacgacgaag actccatcct   120
ggattaatct nacctctntc gcctgnccca ttcctacctc ggaggtggag gccggaaagg   180
tcncaccaag aganaanctg ctgccaacac caaccgcccc agccctggcg ggcacganag   240
gaaactggtg accaatctgc agaattctna gaggaanaag cnaggggccc cgcgctnaga   300
cagagctgga tatgangcca gaccatggac nctacncccn ncaatncana cgggactgcg   360
gaagatggan gacccncgac nngatcaggc cngctnncca nccccccacc cctatgaatt   420
attcccgctg aangaatctc tgannggctt ccannaaagc gcctcccnc caacgnaan    480 tncaacatng ggattanang ctgggaactg naagggcaa anccttnnaat atccccagaa   540 acaanctctc ccnaanaaac tggggcncct catnggtggn accaactatt aactaaaccg   600
cacgccaagn aantataaaa gggggcccc tccncggnng accccctttt gtcccttaat    660
```

```
ganggttatc cnccttgcgt accatggtnc ccnnttctgt ntgnatgttt ccnctcccct      720
ccncctatnt cnagccgaac tcnnatttnc ccggggtgc natcnantng tncnccttn       780 ttngttgncc cngcccttc cgncggaacn cgtttcccg ttantaacgg cacccggggn       840
aagggtgntt ggcccctcc ctccc                                            865
```

<210> SEQ ID NO 72
<211> LENGTH: 560
<212> TYPE: DNA
<213> ORGANISM: Homo sapien
<220> FEATURE:
<221> NAME/KEY: misc_feature
<222> LOCATION: (1)...(560)
<223> OTHER INFORMATION: n = A,T,C or G

<400> SEQUENCE: 72

```
cctggacttg tcttggttcc agaacctgac gacccggcga cggcgacgtc tcttttgact      60
aaaagacagt gtccagtgct ccngcctagg agtctacggg gaccgcctcc cgcgccgcca     120
ccatgcccaa cttctctggc aactggaaaa tcatccgatc ggaaaacttc gangaattgc     180
tcnaantgct gggggtgaat gtgatgctna ngaanattgc tgtggctgca gcgtccaagc     240
cagcagtgga gatcnaacag gagggagaca ctttctacat caaaacctcc accaccgtgc     300
gcaccacaaa gattaacttc nnngttgggg aggantttga ggancaaact gtggatngga     360
ngcctgtnaa aacctggtga atgggagaa tganaataaa atggtctgtg ancanaaact      420
cctgaaagga gaaggccccc anaactcctg gaccngaaaa actgacccnc cnatnggga     480 actgatncttt gaaccctgaa cgggcgggat gancctttt tnttgccncc naangggttc    540 tttccnttc cccaaaaaaa                                                  560
```

<210> SEQ ID NO 73
<211> LENGTH: 379
<212> TYPE: DNA
<213> ORGANISM: Homo sapien
<220> FEATURE:
<221> NAME/KEY: misc_feature
<222> LOCATION: (1)...(379)
<223> OTHER INFORMATION: n = A,T,C or G

<400> SEQUENCE: 73

```
ctggggancc ggcggtnngc nccatntcnn gncgcgaagg tggcaataaa aanccnctga     60
aaccgcncaa naacatgcc naagatatgg acgaggaaga tngngctttc nngnacaanc     120
gnanngagga acanaacaaa ctcnangagc tctcaagcta atgccgcggg aaggggccc     180 ttggccacnn gtggaattaa gaaatctggc aaanngtann tgttccttgt gcctnangag    240
ataagngacc ctttatttca tctgtatta aacctctctn ttccctgnca taacttcttt     300
tnccacgtan agntggaant anttgttgtc ttggactgtt gtncatttta gannaaactt    360
ttgttcaaaa aaaaaataa                                                  379
```

<210> SEQ ID NO 74
<211> LENGTH: 437
<212> TYPE: DNA
<213> ORGANISM: Homo sapien
<220> FEATURE:
<221> NAME/KEY: misc_feature
<222> LOCATION: (1)...(437)
<223> OTHER INFORMATION: n = A,T,C or G

<400> SEQUENCE: 74

```
actagttcag actgccacgc caaccccaga aaataccca catgccagaa aagtgaagtc      60
```

| | |
|---|---|
| ctaggtgttt ccatctatgt ttcaatctgt ccatctacca ggcctcgcga taaaaacaaa | 120 |
| acaaaaaaac gctgccaggt tttanaagca gttctggtct caaaaccatc aggatcctgc | 180 |
| caccagggtt cttttgaaat agtaccacat gtaaaaggga atttggcttt cacttcatct | 240 |
| aatcactgaa ttgtcaggct ttgattgata attgtagaaa taagtagcct tctgttgtgg | 300 |
| gaataagtta taatcagtat tcatctcttt gttttttgtc actcttttct ctctnattgt | 360 |
| gtcatttgta ctgtttgaaa aatatttctt ctataaaatt aaactaacct gccttaaaaa | 420 |
| aaaaaaaaaa aaaaaaa | 437 |

<210> SEQ ID NO 75
<211> LENGTH: 579
<212> TYPE: DNA
<213> ORGANISM: Homo sapien
<220> FEATURE:
<221> NAME/KEY: misc_feature
<222> LOCATION: (1)...(579)
<223> OTHER INFORMATION: n = A,T,C or G

<400> SEQUENCE: 75

| | |
|---|---|
| ctccgtcgcc gccaagatga tgtgcggggc gccctccgcc acgcagccgg ccaccgccga | 60 |
| gacccagcac atcgccgacc aggtgaggtc ccagcttgaa gagaaagaaa acaagaagtt | 120 |
| ccctgtgttt aaggccgtgt cattcaagag ccaggtggtc gcggggacaa actacttcat | 180 |
| caaggtgcac gtcggcgacg aggacttcgt cacctgcga gtgttccaat ctctccctca | 240 |
| tgaaaacaag cccttgacct tatctaacta ccagaccaac aaagccaagc atgatgagct | 300 |
| gacctatttc tgatcctgac tttggacaag gcccttcagc cagaagactg acaaagtcat | 360 |
| cctccgtcta ccagagcgtg cacttgtgat cctaaaataa gcttcatctc cgggctgtgc | 420 |
| ccttggggtg aaggggcan gatctgcact gcttttgcat ttctcttcct aaatttcatt | 480 |
| gtgttgattc tttccttcca ataggtgatc ttnattactt tcagaatatt ttccaaatna | 540 |
| gatatatttt naaaatcctt aaaaaaaaaa aaaaaaaa | 579 |

<210> SEQ ID NO 76
<211> LENGTH: 666
<212> TYPE: DNA
<213> ORGANISM: Homo sapien
<220> FEATURE:
<221> NAME/KEY: misc_feature
<222> LOCATION: (1)...(666)
<223> OTHER INFORMATION: n = A,T,C or G

<400> SEQUENCE: 76

| | |
|---|---|
| gtttatccta tctctccaac cagattgtca gctccttgag ggcaagagcc acagtatatt | 60 |
| tccctgtttc ttccacagtg cctaataata ctgtggaact aggttttaat aatttttaa | 120 |
| ttgatgttgt tatgggcagg atggcaacca gaccattgtc tcagagcagg tgctggctct | 180 |
| ttcctggcta ctccatgttg gctagcctct ggtaacctct tactattat cttcaggaca | 240 |
| ctcactacag ggaccaggga tgatgcaaca tccttgtctt tttatgacag gatgtttgct | 300 |
| cagcttctcc aacaataaaa agcacgtggt aaaacacttg cggatattct ggactgtttt | 360 |
| taaaaaatat acagtttacc gaaaatcata ttatcttaca atgaaaagga ntttatagat | 420 |
| cagccagtga acaaccttt cccaccatac aaaaattcct tttcccgaan gaaaanggct | 480 |
| ttctcaataa ncctcacttt cttaanatct tacaagatag cccganatc ttatcgaaac | 540 |
| tcattttagg caaatatgan ttttattgtn cgttacttgt ttcaaaattt ggtattgtga | 600 |

| | |
|---|---|
| atatcaatta ccaccccat ctcccatgaa anaaangga aanggtgaan ttcntaancg | 660 |
| cttaaa | 666 |

<210> SEQ ID NO 77
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 77

| | |
|---|---|
| ctgcagcccg ggggatccac taatctacca nggttatttg gcagctaatt ctanatttgg | 60 |
| atcattgccc aaagttgcac ttgctggtct cttgggattt ggccttggaa aggtatcata | 120 |
| catanganta tgccanaata aattccattt ttttgaaaat canctccntg gggctggttt | 180 |
| tggtccacag cataacangc actgcctcct tacctgtgag gaatgcaaaa taaagcatgg | 240 |
| attaagtgag aagggagact ctcagccttc agcttcctaa attctgtgtc tgtgactttc | 300 |
| gaagtttttt aaacctctga atttgtacac atttaaaatt tcaagtgtac tttaaaataa | 360 |
| aatacttcta atgggaacaa aaaaaaaaaa aaaaaa | 396 |

<210> SEQ ID NO 78
<211> LENGTH: 793
<212> TYPE: DNA
<213> ORGANISM: Homo sapien
<220> FEATURE:
<221> NAME/KEY: misc_feature
<222> LOCATION: (1)...(793)
<223> OTHER INFORMATION: n = A,T,C or G

<400> SEQUENCE: 78

| | |
|---|---|
| gcatcctagc cgccgactca cacaaggcag gtgggtgagg aaatccagag ttgccatgga | 60 |
| gaaaattcca gtgtcagcat tcttgctcct tgtggccctc tcctacactc tggccagaga | 120 |
| taccacagtc aaacctggag ccaaaaagga cacaaggac tctcgaccca aactgcccca | 180 |
| gaccctctcc agaggttggg gtgaccaact catctggact cagacatatg aagaagctct | 240 |
| atataaatcc aagacaagca acaaacccctt gatgattatt catcacttgg atgagtgccc | 300 |
| acacagtcna gctttaaaga aagtgtttgc tgaaaataaa gaaatccaga aattggcaga | 360 |
| gcagtttgtc ctcctcaatc tggtttatga acaactgac aaacacctt ctcctgatgg | 420 |
| ccagtatgtc ccaggattat gtttgttgac ccatctctga cagttgaagc cgatatcctg | 480 |
| ggaagatatt cnaaccgtct ctatgcttac aaactgcaga tacgctctgt tgcttgacac | 540 |
| atgaaaaagc tctcaagttg ctnaaaatga attgtaagaa aaaaaatctc cagccttctg | 600 |
| tctgtcggct tgaaaattga aaccagaaaa atgtgaaaaa tggctattgt ggaacanatn | 660 |
| gacacctgat taggttttgg ttatgttcac cactatttt aanaaaanan nttttaaaat | 720 |
| ttggttcaat tntctttttn aaacaatntg tttctacntt gnganctgat ttctaaaaaa | 780 |
| aataatnttt ggc | 793 |

<210> SEQ ID NO 79
<211> LENGTH: 456
<212> TYPE: DNA
<213> ORGANISM: Homo sapien
<220> FEATURE:
<221> NAME/KEY: misc_feature
<222> LOCATION: (1)...(456)
<223> OTHER INFORMATION: n = A,T,C or G

<400> SEQUENCE: 79

```
actagtatgg ggtgggaggc cccaccette tcccctaggc gctgttcttg ctccaaaggg      60
ctccgtggag agggactggc agagctgang ccacctgggg ctgggatcc cactcttctt     120
gcagctgttg agcgcaccta accactggtc atgcccccac cctgctctc cgcacccgct     180
tcctcccgac cccangacca ggctacttct cccctcctct tgcctccctc ctgcccctgc    240
tgcctctgat cgtangaatt gangantgtc ccgccttgtg gctganaatg gacagtggca    300
ggggctggaa atgggtgtgt gtgtgtgtgt gtgtgtgtgt gtgtgtgtgt gcncccccc     360
tgcaagaccg agattgaggg aaancatgtc tgctgggtgt gaccatgttt cctctccata    420
aantncccct gtgacnctca naaaaaaaaa aaaaaa                              456
```

<210> SEQ ID NO 80
<211> LENGTH: 284
<212> TYPE: DNA
<213> ORGANISM: Homo sapien
<220> FEATURE:
<221> NAME/KEY: misc_feature
<222> LOCATION: (1)...(284)
<223> OTHER INFORMATION: n = A,T,C or G

<400> SEQUENCE: 80

```
ctttgtacct ctagaaaaga taggtattgt gtcatgaaac ttgagtttaa atttatata      60
taaaactaaa agtaatgctc actttagcaa cacatactaa aattggaacc atactgagaa    120
gaatagcatg acctccgtgc aaacaggaca agcaaatttg tgatgtgttg attaaaaaga    180
aataaataaa tgtgtatatg tgtaacttgt atgtttatgt ggaatacaga ttgggaaata    240
aaatgtattt cttactgtga aaaaaaaaaa aaaaaaaaaa aana                     284
```

<210> SEQ ID NO 81
<211> LENGTH: 671
<212> TYPE: DNA
<213> ORGANISM: Homo sapien
<220> FEATURE:
<221> NAME/KEY: misc_feature
<222> LOCATION: (1)...(671)
<223> OTHER INFORMATION: n = A,T,C or G

<400> SEQUENCE: 81

```
gccaccaaca ttccaagcta ccctgggtac ctttgtgcag tagaagctag tgagcatgtg     60
agcaagcggt gtgcacacgg agactcatcg ttataattta ctatctgcca agagtagaaa   120
gaaaggctgg ggatatttgg gttggcttgg ttttgatttt ttgcttgttt gtttgttttg   180
tactaaaaca gtattatctt ttgaatatcg tagggacata agtatataca tgttatccaa   240
tcaagatggc tagaatggtg cctttctgag tgtctaaaac ttgacacccc tggtaaatct   300
ttcaacacac ttccactgcc tgcgtaatga agttttgatt catttttaac cactggaatt   360
tttcaatgcc gtcattttca gttagatnat tttgcactt gagattaaaa tgccatgtct    420
atttgattag tcttattttt ttatttttac aggcttatca gtctcactgt tggctgtcat   480
tgtgacaaag tcaaataaac ccccnaggac aacacacagt atgggatcac atattgtttg   540
acattaagct ttggccaaaa aatgttgcat gtgttttacc tcgacttgct aaatcaatan   600
canaaaggct ggctnataat gttggtggtg aaataattaa tnantaacca aaaaaaaan    660
aaaaaaaaa a                                                          671
```

<210> SEQ ID NO 82

<211> LENGTH: 217
<212> TYPE: DNA
<213> ORGANISM: Homo sapien
<220> FEATURE:
<221> NAME/KEY: misc_feature
<222> LOCATION: (1)...(217)
<223> OTHER INFORMATION: n = A,T,C or G

<400> SEQUENCE: 82

| | | | | |  |
|---|---|---|---|---|---|
| ctgcagatgt | ttcttgaatg | ctttgtcaaa | ttaanaaagt | taaagtgcaa taatgtttga | 60 |
| agacaataag | tggtggtgta | tcttgtttct | aataagataa | acttttttgt ctttgcttta | 120 |
| tcttattagg | gagttgtatg | tcagtgtata | aaacatactg | tgtggtataa caggcttaat | 180 |
| aaattcttta | aaggaaaaa | aaaaaaaaaa | aaaaaaa | | 217 |

<210> SEQ ID NO 83
<211> LENGTH: 460
<212> TYPE: DNA
<213> ORGANISM: Homo sapien
<220> FEATURE:
<221> NAME/KEY: misc_feature
<222> LOCATION: (1)...(460)
<223> OTHER INFORMATION: n = A,T,C or G

<400> SEQUENCE: 83

| | | | | | |
|---|---|---|---|---|---|
| cgcgagtggg | agcaccagga | tctcgggctc | ggaacgagac | tgcacggatt gttttaagaa | 60 |
| aatggcagac | aaaccagaca | tgggggaaat | cgccagcttc | gatnaggcca agctgaanaa | 120 |
| aacggagacg | caggagaaga | acaccctgcc | gaccaaagag | accattgagc angagaagcg | 180 |
| gagtgaaatt | tcctaagatc | ctggaggatt | tcctaccccc | gtcctcttcg agacccagt | 240 |
| cgtgatgtgg | aggaagagcc | acctgcaaga | tggacacgag | ccacaagctg cactgtgaac | 300 |
| ctgggcactc | cgcgccgatg | ccaccggcct | gtgggtctct | gaagggaccc cccccaatcg | 360 |
| gactgccaaa | ttctccggtt | tgccccggga | tattatacaa | nattatttgt atgaataatg | 420 |
| annataaaac | acacctcgtg | gcancaaana | aaaaaaaaa | | 460 |

<210> SEQ ID NO 84
<211> LENGTH: 323
<212> TYPE: DNA
<213> ORGANISM: Homo sapien
<220> FEATURE:
<221> NAME/KEY: misc_feature
<222> LOCATION: (1)...(323)
<223> OTHER INFORMATION: n = A,T,C or G

<400> SEQUENCE: 84

| | | | | | |
|---|---|---|---|---|---|
| tggtggatct | tggctctgtg | gagctgctgg | gacgggatct | aaaagactat tctggaagct | 60 |
| gtggtccaan | gcattttgct | ggcttaacgg | gtcccggaac | aaaggacacc agctctctaa | 120 |
| aattgaagtt | tacccganat | aacaatcttt | tgggcagaga | tgcctatttt aacaaacncc | 180 |
| gtccctgcgc | aacaacnaac | aatctctggg | aaataccggc | catgaacntg ctgtctcaat | 240 |
| cnancatctc | tctagctgac | cgatcatatc | gtcccagatt | actacanatc ataataattg | 300 |
| atttcctgta | naaaaaaaaa | aaa | | | 323 |

<210> SEQ ID NO 85
<211> LENGTH: 771
<212> TYPE: DNA
<213> ORGANISM: Homo sapien
<220> FEATURE:
<221> NAME/KEY: misc_feature
<222> LOCATION: (1)...(771)
<223> OTHER INFORMATION: n = A,T,C or G

<400> SEQUENCE: 85

```
aaactgggta ctcaacactg agcagatctg ttctttgagc taaaaaccat gtgctgtacc      60
aanagtttgc tcctggctgc tttgatgtca gtgctgctac tccacctctg cggcgaatca     120
gaagcaagca actttgactg ctgtcttgga tacacagacc gtattcttca tcctaaattt     180
attgtgggct tcacacggca gctggccaat gaaggctgtg acatcaatgc tatcatcttt     240
cacacaaaga aaaagttgtc tgtgtgcgca atccaaaac agacttgggt gaaatatatt      300
gtgcgtctcc tcagtaaaaa agtcaagaac atgtaaaaac tgtggctttt ctggaatgga     360
attggacata gcccaagaac agaaagaact tgctggggtt ggaggtttca cttgcacatc     420
atgganggtt tagtgcttat cttatttgtg cctcctggac ttgtccaatt natgaagtta     480
atcatattgc atcatanttt gctttgttta acatcacatt naaattaaac tgtattttat     540
gttatttata gctntaggtt ttctgtgttt aacttttttat acnaantttc ctaaactatt    600
ttggtntant gcaanttaaa aattatattt gggggggaa taaatattgg antttctgca      660
gccacaagct ttttttaaaa aaccantaca nccnngttaa atggtnggtc ccnaatggtt     720
tttgcttttn antagaaaat ttnttagaac natttgaaaa aaaaaaaaaa a              771
```

<210> SEQ ID NO 86
<211> LENGTH: 628
<212> TYPE: DNA
<213> ORGANISM: Homo sapien
<220> FEATURE:
<221> NAME/KEY: misc_feature
<222> LOCATION: (1)...(628)
<223> OTHER INFORMATION: n = A,T,C or G

<400> SEQUENCE: 86

```
actagtttgc tttacatttt tgaaaagtat tattttttgtc caagtgctta tcaactaaac     60
cttgtgttag gtaagaatgg aatttattaa gtgaatcagt gtgacccttc ttgtcataag    120
attatcttaa agctgaagcc aaaatatgct tcaaaagaaa angactttat tgttcattgt    180
agttcataca ttcaaagcat ctgaactgta gtttctatag caagccaatt acatccataa    240
gtggagaang aaatagatta atgtcnaagt atgattggtg gagggagcaa ggttgaagat    300
aatctggggt tgaaattttc tagttttcat tctgtacatt tttagttnga catcagattt    360
gaaatattaa tgtttacctt tcaatgtgtg gtatcagctg gactcantaa caccccttttc   420
ttccctnggg gatggggaat ggattattgg aaaatgaaa gaaaaaagta cttaaagcct     480
tcctttcnca gtttctggct cctaccctac tgatttancc agaataagaa aacattttat    540
catcntctgc tttattccca ttaatnaant tttgatgaat aaatctgctt ttatgcnnac    600
ccaaggaatt nagtggnttc ntcnttgt                                        628
```

<210> SEQ ID NO 87
<211> LENGTH: 518
<212> TYPE: DNA
<213> ORGANISM: Homo sapien
<220> FEATURE:
<221> NAME/KEY: misc_feature
<222> LOCATION: (1)...(518)
<223> OTHER INFORMATION: n = A,T,C or G

<400> SEQUENCE: 87

```
tttttttattt ttttagaga gtagttcagc tttatttat aaatttattg cctgttttat       60
tataacaaca ttatactgtt tatggtttaa tacatatggt tcaaaatgta taatacatca    120
```

| | |
|---|---:|
| agtagtacag ttttaaaatt ttatgcttaa acaagtttt gtgtaaaaaa tgcagataca | 180 |
| ttttacatgg caaatcaatt tttaagtcat cctaaaaatt gattttttt tgaaatttaa | 240 |
| aaacacattt aatttcaatt tctctcttat ataaccttta ttactatagc atggtttcca | 300 |
| ctacagttta acaatgcagc aaaattccca tttcacggta aattgggttt taagcggcaa | 360 |
| ggttaaaatg ctttgaggat cctnaatacc ctttgaactt caaatgaagg ttatggttgt | 420 |
| naatttaacc ctcatgccat aagcagaagc acaagtttag ctgcattttg ctctaaactg | 480 |
| taaaancgag cccccgttg aaaaagcaaa agggaccc | 518 |

<210> SEQ ID NO 88
<211> LENGTH: 1844
<212> TYPE: DNA
<213> ORGANISM: Homo sapien

<400> SEQUENCE: 88

| | |
|---|---:|
| gagacagtga atcctagtat caaaggattt ttggcctcag aaaaagttgt tgattatttt | 60 |
| tatttattt tatttttcga gactccgtct caaaaaaaaa aaaaaaaaaa agaatcacaa | 120 |
| ggtatttgct aaagcatttt gagctgcttg gaaaagggga agtagttgca gtagagtttc | 180 |
| ttccatcttc ttggtgctgg gaagccatat atgtgtcttt tactcaagct aaggggtata | 240 |
| agcttatgtg ttgaatttgc tacatctata tttcacatat tctcacaata agagaatttt | 300 |
| gaaatagaaa tatcatagaa catttaagaa agtttagtat aaataatatt ttgtgtgttt | 360 |
| taatcccttt gaagggatct atccaaagaa aatattttac actgagctcc ttcctacacg | 420 |
| tctcagtaac agatcctgtg ttagtctttg aaaatagctc attttttaaa tgtcagtgag | 480 |
| tagatgtagc atacatatga tgtataatga cgtgtattat gttaacaatg tctgcagatt | 540 |
| ttgtaggaat acaaacatg gccttttta taagcaaaac gggccaatga ctagaataac | 600 |
| acatagggca atctgtgaat atgtattata agcagcattc cagaaaagta gttggtgaaa | 660 |
| taattttcaa gtcaaaaagg gatatggaaa gggaattatg agtaacctct attttttaag | 720 |
| ccttgctttt aaattaaacg ctacagccat ttaagccttg aggataataa agcttgagag | 780 |
| taataatgtt aggttagcaa aggtttagat gtatcacttc atgcatgcta ccatgatagt | 840 |
| aatgcagctc ttcgagtcat ttctggtcat tcaagatatt caccctttg cccatagaaa | 900 |
| gcaccctacc tcacctgctt actgacattg tcttagctga tcacaagatc attatcagcc | 960 |
| tccattattc cttactgtat ataaaataca gagttttata ttttcctttc ttcgtttttc | 1020 |
| accatattca aaacctaaat ttgttttgc agatggaatg caaagtaatc aagtgttcgt | 1080 |
| gctttcacct agaagggtgt ggtcctgaag gaaagaggtc cctaaatatc ccccacctg | 1140 |
| ggtgctcctc cttccctggt accctgacta ccagaagtca ggtgctagag cagctggaga | 1200 |
| agtgcagcag cctgtgcttc cacagatggg ggtgctgctg caacaaggct ttcaatgtgc | 1260 |
| ccatcttagg gggagaagct agatcctgtg cagcagcctg gtaagtcctg aggaggttcc | 1320 |
| attgctcttc ctgctgctgt cctttgcttc tcaacggggc tcgctctaca gtctagagca | 1380 |
| catgcagcta acttgtgcct ctgcttatgc atgagggtta aattaacaac cataaccttc | 1440 |
| atttgaagtt caaggtgta ttcaggatcc tcaaagcatt ttaaccttgc cgcttaaaac | 1500 |
| ccaatttacc gtgaaatggg aattttgctg cattgttaaa ctgtagtgga aaccatgcta | 1560 |
| tagtaataaa ggttatataa gagagaaatt gaaattaaat gtgttttaa atttcaaaaa | 1620 |
| aaaatcaatc tttaggatga cttaaaaatt gatttgccat gtaaaatgta tctgcatttt | 1680 |
| ttacacaaaa cttgttttaa gcataaaatt ttaaaactgt actacttgat gtattataca | 1740 | ttttgaacca tatgtattaa accataaaca gtataatgtt gttataataa aacaggcaat    1800 aaatttataa ataaaagctg aaaaaaaaaa aaaaaaaaaa aaaa                    1844

<210> SEQ ID NO 89
<211> LENGTH: 523
<212> TYPE: DNA
<213> ORGANISM: Homo sapien
<220> FEATURE:
<221> NAME/KEY: misc_feature
<222> LOCATION: (1)...(523)
<223> OTHER INFORMATION: n = A,T,C or G

<400> SEQUENCE: 89 ttttttttttt tttttttagt caatccacat ttattgatca cttattatgt accaggcact    60
gggataaaga tgactgttag tcactcacag taaggaagaa aactagcaaa taagacgatt   120
acaatatgat gtagaaaatg ctaagccaga gatatagaaa ggtcctattg ggtccttctg   180
tcaccttgtc tttccacatc cctacccttc acaggccttc cctccagctt cctgcccccg   240
ctccccactg cagatcccct gggattttgc ctagagctaa acgagganat gggcccctg    300 gccctggcat gacttgaacc caaccacaga ctgggaaagg gagcctttcg anagtggatc   360
actttgatna gaaacacat agggaattga agagaaantc cccaaatggc cacccgtgct    420
ggtgctcaag aaaagtttgc agaatggata aatgaaggat caagggaatt aatanatgaa   480
taattgaatg gtggctcaat aagaatgact ncnttgaatg acc                      523

<210> SEQ ID NO 90
<211> LENGTH: 604
<212> TYPE: DNA
<213> ORGANISM: Homo sapien
<220> FEATURE:
<221> NAME/KEY: misc_feature
<222> LOCATION: (1)...(604)
<223> OTHER INFORMATION: n = A,T,C or G

<400> SEQUENCE: 90
ccagtgtggt ggaatgcaaa gattaccccg gaagctttcg agaagctggg attccctgca    60
gcaaaggaaa tagccaatat gtgtcgtttc tatgaaatga agccagaccg agatgtcaat   120
ctcacccacc aactaaatcc caaagtcaaa agcttcagcc agtttatctc agagaaccag   180
gggagccttc aagggcatgt agaaaatcag ctgttcagat aggcctctgc accacacagc   240
ctctttcctc tctgatcctt ttcctcttta cggcacaaca ttcatgtttg acagaacatg   300
ctggaatgca attgtttgca acaccgaagg atttcctgcg gtcgcctctt cagtaggaag   360
cactgcattg gtgataggac acggtaattt gattcacatt taacttgcta gttagtgata   420 agggggtggta cacctgtttg gtaaaatgag aagcctcgga aacttgggag cttctctcct   480
accactaatg gggagggcag attattactg ggatttctcc tggggtgaat taatttcaag   540
ccctaattgc tgaaattccc ctnggcaggc tccagttttc tcaactgcat tgcaaaattc    600
cccc                                                                604

<210> SEQ ID NO 91
<211> LENGTH: 858
<212> TYPE: DNA
<213> ORGANISM: Homo sapien
<220> FEATURE:
<221> NAME/KEY: misc_feature
<222> LOCATION: (1)...(858)
<223> OTHER INFORMATION: n = A,T,C or G

<400> SEQUENCE: 91

```
tttttttttt ttttttttta tgattattat ttttttttatt gatctttaca tcctcagtgt    60
tggcagagtt tctgatgctt aataaacatt tgttctgatc agataagtgg aaaaaattgt    120
catttcctta ttcaagccat gcttttctgt gatattctga tcctagttga acatacagaa    180
ataaatgtct aaaacagcac ctcgattctc gtctataaca ggactaagtt cactgtgatc    240
ttaaataagc ttggctaaaa tgggacatga gtggaggtag tcacacttca gcgaagaaag    300
agaatctcct gtataatctc accaggagat tcaacgaatt ccaccacact ggactagtgg    360
atccccggg ctgcaggaat tcgatatcaa gcttatcgat accgtcgacc tcgaggggg    420
gcccggtacc caattcgccc tatagtgagt cgtattacgc gcgctcactg gccgtcgttt    480
tacaacgtcg tgactgggaa accctggcg ttacccaact taatcgcctt gcagcacatc    540
ccctttcgc cagctggcgt aatagcgaan agcccgcacc gatcgccctt ncaacgttg    600
cgcagcctga atggcgaatg ggacgcgccc tgtagcggcg cattaaagcg ggcngggtg    660
tggnggntcc cccacgtgac cgntacactt ggcagcgcct tacgccggtc nttcgctttc    720
ttccttcct ttctcgcacc gttcgccggg tttccccgnn agctnttaat cggggncctc    780
cctttagggg tncnaattaa nggnttacng gaccttngan cccaaaaact ttgattaggg    840
ggaaggtccc cgaaggg                                                   858
```

<210> SEQ ID NO 92
<211> LENGTH: 585
<212> TYPE: DNA
<213> ORGANISM: Homo sapien
<220> FEATURE:
<221> NAME/KEY: misc_feature
<222> LOCATION: (1)...(585)
<223> OTHER INFORMATION: n = A,T,C or G

<400> SEQUENCE: 92

```
gttgaatctc ctggtgagat tatacaggag attctctttc ttcgctgaag tgtgactacc    60
tccactcatg tcccatttta gccaagctta tttaagatca cagtgaactt agtcctgtta    120
tagacgagaa tcgaggtgct gttttagaca tttatttctg tatgttcaac taggatcaga    180
atatcacaga aaagcatggc ttgaataagg aaatgacaat tttttccact tatctgatca    240
gaacaaatgt ttattaagca tcagaaactc tgccaacact gaggatgtaa agatcaataa    300
aaaaaataat aatcatnann naaanannan nngaagggcg gccgccaccg cggtggagct    360
ccagcttttg ttccctttag tgagggttaa ttgcgcgctt ggcgttaatc atggtcatag    420
ctgtttcctg tgtgaaattg ttatccggct cacaattccn cncaacatac gagccgggaa    480
gcntnangtg taaaagcctg ggggtgccta attgagtgag ctnactcaca ttaattgngt    540
tgcgctccac ttgcccgctt ttccantccg ggaaacctgt tcgnc                     585
```

<210> SEQ ID NO 93
<211> LENGTH: 567
<212> TYPE: DNA
<213> ORGANISM: Homo sapien
<220> FEATURE:
<221> NAME/KEY: misc_feature
<222> LOCATION: (1)...(567)
<223> OTHER INFORMATION: n = A,T,C or G

<400> SEQUENCE: 93

```
cggcagtgtt gctgtctgcg tgtccacctt ggaatctggc tgaactggct gggaggacca    60
agactgcggc tggggtgggc anggaaggga accgggggct gctgtgaagg atcttggaac   120
```

```
ttccctgtac ccaccttccc cttgcttcat gtttgtanag gaaccttgtg ccggccaagc    180
ccagtttcct tgtgtgatac actaatgtat ttgcttttt tgggaaatan anaaaaatca    240
attaaattgc tantgtttct ttgaannnnn nnnnnnnnn nnnnnngggg ggggncgccc    300
ccncggngga aacncccct tttgttccct ttaattgaaa ggttaattng cncncntggc    360
gttaanccnt gggccaaanc tngttncccg tgntgaaatt gttatcccc tcccaaattc    420 cccccnncc ttccaaaccc ggaaanccta annntgttna anccggggg gttgcctaan    480 ngnaattnaa ccnaaccccc ntttaaatng nntttgcncn ccacnngccc cncttcccca    540
nttcggggaa aaccctntcc gtgccca                                       567
```

<210> SEQ ID NO 94
<211> LENGTH: 620
<212> TYPE: DNA
<213> ORGANISM: Homo sapien
<220> FEATURE:
<221> NAME/KEY: misc_feature
<222> LOCATION: (1)...(620)
<223> OTHER INFORMATION: n = A,T,C or G

<400> SEQUENCE: 94

```
actagtcaaa aatgctaaaa taatttggga gaaatatatt tttaagtagt gttatagttt     60
catgtttatc ttttattatg ttttgtgaag ttgtgtcttt tcactaatta cctatactat    120
gccaatattt cctatatatct atccataaca tttatactac atttgtaana naatatgcac    180
gtgaaactta acactttata aggtaaaaat gaggtttcca anatttaata atctgatcaa    240
gttcttgtta tttccaaata gaatggactt ggtctgttaa gggctaagga gaagaggaag    300
ataaggttaa aagttgttaa tgaccaaaca ttctaaaaga aatgcaaaaa aaaagtttat    360
tttcaagcct tcgaactatt taaggaaagc aaaatcattt cctaaatgca tatcatttgt    420
gagaatttct cattaatatc ctgaatcatt catttcacta aggctcatgt tnactccgat    480
atgtctctaa gaaagtacta tttcatggtc caaacctggt tgccatantt gggtaaaggc    540
tttcccttaa gtgtgaaant atttaaaatg aaattttcct ctttttaaaa attctttana    600
agggttaagg gtgttgggga                                               620
```

<210> SEQ ID NO 95
<211> LENGTH: 470
<212> TYPE: DNA
<213> ORGANISM: Homo sapien
<220> FEATURE:
<221> NAME/KEY: misc_feature
<222> LOCATION: (1)...(470)
<223> OTHER INFORMATION: n = A,T,C or G

<400> SEQUENCE: 95

```
ctcgaccttc tctgcacagc ggatgaaccc tgagcagctg aagaccagaa aagccactat     60
nactttntgc ttaattcang agcttacang attcttcaaa gagtgngtcc agcatccttt    120
gaaacatgag ttcttaccag cagaagcaga cctttacccc accacctcag cttcaacagc    180
agcaggtgaa acaacccatc cagcctccac ctnaggaaat atttgttccc acaaccaagg    240
agccatgcca ctcaaaggtt ccacaacctg naaacacaaa nattccagag ccaggctgta    300
ccaaggtccc tgagccaggg ctgtaccaan gtccctgagc caggttgtac caangtccct    360
gagccaggat gtaccaaggt ccctgancca ggttgtccaa ggtccctgag ccaggctaca    420
ccaagggcct gngccaggca gcatcaangt ccctgaccaa ggcttatcaa                470
```

<210> SEQ ID NO 96
<211> LENGTH: 660
<212> TYPE: DNA
<213> ORGANISM: Homo sapien
<220> FEATURE:
<221> NAME/KEY: misc_feature
<222> LOCATION: (1)...(660)
<223> OTHER INFORMATION: n = A,T,C or G

<400> SEQUENCE: 96

| | | | | | |
|---|---|---|---|---|---|
| tttttttttt | tttttttttt | ggaattaaaa | gcaatttaat | gagggcagag | caggaaacat | 60 |
| gcatttcttt | tcattcgaat | cttcagatga | accctgagca | gccgaagacc | agaaaagcca | 120 |
| tgaagacttt | ctgcttaatt | caggggctta | caggattctt | cagagtgtgt | gtgaacaaaa | 180 |
| gctttatagt | acgtattttt | aggatacaaa | taagagagag | actatggctt | ggggtgagaa | 240 |
| tgtactgatt | acaaggtcta | cagacaatta | agacacagaa | acagatggga | agagggtgnc | 300 |
| cagcatctgg | nggttggctt | ctcaagggct | tgtctgtgca | ccaaattact | tctgcttggn | 360 |
| cttctgctga | gctgggcctg | gagtgaccgt | tgaaggacat | ggctctggta | cctttgtgta | 420 |
| gcctgncaca | ggaactttgg | tgtatccttg | ctcaggaact | ttgatggcac | ctggctcagg | 480 |
| aaacttgatg | aagccttggt | caagggacct | tgatgcttgc | tggctcaggg | accttggngn | 540 |
| anccctgggct | canggacctt | tgncncaacc | ttggcttcaa | gggacccttg | gnacatcctg | 600 |
| gcnnagggac | ccttgggncc | aaccctgggc | ttnagggacc | ctttggntnc | nanccttggc | 660 |

<210> SEQ ID NO 97
<211> LENGTH: 441
<212> TYPE: DNA
<213> ORGANISM: Homo sapien
<220> FEATURE:
<221> NAME/KEY: misc_feature
<222> LOCATION: (1)...(441)
<223> OTHER INFORMATION: n = A,T,C or G

<400> SEQUENCE: 97

| | | | | | |
|---|---|---|---|---|---|
| gggaccatac | anagtattcc | tctcttcaca | ccaggaccag | ccactgttgc | agcatgagtt | 60 |
| cccagcagca | gaagcagccc | tgcatcccac | cccctcagct | tcagcagcag | caggtgaaac | 120 |
| agccttgcca | gcctccacct | caggaaccat | gcatccccaa | aaccaaggag | ccctgccacc | 180 |
| ccaaggtgcc | tgagccctgc | caccccaaag | tgcctgagcc | ctgccagccc | aaggttccag | 240 |
| agccatgcca | ccccaaggtg | cctgagccct | gcccttcaat | agtcactcca | gcaccagccc | 300 |
| agcagaanac | caagcagaag | taatgtggtc | cacagccatg | cccttgagga | gccggccacc | 360 |
| agatgctgaa | tcccctatcc | cattctgtgt | atgagtccca | tttgccttgc | aattagcatt | 420 |
| ctgtctcccc | caaaaaaaaa | a | | | | 441 |

<210> SEQ ID NO 98
<211> LENGTH: 600
<212> TYPE: DNA
<213> ORGANISM: Homo sapien
<220> FEATURE:
<221> NAME/KEY: misc_feature
<222> LOCATION: (1)...(600)
<223> OTHER INFORMATION: n = A,T,C or G

<400> SEQUENCE: 98

| | | | | | |
|---|---|---|---|---|---|
| gtattcctct | cttcacacca | ggaccagcca | ctgttgcagc | atgagttccc | agcagcagaa | 60 |
| gcagccctgc | atcccacccc | ctcagcttca | gcagcagcag | gtgaaacagc | cttgccagcc | 120 |
| tccacctcag | gaaccatgca | tccccaaaac | caaggagccc | tgccacccca | aggtgcctga | 180 |

```
gccctgccac cccaaagtgc ctgagccctg ccagcccaag gttccagagc catgccaccc    240
caaggtgcct gagccctgcc cttcaatagt cactccagca ccagcccagc agaanaccaa    300
gcagaagtaa tgtggtccac agccatgccc ttgaggagcc ggccaccana tgctgaatcc    360
cctatcccat tctgtgtatg agtcccattt gccttgcaat tagcattctg tctcccccaa    420
aaaagaatgt gctatgaagc tttctttcct acacactctg agtctctgaa tgaagctgaa    480
ggtcttaant acaganctag ttttcagctg ctcagaattc tctgaagaaa agatttaaga    540
tgaaaggcaa atgattcagc tccttattac cccattaaat tcnctttcaa ttccaaaaaa    600
```

<210> SEQ ID NO 99
<211> LENGTH: 667
<212> TYPE: DNA
<213> ORGANISM: Homo sapien
<220> FEATURE:
<221> NAME/KEY: misc_feature
<222> LOCATION: (1)...(667)
<223> OTHER INFORMATION: n = A,T,C or G

<400> SEQUENCE: 99

```
actagtgact gagttcctgg caaagaaatt tgacctggac cagttgataa ctcatgtttt     60
accatttaaa aaaatcagtg aaggatttga gctgctcaat tcaggacaaa gcattcgaac    120
ggtcctgacg ttttgagatc caaagtggca ggaggtctgt gttgtcatgg tgaactggag    180
tttctcttgt gagagttccc tcatctgaaa tcatgtatct gtctcacaaa tacaagcata    240
agtagaagat ttgttgaaga catagaaccc ttataaagaa ttattaacct ttataaacat    300
ttaaagtctt gtgagcacct gggaattagt ataataacaa tgttnatatt tttgatttac    360
attttgtaag gctataattg tatcttttaa gaaaacatac cttggatttc tatgttgaaa    420
tggagatttt taagagtttt aaccagctgc tgcagatata ttactcaaaa cagatatagc    480
gtataaagat atagtaaatg catctcctag agtaatattc acttaacaca ttggaaacta    540 ttattttta gatttgaata tnaatgttat tttttaaaca cttgttatga gttacttggg    600
attacatttt gaaatcagtt cattccatga tgcanattac tgggattaga ttaagaaaga    660
cggaaaa                                                              667
```

<210> SEQ ID NO 100
<211> LENGTH: 583
<212> TYPE: DNA
<213> ORGANISM: Homo sapien
<220> FEATURE:
<221> NAME/KEY: misc_feature
<222> LOCATION: (1)...(583)
<223> OTHER INFORMATION: n = A,T,C or G

<400> SEQUENCE: 100

```
gttttgtttg taagatgatc acagtcatgt tacactgatc taaaggacat atatataacc     60
ctttaaaaaa aaaatcactg cctcattctt atttcaagat gaatttctat acagactaga    120 tgttttctg aagatcaatt agacattttg aaaatgattt aaagtgtttt ccttaatgtt    180
ctctgaaaac aagtttcttt tgtagtttta accaaaaaag tgccctttt gtcactggat    240 tctcctagca ttcatgattt ttttttcata caatgaaatt aaaattgcta aaatcatgga    300
ctggctttct ggttggattt caggtaagat gtgtttaagg ccagagcttt tctcagtatt    360 tgatttttt ccccaatatt tgatttttta aaaatataca catnggtgct gcatttatat    420
ctgctggttt aaaattctgt catatttcac ttctagcctt ttagttatgg caaatcatat    480
```

```
tttacttttta cttaaagcat ttggtnattt ggantatctg gttctannct aaaaaaanta      540
attctatnaa ttgaantttt ggtactcnnc catatttgga tcc                        583

<210> SEQ ID NO 101
<211> LENGTH: 592
<212> TYPE: DNA
<213> ORGANISM: Homo sapien
<220> FEATURE:
<221> NAME/KEY: misc_feature
<222> LOCATION: (1)...(592)
<223> OTHER INFORMATION: n = A,T,C or G

<400> SEQUENCE: 101
gtggagacgt acaaagagca gccgctcaag acacctggga agaaaaagaa aggcaagccc       60
gggaaacgca aggagcagga aaagaaaaaa cggcgaactc gctctgcctg gttagactct      120
ggagtgactg ggagtgggct agaaggggac cacctgtctg acacctccac aacgtcgctg      180
gagctcgatt cacggaggca ttgaaatttt cagcaganac cttccaagga catattgcag      240
gattctgtaa tagtgaacat atggaaagta ttagaaatat ttattgtctg taaatactgt      300
aaatgcattg gaataaaact gtctccccca ttgctctatg aaactgcaca ttggtcattg      360
tgaatatttt ttttttttgcc aaggctaatc caattattat tatcacattt accataattt      420
attttgtcca ttgatgtatt tattttgtaa atgtatcttg gtgctgctga atttctatat      480
tttttgtaca taatgcnttt anatatacct atcaagtttg ttgataaatg acncaatgaa      540
gtgncncnan ttggnggttg aatttaatga atgcctaatt ttattatccc aa              592

<210> SEQ ID NO 102
<211> LENGTH: 587
<212> TYPE: DNA
<213> ORGANISM: Homo sapien
<220> FEATURE:
<221> NAME/KEY: misc_feature
<222> LOCATION: (1)...(587)
<223> OTHER INFORMATION: n = A,T,C or G

<400> SEQUENCE: 102
cgtcctaagc acttagacta catcagggaa gaacacagac cacatccctg tcctcatgcg       60
gcttatgttt tctggaagaa agtggagacc nagtccttgg ctttagggct ccccggctgg      120
gggctgtgca ntccggtcag ggcgggaagg gaaatgcacc gctgcatgtg aacttacagc      180
ccaggcggat gccccttccc ttagcactac ctggcctcct gcatcccctc gcctcatgtt      240
cctcccacct tcaaanaatg aanaacccca tgggcccagc cccttgccct ggggaaccaa      300
ggcagccttc caaaactcag gggctgaagc anactattag ggcaggggct gactttgggt      360
gacactgccc attccctctc agggcagctc angtcacccn ggnctcttga acccagcctg      420
ttcctttgaa aaagggcaaa actgaaaagg gcttttccta naaaaagaaa accagggaa       480 ctttgccagg gcttcnntnt taccaaaacn ncttctcnng gatttttaat tccccattng      540
gcctccactt accnggggcn atgccccaaa attaanaatt tcccatc                    587

<210> SEQ ID NO 103
<211> LENGTH: 496
<212> TYPE: DNA
<213> ORGANISM: Homo sapien
<220> FEATURE:
<221> NAME/KEY: misc_feature
<222> LOCATION: (1)...(496)
<223> OTHER INFORMATION: n = A,T,C or G

<400> SEQUENCE: 103
```

```
anaggactgg ccctacntgc tctctctcgt cctacctatc aatgcccaac atggcagaac    60
ctgcanccct tggncactgc anatggaaac ctctcagtgt cttgacatca ccctacccnt   120
gcggtgggtc tccaccacaa ccactttgac tctgtggtcc ctgnanggtg gnttctcctg   180
actggcagga tggaccttan ccacatatc cctctgttcc ctctgctnag anaaagaatt    240
cccttaacat gatataatcc acccatgcaa ntngctactg gcccagctac catttaccat   300
ttgcctacag aatttcattc agtctacact ttggcattct ctctggcgat agagtgtggc   360
tgggctgacc gcaaaaggtg ccttacacac tggcccccac cctcaaccgt tgacncatca   420
gangcttgcc tcctccttct gattnncccc catgttggat atcagggtgc tcnagggatt   480
ggaaaagaaa caaaac                                                   496

<210> SEQ ID NO 104
<211> LENGTH: 575
<212> TYPE: DNA
<213> ORGANISM: Homo sapien
<220> FEATURE:
<221> NAME/KEY: misc_feature
<222> LOCATION: (1)...(575)
<223> OTHER INFORMATION: n = A,T,C or G

<400> SEQUENCE: 104
gcacctgctc tcaatccnnc tctcaccatg atcctccgcc tgcanaaact cctctgccaa    60
ctatggangt ggtttcnggg gtggctcttg ccaactggga agaagccgtg gtgtctctac   120
ctgttcaact cngtttgtgt ctgggggatc aactnggggc tatggaagcg gctnaactgt   180
tgttttggtg gaagggctgg taattggctt tgggaagtng cttatngaag ttggcctngg   240
gaagttgcta ttgaaagtng ccntggaagt ngntttggtg gggggttttg ctggtggcct   300
ttgttnaatt tgggtgcttt gtnaatggcg gcccctcnc ctgggcaatg aaaaaaatca    360
ccnatgcngn aaacctcnac nnaacagcct gggcttccct cacctcgaaa aagttgctc   420 ccccccaaa aaaggncaan ccctcaann tggaangttg aaaaaatcct cgaatgggga    480
ncccnaaaac aaaaancccc ccntttcccn gnaanggggg aaataccncc ccccactta   540 cnaaaaccct tntaaaaaac ccccgggaa aaaaa                              575

<210> SEQ ID NO 105
<211> LENGTH: 619
<212> TYPE: DNA
<213> ORGANISM: Homo sapien
<220> FEATURE:
<221> NAME/KEY: misc_feature
<222> LOCATION: (1)...(619)
<223> OTHER INFORMATION: n = A,T,C or G

<400> SEQUENCE: 105
cactagtagg atagaaacac tgtgtcccga gagtaaggag agaagctact attgattaga    60
gcctaaccca ggttaactgc aagaagaggc gggatacttt cagctttcca tgtaactgta   120
tgcataaagc caatgtagtc cagtttctaa gatcatgttc caagctaact gaatcccact   180
tcaatacaca ctcatgaact cctgatggaa caataacagg cccaagcctg tggtatgatg   240
tgcacacttg ctagactcan aaaaaatact actctcataa atgggtggga gtattttggt   300
gacaacctac tttgcttggc tgagtgaagg aatgatattc atatattcat ttattccatg   360
gacatttagt tagtgctttt tatataccag gcatgatgct gagtgacact cttgtgtata   420
tttccaaatt tttgtacagt cgctgcacat atttgaaatc atatattaag acttccaaaa   480
```

```
aatgaagtcc ctggtttttc atggcaactt gatcagtaaa ggattcncct ctgtttggta    540
cttaaaacat ctactatatn gttnanatga aattccttttt cccncctcc cgaaaaaana    600 aagtggtggg gaaaaaaaa                                                  619
```

<210> SEQ ID NO 106
<211> LENGTH: 506
<212> TYPE: DNA
<213> ORGANISM: Homo sapien
<220> FEATURE:
<221> NAME/KEY: misc_feature
<222> LOCATION: (1)...(506)
<223> OTHER INFORMATION: n = A,T,C or G

<400> SEQUENCE: 106

```
cattggtnct ttcatttgct ntggaagtgt nnatctctaa cagtggacaa agttcccngt     60
gccttaaact ctgtnacact tttgggaant gaaaanttng tantatgata ggttattctg    120
angtanagat gttctggata ccattanatn tgccccngt gtcagaggct catattgtgt     180
tatgtaaatg gtatntcatt cgctactatn antcaattng aaatanggtc tttgggttat    240
gaatantnng cagcncanct nanangctgt ctgtngtatt cattgtggtc atagcacctc    300
acancattgt aacctcnatc nagtgagaca nactagnaan ttcctagtga tggctcanga    360
ttccaaatgg nctcatntcn aatgtttaaa agttanttaa gtgtaagaaa tacagactgg    420
atgttccacc aactagtacc tgtaatgacn ggcctgtccc aacacatctc cctttttccat  480 gactgtggta ncccgcatcg gaaaaa                                         506
```

<210> SEQ ID NO 107
<211> LENGTH: 452
<212> TYPE: DNA
<213> ORGANISM: Homo sapien
<220> FEATURE:
<221> NAME/KEY: misc_feature
<222> LOCATION: (1)...(452)
<223> OTHER INFORMATION: n = A,T,C or G

<400> SEQUENCE: 107

```
gttgagtctg tactaaacag taagatatct caatgaacca taaattcaac tttgtaaaaa     60
tcttttgaag catagataat attgtttggt aaatgtttct tttgtttggt aaatgtttct    120
tttaaagacc ctcctattct ataaaactct gcatgtagag gcttgtttac ctttctctct    180
ctaaggttta caataggagt ggtgatttga aaaatataaa attatgagat tggttttcct    240
gtggcataaa ttgcatcact gtatcatttt cttttttaac cggtaagant ttcagtttgt    300
tggaaagtaa ctgtganaac ccagtttccc gtccatctcc cttagggact acccatagaa    360
catgaaaagg tccccacnga agcaagaaga taagtctttc atggctgctg gttgcttaaa    420
ccactttaaa accaaaaaat tccccttgga aa                                  452
```

<210> SEQ ID NO 108
<211> LENGTH: 502
<212> TYPE: DNA
<213> ORGANISM: Homo sapien
<220> FEATURE:
<221> NAME/KEY: misc_feature
<222> LOCATION: (1)...(502)
<223> OTHER INFORMATION: n = A,T,C or G

<400> SEQUENCE: 108

```
atcttcttcc cttaattagt tnttatttat ntattaaatt ttattgcatg tcctggcaaa     60
caaaaagaga ttgtagattg gcttctggct ccccaaaagc ccataacaga aagtaccaca    120
```

```
agaccncaac tgaagcttaa aaaatctatc acatgtataa tacctttnga agaacattaa        180
tanagcatat aaaacttta acatntgctt aatgttgtnc aattataaaa ntaatngaaa         240
aaaatgtccc tttaacatnc aatatcccac atagtgttat ttnagggat taccnngnaa         300 naaaaaagg gtagaaggga tttaatgaaa actctgcttn ccatttctgt ttanaaacgt         360
ctccagaaca aaaacttntc aantctttca gctaaccgca tttgagctna ggccactcaa       420
aaactccatt agncccactt tctaangtc tctanagctt actaancctt ttgaccctt         480 accctggnta ctcctgccct ca                                                 502
```

<210> SEQ ID NO 109
<211> LENGTH: 1308
<212> TYPE: DNA
<213> ORGANISM: Homo sapien

<400> SEQUENCE: 109

```
acccgaggtc tcgctaaaat catcatggat tcacttggcg ccgtcagcac tcgacttggg        60
tttgatcttt tcaaagagct gaagaaaaca atgatggca acatcttctt ttcccctgtg       120
ggcatcttga ctgcaattgg catggtcctc ctggggaccc gaggagccac cgcttcccag       180
ttggaggagt gtttcactc tgaaaaagag acgaagagct caagaataaa ggctgaagaa       240 aagaggtga ttgagaacac agaagcagta catcaacaat tccaaaagtt tttgactgaa       300
ataagcaaac tcactaatga ttatgaactg aacataacca acaggctgtt tggagaaaaa       360
acatacctct tccttcaaaa atacttagat tatgttgaaa aatattatca tgcatctctg       420
gaacctgttg atttttgtaaa tgcagccgat gaaagtcgaa agaagattaa ttcctggggtt       480 gaaagcaaaa caaatgaaaa aatcaaggac ttgttcccag atggctctat tagtagctct       540
accaagctgg tgctggtgaa catggtttat tttaaagggc aatgggacag ggagtttaag       600
aaagaaaata ctaaggaaga gaaattttgg atgaataaga gcacaagtaa atctgtacag       660
atgatgacac agagccattc ctttagcttc actttcctgg aggacttgca ggccaaaatt       720
ctagggattc catataaaaa caacgaccta agcatgtttg tgcttctgcc caacgacatc       780
gatggcctgg agaagataat agataaaata agtcctgaga aattggtaga gtggactagt       840
ccagggcata tggaagaaag aaaggtgaat ctgcacttgc cccggtttga ggtggaggac       900
agttacgatc tagaggcggt cctggctgcc atggggatgg gcgatgcctt cagtgagcac       960
aaagccgact actcgggaat gtcgtcaggc tccggttgt acgcccagaa gttcctgcac      1020
agttcctttg tggcagtaac tgaggaaggc accgaggctg cagctgccac tggcataggc      1080
tttactgtca catccgcccc aggtcatgaa aatgttcact gcaatcatcc cttcctgttc      1140
ttcatcaggc acaatgaatc caacagcatc ctcttcttcg gcagatttc ttctccttaa      1200 gatgatcgtt gccatggcat tgctgctttt agcaaaaac aactaccagt gttactcata      1260
tgattatgaa aatcgtccat tcttttaaat ggtggctcac ttgcattt                   1308
```

<210> SEQ ID NO 110
<211> LENGTH: 391
<212> TYPE: PRT
<213> ORGANISM: Homo sapien

<400> SEQUENCE: 110

```
Met Asp Ser Leu Gly Ala Val Ser Thr Arg Leu Gly Phe Asp Leu Phe
  1               5                  10                  15

Lys Glu Leu Lys Lys Thr Asn Asp Gly Asn Ile Phe Phe Ser Pro Val
```

-continued

```
            20                  25                  30
Gly Ile Leu Thr Ala Ile Gly Met Val Leu Gly Thr Arg Gly Ala
                35                  40                  45
Thr Ala Ser Gln Leu Glu Val Phe His Ser Glu Lys Glu Thr Lys
 50                  55                  60
Ser Ser Arg Ile Lys Ala Glu Lys Glu Val Ile Glu Asn Thr Glu
 65                  70                  75                  80
Ala Val His Gln Gln Phe Gln Lys Phe Leu Thr Glu Ile Ser Lys Leu
                 85                  90                  95
Thr Asn Asp Tyr Glu Leu Asn Ile Thr Asn Arg Leu Phe Gly Glu Lys
                100                 105                 110
Thr Tyr Leu Phe Leu Gln Lys Tyr Leu Asp Tyr Val Glu Lys Tyr Tyr
                115                 120                 125
His Ala Ser Leu Glu Pro Val Asp Phe Val Asn Ala Ala Asp Glu Ser
                130                 135                 140
Arg Lys Lys Ile Asn Ser Trp Val Glu Ser Lys Thr Asn Glu Lys Ile
145                 150                 155                 160
Lys Asp Leu Phe Pro Asp Gly Ser Ile Ser Ser Thr Lys Leu Val
                165                 170                 175
Leu Val Asn Met Val Tyr Phe Lys Gly Gln Trp Asp Arg Glu Phe Lys
                180                 185                 190
Lys Glu Asn Thr Lys Glu Glu Lys Phe Trp Met Asn Lys Ser Thr Ser
                195                 200                 205
Lys Ser Val Gln Met Met Thr Gln Ser His Ser Phe Ser Phe Thr Phe
                210                 215                 220
Leu Glu Asp Leu Gln Ala Lys Ile Leu Gly Ile Pro Tyr Lys Asn Asn
225                 230                 235                 240
Asp Leu Ser Met Phe Val Leu Leu Pro Asn Asp Ile Asp Gly Leu Glu
                245                 250                 255
Lys Ile Ile Asp Lys Ile Ser Pro Glu Lys Leu Val Glu Trp Thr Ser
                260                 265                 270
Pro Gly His Met Glu Glu Arg Lys Val Asn Leu His Leu Pro Arg Phe
                275                 280                 285
Glu Val Glu Asp Ser Tyr Asp Leu Glu Ala Val Leu Ala Ala Met Gly
                290                 295                 300
Met Gly Asp Ala Phe Ser Glu His Lys Ala Asp Tyr Ser Gly Met Ser
305                 310                 315                 320
Ser Gly Ser Gly Leu Tyr Ala Gln Lys Phe Leu His Ser Ser Phe Val
                325                 330                 335
Ala Val Thr Glu Glu Gly Thr Glu Ala Ala Ala Thr Gly Ile Gly
                340                 345                 350
Phe Thr Val Thr Ser Ala Pro Gly His Glu Asn Val His Cys Asn His
                355                 360                 365
Pro Phe Leu Phe Phe Ile Arg His Asn Glu Ser Asn Ser Ile Leu Phe
                370                 375                 380
Phe Gly Arg Phe Ser Ser Pro
385                 390
```

<210> SEQ ID NO 111
<211> LENGTH: 1419
<212> TYPE: DNA
<213> ORGANISM: Homo sapien

<400> SEQUENCE: 111

-continued

```
ggagaactat aaattaagga tcccagctac ttaattgact tatgcttcct agttcgttgc    60
ccagccacca ccgtctctcc aaaaacccga ggtctcgcta aaatcatcat ggattcactt   120
ggcgccgtca gcactcgact tgggtttgat cttttcaaag agctgaagaa acaaatgat    180
ggcaacatct tcttttcccc tgtgggcatc ttgactgcaa ttggcatggt cctcctgggg   240
acccgaggag ccaccgcttc ccagttggag gaggtgtttc actctgaaaa agagacgaag   300
agctcaagaa taaaggctga gaaaaagag gtggtaagaa taaaggctga aggaaaagag    360
attgagaaca cagaagcagt acatcaacaa ttccaaaagt ttttgactga ataagcaaa    420
ctcactaatg attatgaact gaacataacc aacaggctgt ttggagaaaa acataccct    480
ttccttcaaa aatacttaga ttatgttgaa aaatattatc atgcatctct ggaacctgtt   540
gattttgtaa atgcagccga tgaaagtcga agaagatta ttcctgggt tgaaagcaaa     600
acaaatgaaa aaatcaagga cttgttccca gatggctcta ttagtagctc taccaagctg   660
gtgctggtga acatggttta ttttaagggg caatgggaca gggagtttaa gaaagaaaat   720
actaaggaag agaaattttg gatgaataag agcacaagta aatctgtaca gatgatgaca   780
cagagccatt cctttagctt cactttcctg gaggacttgc aggccaaaat tctagggatt   840
ccatataaaa acaacgacct aagcatgttt gtgcttctgc ccaacgacat cgatggcctg   900
gagaagataa tagataaaat aagtcctgag aaattggtag agtggactag tccagggcat   960
atggaagaaa gaaggtgaa tctgcacttg ccccggtttg aggtggagga cagttacgat  1020
ctagaggcgg tcctggctgc catggggatg ggcgatgcct tcagtgagca aaagccgac   1080
tactcgggaa tgtcgtcagg ctccggggttg tacgcccaga agttcctgca cagttccttt  1140
gtggcagtaa ctgaggaagg caccgaggct gcagctgcca ctggcatagg ctttactgtc  1200
acatccgccc caggtcatga aaatgttcac tgcaatcatc ccttcctgtt cttcatcagg  1260
cacaatgaat ccaacagcat cctcttcttc ggcagatttt cttctcctta agatgatcgt  1320
tgccatggca ttgctgcttt tagcaaaaaa caactaccag tgttactcat atgattatga  1380
aaatcgtcca ttcttttaaa tggtggctca cttgcattt                         1419
```

<210> SEQ ID NO 112
<211> LENGTH: 400
<212> TYPE: PRT
<213> ORGANISM: Homo sapien

<400> SEQUENCE: 112

```
Met Asp Ser Leu Gly Ala Val Ser Thr Arg Leu Gly Phe Asp Leu Phe
 1               5                  10                  15
Lys Glu Leu Lys Lys Thr Asn Asp Gly Asn Ile Phe Phe Ser Pro Val
                20                  25                  30
Gly Ile Leu Thr Ala Ile Gly Met Val Leu Leu Gly Thr Arg Gly Ala
            35                  40                  45
Thr Ala Ser Gln Leu Glu Glu Val Phe His Ser Glu Lys Glu Thr Lys
        50                  55                  60
Ser Ser Arg Ile Lys Ala Glu Lys Glu Val Val Arg Ile Lys Lys Ala
65                  70                  75                  80
Glu Gly Lys Glu Ile Glu Asn Thr Glu Ala Val His Gln Gln Phe Gln
                85                  90                  95
Lys Phe Leu Thr Glu Ile Ser Lys Leu Thr Asn Asp Tyr Glu Leu Asn
                100                 105                 110
Ile Thr Asn Arg Leu Phe Gly Glu Lys Thr Tyr Leu Phe Leu Gln Lys
            115                 120                 125
```

```
Tyr Leu Asp Tyr Val Glu Lys Tyr Tyr His Ala Ser Leu Glu Pro Val
    130                 135                 140

Asp Phe Val Asn Ala Ala Asp Glu Ser Arg Lys Lys Ile Asn Ser Trp
145                 150                 155                 160

Val Glu Ser Lys Thr Asn Glu Lys Ile Lys Asp Leu Phe Pro Asp Gly
                165                 170                 175

Ser Ile Ser Ser Ser Thr Lys Leu Val Leu Val Asn Met Val Tyr Phe
                180                 185                 190

Lys Gly Gln Trp Asp Arg Glu Phe Lys Lys Glu Asn Thr Lys Glu Glu
                195                 200                 205

Lys Phe Trp Met Asn Lys Ser Thr Ser Lys Ser Val Gln Met Met Thr
210                 215                 220

Gln Ser His Ser Phe Ser Phe Thr Phe Leu Glu Asp Leu Gln Ala Lys
225                 230                 235                 240

Ile Leu Gly Ile Pro Tyr Lys Asn Asn Asp Leu Ser Met Phe Val Leu
                245                 250                 255

Leu Pro Asn Asp Ile Asp Gly Leu Glu Lys Ile Ile Asp Lys Ile Ser
                260                 265                 270

Pro Glu Lys Leu Val Glu Trp Thr Ser Pro Gly His Met Glu Glu Arg
                275                 280                 285

Lys Val Asn Leu His Leu Pro Arg Phe Glu Val Glu Asp Ser Tyr Asp
290                 295                 300

Leu Glu Ala Val Leu Ala Ala Met Gly Met Gly Asp Ala Phe Ser Glu
305                 310                 315                 320

His Lys Ala Asp Tyr Ser Gly Met Ser Ser Gly Ser Gly Leu Tyr Ala
                325                 330                 335

Gln Lys Phe Leu His Ser Ser Phe Val Ala Val Thr Glu Glu Gly Thr
                340                 345                 350

Glu Ala Ala Ala Ala Thr Gly Ile Gly Phe Thr Val Thr Ser Ala Pro
                355                 360                 365

Gly His Glu Asn Val His Cys Asn His Pro Phe Leu Phe Phe Ile Arg
                370                 375                 380

His Asn Glu Ser Asn Ser Ile Leu Phe Phe Gly Arg Phe Ser Ser Pro
385                 390                 395                 400

<210> SEQ ID NO 113
<211> LENGTH: 957
<212> TYPE: DNA
<213> ORGANISM: Homo sapien

<400> SEQUENCE: 113
ctcgaccttc tctgcacagc ggatgaaccc tgagcagctg aagaccagaa aagccactat     60
gactttctgc ttaattcagg agcttacagg attcttcaaa gagtgtgtcc agcatccttt    120
gaaacatgag ttcttaccag cagaagcaga cctttacccc accacctcag cttcaacagc    180
agcaggtgaa acaacccagc cagcctccac ctcaggaaat atttgttccc acaaccaagg    240
agccatgcca ctcaaaggtt ccacaacctg gaaacacaaa gattccagag ccaggctgta    300
ccaaggtccc tgagccaggc tgtaccaagg tccctgagcc aggttgtacc aaggtccctg    360
agccaggatg taccaaggtc cctgagccag gttgtaccaa ggtccctgag ccaggctaca    420
ccaaggtccc tgagccaggc agcatcaagg tccctgacca aggcttcatc aagtttcctg    480
agccaggtgc catcaaagtt cctgagcaag atacaccaa agttcctgtg ccaggctaca    540
caaaggtacc agagccatgt ccttcaacgg tcactccagg cccagctcag cagaagacca    600
```

```
agcagaagta atttggtgca cagacaagcc cttgagaagc caaccaccag atgctggaca    660
ccctcttccc atctgtttct gtgtcttaat tgtctgtaga ccttgtaatc agtacattct    720
caccccaagc catagtctct ctcttatttg tatcctaaaa atacggtact ataaagcttt    780
tgttcacaca cactctgaag aatcctgtaa gcccctgaat taagcagaaa gtcttcatgg    840
cttttctggt cttcggctgc tcagggttca tctgaagatt cgaatgaaaa gaaatgcatg    900
tttcctgctc tgccctcatt aaattgcttt taattccaaa aaaaaaaaaa aaaaaaa      957
```

<210> SEQ ID NO 114
<211> LENGTH: 161
<212> TYPE: PRT
<213> ORGANISM: Homo sapien

<400> SEQUENCE: 114

```
Met Ser Ser Tyr Gln Gln Lys Gln Thr Phe Thr Pro Pro Gln Leu
 1               5                  10                  15

Gln Gln Gln Gln Val Lys Gln Pro Ser Gln Pro Pro Gln Glu Ile
                20                  25                  30

Phe Val Pro Thr Thr Lys Glu Pro Cys His Ser Lys Val Pro Gln Pro
                35                  40                  45

Gly Asn Thr Lys Ile Pro Glu Pro Gly Cys Thr Lys Val Pro Glu Pro
        50                  55                  60

Gly Cys Thr Lys Val Pro Glu Pro Gly Cys Thr Lys Val Pro Glu Pro
65                  70                  75                  80

Gly Cys Thr Lys Val Pro Glu Pro Gly Cys Thr Lys Val Pro Glu Pro
                85                  90                  95

Gly Tyr Thr Lys Val Pro Glu Pro Gly Ser Ile Lys Val Pro Asp Gln
                100                 105                 110

Gly Phe Ile Lys Phe Pro Glu Pro Gly Ala Ile Lys Val Pro Glu Gln
            115                 120                 125

Gly Tyr Thr Lys Val Pro Val Pro Gly Tyr Thr Lys Val Pro Glu Pro
        130                 135                 140

Cys Pro Ser Thr Val Thr Pro Gly Pro Ala Gln Gln Lys Thr Lys Gln
145                 150                 155                 160

Lys
```

<210> SEQ ID NO 115
<211> LENGTH: 506
<212> TYPE: DNA
<213> ORGANISM: Homo sapien
<220> FEATURE:
<221> NAME/KEY: misc_feature
<222> LOCATION: (1)...(506)
<223> OTHER INFORMATION: n = A,T,C or G

<400> SEQUENCE: 115

```
cattggtnct ttcatttgct ntggaagtgt nnatctctaa cagtggacaa agttcccngt     60
gccttaaact ctgtnacact tttgggaant gaaaanttng tantatgata ggttattctg    120
angtanagat gttctggata ccattanatn tgcccccngt gtcagaggct catattgtgt    180
tatgtaaatg gtatntcatt cgctactatn antcaattng aaatanggtc tttgggttat    240
gaatantnng cagcncanct nanangctgt ctgtngtatt cattgtgtc atagcacctc     300 acancattgt aacctcnatc nagtgagaca nactagnaan ttcctagtga tggctcanga    360
ttccaaatgg nctcatntcn aatgtttaaa agttanttaa gtgtaagaaa tacagactgg    420
```

| atgttccacc aactagtacc tgtaatgacn ggcctgtccc aacacatctc cctttccat | 480 |
| gactgtggta ncccgcatcg gaaaaa | 506 |

<210> SEQ ID NO 116
<211> LENGTH: 3079
<212> TYPE: DNA
<213> ORGANISM: Homo sapien

<400> SEQUENCE: 116

| ggatccccgg gtttcctaaa cccccacag agtcctgccc aggccaaaga gcaaggaaaa | 60 |
| ggtcaaaggg cagaaaaaat gctgagttag gaggagctat ggaaggataa acctggcctt | 120 |
| aaagaggtca aagtggttta taggggcgc tgagggcttc ccacattctc tggcctaaac | 180 |
| cttgcaggca gatctgccca gtgggctctg ggatagctgt gccttcccta acaaaaaaat | 240 |
| tgtgcacaaa aggatgaaac tctattttcc ctctagcaca taaccaagaa tataaggcta | 300 |
| cagattgcct ttcccagagg gaaaaccctg cagcaacctg ctgcctggaa aagtgtaaga | 360 |
| gcagatcact ggggaatcgt ttgccccccg ctgatgaca gcttcccaa gctccaaggg | 420 |
| caggtgctca gcatgtaccg tactgggatg gttgtcaata ctcctggtcc tgtaagagtc | 480 |
| ccaggacact gccatgccaa tgcccccctca gttcctggca tccttttttgg gctgctcaca | 540 |
| gccccagcct ctatggtgaa acatacttg ctagcagcgt caccaacttg ttgccaagag | 600 |
| atcagtgctc gaaggcaagg ttatttctaa ctgagcagag cctgccagga agaaagcgtt | 660 |
| tgcaccccac accactgtgc aggtgtgacc ggtgagctca cagctgcccc ccaggcatgc | 720 |
| ccagcccact taatcatcac agctcgacag ctctctcgcc cagcccagtt ctggaaggga | 780 |
| taaaagggg catcaccgtt cctgggtaac agagccacct tctgcgtcct gctgagctct | 840 |
| gttctctcca gcacctccca acccactagt gcctggttct cttgctccac caggaacaag | 900 |
| ccaccatgtc tcgccagtca agtgtgtctt ccggagcggg gggcagtcgt agcttcagca | 960 |
| ccgcctctgc catcacccg tctgtctccc gcaccagctt cacctccgtg tcccggtccg | 1020 |
| ggggtggcgg tggtggtggc ttcggcaggg tcagccttgc gggtgcttgt ggagtgggtg | 1080 |
| gctatggcag ccggagcctc tacaacctgg ggggctccaa gaggatatcc atcagcacta | 1140 |
| gtggtggcag cttcaggaac cggtttggtg ctggtgctgg aggcggctat ggctttggag | 1200 |
| gtggtgccgg tagtggatt ggtttcggcg gtggagctgg tggtggcttt gggctcggtg | 1260 |
| gcggagctgg cttttggaggt ggcttcggtg gccctggctt tcctgtctgc cctcctggag | 1320 |
| gtatccaaga ggtcactgtc aaccagagtc tcctgactcc cctcaacctg caaatcgacc | 1380 |
| ccagcatcca gagggtgagg accgaggagc gcgagcagat caagaccctc aacaataagt | 1440 |
| ttgcctcctt catcgacaag gtgcggttcc tggagcagca gaacaaggtt ctggaaacaa | 1500 |
| agtggaccct gctgcaggag cagggcacca agactgtgag gcagaacctg gagccgttgt | 1560 |
| tcgagcagta catcaacaac ctcaggaggc agctggacag catcgtgggg aacgggggcc | 1620 |
| gcctggacte agagctgaga aacatgcagg acctggtgga agacttcaag aacaagtatg | 1680 |
| aggatgaaat caacaagcgt accactgctg agaatgagtt tgtgatgctg aagaaggatg | 1740 |
| tagatgctgc ctacatgaac aaggtggagc tggaggccaa ggttgatgca ctgatggatg | 1800 |
| agattaactt catgaagatg ttctttgatg cggagctgtc ccagatgcag acgcatgtct | 1860 |
| ctgacacctc agtggtcctc tccatggaca caaccgcaa cctggacctg atagcatca | 1920 |
| tcgctgaggt caaggcccag tatgaggaga ttgccaaccg cagccggaca gaagccgagt | 1980 |

-continued

```
cctggtatca gaccaagtat gaggagctgc agcagacagc tggccggcat ggcgatgacc    2040
tccgcaacac caagcatgag atctctgaga tgaaccggat gatccagagg ctgagagccg    2100
agattgacaa tgtcaagaaa cagtgcgcca atctgcagaa cgccattgcg gatgccgagc    2160
agcgtgggga gctggccctc aaggatgcca ggaacaagct ggccgagctg aggaggccc     2220 tgcagaaggc caagcaggac atggcccggc tgctgcgtga gtaccaggag ctcatgaaca    2280
ccaagctggc cctggacgtg gagatcgcca cttaccgcaa gctgctggag ggcgaggaat    2340
gcagactcag tggagaagga gttggaccag tcaacatctc tgttgtcaca agcagtgttt    2400
cctctggata tggcagtggc agtggctatg gcggtggcct cggtggaggt cttggcggcg    2460
gcctcggtgg aggtcttgcc ggaggtagca gtggaagcta ctactccagc agcagtgggg    2520
gtgtcggcct aggtggtggg ctcagtgtgg ggggctctgg cttcagtgca agcagtagcc    2580
gagggctggg ggtgggcttt ggcagtgcg ggggtagcag ctccagcgtc aaatttgtct      2640
ccaccacctc ctcctcccgg aagagcttca agagctaaga acctgctgca agtcactgcc    2700
ttccaagtgc agcaacccag cccatggaga ttgcctcttc taggcagttg ctcaagccat    2760
gttttatcct tttctggaga gtagtctaga ccaagccaat tgcagaacca cattctttgg    2820
ttcccaggag agccccattc ccagcccctg gtctcccgtg ccgcagttct atattctgct    2880
tcaaatcagc cttcaggttt cccacagcat ggcccctgct gacacgagaa cccaaagttt    2940
tcccaaatct aaatcatcaa aacagaatcc caccccaat cccaattttt gttttggttc      3000
taactacctc cagaatgtgt tcaataaaat gttttataat ataagctggt gtgcagaatt    3060
gttttttttt tctacccaa                                                  3079
```

<210> SEQ ID NO 117
<211> LENGTH: 6921
<212> TYPE: DNA
<213> ORGANISM: Homo sapien

<400> SEQUENCE: 117

```
aattctgac tgtccactca aaacttctat tccgatcaaa gctatctgtg actacagaca       60 attgagata accatttaca aagacgatga atgtgttttg gcgaataact ctcatcgtgc      120 aaatggaag gtcattagtc ctactgggaa tgaggctatg gtcccatctg tgtgcttcac      180 gttcctcca ccaaacaaag aagcggtgga ccttgccaac agaattgagc aacagtatca     240 aatgtcctg actctttggc atgagtctca cataaacatg aagagtgtag tatcctggca     300 tatctcatc aatgaaattg atagaattcg agctagcaat gtggcttcaa taaagacaat     360 ctacctggt gaacatcagc aagttctaag taatctacaa tctcgttttg aagattttct     420 gaagatagc caggaatccc aagtctttc aggctcagat ataacacaac tggaaaagga      480 gttaatgta tgtaagcagt attatcaaga acttcttaaa tctgcagaaa gagaggagca     540 gaggaatca gtttataatc tctacatctc tgaagttcga acattagac ttcggttaga       600 aactgtgaa gatcggctga ttagacagat tcgaactccc ctggaaagag atgatttgca     660 gaaagtgtg ttcagaatca cagaacagga gaactaaag aaagagctgg aacgacttaa      720 gatgatttg ggaacaatca caaataagtg tgaggagttt tcagtcaag cagcagcctc      780 tcatcagtc cctaccctac gatcagagct taatgtggtc cttcagaaca tgaaccaagt    840 tattctatg tcttccactt acatagataa gttgaaaact gttaacttgg tgttaaaaaa    900 actcaagct gcagaagccc tcgtaaaact ctatgaaact aaactgtgtg aagaagaagc    960 gttatagct gacaagaata atattgagaa tctaataagt actttaaagc aatggagatc    1020
```

-continued

```
gaagtagat gaaaagagac aggtattcca tgccttagag gatgagttgc agaaagctaa      1080 gccatcagt gatgaaatgt ttaaaacgta taaagaacgg gaccttgatt ttgactggca      1140 aaagaaaaa gcagatcaat tagttgaaag gtggcaaaat gttcatgtgc agattgacaa      1200 aggttacgg gacttagagg gcattggcaa atcactgaag tactacagag acacttacca      1260 cctttagat gattggatcc agcaggttga aactactcag agaaagattc aggaaaatca      1320 cctgaaaat agtaaaaccc tagccacaca gttgaatcaa cagaagatgc tggtgtccga      1380 atagaaatg aaacagagca aaatggacga gtgtcaaaaa tatgcagaac agtactcagc      1440 acagtgaag gactatgaat tacaaacaat gacctaccgg gccatggtag attcacaaca      1500 aaatctcca gtgaaacgcc gaagaatgca gagttcagca gatctcatta ttcaagagtt      1560 atggaccta aggactcgat atactgccct ggtcactctc atgacacaat atattaaatt      1620 gctggtgat tcattgaaga ggctggaaga ggaggagatt aaaaggtgta aggagacttc      1680 gaacatggg gcatattcag atctgcttca gcgtcagaag gcaacagtgc ttgagaatag      1740 aaacttaca ggaaagataa gtgagttgga agaatggta gctgaactaa agaaacaaaa      1800 tcccgagta gaggaagaac ttccgaaggt cagggaggct gcagaaaatg aattgagaaa      1860 cagcagaga aatgtagaag atatctctct gcagaagata agggctgaaa gtgaagccaa      1920 cagtaccgc agggaacttg aaaccattgt gagagagaag gaagccgctg aaagagaact      1980 gagcgggtg aggcagctca ccatagaggc cgaggctaaa agagctgccg tggaagagaa      2040 ctcctgaat tttcgcaatc agttggagga aaacaccttt accagacgaa cactggaaga      2100 catcttaaa agaaaagatt taagtctcaa tgatttggag caacaaaaaa ataaattaat      2160 gaagaatta agaagaaaga gagacaatga ggaagaactc ttgaagctga taaagcagat      2220 gaaaaagac cttgcatttc agaaacaggt agcagagaaa cagttgaaag aaaagcagaa      2280 attgaattg gaagcaagaa gaaaaataac tgaaattcag tatacatgta gagaaaatgc      2340 ttgccagtg tgtccgatca cacaggctac atcatgcagg gcagtaacgg gtctccagca      2400 gaacatgac aagcagaaag cagaagaact caaacagcag gtagatgaac taacagctgc      2460 aatagaaag gctgaacaag acatgagaga gctgacatat gaacttaatg ccctccagct      2520 gaaaaacg tcatctgagg aaaaggctcg tttgctaaaa gataaactag atgaaacaaa      2580 aatacactc agatgcctta agttggagct ggaaaggaag gatcaggcgg agaaagggta      2640 tctcaacaa ctcagagagc ttggtaggca attgaatcaa accacaggta aagctgaaga      2700 gccatgcaa gaagctagtg atctcaagaa aataaagcgc aattatcagt tagaattaga      2760 tctcttaat catgaaaaag ggaaactaca aagagaagta gacagaatca caagggcaca      2820 gctgtagct gagaagaata ttcagcattt aaattcacaa attcattctt ttcgagatga      2880 aaagaatta gaaagactac aaatctgcca gagaaaatca gatcatctaa aagaacaatt      2940 gagaaaagc catgagcagt tgcttcaaaa tatcaaagct gaaaagaaaa ataatgataa      3000 atccaaagg ctcaatgaag aattggagaa aagtaatgag tgtgcagaga tgctaaaaca      3060 aagtagag gagcttacta ggcagaataa tgaaaccaaa ttaatgatgc agagaattca      3120 gcagaatca gagaatatag ttttagagaa acaaactatc cagcaaagat gtgaagcact      3180 aaaattcag gcagatggtt ttaaagatca gctacgcagc acaaatgaac acttgcataa      3240 cagacaaaa acagagcagg atttttcaaag aaaaattaaa tgcctagaag aagacctggc      3300 aaaagtcaa aatttggtaa gtgaatttaa gcaaaagtgt gaccaacaga acattatcat      3360
```

```
cagaatacc aagaaagaag ttagaaatct gaatgcggaa ctgaatgctt ccaaagaaga      3420 aagcgacgc ggggagcaga aagttcagct acaacaagct caggtgcaag agttaaataa      3480 aggttgaaa aaagtacaag acgaattaca cttaaagacc atagaggagc agatgaccca      3540 agaaagatg gttctgtttc aggaagaatc tggtaaattc aaacaatcag cagaggagtt      3600 cggaagaag atggaaaaat taatggagtc caaagtcatc actgaaaatg atatttcagg      3660 attaggctt gactttgtgt ctcttcaaca agaaaactct agagcccaag aaaatgctaa      3720 ctttgtgaa acaaacatta agaacttga aagacagctt caacagtatc gtgaacaaat      3780 cagcaaggg cagcacatgg aagcaaatca ttaccaaaaa tgtcagaaac ttgaggatga      3840 ctgatagcc cagaagcgtg aggttgaaaa cctgaagcaa aaatggacc aacagatcaa      3900 gagcatgaa catcaattag ttttgctcca gtgtgaaatt caaaaaaaga gcacagccaa      3960 gactgtacc ttcaaaccag attttgagat acagtgaag gagtgccagc actctggaga      4020 ctgtcctct agaaacactg gacaccttca cccaacaccc agatcccctc tgttgagatg      4080 actcaagaa ccacagccat ggaagagaa gtggcagcat cgggttgttg aacagatacc      4140 aaagaagtc caattccagc caccagggc tccactcgag aaagagaaaa gccagcagtg      4200 tactctgag tactttctc agacaagcac cgagttacag ataactttg atgagacaaa      4260 cccattaca agactgtctg aaattgagaa gataagagac caagccctga acaattctag      4320 ccacctgtt aggtatcaag ataacgcatg tgaaatggaa ctggtgaagg ttttgacacc      4380 ttagagata gctaagaaca agcagtatga tatgcataca gaagtcacaa cattaaaaca      4440 gaaaagaac ccagttccca gtgctgaaga atggatgctt gaagggtgca gagcatctgg      4500 ggactcaag aaaggggatt tccttaagaa gggcttagaa ccagagacct tccagaactt      4560 gatggtgat catgcatgtt cagtcaggga tgatgaattt aaattccaag ggcttaggca      4620 actgtgact gccaggcagt tggtggaagc taagcttctg gacatgagaa caattgagca      4680 ctgcgactc ggtcttaaga ctgttgaaga agttcagaaa actcttaaca agtttctgac      4740 aaagccacc tcaattgcag ggctttacct agaatctaca aaagaaaaga tttcatttgc      4800 tcagcggcc gagagaatca taatagacaa aatggtggct ttggcatttt tagaagctca      4860 gctgcaaca ggttttataa ttgatcccat ttcaggtcag acatattctg ttgaagatgc      4920 gttcttaaa ggagttgttg accccgaatt cagaattagg cttcttgagg cagagaaggc      4980 gctgtggga tattcttatt cttctaagac attgtcagtg tttcaagcta tggaaaatag      5040 atgcttgac agacaaaaag gtaaacatat cttggaagcc cagattgcca gtggggtgt      5100 attgaccct gtgagaggca ttcgtgttcc tccagaaatt gctctgcagc agggggttgtt      5160 aataatgcc atcttacagt ttttacatga gccatccagc aacacaagag ttttccctaa      5220 cccaataac aagcaagctc tgtattactc agaattactg cgaatgtgtg tatttgatgt      5280 gagtcccaa tgctttctgt ttccatttgg ggagaggaac atttccaatc tcaatgtcaa      5340 aaaacacat agaatttctg tagtagatac taaaacagga tcagaattga ccgtgtatga      5400 gctttccag agaaacctga ttgagaaaag tatatatctt gaactttcag ggcagcaata      5460 cagtggaag gaagctatgt tttttgaatc ctatgggcat tcttctcata tgctgactga      5520 actaaaaca ggattacact tcaatattaa tgaggctata gagcagggaa caattgacaa      5580 gccttggtc aaaaagtatc aggaaggcct catcacactt acagaacttg ctgattcttt      5640 ctgagccgg ttagtcccca agaaagattt gcacagtcct gttgcagggt attggctgac      5700 gctagtggg gaaaggatct ctgtactaaa agcctcccgt agaaatttgg ttgatcggat      5760
```

| | |
|---|---|
| actgccctc cgatgccttg aagcccaagt cagtacaggg ggcataattg atcctcttac | 5820 |
| ggcaaaaag taccgggtgg ccgaagcttt gcatagaggc ctggttgatg aggggtttgc | 5880 |
| cagcagctg cgacagtgtg aattagtaat cacagggatt ggccatccca tcactaacaa | 5940 |
| atgatgtca gtggtggaag ctgtgaatgc aaatattata ataaggaaa tgggaatccg | 6000 |
| tgtttggaa tttcagtact tgacaggagg gttgatagag ccacaggttc actctcggtt | 6060 |
| tcaatagaa gaggctctcc aagtaggtat tatagatgtc ctcattgcca caaaactcaa | 6120 |
| gatcaaaag tcatatgtca gaaatataat atgccctcag acaaaaagaa agttgacata | 6180 |
| aaagaagcc ttagaaaaag ctgatttga tttccacaca ggacttaaac tgttagaagt | 6240 |
| tctgagccc ctgatgacag gaatttctag cctctactat tcttcctaat gggacatgtt | 6300 |
| aaataactg tgcaaggggt gatgcaggct ggttcatgcc acttttcag agtatgatga | 6360 |
| atcggctac atatgcagtc tgtgaattat gtaacatact ctatttcttg agggctgcaa | 6420 |
| ttgctaagt gctcaaaata gagtaagttt taaattgaaa attacataag atttaatgcc | 6480 |
| ttcaaatgg tttcatttag ccttgagaat ggttttttga aacttggcca cactaaaatg | 6540 |
| tttttttt tttacgtaga atgtgggata aacttgatga actccaagtt cacagtgtca | 6600 |
| ttcttcaga actcccttc attgaatagt gatcatttat taaatgataa attgcactcg | 6660 |
| tgaaagagc acgtcatgaa gcaccatgga atcaaagaga agatataaa ttcgttccca | 6720 |
| agccttcaa gctgcagtgt tttagattgc ttcaaaaaat gaaaagttt tgccttttc | 6780 |
| atatagtga ccttctttgc atattaaat gtttaccaca atgtcccatt tctagttaag | 6840 |
| cttcgcact tgaaagctaa cattatgaat attatgtgtt ggaggagggg aaggattttc | 6900 |
| tcattctgt gtattttccg g | 6921 |

<210> SEQ ID NO 118
<211> LENGTH: 946
<212> TYPE: DNA
<213> ORGANISM: Homo sapien

<400> SEQUENCE: 118

| | |
|---|---|
| cttctgactg ggctcaggct gacaggtaga gctcaccatg gcttcttgtg tccttgtccc | 60 |
| ctccccatca cagctgtggt gcagtccacc gtctccagtg gctatggcgg tgccagtggt | 120 |
| gtcggcagtg gcttaggcct gggtggagga agcagctact cctatggcag tggtcttggc | 180 |
| gttggaggtg gcttcagttc cagcagtggc agagccattg ggggtggcct cagctctgtt | 240 |
| ggaggcggca gttccaccat caagtacacc accacctcct cctccagcag gaagagctat | 300 |
| aagcactaaa gtgcgtctgc tagctctcgg tcccacagtc ctcaggcccc tctctggctg | 360 |
| cagagccctc tcctcaggtt gcctgtcctc tcctggcctc cagtctcccc tgctgtccca | 420 |
| ggtagagctg gggatgaatg cttagtgccc tcacttcttc tctctctctc tataccatct | 480 |
| gagcacccat tgctcaccat cagatcaacc tctgattta catcatgatg taatcaccac | 540 |
| tggagcttca ctgttactaa attattaatt tcttgcctcc agtgttctat ctctgaggct | 600 |
| gagcattata agaaaatgac ctctgctcct tttcattgca gaaaattgcc aggggcttat | 660 |
| ttcagaacaa cttccactta cttttccactg gctctcaaac tctctaactt ataagtgttg | 720 |
| tgaacccca cccaggcagt atccatgaaa gcacaagtga ctagtcctat gatgtacaaa | 780 |
| gcctgtatct ctgtgatgat ttctgtgctc ttcactgttt gcaattgcta aataaagcag | 840 |
| atttataata catatattct tttactttgc cttgctttgg ggccaaagtt ttgggcttaa | 900 |

-continued acttttttat ctgataagtg aatagttgtt tttaaaagat aatcta     946

<210> SEQ ID NO 119
<211> LENGTH: 8948
<212> TYPE: DNA
<213> ORGANISM: Homo sapien

<400> SEQUENCE: 119

```
caacagccc ctgctccttg ggcccctcca tgccatgccg taatctctcc cacccgacca     60
caccaacac ccagctccga cgcagctcct ctgcgccctt gccgccctcc gagccacagc    120
ttcctcccg ctcctgcccc cggcccgtcg ccgtctccgc gctcgcagcg gcctcgggag    180
gcccaggta gcgagcagcg acctcgcgag ccttccgcac tcccgcccgg ttccccggcc    240
tccgcctat ccttggcccc ctccgctttc tccgcgccgg cccgcctcgc ttatgcctcg    300
cgctgagcc gctctcccga ttgcccgccg acatgagctg caacggaggc tcccacccgc    360
gatcaacac tctgggccgc atgatccgcg ccgagtctgg cccggacctg cgctacgagg    420
gaccagcgg cggcgggggc accagcagga tgtactattc tcggcgcggc gtgatcaccg    480
ccagaactc ggacggctac tgtcaaaccg gcacgatgtc caggcaccag aaccagaaca    540
catccagga gctgctgcag aactgctccg actgcttgat gcgagcagag ctcatcgtgc    600
gcctgaatt gaagtatgga gatggaatac aactgactcg gagtcgagaa ttggatgagt    660
ttttgccca ggccaatgac caaatggaaa tcctcgacag cttgatcaga gagatgcggc    720
gatgggcca gccctgtgat gcttaccaga aaaggcttct tcagctccaa gagcaaatgc    780
agccccttta taaagccatc agtgtccctc gagtccgcag ggccagctcc aagggtggtg    840
aggctacac ttgtcagagt ggctctggct gggatgagtt caccaaacat gtcaccagtg    900
atgtttggg gtggatgagg cagcaagggc ggagatggga catggtggcc tggggtgtgg    960
cctggcctc agtggagcag cacattaaca gccaccgggg catccacaac tccatcggcg   1020
ctatcgctg gcagctggac aaaatcaaag ccgacctgcg cgagaaatct gcgatctacc   1080
gttggagga ggagtatgaa aacctgctga agcgtccctt tgagaggatg gatcacctgc   1140
acagctgca gaacatcatt caggccacgt ccagggagat catgtggatc aatgactgcg   1200
ggaggagga gctgctgtac gactggagcg acaagaacac caacatcgct cagaaacagg   1260
ggccttctc catacgcatg agtcaactgg aagttaaaga aaaagagctc aataagctga   1320
acaagaaag tgaccaactt gtcctcaatc agcatccagc ttcagacaaa attgaggcct   1380
tatggacac tctgcagacg cagtggagtt ggattcttca gatcaccaag tgcattgatg   1440
tcatctgaa agaaaatgct gcctactttc agttttttga agaggcgcag tctactgaag   1500
atacctgaa ggggctccag gactccatca ggaagaagta cccctgcgac aagaacatgc   1560
cctgcagca cctgctggaa cagatcaagg agctggagaa agaacgagag aaaatccttg   1620
atacaagcg tcaggtgcag aacttggtaa acaagtctaa gaagattgta cagctgaagc   1680
tcgtaaccc agactacaga agcaataaac ccattattct cagagctctc tgtgactaca   1740
acaagatca gaaaatcgtg cataaggggg atgagtgtat cctgaaggac aacaacgagc   1800
cagcaagtg gtacgtgacg ggcccgggag gcgttgacat gcttgttccc tctgtgggc   1860
gatcatccc tcctccgaac ccactggccg tggacctctc ttgcaagatt gagcagtact   1920
cgaagccat cttggctctg tggaaccagc tctacatcaa catgaagagc ctggtgtcct   1980
gcactactg catgattgac atagagaaga tcagggcat gacaatcgcc aagctgaaaa   2040
aatgcggca ggaagattac atgaagacga tagccgacct tgagttacat taccaagagt   2100
```

| | |
|---|---:|
| catcagaaa tagccaaggc tcagagatgt ttggagatga tgacaagcgg aaaatacagt | 2160 |
| tcagttcac cgatgcccag aagcattacc agaccctggt cattcagctc cctggctatc | 2220 |
| ccagcacca gacagtgacc acaactgaaa tcactcatca tggaacctgc caagatgtca | 2280 |
| ccataataa agtaattgaa accaacagag aaaatgacaa gcaagaaaca tggatgctga | 2340 |
| ggagctgca gaagattcgc aggcagatag agcactgcga gggcaggatg actctcaaaa | 2400 |
| cctccctct agcagaccag gggtcttctc accacatcac agtgaaaatt aacgagctta | 2460 |
| gagtgtgca gaatgattca caagcaattg ctgaggttct caaccagctt aaagatatgc | 2520 |
| tgccaactt cagaggttct gaaaagtact gctatttaca gaatgaagta tttggactat | 2580 |
| tcagaaact ggaaaatatc aatggtgtta cagatggcta cttaaatagc ttatgcacag | 2640 |
| aagggcact gctccaggct attctccaaa cagaagacat gttaaaggtt tatgaagcca | 2700 |
| gctcactga ggaggaaact gtctgcctgg acctggataa agtggaagct taccgctgtg | 2760 |
| actgaagaa aataaaaaat gacttgaact tgaagaagtc gttgttggcc actatgaaga | 2820 |
| agaactaca gaaagcccag cagatccact ctcagacttc acagcagtat ccactttatg | 2880 |
| tctggactt gggcaagttc ggtgaaaaag tcacacagct gacagaccgc tggcaaagga | 2940 |
| agataaaca gatcgacttt agattatggg acctggagaa acaaatcaag caattgagga | 3000 |
| ttatcgtga taactatcag gctttctgca agtggctcta tgatcgtaaa cgccgccagg | 3060 |
| ttccttaga atccatgaaa tttggagatt ccaacacagt catgcggttt ttgaatgagc | 3120 |
| gaagaactt gcacagtgaa atatctggca acgagacaa atcagaggaa gtacaaaaaa | 3180 |
| tgctgaact ttgcgccaat tcaattaagg attatgagct ccagctggcc tcatacacct | 3240 |
| aggactgga aactctgctg aacatacc ta tcaagaggac catgattcag tccccttctg | 3300 |
| ggtgattct gcaagaggct gcagatgttc atgctcggta cattgaacta cttacaagat | 3360 |
| tggagacta ttacaggttc ttaagtgaga tgctgaagag tttggaagat ctgaagctga | 3420 |
| aaataccaa gatcgaagtt ttggaagagg agctcagact ggcccgagat gccaactcgg | 3480 |
| aaactgtaa taagaacaaa ttcctggatc agaacctgca gaaataccag gcagagtgtt | 3540 |
| ccagttcaa agcgaagctt gcgagcctgg aggagctgaa gagacaggct gagctggatg | 3600 |
| gaagtcggc taagcaaaat ctagacaagt gctacggcca aataaagaa ctcaatgaga | 3660 |
| gatcacccg actgacttat gagattgaag atgaaaagag aagaagaaaa tctgtggaag | 3720 |
| cagatttga ccaacagaag aatgactatg accaactgca gaaagcaagg caatgtgaaa | 3780 |
| ggagaacct tggttggcag aaattagagt ctgagaaagc catcaaggag aaggagtacg | 3840 |
| gattgaaag gttgagggtt ctactgcagg aagaaggcac ccggaagaga gaatatgaaa | 3900 |
| tgagctggc aaaggtaaga aaccactata tgaggagat gagtaattta aggaacaagt | 3960 |
| tgaaacaga gattaacatt acgaagacca ccatcaagga gatatccatg caaaaagagg | 4020 |
| tgattccaa aaatcttaga aaccagcttg atagactttc aagggaaaat cgagatctga | 4080 |
| ggatgaaat tgtcaggctc aatgacagca tcttgcaggc cactgagcag cgaaggcgag | 4140 |
| tgaagaaaa cgcccttcag caaaaggcct gtggctctga taatgcag aagaagcagc | 4200 |
| tctggagat agaactgaag caggtcatgc agcagcgctc tgaggacaat gcccggcaca | 4260 |
| gcagtccct ggaggaggct gccaagacca ttcaggacaa aaataaggag atcgagagac | 4320 |
| caaagctga gtttcaggag gaggccaagc gccgctggga atatgaaaat gaactgagta | 4380 |
| ggtaagaaa caattatgat gaggagatca ttagcttaaa aaatcagttt gagaccgaga | 4440 |

-continued

```
caacatcac caagaccacc atccaccagc tcaccatgca gaaggaagag gataccagtg    4500 ctaccgggc tcagatagac aatctcaccc gagaaaacag gagcttatct gaagaaataa    4560 gaggctgaa gaacactcta acccagacca cagagaatct caggagggtg gaagaagaca    4620 ccaacagca aaaggccact ggctctgagg tgtctcagag gaaacagcag ctggaggttg    4680 gctgagaca agtcactcag atgcgaacag aggagagcgt aagatataag caatctcttg    4740 tgatgctgc caaaaccatc caggataaaa acaaggagat agaaaggtta aaacaactga    4800 cgacaaaga aacaaatgac cggaaatgcc tggaagatga aaacgcgaga ttacaaaggg    4860 ccagtatga cctgcagaaa gcaaacagta gtgcgacgga gacaataaac aaactgaagg    4920 tcaggagca agaactgaca cgcctgagga tcgactatga aagggtttcc caggagagga    4980 tgtgaagga ccaggatatc acgcggttcc agaactctct gaaagagctg cagctgcaga    5040 gcagaaggt ggaagaggag ctgaatcggc tgaagaggac cgcgtcagaa gactcctgca    5100 gaggaagaa gctggaggaa gagctggaag gcatgaggag gtcgctgaag gagcaagcca    5160 caaaatcac caacctgacc cagcagctgg agcaggcatc cattgttaag aagaggagtg    5220 ggatgacct ccggcagcag agggacgtgc tggatggcca cctgagggaa aagcagagga    5280 ccaggaaga gctgaggagg ctctcttctg aggtcgaggc cctgaggcgg cagttactcc    5340 ggaacagga aagtgtcaaa caagctcact tgaggaatga gcatttccag aaggcgatag    5400 agataaaag cagaagctta aatgaaagca aaatagaaat tgagaggctg cagtctctca    5460 agagaacct gaccaaggag cacttgatgt tagaagaaga actgcggaac ctgaggctgg    5520 gtacgatga cctgaggaga ggacgaagcg aagcggacag tgataaaaat gcaaccatct    5580 ggaactaag gagccagctg cagatcagca acaaccggac cctggaactg caggggctga    5640 taatgattt acagagagag agggaaaatt tgagacagga aattgagaaa ttccaaaagc    5700 ggctttaga ggcatctaat aggattcagg aatcaaagaa tcagtgtact caggtggtac    5760 ggaaagaga gagccttctg gtgaaaatca aagtcctgga gcaagacaag gcaaggctgc    5820 gaggctgga ggatgagctg aatcgtgcaa aatcaactct agaggcagaa accagggtga    5880 acagcgcct ggagtgtgag aaacagcaaa ttcagaatga cctgaatcag tggaagactc    5940 atattcccg caaggaggag gctattagga agatagaatc ggaaagagaa aagagtgaga    6000 agagaagaa cagtcttagg agtgagatcg aaagactcca agcagagatc aagagaattg    6060 agagaggtg caggcgtaag ctggaggatt ctaccaggga gacacagtca cagttagaaa    6120 agaacgctc ccgatatcag agggagattg ataaactcag acagcgccca tatgggtccc    6180 tcgagagac ccagactgag tgtgagtgga ccgttgcac ctccaagctg gtgtttgatg    6240 gctgaggaa gaaggtgaca gcaatgcagc tctatgagtg tcagctgatc gacaaaacaa    6300 cttggacaa actattgaag gggaagaagt cagtggaaga agttgcttct gaaatccagc    6360 attccttcg gggtgcagga tctatcgctg gagcatctgc ttctcctaag gaaaaatact    6420 tttggtaga ggccaagaga aagaaattaa tcagcccaga atccacagtc atgcttctgg    6480 ggcccaggc agctacaggt ggtataattg atccccatcg gaatgagaag ctgactgtcg    6540 cagtgccat agctcgggac ctcattgact tcgatgaccg tcagcagata tatgcagcag    6600 aaaagctat cactggtttt gatgatccat tttcaggcaa gacagtatct gtttcagaag    6660 catcaagaa aaatttgatt gatagagaaa ccggaatgcg cctgctggaa gcccagattg    6720 ttcagggg tgtagtagac cctgtgaaca gtgtctttt gccaaaagat gtcgccttgg    6780 ccgggggct gattgataga gatttgtatc gatccctgaa tgatccccga gatagtcaga    6840
```

```
aaactttgt ggatccagtc accaaaaaga aggtcagtta cgtgcagctg aaggaacggt      6900 cagaatcga accacatact ggtctgctct tgctttcagt acagaagaga agcatgtcct      6960 ccaaggaat cagacaacct gtgaccgtca ctgagctagt agattctggt atattgagac      7020 gtccactgt caatgaactg gaatctggtc agatttctta tgacgaggtt ggtgagagaa      7080 taaggactt cctccagggt tcaagctgca tagcaggcat atacaatgag accacaaaac      7140 gaagcttgg catttatgag gccatgaaaa ttggcttagt ccgacctggt actgctctgg      7200 gttgctgga agcccaagca gctactggct ttatagtgga tcctgttagc aacttgaggt      7260 accagtgga ggaagcctac aagagaggtc tggtgggcat tgagttcaaa gagaagctcc      7320 gtctgcaga acgagctgtc actgggtata atgatcctga aacaggaaac atcatctctt      7380 gttccaagc catgaataag gaactcatcg aaaagggcca cggtattcgc ttattagaag      7440 acagatcgc aaccggggg atcattgacc caaaggagag ccatcgttta ccagttgaca      7500 agcatataa gagggctat ttcaatgagg aactcagtga gattctctca gatccaagtg      7560 tgataccaa aggattttttt gaccccaaca ctgaagaaaa tcttacctat ctgcaactaa      7620 agaaagatg cattaaggat gaggaaacag ggctctgtct tctgcctctg aaagaaaaga      7680 gaaacaggt gcagacatca caaaagaata ccctcaggaa gcgtagagtg tcatagttg      7740 cccagaaac caataaagaa atgtctgttc aggaggccta caagaagggc ctaattgatt      7800 tgaaacctt caaagaactg tgtgagcagg aatgtgaatg ggaagaaata accatcacgg      7860 atcagatgg ctccaccagg gtggtcctgg tagatagaaa gacaggcagt cagtatgata      7920 tcaagatgc tattgacaag ggccttgttg acaggaagtt ctttgatcag taccgatccg      7980 cagcctcag cctcactcaa tttgctgaca tgatctcctt gaaaaatggt gtcggcacca      8040 cagcagcat gggcagtggt gtcagcgatg atgtttttag cagctcccga catgaatcag      8100 aagtaagat ttccaccata tccagcgtca ggaatttaac cataaggagc agctctttttt      8160 agacaccct ggaagaatcg agccccattg cagccatctt tgacacagaa aacctggaga      8220 aatctccat tacagaaggt atagagcggg gcatcgttga cagcatcacg ggtcagaggc      8280 tctggaggc tcaggcctgc acaggtggca tcatccaccc aaccacgggc cagaagctgt      8340 acttcagga cgcagtctcc cagggtgtga ttgaccaaga catggccacc agcgtgaagc      8400 tgctcagaa agccttcata ggcttcgagg gtgtgaaggg aaagaagaag atgtcagcag      8460 agaggcagt gaaagaaaaa tggctcccgt atgaggctgg ccagcgcttc ctggagttcc      8520 gtacctcac gggaggtctt gttgacccgg aagtgcatgg gaggataagc accgaagaag      8580 catccggaa gggggttcata gatggccgcg ccgcacagag gctgcaagac accagcagct      8640 tgccaaaat cctgacctgc cccaaaacca aattaaaaat atcctataag gatgccataa      8700 tcgctccat ggtagaagat atcactgggc tgcgccttct ggaagccgcc tccgtgtcgt      8760 caagggctt acccagccct tacaacatgt cttcggctcc ggggtcccgc tccggctccc      8820 ctcgggatc tcgctccgga tctcgctccg ggtccgcag tgggtcccgg agaggaagct      8880 tgacgccac agggaattct tcctactctt attcctactc atttagcagt agttctattg      8940
gcactag                                                              8948
```

<210> SEQ ID NO 120
<211> LENGTH: 587
<212> TYPE: DNA
<213> ORGANISM: Homo sapien
<220> FEATURE:

<221> NAME/KEY: misc_feature
<222> LOCATION: (1)...(587)
<223> OTHER INFORMATION: n = A,T,C or G

<400> SEQUENCE: 120

| | | |
|---|---|---|
| cgtcctaagc acttagacta catcagggaa gaacacagac cacatccctg tcctcatgcg | 60 |
| gcttatgttt tctggaagaa agtggagacc nagtccttgg ctttagggct ccccggctgg | 120 |
| gggctgtgca ntccggtcag ggcgggaagg gaaatgcacc gctgcatgtg aacttacagc | 180 |
| ccaggcggat gccccttccc ttagcactac ctggcctcct gcatcccctc gcctcatgtt | 240 |
| cctcccacct tcaaanaatg aanaacccca tgggcccagc cccttgccct ggggaaccaa | 300 |
| ggcagccttc caaaactcag gggctgaagc anactattag ggcaggggct gactttgggt | 360 |
| gacactgccc attccctctc agggcagctc angtcacccn ggnctcttga acccagcctg | 420 |
| ttcctttgaa aaagggcaaa actgaaaagg gcttttccta naaaaagaaa accagggaa | 480 |
| ctttgccagg gcttcnntnt taccaaaacn ncttctcnng gattttaat tccccattng | 540 |
| gcctccactt accngggggcn atgccccaaa attaanaatt tcccatc | 587 |

<210> SEQ ID NO 121
<211> LENGTH: 619
<212> TYPE: DNA
<213> ORGANISM: Homo sapien
<220> FEATURE:
<221> NAME/KEY: misc_feature
<222> LOCATION: (1)...(619)
<223> OTHER INFORMATION: n = A,T,C or G

<400> SEQUENCE: 121

| | | |
|---|---|---|
| cactagtagg atagaaacac tgtgtcccga gagtaaggag agaagctact attgattaga | 60 |
| gcctaaccca ggttaactgc aagaagaggc gggatacttt cagcttttcca tgtaactgta | 120 |
| tgcataaagc caatgtagtc cagtttctaa gatcatgttc caagctaact gaatcccact | 180 |
| tcaatacaca ctcatgaact cctgatggaa caataacagg cccaagcctg tggtatgatg | 240 |
| tgcacacttg ctagactcan aaaaaatact actctcataa atgggtggga gtattttggt | 300 |
| gacaacctac tttgcttggc tgagtgaagg aatgatattc atatattcat ttattccatg | 360 |
| gacatttagt tagtgctttt tatataccag gcatgatgct gagtgacact cttgtgtata | 420 |
| tttccaaatt tttgtacagt cgctgcacat atttgaaatc atatattaag acttccaaaa | 480 |
| aatgaagtcc ctggtttttc atggcaactt gatcagtaaa ggattcncct ctgtttggta | 540 |
| cttaaaacat ctactatatn gttnanatga aattccttt cccncctcc cgaaaaaana | 600 |
| aagtggtggg gaaaaaaaa | 619 |

<210> SEQ ID NO 122
<211> LENGTH: 1475
<212> TYPE: DNA
<213> ORGANISM: Homo sapien

<400> SEQUENCE: 122

| | | |
|---|---|---|
| tccacctgtc cccgcagcgc cggctcgcgc cctcctgccg cagccaccga gccgccgtct | 60 |
| agcgccccga cctcgccacc atgagagccc tgctggcgcg cctgcttctc tgcgtcctgg | 120 |
| tcgtgagcga ctccaaaggc agcaatgaac ttcatcaagt tccatcgaac tgtgactgtc | 180 |
| taaatggagg aacatgtgtg tccaacaagt acttctccaa cattcactgg tgcaactgcc | 240 |
| caaagaaatt cggagggcag cactgtgaaa tagataagtc aaaaacctgc tatgagggaa | 300 |
| atggtcactt ttaccgagga aaggccagca ctgacaccat gggccggccc tgcctgccct | 360 |

```
ggaactctgc cactgtcctt cagcaaacgt accatgccca cagatctgat gctcttcagc    420
tgggcctggg gaaacataat tactgcagga acccagacaa ccggaggcga ccctggtgct    480
atgtgcaggt gggcctaaag ccgcttgtcc aagagtgcat ggtgcatgac tgcgcagatg    540
gaaaaaagcc ctcctctcct ccagaagaat taaaatttca gtgtggccaa aagactctga    600
ggccccgctt taagattatt gggggagaat tcaccaccat cgagaaccag ccctggtttg    660
cggccatcta caggaggcac cggggggggct ctgtcaccta cgtgtgtgga ggcagcctca   720
tcagcccttg ctgggtgatc agcgccacac actgcttcat tgattaccca aagaaggag    780 actacatcgt ctacctgggt cgctcaaggc ttaactccaa cacgcaaggg gagatgaagt    840
ttgaggtgga aaacctcatc ctacacaagg actacagcgc tgacacgctt gctcaccaca    900
acgacattgc cttgctgaag atccgttcca aggagggcag gtgtgcgcag ccatcccgga    960
ctatacagac catctgcctg ccctcgatgt ataacgatcc ccagtttggc acaagctgtg   1020
agatcactgg cttttggaaaa gagaattcta ccgactatct ctatccggag cagctgaaga   1080
tgactgttgt gaagctgatt tccaccggg agtgtcagca gccccactac tacggctctg   1140
aagtcaccac caaaatgctg tgtgctgctg acccacagtg gaaaacagat tcctgccagg   1200
gagactcagg ggacccctc gtctgttccc tccaaggccg catgactttg actggaattg   1260
tgagctgggg ccgtggatgt gccctgaagg acaagccagg cgtctacacg agagtctcac   1320
acttcttacc ctggatccgc agtcacacca aggaagagaa tggcctggcc ctctgagggt   1380
ccccagggag gaaacgggca ccacccgctt tcttgctggt tgtcattttt gcagtagagt   1440
catctccatc agctgtaaga gagactggg aagat                                 1475
```

<210> SEQ ID NO 123
<211> LENGTH: 2294
<212> TYPE: DNA
<213> ORGANISM: Homo sapien

<400> SEQUENCE: 123

```
cagcgccggc tcgcgccctc ctgccgcagc caccgagccg ccgtctagcg ccccgacctc     60
gccaccatga gagccctgct ggcgcgcctg cttctctgcg tcctggtcgt gagcgactcc    120
aaaggcagca atgaacttca tcaagttcca tcgaactgtg actgtctaaa tggaggaaca    180
tgtgtgtcca acaagtactt ctccaacatt cactggtgca actgcccaaa gaaattcgga    240
gggcagcact gtgaaataga taagtcaaaa acctgctatg aggggaatgg tcacttttac    300
cgaggaaagg ccagcactga caccatgggc cggccctgcc tgccctggaa ctctgccact    360
gtccttcagc aaacgtacca tgcccacaga tctgatgctc ttcagctggg cctggggaaa    420
cataattact gcaggaaccc agacaaccgg aggcgaccct ggtgctatgt gcaggtgggc    480
ctaaagccgc ttgtccaaga gtgcatggtg catgactgcg cagatggaaa aaagccctcc    540
tctcctccag aagaattaaa atttcagtgt ggccaaaaga ctctgaggcc ccgctttaag    600
attattgggg gagaattcac caccatcgag aaccagcccc ggtttgcggc catctacagg    660
aggcaccggg ggggctctgt cacctacgtg tgtggaggca gcctcatcag cccttgctgg    720
gtgatcagcg ccacacactg cttcattgat tacccaaaga aggaggacta catcgtctac    780
ctgggtcgct caaggcttaa ctccaacacg caaggggaga tgaagtttga ggtggaaaac    840
ctaatcctac acaaggacta cagcgctgac acgcttgctc accaacga cattgccttg    900 ctgaagatcc gttccaagga gggcaggtgt gcgcagccat cccggactat acagaccatc    960
```

-continued

```
tgcctgccct cgatgtataa cgatccccag tttggcacaa gctgtgagat cactggcttt    1020
ggaaaagaga attctaccga ctatctctat ccggagcagc tgaaaatgac tgttgtgaag    1080
ctgatttccc accgggagtg tcagcagccc cactactacg gctctgaagt caccaccaaa    1140
atgctgtgtg ctgctgaccc acagtggaaa acagattcct gccagggaga ctcaggggga    1200
cccctcgtct gttccctcca aggccgcatg actttgactg gaattgtgag ctggggccgt    1260
ggatgtgccc tgaaggacaa gccaggcgtc tacacgagag tctcacactt cttaccctgg    1320
atccgcagtc acaccaagga agagaatggc ctggccctct gagggtcccc agggaggaaa    1380
cgggcaccac ccgctttctt gctggttgct attttgcagt agagtcatct ccatcagctg    1440
taagaagagc tgggaatata ggctctgcac agatggattt gcctgtgcca ccaccagggc    1500
gaacgacaat agctttaccc tcaggcatag gcctgggtgc tggctgccca gacccctctg    1560
gccaggatgg aggggtggtc ctgactcaac atgttactga ccagcaactt gtcttttttct    1620 ggactgaagc ctgcaggagt taaaaagggc agggcatctc ctgtgcatgg gctcgaaggg    1680
agagccagct cccccgaccg gtgggcattt gtgaggccca tggttgagaa atgaataatt    1740
tcccaattag gaagtgtaag cagctgaggt ctcttgaggg agcttagcca atgtgggagc    1800
agcggtttgg ggagcagaga cactaacgac ttcagggcag ggctctgata ttccatgaat    1860
gtatcaggaa atatatatgt gtgtgtatgt ttgcacactt gtgtgtgggc tgtgagtgta    1920
agtgtgagta agagctggtg tctgattgtt aagtctaaat atttccttaa actgtgtgga    1980
ctgtgatgcc acacagagtg gtctttctgg agaggttata ggtcactcct ggggcctctt    2040 gggtcccca cgtgacagtg cctgggaatg tattattctg cagcatgacc tgtgaccagc    2100
actgtctcag tttcactttc acatagatgt ccctttcttg gccagttatc ccttcctttt    2160
agcctagttc atccaatcct cactgggtgg ggtgaggacc actcctgtac actgaatatt    2220
tatatttcac tattttattt tatattttg taattttaaa taaaagtgat caataaaatg    2280
tgatttttct gatg                                                     2294
```

<210> SEQ ID NO 124
<211> LENGTH: 956
<212> TYPE: DNA
<213> ORGANISM: Homo sapien

<400> SEQUENCE: 124

```
gatgagttcc gcaccaagtt tgagacagac caggccctgc gcctgagtgt ggaggccgac      60
atcaatggcc tgcgcagggt gctggatgag ctgaccctgg ccagagccga cctggagatg     120
cagattgaga acctcaagga ggagctggcc tacctgaaga gaaccacga ggaggagatg      180 aacgccctgc gaggccaggt gggtggtgag atcaatgtgg agatggacgc tgccccaggc     240
gtggacctga gccgcatcct caacgagatg cgtgaccagt atgagaagat ggcagagaag     300
aaccgcaagg atgccgagga ttggttcttc agcaagacag aggaactgaa ccgcgaggtg     360
gccaccaaca gtgagctggt gcagagtggc aagagtgaga tctcggagct ccggcgcacc     420
atgcaggcct tggagataga gctgcagtcc cagctcagca tgaaagcatc cctggagggc     480
aacctggcgg agacagagaa ccgctactgc gtgcagctgt cccagatcca ggggctgatt     540
ggcagcgtgg aggagcagct ggcccagctt cgctgcgaga tggagcagca gaaccaggaa     600
tacaaaatcc tgctggatgt gaagacgcgc tggagcagg agattgccac ctaccgccgc     660
ctgctggagg gagaggatgc ccacctgact cagtacaaga agaaccggt gaccacccgt     720 caggtgcgta ccattgtgga agaggtccag gatggcaagg tcatctcctc ccgcgagcag     780
```

| | |
|---|---|
| gtccaccaga ccaccegctg aggactcagc taccccggcc ggccacccag gaggcaggga | 840 |
| cgcagccgcc ccatctgccc cacagtctcc ggcctctcca gcctcagccc cctgcttcag | 900 |
| tcccttcccc atgcttcctt gcctgatgac aataaaagct tgttgactca gctatg | 956 |

<210> SEQ ID NO 125
<211> LENGTH: 486
<212> TYPE: DNA
<213> ORGANISM: Homo sapien
<220> FEATURE:
<221> NAME/KEY: misc_feature
<222> LOCATION: (1)...(486)
<223> OTHER INFORMATION: n = A,T,C or G

<400> SEQUENCE: 125

| | |
|---|---|
| aaattatata tagtgnttca gctcccattg tggtgttcat agtcttctag gaacagataa | 60 |
| acttaagtat tcaattcact cttggcattt tttcttaat ataggctttt tagcctattt | 120 |
| ttggaaaact gctttcttc tgagaacctt attctgaatg tcatcaactt taccaaacct | 180 |
| tctaagtcca gagctaactt agtactgttt aagttactat tgactgaatt ttcttcattt | 240 |
| tctgtttagc cagtgttacc aaggtaagct ggggaatgaa gtataccaac ttctttcaga | 300 |
| gcattttagg acattatggc agctttagaa ggctgtcttg tttctagcca agggagagcc | 360 |
| agcgcaggtt ttggatacta gagaaagtca tttgcttgta ctattgccat tttagaaagc | 420 |
| tctgatgtga attcaaattt tacctctgtt acttaaagcc aacaattta aggcagtagt | 480 |
| tttact | 486 |

<210> SEQ ID NO 126
<211> LENGTH: 3552
<212> TYPE: DNA
<213> ORGANISM: Homo sapien

<400> SEQUENCE: 126

| | |
|---|---|
| cggcaggcag gtctcgtctc ggcaccctcc cggcgcccgc gttctcctgg ccctgcccgg | 60 |
| catcccgatg gccgccgctg ggccccggcg ctccgtgcgc ggagccgtct gcctgcatct | 120 |
| gctgctgacc ctcgtgatct tcagtcgtgc tggtgaagcc tgcaaaaagg tgatacttaa | 180 |
| tgtaccttct aaactagagg cagacaaaat aattggcaga gttaatttgg aagagtgctt | 240 |
| caggtctgca gacctcatcc ggtcaagtga tcctgatttc agagttctaa atgatgggtc | 300 |
| agtgtacaca gccagggctg ttgcgctgtc tgataagaaa agatcattta ccatatggct | 360 |
| ttctgacaaa aggaaacaga cacagaaaga ggttactgtg ctgctagaac atcagaagaa | 420 |
| ggtatcgaag acaagacaca ctagagaaac tgttctcagg cgtgccaaga ggagatgggc | 480 |
| acctattcct tgctctatgc aagagaattc cttgggccct tcccattgt ttcttcaaca | 540 |
| agttgaatct gatgcagcac agaactatac tgtcttctac tcaataagtg gacgtggagt | 600 |
| tgataaagaa cctttaaatt tgttttatat agaaagagac actggaaatc tattttgcac | 660 |
| tcggcctgtg gatcgtgaag aatatgatgt ttttgatttg attgcttatg cgtcaactgc | 720 |
| agatggatat tcagcagatc tgcccctccc actacccatc agggtagagg atgaaaatga | 780 |
| caaccaccct gttttcacag aagcaattta aatttttgaa gttttggaaa gtagtagacc | 840 |
| tggtactaca gtgggggtgg tttgtgccac agacagagat gaaccggaca caatgcatac | 900 |
| gcgcctgaaa tacagcattt tgcagcagac accaaggtca cctgggctct tttctgtgca | 960 |
| tcccagcaca ggcgtaatca ccacagtctc tcattatttg gacagagagg ttgtagacaa | 1020 |

```
gtactcattg ataatgaaag tacaagacat ggatggccag ttttttggat tgataggcac    1080
atcaacttgt atcataacag taacagattc aaatgataat gcacccactt tcagacaaaa    1140
tgcttatgaa gcatttgtag aggaaaatgc attcaatgtg gaaatcttac gaataccatt    1200
agaagataag gatttaatta acactgccaa ttggagagtc aattttacca ttttaagggg    1260
aaatgaaaat ggacatttca aaatcagcac agacaaagaa actaatgaag gtgttctttc    1320
tgttgtaaag ccactgaatt atgaagaaaa ccgtcaagtg aacctggaaa ttggagtaaa    1380
caatgaagcg ccatttgcta gagatattcc cagagtgaca gccttgaaca gagccttggt    1440
tacagttcat gtgagggatc tggatgaggg gcctgaatgc actcctgcag cccaatatgt    1500
gcggattaaa gaaaacttag cagtggggtc aaagatcaac ggctataagg catatgaccc    1560
cgaaaataga aatggcaatg gtttaaggta caaaaaattg catgatccta aaggttggat    1620
caccattgat gaaatttcag ggtcaatcat aacttccaaa atcctggata gggaggttga    1680
aactcccaaa atgagttgt ataatattac agtcctggca atagacaaag atgatagatc    1740
atgtactgga acacttgctg tgaacattga agatgtaaat gataatccac cagaaatact    1800
tcaagaatat gtagtcattt gcaaaccaaa aatggggtat accgacattt tagctgttga    1860
tcctgatgaa cctgtccatg gagctccatt ttatttcagt ttgcccaata cttctccaga    1920
aatcagtaga ctgtggagcc tcaccaaagt taatgataca gctgcccgtc tttcatatca    1980
gaaaaatgct ggatttcaag aatataccat tcctattact gtaaaagaca gggccggcca    2040
agctgcaaca aaattattga gagttaatct gtgtgaatgt actcatccaa ctcagtgtcg    2100
tgcgacttca aggagtacag gagtaatact tggaaaatgg gcaatccttg caatattact    2160
gggtatagca ctgctctttt ctgtattgct aactttagta tgtggagttt ttggtgcaac    2220
taaagggaaa cgttttcctg aagatttagc acagcaaaac ttaattatat caaacacaga    2280
agcacctgga gacgatagag tgtgctctgc caatggattt atgacccaaa ctaccaacaa    2340
ctctagccaa ggttttttgtg gtactatggg atcaggaatg aaaaatggag ggcaggaaac    2400
cattgaaatg atgaaaggag gaaaccagac cttggaatcc tgccgggggg ctgggcatca    2460 tcatacccctg gactcctgca ggggaggaca cacggaggtg gacaactgca gatacactta    2520
ctcggagtgg cacagtttta ctcaaccccg tctcggtgaa aaattgcatc gatgtaatca    2580
gaatgaagac cgcatgccat cccaagatta tgtcctcact tataactatg agggaagagg    2640
atctccagct ggttctgtgg gctgctgcag tgaaaagcag gaagaagatg gccttgactt    2700
tttaaataat ttggaaccca aatttattac attagcagaa gcatgcacaa agagataatg    2760
tcacagtgct acaattaggt ctttgtcaga cattctggag gtttccaaaa ataatattgt    2820
aaagttcaat ttcaacatgt atgtatatga tgatttttt ctcaattttg aattatgcta    2880
ctcaccaatt tatattttta aagcaagttg ttgcttatct ttttcaaaaa gtgaaaaatg    2940
ttaaaacaga caactggtaa atctcaaact ccagcactgg aattaaggtc tctaaagcat    3000
ctgctctttt ttttttttac agatatttta gtaataaata tgctggataa atattagtcc    3060
aacaatagct aagttatgct aatatcacat tattatgtat tcactttaag tgatagttta    3120
aaaaataaac aagaaatatt gagtatcact atgtgaagaa agttttggaa agaaacaatt    3180
gaagactgaa ttaaattaaa aatgttgcag ctcataaaga attggactca ccctactgc    3240 actaccaaat tcatttgact ttggaggcaa aatgtgttga agtgccctat gaagtagcaa    3300
ttttctatag gaatatagtt ggaaataaat gtgtgtgtgt atattattat taatcaatgc    3360
aatatttaaa tgaaatgaga acaaagagga aaatggtaaa aacttgaaat gaggctgggg    3420
```

| | |
|---|---|
| tatagtttgt cctacaatag aaaaaagaga gagcttccta ggcctgggct cttaaatgct | 3480 |
| gcattataac tgagtctatg aggaaatagt tcctgtccaa tttgtgtaat ttgttaaaa | 3540 |
| ttgtaaataa at | 3552 |

<210> SEQ ID NO 127
<211> LENGTH: 754
<212> TYPE: DNA
<213> ORGANISM: Homo sapien

<400> SEQUENCE: 127

| | |
|---|---|
| ttttttttt ttgtcattgt tcattgattt taatgagaaa gctaagagag gaaataagta | 60 |
| gcctttcaaa ggtcacacag aagtaagtga cagatccagg attcatatcc aagcattctg | 120 |
| gctctagtgt ccatgcttct caaccattat gacccaatat tcaaccaaat caatactgaa | 180 |
| ggacacgtga aatgtatccg gtattttact attacaaaca aaaatccaat gaacattctt | 240 |
| gaagacatac acaaaaataa tggttacaat agaagttact ggaattgaaa ttttggttca | 300 |
| acctatatta aaatgtaagg cttttgatat agctaataga ttttttgaaat gatcagtctt | 360 |
| aacgtttgta ggggagcaca ctcctgcatg gggaaaagat tcactgtgaa gcacagagca | 420 |
| cctttatggt tggatcatct tgtcattaaa gttcaggcgt tatctatcct gtaagtggca | 480 |
| gaatcaagac tgcaatatcg cctgcttttc ttttaactc atgttttccc ttgactacac | 540 |
| tggtcctcaa agtaaaaccc ctgtgtcagt gtactattca tggaatactc tgcaattata | 600 |
| accaccttct aatacttta atacccaatc aaaatttatt atacatatgt atcatagata | 660 |
| ctcatctgta aagctgtgct tcaaaatagt gatctcttcc caacattaca atatatatta | 720 |
| atgatgtcga acctgcccgg gcggccgctc gaag | 754 |

<210> SEQ ID NO 128
<211> LENGTH: 374
<212> TYPE: DNA
<213> ORGANISM: Homo sapien

<400> SEQUENCE: 128

| | |
|---|---|
| aggttttgat taaaaaggca aatgatttta ttgttcgata atcttttaaa aaaataagag | 60 |
| gaaggagtaa aattaaagat gaaagatgat ttttatttcc ttgtgacctc tatatccccc | 120 |
| ttccctgcc cttggtaagt aactcttgat ggagaaagga ttaaagactc ttatttaacc | 180 |
| aaaaacaga gccagctaat catttccaaa ggttagtatc tccctgctga cctcttcttt | 240 |
| ggtttaattg aataaaacta tatgttcata tatgtattaa acaactcag aataacatct | 300 |
| tttcttcctt agttaaggca ttataagggc tatactatca tccataataa ccaaggcaat | 360 |
| aacttaaaaa gctg | 374 |

<210> SEQ ID NO 129
<211> LENGTH: 546
<212> TYPE: DNA
<213> ORGANISM: Homo sapien

<400> SEQUENCE: 129

| | |
|---|---|
| agtgtgatgg atatctgcag aattcgggct aagcgtggtc gcggcccgag gtctggaact | 60 |
| tcccagcacy tgaaaaggag cctcctgagc tgactcggct aaagccccac tttcgctcct | 120 |
| cctcatttct gcctactgat ttccttggag cattcatctg aatattaccg tttgctgtgt | 180 |
| aacctggtac atacatagca tgactccctg gaatagagtg ggctggggtg cttatgctgg | 240 |

| | |
|---|---|
| gagagtgatt gacatgcact ttcaagctat atctaccatt tgcagcaaag gagaaaaaat | 300 |
| acctcgagta aattccatca tttttttataa catcagcacc tgctccatca tcaaggagtc | 360 |
| tcagcgtaac aggatctcca gtctctggct caactgtggc agtgacagtg cattaagaa | 420 |
| tgggataaaa tccctgtttc acattggcat aaatcatcac aggatgagga aaatggaggc | 480 |
| tgtctctttc cacaaaggct tccacagtgg ctgggggcac agacctgccc gggcggccgc | 540 |
| tcgaaa | 546 |

<210> SEQ ID NO 130
<211> LENGTH: 5156
<212> TYPE: DNA
<213> ORGANISM: Homo sapien

<400> SEQUENCE: 130

| | |
|---|---|
| ccaaccgag gcgccgggca gcgacccctg cagcggagac agagactgag cggcccggca | 60 |
| cgccatgcc tgcgctctgg ctgggctgct gcctctgctt gtcgctcctc ctgcccgcag | 120 |
| ccgggccac ctccaggagg gaagtctgtg attgcaatgg gaagtccagg cagtgtatct | 180 |
| tgatcggga acttcacaga caaactggta atggattccg ctgcctcaac tgcaatgaca | 240 |
| cactgatgg cattcactgc gagaagtgca agaatggctt ttaccggcac agagaaaggg | 300 |
| ccgctgttt gccctgcaat tgtaactcca aaggttctct tagtgctcga tgtgacaact | 360 |
| cggacggtg cagctgtaaa ccaggtgtga caggagccag atgcgaccga tgtctgccag | 420 |
| cttccacat gctcacggat gcggggtgca cccaagacca gagactgcta gactccaagt | 480 |
| tgactgtga cccagctggc atcgcagggc cctgtgacgc gggccgctgt gtctgcaagc | 540 |
| agctgtcac tggagaacgc tgtgataggt gtcgatcagg ttactataat ctggatgggg | 600 |
| gaaccctga gggctgtacc cagtgtttct gctatggca ttcagccagc tgccgcagct | 660 |
| tgcagaata cagtgtccat aagatcacct ctacctttca tcaagatgtt gatggctgga | 720 |
| ggctgtcca acgaaatggg tctcctgcaa agctccaatg gtcacagcgc catcaagatg | 780 |
| gtttagctc agcccaacga ctagaccctg tctatttgt ggctcctgcc aaatttcttg | 840 |
| gaatcaaca ggtgagctat ggtcaaagcc tgtcctttga ctaccgtgtg acagaggag | 900 |
| cagacaccc atctgcccat gatgtgattc tggaaggtgc tggtctacgg atcacagctc | 960 |
| cttgatgcc acttggcaag acactgcctt gtgggctcac caagacttac acattcaggt | 1020 |
| aaatgagca tccaagcaat aattggagcc cccagctgag ttactttgag tatcgaaggt | 1080 |
| actgcggaa tctcacagcc ctccgcatcc gagctacata tggagaatac agtactgggt | 1140 |
| cattgacaa tgtgaccctg atttcagccc gccctgtctc tggagcccca gcaccctggg | 1200 |
| tgaacagtg tatatgtcct gttgggtaca aggggcaatt ctgccaggat tgtgcttctg | 1260 |
| ctacaagag agattcagcg agactggggc cttttggcac ctgtattcct tgtaactgtc | 1320 |
| aggggagg ggcctgtgat ccagacacag gagattgtta ttcagggat gagaatcctg | 1380 |
| cattgagtg tgctgactgc ccaattggtt tctacaacga tccgcacgac ccccgcagct | 1440 |
| caagccatg tccctgtcat aacgggttca gctgctcagt gatgccggag acggaggagg | 1500 |
| ggtgtgcaa taactgcccc tcccggggtca ccggtgcccg ctgtgagctc tgtgctgatg | 1560 |
| ctactttgg ggacccctt ggtgaacatg gcccagtgag gccttgtcag ccctgtcaat | 1620 |
| caacaacaa tgtggacccc agtgcctctg ggaattgtga ccggctgaca ggcaggtgtt | 1680 |
| gaagtgtat ccacaacaca gccggcatct actgcgacca gtgcaaagca ggctacttcg | 1740 |
| ggacccatt ggctcccaac ccagcagaca gtgtcgagc ttgcaactgt aaccccatgg | 1800 |

-continued

```
ctcagagcc tgtaggatgt cgaagtgatg gcacctgtgt ttgcaagcca ggatttggtg      1860
ccccaactg tgagcatgga gcattcagct gtccagcttg ctataatcaa gtgaagattc      1920
gatggatca gtttatgcag cagcttcaga gaatggaggc cctgatttca aaggctcagg      1980
tggtgatgg agtagtacct gatacagagc tggaaggcag gatgcagcag gctgagcagg      2040
ccttcagga cattctgaga gatgcccaga tttcagaagg tgctagcaga tcccttggtc      2100
ccagttggc caaggtgagg agccaagaga acagctacca gagccgcctg gatgacctca      2160
gatgactgt ggaaagagtt cgggctctgg gaagtcagta ccagaaccga gttcgggata      2220
tcacaggct catcactcag atgcagctga gcctggcaga aagtgaagct tccttgggaa      2280
cactaacat tcctgcctca gaccactacg tggggccaaa tggctttaaa agtctggctc      2340
ggaggccac aagattagca gaaagccacg ttgagtcagc cagtaacatg gagcaactga      2400
aagggaaac tgaggactat tccaaacaag ccctctcact ggtgcgcaag gccctgcatg      2460
aggagtcgg aagcggaagc ggtagcccgg acggtgctgt ggtgcaaggg cttgtggaaa      2520
attggagaa aaccaagtcc ctggcccagc agttgacaag ggaggccact caagcggaaa      2580
tgaagcaga taggtcttat cagcacagtc tccgcctcct ggattcagtg tctcggcttc      2640
gggagtcag tgatcagtcc tttcaggtgg aagaagcaaa gaggatcaaa caaaaagcgg      2700
ttcactctc aagcctggta accaggcata tggatgagtt caagcgtaca cagaagaatc      2760
gggaaactg gaaagaagaa gcacagcagc tcttacgaaa tggaaaaagt gggagagaga      2820
atcagatca gctgctttcc cgtgccaatc ttgctaaaag cagagcacaa gaagcactga      2880
tatgggcaa tgccactttt tatgaagttg agagcatcct taaaaacctc agagagtttg      2940
cctgcaggt ggacaacaga aaagcagaag ctgaagaagc catgaagaga ctctcctaca      3000
cagccagaa ggtttcagat gccagtgaca agacccagca agcagaaaga gccctgggga      3060
cgctgctgc tgatgcacag agggcaaaga atggggccgg ggaggccctg gaaatctcca      3120
tgagattga acaggagatt gggagtctga acttggaagc caatgtgaca gcagatggag      3180
cttggccat ggaaaaggga ctggcctctc tgaagagtga gatgagggaa gtggaaggag      3240
gctggaaag gaaggagctg gagtttgaca cgaatatgga tgcagtacag atggtgatta      3300
agaagccca gaaggttgat accagagcca agaacgctgg ggttacaatc caagacacac      3360
caacacatt agacggcctc ctgcatctga tggaccagcc tctcagtgta gatgaagagg      3420
gctggtctt actggagcag aagctttccc gagccaagac ccagatcaac agccaactgc      3480
gcccatgat gtcagagctg gaagagaggg cacgtcagca gaggggccac ctccatttgc      3540
ggagacaag catagatggg attctggctg atgtgaagaa cttggagaac attagggaca      3600
cctgccccc aggctgctac aatacccagg ctcttgagca acagtgaagc tgccataaat      3660
tttctcaac tgaggttctt gggatacaga tctcaggggct cgggagccat gtcatgtgag      3720
gggtgggat ggggacattt gaacatgttt aatgggtatg ctcaggtcaa ctgacctgac      3780
ccattcctg atccatggcc aggtggttg tcttattgca ccatactcct tgcttcctga      3840
gctgggcaa tgaggcagat agcactgggt gtgagaatga tcaaggatct ggaccccaaa      3900
aatagactg gatggaagaa caaactgcac aggcagatgt ttgcctcata atagtcgtaa      3960
tggagtcct ggaatttgga caagtgctgt tgggatatag tcaacttatt ctttgagtaa      4020
gtgactaaa ggaaaaaact ttgactttgc ccaggcatga aattcttcct aatgtcagaa      4080
agagtgcaa cccagtcaca ctgtggccag taaaatacta ttgcctcata ttgtcctctg      4140
```

-continued

```
aagcttctt gctgatcaga gttcctccta cttacaaccc agggtgtgaa catgttctcc    4200 ttttcaagc tggaagaagt gagcagtgtt ggagtgagga cctgtaaggc aggcccattc    4260 gagctatgg tgcttgctgg tgcctgccac cttcaagttc tggacctggg catgacatcc    4320
ttctttttaa tgatgccatg caacttaga gattgcattt ttattaaagc atttcctacc    4380 gcaaagcaa atgttgggaa agtatttact ttttcggttt caaagtgata gaaaagtgtg    4440 cttgggcat tgaaagaggt aaaattctct agatttatta gtcctaattc aatcctactt    4500 tagaacacc aaaaatgatg cgcatcaatg tattttatct tattttctca atctcctctc    4560 ctttcctcc acccataata agagaatgtt cctactcaca cttcagctgg gtcacatcca    4620 ccctccatt catccttcca tccatctttc catccattac ctccatccat ccttccaaca    4680 atatttatt gagtacctac tgtgtgccag ggctggtgg acagtggtg acatagtctc     4740 gccctcata gagttgattg tctagtgagg aagacaagca ttttaaaaa ataaatttaa     4800 cttacaaac tttgtttgtc acaagtggtg tttattgcaa taaccgcttg gtttgcaacc    4860 ctttgctca acagaacata tgttgcaaga ccctcccatg ggggcacttg agttttggca    4920 ggctgacag agctctgggt tgtgcacatt tctttgcatt ccagctgtca ctctgtgcct    4980 tctacaact gattgcaaca gactgttgag ttatgataac accagtggga attgctggag    5040 aaccagagg cacttccacc ttggctggga agactatggt gctgccttgc ttctgtattt    5100 cttggattt tcctgaaagt gttttaaat aaagaacaat tgttagaaaa aaaaaa       5156
```

<210> SEQ ID NO 131
<211> LENGTH: 671
<212> TYPE: DNA
<213> ORGANISM: Homo sapien

<400> SEQUENCE: 131

```
aggtctggag ggcccacagc cggatgtggg acaccgggaa aaagtggtca tagcacacat    60
ttttgcatcc cggttgcagt gtgttgcaga cgaagtcctc ttgctcgtca ccccacactt   120
cctgggcagc caycacgagg atcatgactc ggaaaataaa gatgactgtg atccacacct   180
tcccgatgct ggtggagtgt ttgttgacac ccccgatgaa agtgtgcagc gtcccccaat   240
ccattgcgct ggtttatccc tgagtcctgt ttccaacgac tgccagtgtt tcagacccaa   300
agaatgaggg caagatccct ctgcgagggt ttcagacctc cttctcctac cccactggag   360
tgcctagaag ccaatgggtg cacagtgatg atacgaatgt caatctttgc tcggtcagtg   420
aggatgtcgc ctggaatatt caaattgaat tacagatgca tgaagagggc gtacaagtta   480 gaattttct ttcgccatac agaaattgtt tagccagatc ttctgtactt cttttccttc     540 cctgacccett cctgctcccc aggaagggag gtcagccccg tttgcaaaac acaggatgcc   600
cgtgacaccg gagacaggtc ttcttcaccg acaggaagtg ccttctggtg cctgcacgtt   660
ttaactgcta t                                                         671
```

<210> SEQ ID NO 132
<211> LENGTH: 590
<212> TYPE: DNA
<213> ORGANISM: Homo sapien

<400> SEQUENCE: 132

```
ctgaatggaa aagcttatgg ctctgtgatg atattagtga ccagcggaga tgataagctt     60
cttggcaatt gcttacccac tgtgctcagc agtggttcaa caattcactc cattgccctg   120
ggttcatctg cagccccaaa tctggaggaa ttatcacgtc ttacaggagg tttaaagttc   180
```

```
tttgttccag atatatcaaa ctccaatagc atgattgatg ctttcagtag aatttcctct      240
ggaactggag acattttcca gcaacatatt cagcttgaaa gtacaggtga aaatgtcaaa      300
cctcaccatc aattgaaaaa cacagtgact gtggataata ctgtgggcaa cgacactatg      360
tttctagtta cgtggcaggc cagtggtcct cctgagatta tattatttga tcctgatgga      420
cgaaaatact acacaaataa ttttatcacc aatctaactt ttcggacagc tagtctttgg      480
attccaggaa cagctaagcc tgggcactgg acttacaccc tgaacaatac ccatcattct      540
ctgcaagccc tgaaagtgac agtgacctct cgcgcctcca actcagacct                590

<210> SEQ ID NO 133
<211> LENGTH: 581
<212> TYPE: DNA
<213> ORGANISM: Homo sapien

<400> SEQUENCE: 133
aggtcctgtc cggggggcact gagaactccc tctggaattc ttgggggggtg ttggggagag      60 actgtgggcc tggagataaa acttgtctcc tctaccacca ccctgtaccc tagcctgcac     120
ctgtcctcat ctctgcaaag ttcagcttcc ttccccaggt ctctgtgcac tctgtcttgg     180
atgctctggg gagctcatgg gtggaggagt ctccaccaga ggggaggctca ggggactggt     240 tgggccaggg atgaatattt gagggataaa aattgtgtaa gagccaaaga attggtagta     300
gggggagaac agagaggagc tgggctatgg gaaatgattt gaataatgga gctgggaata     360
tggctggata tctggtacta aaaaagggtc tttaagaacc tacttcctaa tctcttcccc     420
aatccaaacc atagctgtct gtccagtgct ctcttcctgc ctccagctct gccccaggct     480
cctcctagac tctgtccctg ggctagggca ggggaggagg gagagcaggg ttgggggaga     540
ggctgaggag agtgtgacat gtggggagag gaccagacct c                        581

<210> SEQ ID NO 134
<211> LENGTH: 4797
<212> TYPE: DNA
<213> ORGANISM: Homo sapien
<220> FEATURE:
<221> NAME/KEY: misc_feature
<222> LOCATION: (1)...(4797)
<223> OTHER INFORMATION: n = A,T,C or G

<400> SEQUENCE: 134
cctgggacca aagtgctgcc cagagctgag ggtcctggag ccacatgaga aggcttctcc       60
ctgtgtacct gtgcagcaca gggtagggtg agtccactca gctgtctagg agaggaccca     120
ggagcagcag agacncgcca agcctttact cataccatat tctgatcctt ttccagcaaa     180
ttgtggctac taatttgccc cctgaagatc aagatggctc tggggatgac tctgacaact     240
tctccggctc aggtgcaggt gaggttgtca tggggccccc cccacccaa gacggcaaca     300 ggtcatgcct gggggcagtg gtcaggcagt ctcctgtgtt tactgagcat gtactgagtg     360
caccctgcct gccctgtctc cacccagctg gctccaaagg gcaatgctga ggagaggaat     420
ggggtcgtga gctgctgtta aggagagctc atgcttggag gtgaggtgaa ggctgtgagc     480
tccagaaggc cccagggcgc nctgctgcac gcaggctcat attcactagg aatagcttta     540
ctcactaaga aacctctgga acccccttca gaaggttatt tgactcctga gcctctattt     600
tctcatctgc aaaatgggaa taataccttg acctgataag cttgtggagc tgtaaggcag     660
cacagagcca gctgggggtgt agctcttcca tccaagctcc cttccttact tcccctttcc     720
```

-continued

```
tgtggggact gggggagaga agtccctgag ctggaggtgg tcaggaagc  ttcacagagg     780
aggtggctct tgagtggacc tcaggaagag gggtgagaga gctaaggaag gaggctgagg     840
tcatccctgg ggaagtgacc tagcggaggc ctgagagctg caaggtagga tatctgttgt     900
tggaagtgtc tgttgttgga agtgggggcc ttttttttcag ggagggtggg gccagagaag    960
tgtgtgccct gggataagta ggataaccac agtagttatg ccctaaggg  atgcccaccc    1020
caccctgtg  gtcacagaaa agctttccca ggtggcctag gcacctgtct cgtggctcca    1080
gagacaggct gcacctgaca cacacaatgg aaggacagct ctccttgtcc attttccaag    1140
gagcttagcc tcagctgcct tgtccaggta ctagcctccc tcatagcctg agcttggcca    1200
gcccaggtgc tctggagcct ccccgaccc  acccaacaca ctctgcttct ggtcctcccc    1260
acccccacc  tccccaacac actctgcttc tggtcctgca ggtgctttgc aagatatcac    1320
cttgtcacag cagacccctt ccacttggaa ggacacgcag ctcctgacgg ctattcccac    1380
gtctccagaa cccaccggcc tggaggctac agctgcctcc acctccaccc tgccggctgg    1440
agagggccc  aaggaggag  aggctgtagt cctgccagaa gtggagcctg gcctcaccgc    1500
ccgggagcag gaggccaccc cccgacccag ggagaccaca cagctcccga ccactcatca    1560
ggcctcaacg accacagcca ccacggccca ggagcccgcc acctccaccc ccacaggga    1620
catgcagcct ggccaccatg agacctcaac ccctgcagga cccagccaag ctgaccttca    1680
cactccccac acagaggatg gaggtccttc tgccaccgag agggctgctg aggatggagc    1740
ctccagtcag ctcccagcag cagagggctc tggggagcag gtgagtggcc tctgcattcc    1800
ttgggaaatt gagtgggttg gtcctaatgc ctggcacttg gcaggcccta cacctgtgcc    1860
ctgcgcgatc tcgtattcct caccaggaag acagggcaca ggggccgcct tcccctaccc    1920
ccagggcctc gcagagcagg acagactaac tatgagatca gagcagaagc acccttaaag    1980
atcacccaag agagggctcc caaactcaca atccaaactt gcagccctcg tcgaagagtg    2040
aacgttatac cagtcatttt atttatagct tcgtggattt acgcttacac taaatagtct    2100
gctattcata caaaatgtgt gctttgtatc acttttttgtg atatccatgc catggtccag    2160
ccagggtccg gagttgatgt ggcaagaagg cctggctttc gggccctgtg cgatcctggt    2220
ttgggtgcat ctgagtgggt ggtggcaaag atcaggagg  caggagctgc ttctgggtct    2280
gtagtggagc tggttgctgc tgctggcggt gacctggcca acccaatctg cccctgccct    2340
cccacaggac ttcacctttg aaacctcggg ggagaatacg gctgtagtgg ccgtggagcc    2400
tgaccgccgg aaccagtccc cagtggatca ggggccacg  ggggcctcac agggcctcct    2460
ggacaggaaa gaggtgctgg gaggtgagtt ttctttcagg ggggtagttt ggggtgaatt    2520
gctgctgtgg ggtcagggtg gggctgacca cagccaaggc cactgctttg ggagggtctg    2580
cacgagagcc caaggagccg ctgagctgag ctggccccgt ctacctgccc tagggtcat    2640
tgccggaggc ctcgtggggc tcatctttgc tgtgtgcctg gtgggtttca tgctgtaccg    2700
catgaagaag aaggacgaag gcagctactc cttggaggag ccgaaacaag ccaacgcgg    2760
ggcctaccag aagcccacca acaggagga  attctatgcc tgacgcggga gccatgcgcc    2820
ccctccgccc tgccactcac tagggcccca cttgcctctt ccttgaagaa ctgcaggccc    2880
tggcctcccc tgccaccagg ccacctcccc agcattccag cccctctggt cgctcctgcc    2940
cacgagtcg  tgggtgtgct gggagctcca ctctgcttct ctgacttctg cctggagact    3000
tagggcacca ggggtttctc gcataggacc tttccaccac agccagcacc tggcatcgca    3060
ccattctgac tcggtttctc caaactgaag cagcctctcc ccaggtccag ctctggaggg    3120
```

-continued

```
gaggggatc cgactgcttt ggacctaaat ggcctcatgt ggctggaaga tcctgcgggt      3180
ggggcttggg gctcacacac ctgtagcact tactggtagg accaagcatc ttgggggggt     3240
ggccgctgag tggcagggga caggagtcac tttgtttcgt ggggaggtct aatctagata     3300
tcgacttgtt tttgcacatg tttcctctag ttctttgttc atagcccagt agaccttgtt    3360
acttctgagg taagttaagt aagttgattc ggtatccccc catcttgctt ccctaatcta    3420
tggtcgggag acagcatcag ggttaagaag acttttttttt tttttttaa actaggagaa    3480
ccaaatctgg aagccaaaat gtaggcttag tttgtgtgtt gtctcttgag tttgtcgctc    3540
atgtgtgcaa cagggtatgg actatctgtc tggtggcccc gttctggtgg tctgttggca    3600
ggctggccag tccaggctgc cgtggggccg ccgcctcttt caagcagtcg tgcctgtgtc    3660
catgcgctca gggccatgct gaggcctggg ccgctgccac gttggagaag cccgtgtgag    3720
aagtgaatgc tgggactcag ccttcagaca gagaggactg tagggagggc ggcaggggcc    3780
tggagatcct cctgcaggct cacgcccgtc ctcctgtggc gccgtctcca ggggctgctt    3840
cctcctggaa attgacgagg ggtgtcttgg gcagagctgg ctctgagcgc ctccatccaa    3900
ggccaggttc tccgttagct cctgtggccc caccctgggc cctgggctgg aatcaggaat    3960
attttccaaa gagtgatagt cttttgcttt tggcaaaact ctacttaatc caatgggttt    4020
ttccctgtac agtagatttt ccaaatgtaa taaactttaa tataaagtag tctgtgaatg    4080
ccactgcctt cgcttcttgc ctctgtgctg tgtgtgacgt gaccggactt ttctgcaaac    4140
accaacatgt tgggaaactt ggctcgaatc tctgtgcctt cgtctttccc atggggaggg    4200
attctggttc cagggtccct ctgtgtattt gcttttttgt tttggctgaa attctcctgg    4260
aggtcggtag gttcagccaa ggttttataa ggctgatgtc aatttctgtg ttgccaagct    4320
ccaagcccat cttctaaatg gcaaaggaag gtggatggcc ccagcacagc ttgacctgag    4380
gctgtggtca cagcggaggt gtggagccga ggcctacccc ncagacacct tggacatcct    4440
cctcccaccc ggctgcagag gccagannnc agcccaggt cctgcactta cttgcttatt    4500
tgacaacgtt tcagcgactc cgttggccac tccgagagtg ggccagtctg tggatcagag    4560
atgcaccacc aagccaaggg aacctgtgtc cggtattcga tactgcgact ttctgcctgg    4620
agtgtatgac tgcacatgac tcgggggtgg ggaaaggggt cggctgacca tgctcatctg    4680
ctggtccgtg ggacggtncc caagccagag gtgggttcat ttgtgtaacg acaataaacg    4740
gtacttgtca tttcgggcaa cggctgctgt ggtggtggtt gagtctcttc ttggcct       4797
```

<210> SEQ ID NO 135
<211> LENGTH: 2856
<212> TYPE: DNA
<213> ORGANISM: Homo sapien

<400> SEQUENCE: 135

```
tagtcgcggg tccccgagtg agcacgccag ggagcaggag accaaacgac gggggtcgga      60
gtcagagtcg cagtgggagt ccccggaccg gagcacgagc ctgagcggga gagcgccgct     120
cgcacgcccg tcgccacccg cgtacccggc gcagccagag ccaccagcgc agcgctgcca     180
tggagcccag cagcaagaag ctgacgggtc gcctcatgct ggctgtggga ggagcagtgc    240
ttggctccct gcagtttggc tacaacactg gagtcatcaa tgccccccag aaggtgatcg    300
aggagttcta caaccagaca tgggtccacc gctatgggga gagcatcctg cccaccacgc    360
tcaccacgct ctggtccctc tcagtggcca tcttttctgt tgggggcatg attggctcct    420
```

```
tctctgtggg ccttttcgtt aaccgctttg gccggcggaa ttcaatgctg atgatgaacc    480
tgctggcctt cgtgtccgcc gtgctcatgg gcttctcgaa actgggcaag tcctttgaga    540
tgctgatcct gggccgcttc atcatcggtg tgtactgcgg cctgaccaca ggcttcgtgc    600
ccatgtatgt gggtgaagtg tcacccacag cctttcgtgg ggccctgggc accctgcacc    660
agctgggcat cgtcgtcggc atcctcatcg cccaggtgtt cggcctggac tccatcatgg    720
gcaacaagga cctgtggccc ctgctgctga gcatcatctt catcccggcc ctgctgcagt    780
gcatcgtgct gcccttctgc cccgagagtc ccgcttcct gctcatcaac cgcaacgagg    840
agaaccgggc caagagtgtg ctaaagaagc tgcgcgggac agctgacgtg acccatgacc    900
tgcaggagat gaaggaagag agtcggcaga tgatgcggga agaaggtc accatcctgg    960 agctgttccg ctcccccgcc taccgccagc ccatcctcat cgctgtggtg ctgcagctgt   1020
cccagcagct gtctggcatc aacgctgtct tctattactc cacgagcatc ttcgagaagg   1080 cggggtgca gcagcctgtg tatgccacca ttggctccgg tatcgtcaac acggccttca   1140
ctgtcgtgtc gctgtttgtg gtggagcgag caggccggcg gaccctgcac tcataggcc   1200 tcgctggcat ggcgggttgt gccatactca tgaccatcgc gctagcactg ctggagcagc   1260
taccctggat gtcctatctg agcatcgtgg ccatctttgg cttgtgcc ttctttgaag    1320 tgggtcctgg ccccatccca tggttcatcg tggctgaact cttcagccag ggtccacgtc   1380
cagctgccat tgccgttgca ggcttctcca actggacctc aaatttcatt gtgggcatgt   1440
gcttccagta tgtggagcaa ctgtgtggtc cctacgtctt catcatcttc actgtgctcc   1500
tggttctgtt cttcatcttc acctacttca agttcctga gactaaaggc cggaccttcg   1560
atgagatcgc ttccggcttc cggcagggggg gagccagcca aagtgataag acacccgagg   1620
agctgttcca tcccctgggg gctgattccc aagtgtgagt cgccccagat caccagcccg   1680
gcctgctccc agcagcccta aggatctctc aggagcacag gcagctggat gagacttcca   1740
aacctgacag atgtcagccg agccgggcct ggggctcctt tctccagcca gcaatgatgt   1800
ccagaagaat attcaggact taacggctcc aggattttaa caaaagcaag actgttgctc   1860
aaatctattc agacaagcaa caggttttat aattttttta ttactgattt tgttattttt   1920
atatcagcct gagtctcctg tgcccacatc ccaggcttca ccctgaatgg ttccatgcct   1980
gagggtggag actaagccct gtcgagacac ttgccttctt cacccagcta atctgtaggg   2040
ctggacctat gtcctaagga cacactaatc gaactatgaa ctacaaagct tctatcccag   2100
gaggtggcta tggccacccg ttctgctggc ctggatctcc ccactctagg ggtcaggctc   2160
cattaggatt tgcccttcc catctcttcc tacccaacca ctcaaattaa tctttctta    2220 cctgagacca gttgggagca ctggagtgca gggaggagag gggaagggcc agtctgggct   2280
gccgggttct agtctccttt gcactgaggg ccacactatt accatgagaa gagggcctgt   2340
gggagcctgc aaactcactg ctcaagaaga catggagact cctgccctgt tgtgtataga   2400
tgcaagatat ttatatatat ttttggttgt caatattaaa tacagacact aagttatagt   2460
atatctggac aagccaactt gtaaatacac cacctcactc ctgttactta cctaaacaga   2520
tataaatggc tggttttag aaacatggtt ttgaaatgct tgtggattga gggtaggagg   2580
tttggatggg agtgagacag aagtaagtgg ggttgcaacc actgcaacgg cttagacttc   2640
gactcaggat ccagtccctt acacgtacct ctcatcagtg tcctcttgct caaaaatctg   2700
tttgatccct gttacccaga gaatatatac attctttatc ttgacattca aggcatttct   2760
atcacatatt tgatagttgg tgttcaaaaa aacactagtt ttgtgccagc cgtgatgctc   2820
```

```
aggcttgaaa tcgcattatt ttgaatgtga agggaa                              2856
```

<210> SEQ ID NO 136
<211> LENGTH: 356
<212> TYPE: DNA
<213> ORGANISM: Homo sapien

<400> SEQUENCE: 136

```
ggtggagcca aatgaagaaa atgaagatga aagagacaga cacctcagtt tttctggatc     60
aggcattgat gatgatgaag attttatctc cagcaccatt tcaaccacac cacgggcttt    120
tgaccacaca aaacagaacc aggactggac tcagtggaac ccaagccatt caaatccgga    180
agtgctactt cagacaacca caaggatgac tgatgtagac agaaatggca ccactgctta    240
tgaaggaaac tggaacccag aagcacaccc tcccctcatt caccatgagc atcatgagga    300
agaagagacc ccacattcta caagcacaat ccaggcaact cctagtagta caacgg        356
```

<210> SEQ ID NO 137
<211> LENGTH: 356
<212> TYPE: DNA
<213> ORGANISM: Homo sapien
<220> FEATURE:
<221> NAME/KEY: misc_feature
<222> LOCATION: (1)...(356)
<223> OTHER INFORMATION: n = A,T,C or G

<400> SEQUENCE: 137

```
gcaggtggag aagacatttt attgttcctg ggtctctgg aggcccattg gtggggctgg      60
gtcactggct gcccccggaa cagggcgctg ctccatggct ctgcttgtgg tagtctgtgg    120
ctatgtctcc cagcaaggac agaaactcag aaaaatcaat cttcttatcc tcattcttgt    180
ccttttctc aaagacatcg gcgaggtaat ttgtgccctt tttacctcgg cccgcgacca    240
cgctaaggcc aaanttccag acanayggcc gggccggtnc nataggggan cccaacttgg    300
ggacccaaac tctggcgcgg aaacacangg gcataagctt gnttcctgtg gggaaa        356
```

<210> SEQ ID NO 138
<211> LENGTH: 353
<212> TYPE: DNA
<213> ORGANISM: Homo sapien

<400> SEQUENCE: 138

```
aggtccagtc ctccacttgg cctgatgaga gtggggagtg gcaagggacg tttctcctgc     60
aatagacact tagatttctc tcttgtggga agaaaccacc tgtccatcca ctgactcttc    120
tacattgatg tggaaattgc tgctgctacc accacctcct gaagaggctt ccctgatgcc    180
aatgccagcc atcttggcat cctggccctc gagcaggctg cggtaagtag cgatctcctg    240
ctccagccgt gtctttatgt caagcagcat cttgtactcc tggttctgag cctccatctc    300
gcatcggagc tcactcagac ctcgsccgsg mssmcgctam gccgaattcc agc           353
```

<210> SEQ ID NO 139
<211> LENGTH: 371
<212> TYPE: DNA
<213> ORGANISM: Homo sapien

<400> SEQUENCE: 139

```
agcgtggtcg cggccgaggt ccatccgaag caagattgca gatggcagtg tgaagagaga     60
agacatattc tacacttcaa agctttggtg caattcccat cgaccagagt tggtccgacc    120
```

-continued

| | |
|---|---|
| agccttggaa aggtcactga aaaatcttca attggattat gttgacctct accttattca | 180 |
| ttttccagtg tctgtaaagc caggtgagga agtgatccca aaagatgaaa atggaaaaat | 240 |
| actatttgac acagtggatc tctgtgccac gtgggaggcc gtgagaagt gtaaagatgc | 300 |
| aggattggac ctgcccgggc ggccgctcga agccgaatt ccagcacact ggcggccgtt | 360 |
| actagtggat c | 371 |

<210> SEQ ID NO 140
<211> LENGTH: 370
<212> TYPE: DNA
<213> ORGANISM: Homo sapien

<400> SEQUENCE: 140

| | |
|---|---|
| tagcgtggtc gcggccgagg tccatctccc tttgggaact aggggctgc tggtgggaaa | 60 |
| tgggagccag ggcagatgtt gcattccttt gtgtccctgt aaatgtggga ctacaagaag | 120 |
| aggagctgcc tgagtggtac tttctcttcc tggtaatcct ctggcccagc ctcatggcag | 180 |
| aatagaggta ttttaggct atttttgtaa tatggcttct ggtcaaaatc cctgtgtagc | 240 |
| tgaattccca agccctgcat tgtacagccc cccactcccc tcaccaccta ataaaggaat | 300 |
| agttaacact caaaaaaaaa aaaaaacctg cccgggcggc cgctcgaaag ccgaattcca | 360 |
| gcacactggc | 370 |

<210> SEQ ID NO 141
<211> LENGTH: 371
<212> TYPE: DNA
<213> ORGANISM: Homo sapien

<400> SEQUENCE: 141

| | |
|---|---|
| tagcgtggtc gcggccgagg tcctctgtgc tgcctgtcac agcccgatgg taccagcgca | 60 |
| gggtgtaggc agtgcaggag ccctcatcca gtggcaggga acaggggtca tcactatccc | 120 |
| aaggagcttc aggtcctgg tactcctcca cagaatactc ggagtattca gagtactcat | 180 |
| catcctcagg gggtacccgc tcttcctcct ctgcatgaga gacgcggagc acaggcacag | 240 |
| catggagctg ggagccggca gtgtctgcag cataactagg gaggggtcgt gatccagatg | 300 |
| cgatgaactg gccctggcag gcacagtgct gactcatctc ttggcgacct gcccgggcgg | 360 |
| ccgctcgaag c | 371 |

<210> SEQ ID NO 142
<211> LENGTH: 343
<212> TYPE: DNA
<213> ORGANISM: Homo sapien

<400> SEQUENCE: 142

| | |
|---|---|
| gcgttttgag gccaatggtg taaaggaaa tatcttcaca taaaaactag atggaagcat | 60 |
| tgtcagaaac ctctttgtga tgtttgcttt caactcacag agttgaacat tccttttcat | 120 |
| agagcagttt tgaaacactc ttttgtagaa tttgcaagcg gatgattgga tcgctatgag | 180 |
| gtcttcattg gaaacgggat accttttacat aaaaactaga cagtagcatt ctcagaaatt | 240 |
| tctttgggat gtgggcattc aacccacaga ggagaacttc atttgataga gcagttttga | 300 |
| aacacccttt ttgtagaatc tacaggtgga catttagagt gct | 343 |

<210> SEQ ID NO 143
<211> LENGTH: 354
<212> TYPE: DNA
<213> ORGANISM: Homo sapien

<400> SEQUENCE: 143

```
aggtctgatg gcagaaaaac tcagactgtc tgcaacttta cagatggtgc attggttcag    60
catcaggagt gggatgggaa ggaaagcaca ataacaagaa aattgaaaga tgggaaatta   120
gtggtggagt gtgtcatgaa caatgtcacc tgtactcgga tctatgaaaa agtagaataa   180
aaattccatc atcactttgg acaggagtta attaagagaa tgaccaagct cagttcaatg   240
agcaaatctc catactgttt ctttcttttt tttttcatta ctgtgttcaa ttatctttat   300
cataaacatt ttacatgcag ctatttcaaa gtgtgttgga ttaattagga tcat         354
```

<210> SEQ ID NO 144
<211> LENGTH: 353
<212> TYPE: DNA
<213> ORGANISM: Homo sapien

<400> SEQUENCE: 144

```
ggtcaaggac ctgggggacc cccaggtcca gcagccacat gattctgcag cagacaggga    60
cctagagcac atctggatct cagccccacc cctggcaacc tgcctgccta gagaactccc   120
aagatgacag actaagtagg attctgccat ttagaataat tctggtatcc tgggcgttgc   180
gttaagttgc ttaactttca ttctgtctta cgatagtctt cagaggtggg aacagatgaa   240
gaaaccatgc cccagagaag gttaagtgac ttcctcttta tggagccagt gttccaacct   300
aggtttgcct gataccagac ctgtggcccc acctcccatg caggtctctg tgg          353
```

<210> SEQ ID NO 145
<211> LENGTH: 371
<212> TYPE: DNA
<213> ORGANISM: Homo sapien

<400> SEQUENCE: 145

```
caggtctgtc ataaactggt ctggagtttc tgacgactcc ttgttcacca aatgcaccat    60
ttcctgagac ttgctggcct ctccgttgag tccacttggc tttctgtcct ccacagctcc   120
attgccactg ttgatcacta gcttttctt ctgcccacac cttcttcgac tgttgactgc   180
aatgcaaact gcaagaatca aagccaaggc caagagggat gccaagatga tcagccattc   240
tggaatttgg ggtgtcctta taggaccaga ggttgtgttt gctccacctt cttgactccc   300
atgtgagacc tcggccgcga ccacgctaag ccgaattcca gcacactggc ggcccgttac   360
tagtggatcc g                                                        371
```

<210> SEQ ID NO 146
<211> LENGTH: 355
<212> TYPE: DNA
<213> ORGANISM: Homo sapien

<400> SEQUENCE: 146

```
ggtcctccgt cctcttccca gaggtgtcgg ggcttggccc cagcctccat cttcgtctct    60
caggatggcg agtagcagcg gctccaaggc tgaattcatt gtcggaggga aatataaact   120
ggtacggaag atcgggtctg gctccttcgg ggacatctat ttggcgatca acatcaccaa   180
cggcgaggaa gtggcagtga agctagaatc tcagaaggcc aggcatcccc agttgctgta   240
cgagagcaag ctctataaga ttcttcaagg tggggttggc atcccccaca tacggtggta   300
tggtcaggaa aaagactaca atgtactagt catggatctt ctgggaccta gcctc        355
```

<210> SEQ ID NO 147

<211> LENGTH: 355
<212> TYPE: DNA
<213> ORGANISM: Homo sapien

<400> SEQUENCE: 147

| ggtctgttac | aaaatgaaga | cagacaacac | aacatttact | ctgtggagat | atcctactca | 60 |
| tactatgcac | gtgctgtgat | tttgaacata | actcgtccca | aaaacttgtc | acgatcatcc | 120 |
| tgactttta | ggttggctga | tccatcaatc | ttgcactcaa | ctgttacttc | tttcccagtg | 180 |
| ttgttaggag | caaagctgac | ctgaacagca | accaatggct | gtagataccc | aacatgcagt | 240 |
| tttttcccat | aatatgggaa | atattttaag | tctatcattc | cattatgagg | ataaactgct | 300 |
| acatttggta | tatcttcatt | ctttgaaaca | caatctatcc | ttggcactcc | ttcag | 355 |

<210> SEQ ID NO 148
<211> LENGTH: 369
<212> TYPE: DNA
<213> ORGANISM: Homo sapien

<400> SEQUENCE: 148

| aggtctctct | ccccctctcc | ctctcctgcc | agccaagtga | agacatgctt | acttcccctt | 60 |
| caccttcctt | catgatgtgg | gaagagtgct | gcaacccagc | cctagccaac | accgcatgag | 120 |
| agggagtgtg | ccgagggctt | ctgagaaggt | ttctctcaca | tctagaaaga | agcgcttaag | 180 |
| atgtggcagc | ccctcttctt | caagtggctc | ttgtcctgtt | gccctgggag | ttctcaaatt | 240 |
| gctgcagcag | cctccatcca | gcctgaggat | gacatcaata | cacagaggaa | gaagagtcag | 300 |
| gaaaagatga | gagaagttac | agactctcct | gggcgacccc | gagagcttac | cattcctcag | 360 |
| acttcttca | | | | | | 369 |

<210> SEQ ID NO 149
<211> LENGTH: 620
<212> TYPE: DNA
<213> ORGANISM: Homo sapien
<220> FEATURE:
<221> NAME/KEY: misc_feature
<222> LOCATION: (1)...(620)
<223> OTHER INFORMATION: n = A,T,C or G

<400> SEQUENCE: 149

| actagtcaaa | aatgctaaaa | taatttggga | gaaaatattt | tttaagtagt | gttatagttt | 60 |
| catgtttatc | ttttattatg | ttttgtgaag | ttgtgtctttt | tcactaatta | cctatactat | 120 |
| gccaatattt | ccttatatct | atccataaca | tttatactac | atttgtaana | naatatgcac | 180 |
| gtgaaactta | acactttata | aggtaaaaat | gaggtttcca | anatttaata | atctgatcaa | 240 |
| gttcttgtta | tttccaaata | gaatggactt | ggtctgttaa | gggctaagga | gaagaggaag | 300 |
| ataaggttaa | aagttgttaa | tgaccaaaca | ttctaaaaga | aatgcaaaaa | aaaagtttat | 360 |
| tttcaagcct | tcgaactatt | taaggaaagc | aaaatcattt | cctaaatgca | tatcatttgt | 420 |
| gagaatttct | cattaatatc | ctgaatcatt | catttcacta | aggctcatgt | tnactccgat | 480 |
| atgtctctaa | gaaagtacta | tttcatggtc | caaacctggt | tgccatantt | gggtaaaggc | 540 |
| tttcccttaa | gtgtgaaant | atttaaaatg | aaatttccct | cttttaaaa | attctttana | 600 |
| agggttaagg | gtgttgggga | | | | | 620 |

<210> SEQ ID NO 150
<211> LENGTH: 371
<212> TYPE: DNA
<213> ORGANISM: Homo sapien

<400> SEQUENCE: 150

```
ggtccgatca aaacctgcta cctccccaag actttactag tgccgataaa ctttctcaaa      60
gagcaaccag tatcacttcc ctgtttataa aacctctaac catctctttg ttctttgaac     120
atgctgaaaa ccacctggtc tgcatgtatg cccgaatttg yaattctttt ctctcaaatg     180
aaaatttaat tttagggatt catttctata ttttcacata tgtagtatta ttatttcctt     240
atatgtgtaa ggtgaaattt atggtatttg agtgtgcaag aaaatatatt tttaaagctt     300
tcatttttcc cccagtgaat gatttagaat tttttatgta aatatacaga atgttttttc     360
ttacttttat a                                                          371
```

<210> SEQ ID NO 151
<211> LENGTH: 4655
<212> TYPE: DNA
<213> ORGANISM: Homo sapien

<400> SEQUENCE: 151

```
gggacttgag ttctgttatc ttcttaagta gattcatatt gtaagggtct cggggtgggg      60
gggttggcaa atcctggag ccagaagaaa ggacagcagc attgatcaat cttacagcta     120
acatgttgta cctggaaaac aatgcccaga ctcaatttag tgagccacag tacacgaacc     180
tggggctcct gaacagcatg gaccagcaga ttcagaacgg ctcctcgtcc accagtccct     240
ataacacaga ccacgcgcag aacagcgtca cggcgccctc gccctacgca cagcccagct     300
ccaccttcga tgctctctct ccatcacccg ccatcccctc aacaccgac tacccaggcc     360
cgcacagttt cgacgtgtcc ttccagcagt cgagcaccgc caagtcggcc acctggacgt     420
attccactga actgaagaaa ctctactgcc aaattgcaaa gacatgcccc atccagatca     480
aggtgatgac cccacctcct cagggagctg ttatccgcgc catgcctgtc tacaaaaaag     540
ctgagcacgt cacggaggtg gtgaagcggt gccccaacca tgagctgagc cgtgaattca     600
acgagggaca gattgcccct yctagtcatt tgattcgagt agaggggaac agccatgccc     660
agtatgtaga agatccccatc acaggaagac agagtgtgct ggtaccttat gagccacccc     720
aggttggcac tgaattcacg acagtcttgt acaatttcat gtgtaacagc agttgtgttg     780
gagggatgaa ccgccgtcca attttaatca ttgttactct ggaaaccaga gatgggcaag     840
tcctgggccg acgctgcttt gaggcccgga tctgtgcttg cccaggaaga gacaggaagg     900
cggatgaaga tagcatcaga aagcagcaag tttcggacag tacaaagaac ggtgatggta     960
cgaagcgccc gtttcgtcag aacacacatg gtatccagat gacatccatc aagaaacgaa    1020
gatccccaga tgatgaactg gtatacttac cagtgagggg ccgtgagact tatgaaatgc    1080
tggtgaagat caaagagtcc ctggaactca tgcagtacct tcttcagcac acaattgaaa    1140
cgtacaggca cagcaacag cagcagcacc agcacttact tcagaaacag acctcaatac    1200
agtctccatc ttcatatggt aacagctccc cacctctgaa caaaatgaac agcatgaaca    1260
agctgccttc tgtgagccag cttatcaacc ctcagcagcg caacgccctc actcctacaa    1320
ccattcctga tggcatggga gccaacattc ccatgatggg cacccacatg ccaatggctg    1380
gagacatgaa tggactcagc cccacccagg cactccctcc cccactctcc atgccatcca    1440
cctcccactg cacaccccca cctccgtatc ccacagattg cagcattgtc agtttcttag    1500
cgaggttggg ctgttcatca tgtctggact atttcacgac ccaggggctg accaccatct    1560
atcagattga gcattactcc atggatgatc tggcaagtct gaaaatccct gagcaatttc    1620
```

```
gacatgcgat ctggaagggc atcctggacc accggcagct ccacgaattc tcctcccctt    1680
ctcatctcct gcggacccca agcagtgcct ctacagtcag tgtgggctcc agtgagaccc    1740
ggggtgagcg tgttattgat gctgtgcgat tcaccctccg ccagaccatc tctttcccac    1800
cccgagatga gtggaatgac ttcaactttg acatggatgc tcgccgcaat aagcaacagc    1860
gcatcaaaga ggagggggag tgagcctcac catgtgagct cttcctatcc ctctcctaac    1920
tgccagcccc ctaaaagcac tcctgcttaa tcttcaaagc cttctcccta gctcctcccc    1980
ttcctcttgt ctgatttctt aggggaagga gaagtaagag gcttacttct taccctaacc    2040
atctgacctg gcatctaatt ctgattctgg ctttaagcct tcaaaactat agcttgcaga    2100
actgtagctt gccatggcta gtagaagtg agcaaaaaag agttgggtgt ctccttaagc    2160
tgcagagatt tctcattgac ttttataaag catgttcacc cttatagtct aagactatat    2220
atataaatgt ataaatatac agtatagatt tttgggtggg gggcattgag tattgtttaa    2280
aatgtaattt aaatgaaaga aaattgagtt gcacttattg accatttttt aatttacttg    2340
ttttggatgg cttgtctata ctccttccct taagggtat catgtatggt gataggtatc    2400
tagagcttaa tgctacatgt gagtgacgat gatgtacaga ttctttcagt tctttggatt    2460
ctaaatacat gccacatcaa acctttgagt agatccattt ccattgctta ttatgtaggt    2520
aagactgtag atatgtattc ttttctcagt gttggtatat tttatattac tgacatttct    2580
tctagtgatg atggttcacg ttggggtgat ttaatccagt tataagaaga agttcatgtc    2640
caaacgtcct ctttagtttt tggttgggaa tgaggaaaat tcttaaaagg cccatagcag    2700
ccagttcaaa acacccgac gtcatgtatt tgagcatatc agtaaccccc ttaaatttaa    2760
taccagatac cttatcttac aatattgatt gggaaaacat ttgctgccat tacagaggta    2820
ttaaaactaa atttcactac tagattgact aactcaaata cacatttgct actgttgtaa    2880
gaattctgat tgatttgatt gggatgaatg ccatctatct agttctaaca gtgaagtttt    2940
actgtctatt aatattcagg gtaaatagga atcattcaga aatgttgagt ctgtactaaa    3000
cagtaagata tctcaatgaa ccataaaattc aactttgtaa aaatcttttg aagcatagat    3060
aatattgttt ggtaaatgtt tcttttgttt ggtaaatgtt tcytttaaag accctcctat    3120
tctataaaac tctgcatgta gaggcttgtt tacctttctc tctctaaggt ttacaatagg    3180
agtggtgatt tgaaaaatat aaaattatga gattggtttt cctgtggcat aaattgcatc    3240
actgtatcat tttctttttt aaccggtaag agtttcagtt tgttggaaag taactgtgag    3300
aacccagttt cccgtccatc tcccttaggg actacccata gacatgaaag gtccccacag    3360
agcaagagat aagtctttca tggctgctgt tgcttaaacc acttaaacga agagttccct    3420
tgaaactttg ggaaaacatg ttaatgacaa tattccagat ctttcagaaa ataacacat    3480 ttttttgcat gcatgcaaat gagctctgaa atcttcccat gcattctggt caagggctgt    3540
cattgcacat aagcttccat tttaatttta aagtgcaaaa gggccagcgt ggctctaaaa    3600
ggtaatgtgt ggattgcctc tgaaaagtgt gtatatattt tgtgtgaaat tgcatacttt    3660
gtattttgat tatttttttt tcttcttgg gatagtggga tttccagaac cacacttgaa    3720
accttttttt atcgttttg tatttcatg aaaataccat ttagtaagaa taccacatca    3780
aataagaaat aatgctacaa ttttaagagg ggagggaagg gaaagtttt tttttatta    3840 ttttttaaa attttgtatg ttaaagaaa tgagtccttg atttcaaagt tttgttgtac    3900
ttaaatggta ataagcactg taaacttctg caacaagcat gcagctttgc aaacccatta    3960 agggggaagaa tgaaagctgt tccttggtcc tagtaagaag acaaactgct tcccttactt    4020
```

-continued

```
tgctgagggt ttgaataaac ctaggacttc cgagctatgt cagtactatt caggtaacac    4080
tagggccttg gaaatccctg tactgtgtct catggatttg gcactagcca aagcgaggca    4140
ccccttactg gcttacctcc tcatggcagc ctactctcct tgagtgtatg agtagccagg    4200
gtaaggggta aaaggatagt aagcatagaa accactagaa agtgggctta atggagttct    4260
tgtggcctca gctcaatgca gttagctgaa gaattgaaaa gttttttgttt ggagacgttt    4320 ataaacagaa atggaaagca gagttttcat taaatccttt taccttttttt ttttcttggt    4380 aatcccctaa aataacagta tgtgggatat tgaatgttaa agggatatttt ttttctatta    4440 ttttttataat tgtacaaaat taagcaaatg ttaaaagttt tatatgcttt attaatgttt    4500
tcaaaaggta ttatacatgt gatacatttt ttaagcttca gttgcttgtc ttctggtact    4560
ttctgttatg ggcttttggg gagccagaag ccaatctaca atctcttttt gtttgccagg    4620
acatgcaata aaatttaaaa aataaataaa aacta                                4655
```

<210> SEQ ID NO 152
<211> LENGTH: 586
<212> TYPE: PRT
<213> ORGANISM: Homo sapien

<400> SEQUENCE: 152

```
Met Leu Tyr Leu Glu Asn Asn Ala Gln Thr Gln Phe Ser Glu Pro Gln
 1               5                  10                  15

Tyr Thr Asn Leu Gly Leu Leu Asn Ser Met Asp Gln Gln Ile Gln Asn
            20                  25                  30

Gly Ser Ser Ser Thr Ser Pro Tyr Asn Thr Asp His Ala Gln Asn Ser
        35                  40                  45

Val Thr Ala Pro Ser Pro Tyr Ala Gln Pro Ser Ser Thr Phe Asp Ala
    50                  55                  60

Leu Ser Pro Ser Pro Ala Ile Pro Ser Asn Thr Asp Tyr Pro Gly Pro
65                  70                  75                  80

His Ser Phe Asp Val Ser Phe Gln Gln Ser Ser Thr Ala Lys Ser Ala
                85                  90                  95

Thr Trp Thr Tyr Ser Thr Glu Leu Lys Lys Leu Tyr Cys Gln Ile Ala
            100                 105                 110

Lys Thr Cys Pro Ile Gln Ile Lys Val Met Thr Pro Pro Gln Gly
        115                 120                 125

Ala Val Ile Arg Ala Met Pro Val Tyr Lys Ala Glu His Val Thr
    130                 135                 140

Glu Val Val Lys Arg Cys Pro Asn His Glu Leu Ser Arg Glu Phe Asn
145                 150                 155                 160

Glu Gly Gln Ile Ala Pro Ser His Leu Ile Arg Val Glu Gly Asn
                165                 170                 175

Ser His Ala Gln Tyr Val Glu Asp Pro Ile Thr Gly Arg Gln Ser Val
            180                 185                 190

Leu Val Pro Tyr Glu Pro Pro Gln Val Gly Thr Glu Phe Thr Thr Val
        195                 200                 205

Leu Tyr Asn Phe Met Cys Asn Ser Ser Cys Val Gly Gly Met Asn Arg
    210                 215                 220

Arg Pro Ile Leu Ile Ile Val Thr Leu Glu Thr Arg Asp Gly Gln Val
225                 230                 235                 240

Leu Gly Arg Arg Cys Phe Glu Ala Arg Ile Cys Ala Cys Pro Gly Arg
                245                 250                 255
```

```
Asp Arg Lys Ala Asp Glu Asp Ser Ile Arg Lys Gln Gln Val Ser Asp
            260                 265                 270
Ser Thr Lys Asn Gly Asp Gly Thr Lys Arg Pro Phe Arg Gln Asn Thr
            275                 280                 285
His Gly Ile Gln Met Thr Ser Ile Lys Lys Arg Arg Ser Pro Asp Asp
            290                 295                 300
Glu Leu Val Tyr Leu Pro Val Arg Gly Arg Glu Thr Tyr Glu Met Leu
305                 310                 315                 320
Val Lys Ile Lys Glu Ser Leu Glu Leu Met Gln Tyr Leu Leu Gln His
                325                 330                 335
Thr Ile Glu Thr Tyr Arg Gln Gln Gln Gln Gln His Gln His Leu
            340                 345                 350
Leu Gln Lys Gln Thr Ser Ile Gln Ser Pro Ser Ser Tyr Gly Asn Ser
            355                 360                 365
Ser Pro Pro Leu Asn Lys Met Asn Ser Met Asn Lys Leu Pro Ser Val
            370                 375                 380
Ser Gln Leu Ile Asn Pro Gln Gln Arg Asn Ala Leu Thr Pro Thr Thr
385                 390                 395                 400
Ile Pro Asp Gly Met Gly Ala Asn Ile Pro Met Met Gly Thr His Met
            405                 410                 415
Pro Met Ala Gly Asp Met Asn Gly Leu Ser Pro Thr Gln Ala Leu Pro
            420                 425                 430
Pro Pro Leu Ser Met Pro Ser Thr Ser His Cys Thr Pro Pro Pro
            435                 440                 445
Tyr Pro Thr Asp Cys Ser Ile Val Ser Phe Leu Ala Arg Leu Gly Cys
            450                 455                 460
Ser Ser Cys Leu Asp Tyr Phe Thr Thr Gln Gly Leu Thr Thr Ile Tyr
465                 470                 475                 480
Gln Ile Glu His Tyr Ser Met Asp Asp Leu Ala Ser Leu Lys Ile Pro
            485                 490                 495
Glu Gln Phe Arg His Ala Ile Trp Lys Gly Ile Leu Asp His Arg Gln
            500                 505                 510
Leu His Glu Phe Ser Ser Pro Ser His Leu Leu Arg Thr Pro Ser Ser
            515                 520                 525
Ala Ser Thr Val Ser Val Gly Ser Ser Glu Thr Arg Gly Glu Arg Val
            530                 535                 540
Ile Asp Ala Val Arg Phe Thr Leu Arg Gln Thr Ile Ser Phe Pro Pro
545                 550                 555                 560
Arg Asp Glu Trp Asn Asp Phe Asn Phe Asp Met Asp Ala Arg Arg Asn
            565                 570                 575
Lys Gln Gln Arg Ile Lys Glu Glu Gly Glu
            580                 585

<210> SEQ ID NO 153
<211> LENGTH: 2007
<212> TYPE: DNA
<213> ORGANISM: Homo sapien

<400> SEQUENCE: 153
gaattcgtcg ctgctccagg gaaagttctg ttactccact gactctctct tttcctgata      60
acatggccag caagaaagta attacagtgt ttggagcaac aggagctcaa ggtggctctg     120
tggccagggc aattttggag agcaaaaaat ttgcagtgag agcagtgacc agggatgtga     180
cttgaccaaa tgccctggag ctccagcgcc ttggagctga ggtggtcaaa ggtgacctga     240
```

```
atgataaagc atcggtggac agtgccttaa aaggtgtcta tggggccttc ttggtgacca    300
acttctggga ccctctcaac caagataagg aagtgtgtcg ggggaagctg gtggcagact    360
ccgccaagca cctgggtctg aagcacgtgg tgtacagcgg cctggagaac gtcaagcgac    420
tgacggatgg caagctggag gtgccgcact ttgacagcaa gggcgaggtg gaggagtact    480
tctggtccat tggcatcccc atgaccagtg tccgcgtggc ggcctacttt gaaaactttc    540
tcgcggcgtg gcggcccgtg aaagcctctg atggagatta ctacaccttg gctgtaccga    600
tgggagatgt accaatggat ggtatctctg ttgctgatat tggagcagcc gtctctagca    660 ttttttaattc tccagaggaa ttttttaggca aggccgtggg gctcagtgca gaagcactaa    720
caatacagca atatgctgat gttttgtcca aggctttggg gaaagaagtc cgagatgcaa    780
agattacccc ggaagctttc gagaagctgg gattccctgc agcaaaggaa atagccaata    840
tgtgtcgttt ctatgaaatg aagccagacc gagatgtcaa tctcacccac caactaaatc    900
ccaaagtcaa aagcttcagc cagtttatct cagagaacca gggagccttc aagggcatgt    960
agaaaatcag ctgttcagat aggcctctgc accacacagc ctctttcctc tctgatcctt   1020
ttcctcttta cggcacaaca ttcatgttga cagaacatgc tggaatgcaa ttgtttgcaa   1080
caccgaagga tttcctgcgg tcgcctcttc agtaggaagc actgcattgg tgataggaca   1140
cggtaatttg attcacattt aacttgctag ttagtgataa gggtggtaca actgtttggt   1200
aaaatgagaa gcctcggaac ttggagcttc tctcctacca ctaatgggag ggcagattat   1260
actgggattt ctcctgggtg agtaattcca gccctaatg ctgaaattcc ctaggcagc    1320 tccagttttc tcaactgcat tgcaaaattc ccagtgaact tttaagtact tttaacttaa   1380
aaaaatgaac atctttgtag agaattttct ggggaacatg gtgttcaatg aacaagcaca   1440
agcattggaa atgctaaaat tcagttttgc ctcaagattg gaagtttatt ttctgactca   1500
ttcatgaagt catctattga gccaccattc aattattcat ctattaattc cttgatcctt   1560
catttatcca ttctgcaaac ttttcttgag caccagcacg ggtggccatt tgtggacttc   1620
tcttcattcc tatgtgtttt cttatcaaag tgatccactc tcgaaaggct cctttccagt   1680
ctgtggttgg gttcaagtca tgccagggcc aggggcccca tctcctcgtt tagctctagg   1740
caaaatccag gggatctgca gtggggagcg ggggcaggaa gctggaggga aggcctgtga   1800
agggtaggga tgtggaaaga caaggtgaca gaaggaccca ataggacctt tctatatctc   1860
tggcttagca ttttctacat catattgtaa tcgtcttatt tgctagtttt cttccttact   1920
gtgagtgact aacagtcatc tttatcccag tgcctggtac ataataagtg atcaataaat   1980
gttgattgac taaaaaaaaa aaaaaaa                                      2007
```

<210> SEQ ID NO 154
<211> LENGTH: 2148
<212> TYPE: DNA
<213> ORGANISM: Homo sapien

<400> SEQUENCE: 154

```
gaattcgtcg ctgctccagg gaaagttctg ttactccact gactctctct tttcctgata     60
acatggccag caagaaagta attacagtgt tggagcaac aggagctcaa ggtggctctg    120
tggccagggc aattttggag agcaaaaaat ttgcagtgag agcagtgacc agggatgtga   180
cttgaccaaa tgccctggag ctccagcgcc ttggagctga ggtggtcaaa ggtgacctga   240
atgataaagc atcggtggac agtgccttaa aaggggaagc tggtggcaga ctccgccaag   300
cacctgggtc tgaagcacgt ggtgtacagc ggcctggaga acgtcaagcg actgacggat   360
```

-continued

```
ggcaagctgg aggtgccgca ctttgacagc aagggcgagg tggaggagta cttctggtcc    420
attggcatcc ccatgaccag tgtccgcgtg gcggcctact ttgaaaactt tctcgcggcg    480
tggcggcccg tgaaagcctc tgatggagat tactacacct tggctgtacc gatgggagat    540
gtaccaatgg atggtatctc tgttgctgat attggagcag ccgtctctag cattttaat    600
tctccagagg aattttagg caaggccgtg gggctcagtg cagaagcact aacaatacag    660
caatatgctg atgttttgtc caaggctttg gggaaagaag tccgagatgc aaagactatc    720
tgtgctatag atgaccagaa aacagtgaa gaaggttca tggaagacgt gggcttgagt    780
tggtccttga gggaacatga ccatgtatag acagaggagg catcaagaag gctggcctgg    840
ctaattctgg aataaacacg acaaaccaga ggcagtacgg gaaggaggca aattctggct    900
ctgcctctat ccttgattac cccggaagct ttcgagaagc tgggattccc tgcagcaaag    960
gaaatagcca atatgtgtcg tttctatgaa atgaagccag accgagatgt caatctcacc   1020
caccaactaa atcccaaagt caaaagcttc agccatttta tctcagagaa ccagggagcc   1080
ttcagggca tgtagaaaat cagctgttca gataggcctc tgcaccacac agcctctttc   1140
ctctctgatc cttttcctct ttacggcaca acattcatgt tgacagaaca tgctggaatg   1200
caattgtttg caacaccgaa ggatttcctg cggtcgcctc ttcagtagga agcactgcat   1260
tggtgatagg acacggtaat ttgattcaca tttaacttgc tagttagtga taagggtggt   1320
acaactgttt ggtaaaatga aagcctcgg aacttggagc ttctctccta ccactaatgg   1380
gagggcagat tatactggga tttctcctgg gtgagtaatt tcaagcccta atgctgaaat   1440
tcccctaggc agctccagtt ttctcaactg cattgcaaaa ttcccagtga acttttaagt   1500
acttttaact taaaaaaatg aacatctttg tagagaattt tctggggaac atggtgttca   1560
atgaacaagc acaagcattg gaaatgctaa aattcagttt tgcctcaaga ttggaagttt   1620
attttctgac tcattcatga agtcatctat tgagccacca ttcaattatt catctattaa   1680
ttccttgatc cttcatttat ccattctgca aactttctt gagcaccagc acgggtggcc   1740
atttgtggac ttctcttcat tcctatgtgt tttcttatca aagtgatcca ctctcgaaag   1800
gctcctttcc agtctgtggt tgggttcaag tcatgccagg gccagggggc ccatctcctc   1860
gtttagctct aggcaaaatc cagggatct gcagtgggga gcggggcag gaagctggag   1920
ggaaggcctg tgaagggtag ggatgtggaa agacaaggtg acagaaggac ccaataggac   1980
cttctatat ctctggctta gcattttcta catcatattg taatcgtctt atttgctagt   2040
tttcttcctt actgtgagtg actaacagtc atctttatcc cagtgcctgg tacataataa   2100
gtgatcaata aatgttgatt gactaaatga aaaaaaaaa aaaaaaaa                 2148
```

<210> SEQ ID NO 155
<211> LENGTH: 153
<212> TYPE: PRT
<213> ORGANISM: Homo sapien

<400> SEQUENCE: 155

```
Met Thr Ser Val Arg Val Ala Ala Tyr Phe Glu Asn Phe Leu Ala Ala
 1               5                  10                  15

Trp Arg Pro Val Lys Ala Ser Asp Gly Asp Tyr Tyr Thr Leu Ala Val
            20                  25                  30

Pro Met Gly Asp Val Pro Met Asp Gly Ile Ser Val Ala Asp Ile Gly
        35                  40                  45

Ala Ala Val Ser Ser Ile Phe Asn Ser Pro Glu Glu Phe Leu Gly Lys
```

```
              50                  55                  60
Ala Val Gly Leu Ser Ala Glu Ala Leu Thr Ile Gln Gln Tyr Ala Asp
 65                  70                  75                  80

Val Leu Ser Lys Ala Leu Gly Lys Glu Val Arg Asp Ala Lys Ile Thr
                 85                  90                  95

Pro Glu Ala Phe Glu Lys Leu Gly Phe Pro Ala Ala Lys Glu Ile Ala
                100                 105                 110

Asn Met Cys Arg Phe Tyr Glu Met Lys Pro Asp Arg Asp Val Asn Leu
                115                 120                 125

Thr His Gln Leu Asn Pro Lys Val Lys Ser Phe Ser Gln Phe Ile Ser
130                 135                 140

Glu Asn Gln Gly Ala Phe Lys Gly Met
145                 150

<210> SEQ ID NO 156
<211> LENGTH: 128
<212> TYPE: PRT
<213> ORGANISM: Homo sapien

<400> SEQUENCE: 156

Met Thr Ser Val Arg Val Ala Ala Tyr Phe Glu Asn Phe Leu Ala Ala
  1               5                  10                  15

Trp Arg Pro Val Lys Ala Ser Asp Gly Asp Tyr Tyr Thr Leu Ala Val
                 20                  25                  30

Pro Met Gly Asp Val Pro Met Asp Gly Ile Ser Val Ala Asp Ile Gly
                 35                  40                  45

Ala Ala Val Ser Ser Ile Phe Asn Ser Pro Glu Glu Phe Leu Gly Lys
 50                  55                  60

Ala Val Gly Leu Ser Ala Glu Ala Leu Thr Ile Gln Gln Tyr Ala Asp
 65                  70                  75                  80

Val Leu Ser Lys Ala Leu Gly Lys Glu Val Arg Asp Ala Lys Thr Ile
                 85                  90                  95

Cys Ala Ile Asp Asp Gln Lys Thr Val Glu Glu Gly Phe Met Glu Asp
                100                 105                 110

Val Gly Leu Ser Trp Ser Leu Arg Glu His Asp His Val Ala Gly Ala
                115                 120                 125

<210> SEQ ID NO 157
<211> LENGTH: 424
<212> TYPE: DNA
<213> ORGANISM: Homo sapien
<220> FEATURE:
<221> NAME/KEY: misc_feature
<222> LOCATION: (1)...(424)
<223> OTHER INFORMATION: n = A,T,C or G

<400> SEQUENCE: 157
ctgcagcccg ggggatccac tagtccagtg tggtggaatt cattggtctt tacaagactt      60
ggatacatta cagcagacat ggaaatataa ttttaaaaaa tttctctcca acctccttca     120
aattcagtca ccactgttat attaccttct ccaggaaccc tccagtgggg aaggctgcga     180
tattagattt ccttgtatgc aaagtttttg ttgaaagctg tgctcagagg aggtgagagg     240
agaggaagga gaaaactgca tcataacttt acagaattga atctagagtc ttccccgaaa     300
agcccagaaa cttctctgcn gnatctggct tgtccatctg gtctaaggtg gctgcttctt     360
ccccagccat cgagtcagtt tgtgcccatg aataatacac gacctgctat ttcccatgac     420
tgct                                                                  424
```

<210> SEQ ID NO 158
<211> LENGTH: 2099
<212> TYPE: DNA
<213> ORGANISM: Homo sapien

<400> SEQUENCE: 158

```
ccgcggttaa aaggcgcagc aggtgggagc cggggccttc acccgaaacc cgacgagagc      60
ccgacagccg gcggcgcccg agcccgacct gcctgcccag ccggagcgaa gggcgccgcc     120
ccgcgcagag cccgcgccag ggccgccggc cgcagagcag ttaaaacgtg caggcaccag     180
aaggcacttc ctgtcggtga agaagacctg tctccggtgt cacgggcatc ctgtgttttg     240
caaacggggc tgacctccct tcctggggag caggaagggt cagggaagga aagaagtac      300
agaagatctg gctaaacaat ttctgtatgg cgaaagaaaa attctaactt gtacgccctc     360
ttcatgcatc tttaattcaa tttgaatatt ccaggcgaca tcctcactga ccgagcaaag     420
attgacattc gtatcatcac tgtgcaccat ggcttctag gcactccagt ggggtaggag      480
aaggaggtct gaaaccctcg cagagggatc ttgccctcat tctttgggtc tgaaacactg     540
gcagtcgttg aaacaggac tcaggataa accagcgcaa tggattgggg gacgctgcac      600
actttcatcg ggggtgtcaa caaacactcc accagcatcg ggaaggtgtg gatcacagtc     660
atctttattt ccgagtcat gatcctcgtg gtggctgccc aggaagtgtg gggtgacgag      720
caagaggact tcgtctgcaa cacactgcaa ccgggatgca aaaatgtgtg ctatgaccac     780
tttttcccgg tgtcccacat ccggctgtgg gccctccagc tgatcttcgt ctccacccca     840
gcgctgctgg tggccatgca gtggcctac taggcacg aaaccactcg caagttcagg       900
cgaggagaga agaggaatga tttcaaagac atagaggaca ttaaaaagca gaaggttcgg     960
atagagggggg cgctgtggtg gacgtacacc agcagcatct ttttccgaat catctttgaa    1020
gcagccttta tgtatgtgtt ttacttcctt tacaatgggt accacctgcc ctgggtgttg    1080
aaatgtggga ttgaccccctg ccccaacctt gttgactgct ttatttctag gccaacagag    1140
aagaccgtgt ttaccatttt tatgatttct gcgtctgtga tttgcatgct gcttaacgtg    1200
gcagagttgt gctacctgct gctgaaagtg tgttttagga gatcaaagag agcacagacg    1260
caaaaaaatc accccaatca tgccctaaag gagagtaagc agaatgaaat gaatgagctg    1320
atttcagata gtggtcaaaa tgcaatcaca ggttcccaag ctaaacattt caaggtaaaa    1380
tgtagctgcg tcataaggag acttctgtct tctccagaag gcaataccaa cctgaaagtt    1440
ccttctgtag cctgaagagt ttgtaaatga cttttcataat aaatagacac ttgagttaac    1500
tttttgtagg atacttgctc cattcataca caacgtaatc aaatatgtgg tccatctctg    1560
aaaacaagag actgcttgac aaaggagcat gcagtcact ttgacaggtt cctttttaagt     1620
ggactctctg acaaagtggg tactttctga aaatttatat aactgttgtt gataaggaac    1680
atttatccag gaattgatac gtttattagg aaaagatatt tttataggct tggatgtttt    1740
tagttctgac tttgaattta tataaagtat ttttataatg actggtcttc cttacctgga    1800
aaaacatgcg atgttagttt tagaattaca ccacaagtat ctaaatttgg aacttacaaa    1860
gggtctatct tgtaaatatt gttttgcatt gtctgttggc aaatttgtga actgtcatga    1920
tacgcttaag gtggaaagtg ttcattgcac aatatatttt tactgctttc tgaatgtaga    1980
cggaacagtg tggaagcaga aggcttttt aactcatccg tttgccaatc attgcaaaca     2040
actgaaatgt ggatgtgatt gcctcaataa agctcgtccc cattgcttaa aaaaaaaaa     2099
```

```
<210> SEQ ID NO 159
<211> LENGTH: 291
<212> TYPE: PRT
<213> ORGANISM: Homo sapien

<400> SEQUENCE: 159

Met Asp Trp Gly Thr Leu His Thr Phe Ile Gly Val Asn Lys His
 1               5                  10                  15

Ser Thr Ser Ile Gly Lys Val Trp Thr Val Ile Phe Ile Phe Arg
                20                  25                  30

Val Met Ile Leu Val Val Ala Ala Gln Glu Val Trp Gly Asp Glu Gln
                35                  40                  45

Glu Asp Phe Val Cys Asn Thr Leu Gln Pro Gly Cys Lys Asn Val Cys
 50                  55                  60

Tyr Asp His Phe Phe Pro Val Ser His Ile Arg Leu Trp Ala Leu Gln
 65                  70                  75                  80

Leu Ile Phe Val Ser Thr Pro Ala Leu Leu Val Ala Met His Val Ala
                85                  90                  95

Tyr Tyr Arg His Glu Thr Thr Arg Lys Phe Arg Arg Gly Glu Lys Arg
                100                 105                 110

Asn Asp Phe Lys Asp Ile Glu Asp Ile Lys Lys Gln Lys Val Arg Ile
                115                 120                 125

Glu Gly Ser Leu Trp Trp Thr Tyr Thr Ser Ser Ile Phe Phe Arg Ile
130                 135                 140

Ile Phe Glu Ala Ala Phe Met Tyr Val Phe Tyr Phe Leu Tyr Asn Gly
145                 150                 155                 160

Tyr His Leu Pro Trp Val Leu Lys Cys Gly Ile Asp Pro Cys Pro Asn
                165                 170                 175

Leu Val Asp Cys Phe Ile Ser Arg Pro Thr Glu Lys Thr Val Phe Thr
                180                 185                 190

Ile Phe Met Ile Ser Ala Ser Val Ile Cys Met Leu Leu Asn Val Ala
                195                 200                 205

Glu Leu Cys Tyr Leu Leu Leu Lys Val Cys Phe Arg Arg Ser Lys Arg
210                 215                 220

Ala Gln Thr Gln Lys Asn His Pro Asn His Ala Leu Lys Glu Ser Lys
225                 230                 235                 240

Gln Asn Glu Met Asn Glu Leu Ile Ser Asp Ser Gly Gln Asn Ala Ile
                245                 250                 255

Thr Gly Ser Gln Ala Lys His Phe Lys Val Lys Cys Ser Cys Val Ile
                260                 265                 270

Arg Arg Leu Leu Ser Ser Pro Glu Gly Asn Thr Asn Leu Lys Val Pro
                275                 280                 285

Ser Val Ala
    290

<210> SEQ ID NO 160
<211> LENGTH: 3951
<212> TYPE: DNA
<213> ORGANISM: Homo sapien

<400> SEQUENCE: 160
tctgcatcca tattgaaaac ctgacacaat gtatgcagca ggctcagtgt gagtgaactg     60
gaggcttctc tacaacatga cccaaaggag cattgcaggt cctatttgca acctgaagtt    120
tgtgactctc ctggttgcct taagttcaga actcccattc ctgggagctg gagtacagct    180
```

-continued

```
tcaagacaat gggtataatg gattgctcat tgcaattaat cctcaggtac ctgagaatca    240
gaacctcatc tcaaacatta aggaaatgat aactgaagct tcattttacc tatttaatgc    300
taccaagaga agagtatttt tcagaaatat aaagatttta atacctgcca catggaaagc    360
taataataac agcaaaataa aacaagaatc atatgaaaag gcaaatgtca tagtgactga    420
ctggtatggg gcacatggag atgatccata caccctacaa tacagagggt gtggaaaaga    480
gggaaaatac attcatttca cacctaattt cctactgaat gataacttaa cagctggcta    540
cggatcacga ggccgagtgt tgtccatga atgggcccac ctccgttggg gtgtgttcga    600
tgagtataac aatgacaaac ctttctacat aaatgggcaa aatcaaatta aagtgacaag    660
gtgttcatct gacatcacag gcattttttgt gtgtgaaaaa ggtccttgcc cccaagaaaa    720
ctgtattatt agtaagcttt ttaaagaagg atgcaccttt atctacaata gcacccaaaa    780
tgcaactgca tcaataatgt tcatgcaaag tttatcttct gtggttgaat tttgtaatgc    840
aagtacccac aaccaagaag caccaaacct acagaaccag atgtgcagcc tcagaagtgc    900
atgggatgta atcacagact ctgctgactt tcaccacagc tttcccatga acgggactga    960
gcttccacct cctcccacat tctcgcttgt agaggctggt gacaaagtgg tctgtttagt   1020
gctggatgtg tccagcaaga tggcagaggc tgacagactc cttcaactac aacaagccgc   1080
agaattttat ttgatgcaga ttgttgaaat tcataccttc gtgggcattg ccagtttcga   1140
cagcaaagga gagatcagag cccagctaca ccaaattaac agcaatgatg atcgaaagtt   1200
gctggtttca tatctgccca ccactgtatc agctaaaaca gacatcagca tttgttcagg   1260
gcttaagaaa ggatttgagg tggttgaaaa actgaatgga aaagcttatg gctctgtgat   1320
gatattagtg accagcggag atgataagct tcttggcaat tgcttaccca ctgtgctcag   1380
cagtggttca acaattcact ccattgccct gggttcatct gcagcccaaa atctggagga   1440
attatcacgt cttacaggag gttttaaagtt ctttgttcca gatatatcaa actccaatag   1500
catgattgat gctttcagta gaatttcctc tggaactgga gacattttcc agcaacatat   1560
tcagcttgaa agtacaggtg aaaatgtcaa acctcaccat caattgaaaa acacagtgac   1620
tgtggataat actgtgggca acgacactat gtttctagtt acgtggcagg ccagtggtcc   1680
tcctgagatt atattatttg atcctgatgg acgaaaatac tacacaaata atttttatcac   1740 caatctaact tttcggacag ctagtctttg gattccagga acagctaagc ctgggcactg   1800
gacttacacc ctgaacaata cccatcattc tctgcaagcc ctgaaagtga cagtgacctc   1860
tcgcgcctcc aactcagctg tgcccccagc cactgtggaa gcctttgtgg aaagagacag   1920
cctccatttt cctcatcctg tgatgattta tgccaatgtg aaacagggat ttatcccat    1980 tcttaatgcc actgtcactg ccacagttga gccagagact ggagatcctg ttacgctgag   2040
actccttgat gatggagcag gtgctgatgt tataaaaaat gatggaattt actcgaggta   2100
ttttttctcc tttgctgcaa atggtagata tagcttgaaa gtgcatgtca atcactctcc   2160
cagcataagc accccagccc actctattcc agggagtcat gctatgtatg taccaggtta   2220
cacagcaaac ggtaatattc agatgaatgc tccaaggaaa tcagtaggca gaaatgagga   2280
ggagcgaaag tggggcttta gccgagtcag ctcaggaggc tccttttcag tgctgggagt   2340
tccagctggc ccccaccctg atgtgtttcc accatgcaaa attattgacc tggaagctgt   2400
aaaagtagaa gaggaattga ccctatcttg gacagcacct ggagaagact ttgatcaggg   2460
ccaggctaca agctatgaaa taagaatgag taaaagtcta cagaatatcc aagatgactt   2520
taacaatgct attttagtaa atacatcaaa gcgaaatcct cagcaagctg gcatcaggga   2580
```

```
gatatttacg ttctcacccc aaatttccac gaatggacct gaacatcagc caaatggaga    2640
aacacatgaa agccacagaa tttatgttgc aatacgagca atggatagga actccttaca    2700
gtctgctgta tctaacattg cccaggcgcc tctgtttatt cccccccaatt ctgatcctgt   2760 acctgccaga gattatctta tattgaaagg agttttaaca gcaatgggtt tgataggaat   2820
catttgcctt attatagttg tgacacatca tactttaagc aggaaaaaga gagcagacaa   2880
gaaagagaat ggaacaaaat tattataaat aaatatccaa agtgtcttcc ttcttagata   2940
taagacccat ggccttcgac tacaaaaaca tactaacaaa gtcaaattaa catcaaaact   3000
gtattaaaat gcattgagtt tttgtacaat acagataaga ttttacatg gtagatcaac    3060 aaattctttt tgggggtaga ttagaaaacc cttacacttt ggctatgaac aaataataaa   3120
aattattctt taaagtaatg tctttaaagg caaagggaag ggtaaagtcg gaccagtgtc   3180
aaggaaagtt tgtttttattg aggtggaaaa atagccccaa gcagagaaaa ggagggtagg  3240
tctgcattat aactgtctgt gtgaagcaat catttagtta ctttgattaa ttttttctttt 3300 ctccttatct gtgcagaaca ggttgcttgt ttacaactga agatcatgct atatttcata   3360
tatgaagccc ctaatgcaaa gctctttacc tcttgctatt ttgttatata tattacagat   3420
gaaatctcac tgctaatgct cagagatctt ttttcactgt aagaggtaac ctttaacaat   3480
atgggtatta cctttgtctc ttcataccgg ttttatgaca aaggtctatt gaatttattt   3540
gtttgtaagt ttctactccc atcaaagcag cttttttaagt tattgccttg gttattatgg  3600
atgatagtta tagcccttat aatgccttaa ctaaggaaga aaagatgtta ttctgagttt   3660
gttttaatac atatatgaac atatagtttt attcaattaa accaaagaag aggtcagcag   3720
ggagatacta acctttggaa atgattagct ggctctgttt tttggttaaa taagagtctt   3780
taatcctttc tccatcaaga gttacttacc aagggcaggg gaaggggat atagaggtcc    3840 caaggaaata aaaatcatct ttcatcttta attttactcc ttcctcttat ttttttaaaa   3900
gattatcgaa caataaaatc atttgccttt ttaattaaaa acataaaaaa a            3951
```

<210> SEQ ID NO 161
<211> LENGTH: 943
<212> TYPE: PRT
<213> ORGANISM: Homo sapien

<400> SEQUENCE: 161

```
Met Thr Gln Arg Ser Ile Ala Gly Pro Ile Cys Asn Leu Lys Phe Val
 1               5                  10                  15

Thr Leu Val Ala Leu Ser Ser Glu Leu Pro Phe Leu Gly Ala Gly
            20                  25                  30

Val Gln Leu Gln Asp Asn Gly Tyr Asn Gly Leu Leu Ile Ala Ile Asn
        35                  40                  45

Pro Gln Val Pro Glu Asn Gln Asn Leu Ile Ser Asn Ile Lys Glu Met
    50                  55                  60

Ile Thr Glu Ala Ser Phe Tyr Leu Phe Asn Ala Thr Lys Arg Arg Val
65                  70                  75                  80

Phe Phe Arg Asn Ile Lys Ile Leu Ile Pro Ala Thr Trp Lys Ala Asn
                85                  90                  95

Asn Asn Ser Lys Ile Lys Gln Glu Ser Tyr Glu Lys Ala Asn Val Ile
            100                 105                 110

Val Thr Asp Trp Tyr Gly Ala His Gly Asp Asp Pro Tyr Thr Leu Gln
        115                 120                 125
```

-continued

```
Tyr Arg Gly Cys Gly Lys Glu Gly Lys Tyr Ile His Phe Thr Pro Asn
    130                 135                 140

Phe Leu Asn Asp Asn Leu Thr Ala Gly Tyr Gly Ser Arg Gly Arg
145                 150                 155                 160

Val Phe Val His Glu Trp Ala His Leu Arg Trp Gly Val Phe Asp Glu
                165                 170                 175

Tyr Asn Asn Asp Lys Pro Phe Tyr Ile Asn Gly Gln Asn Gln Ile Lys
                180                 185                 190

Val Thr Arg Cys Ser Ser Asp Ile Thr Gly Ile Phe Val Cys Glu Lys
            195                 200                 205

Gly Pro Cys Pro Gln Glu Asn Cys Ile Ile Ser Lys Leu Phe Lys Glu
        210                 215                 220

Gly Cys Thr Phe Ile Tyr Asn Ser Thr Gln Asn Ala Thr Ala Ser Ile
225                 230                 235                 240

Met Phe Met Gln Ser Leu Ser Ser Val Val Glu Phe Cys Asn Ala Ser
                245                 250                 255

Thr His Asn Gln Glu Ala Pro Asn Leu Gln Asn Gln Met Cys Ser Leu
                260                 265                 270

Arg Ser Ala Trp Asp Val Ile Thr Asp Ser Ala Asp Phe His His Ser
            275                 280                 285

Phe Pro Met Asn Gly Thr Glu Leu Pro Pro Pro Thr Phe Ser Leu
        290                 295                 300

Val Glu Ala Gly Asp Lys Val Val Cys Leu Val Leu Asp Val Ser Ser
305                 310                 315                 320

Lys Met Ala Glu Ala Asp Arg Leu Leu Gln Leu Gln Ala Ala Glu
                325                 330                 335

Phe Tyr Leu Met Gln Ile Val Glu Ile His Thr Phe Val Gly Ile Ala
                340                 345                 350

Ser Phe Asp Ser Lys Gly Glu Ile Arg Ala Gln Leu His Gln Ile Asn
            355                 360                 365

Ser Asn Asp Asp Arg Lys Leu Leu Val Ser Tyr Leu Pro Thr Thr Val
        370                 375                 380

Ser Ala Lys Thr Asp Ile Ser Ile Cys Ser Gly Leu Lys Lys Gly Phe
385                 390                 395                 400

Glu Val Val Glu Lys Leu Asn Gly Lys Ala Tyr Gly Ser Val Met Ile
                405                 410                 415

Leu Val Thr Ser Gly Asp Asp Lys Leu Leu Gly Asn Cys Leu Pro Thr
            420                 425                 430

Val Leu Ser Ser Gly Ser Thr Ile His Ser Ile Ala Leu Gly Ser Ser
        435                 440                 445

Ala Ala Pro Asn Leu Glu Glu Leu Ser Arg Leu Thr Gly Gly Leu Lys
    450                 455                 460

Phe Phe Val Pro Asp Ile Ser Asn Ser Asn Ser Met Ile Asp Ala Phe
465                 470                 475                 480

Ser Arg Ile Ser Ser Gly Thr Gly Asp Ile Phe Gln Gln His Ile Gln
                485                 490                 495

Leu Glu Ser Thr Gly Glu Asn Val Lys Pro His His Gln Leu Lys Asn
            500                 505                 510

Thr Val Thr Val Asp Asn Thr Val Gly Asn Asp Thr Met Phe Leu Val
        515                 520                 525

Thr Trp Gln Ala Ser Gly Pro Pro Glu Ile Ile Leu Phe Asp Pro Asp
    530                 535                 540

Gly Arg Lys Tyr Tyr Thr Asn Asn Phe Ile Thr Asn Leu Thr Phe Arg
```

-continued

```
545                 550                 555                 560
Thr Ala Ser Leu Trp Ile Pro Gly Thr Ala Lys Pro Gly His Trp Thr
                565                 570                 575
Tyr Thr Leu Asn Asn Thr His His Ser Leu Gln Ala Leu Lys Val Thr
                580                 585                 590
Val Thr Ser Arg Ala Ser Asn Ser Ala Val Pro Pro Ala Thr Val Glu
                595                 600                 605
Ala Phe Val Glu Arg Asp Ser Leu His Phe Pro His Pro Val Met Ile
                610                 615                 620
Tyr Ala Asn Val Lys Gln Gly Phe Tyr Pro Ile Leu Asn Ala Thr Val
625                 630                 635                 640
Thr Ala Thr Val Glu Pro Glu Thr Gly Asp Pro Val Thr Leu Arg Leu
                645                 650                 655
Leu Asp Asp Gly Ala Gly Ala Asp Val Ile Lys Asn Asp Gly Ile Tyr
                660                 665                 670
Ser Arg Tyr Phe Phe Ser Phe Ala Ala Asn Gly Arg Tyr Ser Leu Lys
                675                 680                 685
Val His Val Asn His Ser Pro Ser Ile Ser Thr Pro Ala His Ser Ile
                690                 695                 700
Pro Gly Ser His Ala Met Tyr Val Pro Gly Tyr Thr Ala Asn Gly Asn
705                 710                 715                 720
Ile Gln Met Asn Ala Pro Arg Lys Ser Val Gly Arg Asn Glu Glu Glu
                725                 730                 735
Arg Lys Trp Gly Phe Ser Arg Val Ser Ser Gly Gly Ser Phe Ser Val
                740                 745                 750
Leu Gly Val Pro Ala Gly Pro His Pro Asp Val Phe Pro Pro Cys Lys
                755                 760                 765
Ile Ile Asp Leu Glu Ala Val Lys Val Glu Glu Leu Thr Leu Ser
                770                 775                 780
Trp Thr Ala Pro Gly Glu Asp Phe Asp Gln Gly Gln Ala Thr Ser Tyr
785                 790                 795                 800
Glu Ile Arg Met Ser Lys Ser Leu Gln Asn Ile Gln Asp Asp Phe Asn
                805                 810                 815
Asn Ala Ile Leu Val Asn Thr Ser Lys Arg Asn Pro Gln Gln Ala Gly
                820                 825                 830
Ile Arg Glu Ile Phe Thr Phe Ser Pro Gln Ile Ser Thr Asn Gly Pro
                835                 840                 845
Glu His Gln Pro Asn Gly Glu Thr His Glu Ser His Arg Ile Tyr Val
                850                 855                 860
Ala Ile Arg Ala Met Asp Arg Asn Ser Leu Gln Ser Ala Val Ser Asn
865                 870                 875                 880
Ile Ala Gln Ala Pro Leu Phe Ile Pro Pro Asn Ser Asp Pro Val Pro
                885                 890                 895
Ala Arg Asp Tyr Leu Ile Leu Lys Gly Val Leu Thr Ala Met Gly Leu
                900                 905                 910
Ile Gly Ile Ile Cys Leu Ile Ile Val Val Thr His His Thr Leu Ser
                915                 920                 925
Arg Lys Lys Arg Ala Asp Lys Lys Glu Asn Gly Thr Lys Leu Leu
                930                 935                 940

<210> SEQ ID NO 162
<211> LENGTH: 498
<212> TYPE: DNA
<213> ORGANISM: Homo sapien
```

<400> SEQUENCE: 162

```
tggagaacca cgtggacagc accatgaaca tgttgggcgg gggaggcagt gctggccgga      60
agcccctcaa gtcgggtatg aaggagctgg ccgtgttccg ggagaaggtc actgagcagc     120
accggcagat gggcaagggt ggcaagcatc accttggcct ggaggagccc aagaagctgc     180
gaccaccccc tgccaggact ccctgccaac aggaactgga ccaggtcctg gagcggatct     240
ccaccatgcg ccttccggat gagcggggcc ctctggagca cctctactcc ctgcacatcc     300
ccaactgtga caagcatggc ctgtacaacc tcaaacagtg gcaagatgtc tctgaacggg     360
cagcgtgggg agtgctggtg tgtgaacccc aacaccggga agctgatcca gggagccccc     420
accatccggg gggaccccga gtgtcatctc ttctacaatg agcagcagga ggctcgcggg     480
gtgcacaccc cagcggat                                                   498
```

<210> SEQ ID NO 163
<211> LENGTH: 1128
<212> TYPE: DNA
<213> ORGANISM: Homo sapien

<400> SEQUENCE: 163

```
gccacctggc cctcctgatc gacgacacac gcacttgaaa cttgttctca gggtgtgtgg      60
aatcaacttt ccggaagcaa ccagcccacc agaggaggtc ccgagcgcga gcggagacga     120
tgcagcggag actggttcag cagtggacgc tcgcggtgtt cctgctgagc tacgcggtgc     180
cctcctgcgg gcgctcggtg gagggtctca gccgccgcct caaaagagct gtgtctgaac     240
atcagctcct ccatgacaag gggaagtcca tccaagattt acggcgacga ttcttccttc     300
accatctgat cgcagaaatc cacacagctg aaatcagagc tacctcggag gtgtcccta     360
actccaagcc ctctcccaac acaaagaacc accccgtccg atttgggtct gatgatgagg     420
gcagataacct aactcaggaa actaacaagg tggagacgta caaagagcag ccgctcaaga     480
cacctgggaa gaaaagaaa ggcaagcccg ggaaacgcaa ggagcaggaa aagaaaaaac     540
ggcgaactcg ctctgcctgg ttagactctg gagtgactgg gagtgggcta aaggggacc     600
acctgtctga cacctccaca acgtcgctgg agctcgattc acggaggcat tgaaattttc     660
agcagagacc ttccaaggac atattgcagg attctgtaat agtgaacata tggaaagtat     720
tagaaatatt tattgtctgt aaatactgta aatgcattgg aataaaactg tctcccccat     780
tgctctatga aactgcacat tggtcattgt gaatattttt ttttttgcca aggctaatcc     840
aattattatt atcacattta ccataattta ttttgtccat tgatgtattt attttgtaaa     900
tgtatcttgg tgctgctgaa tttctatatt ttttgtaaca taatgcactt tagatataca     960
tatcaagtat gttgataaat gacacaatga agtgtctcta ttttgtggtt gatttaatg    1020
aatgcctaaa tataattatc caaattgatt tcctttgtg catgtaaaaa taacagtatt    1080
ttaaatttgt aaagaatgtc taataaaata taatctaatt acatcatg              1128
```

<210> SEQ ID NO 164
<211> LENGTH: 1310
<212> TYPE: DNA
<213> ORGANISM: Homo sapien

<400> SEQUENCE: 164

```
gggcctggtt cgcaaagaag ctgacttcag aggggaaac tttcttcttt taggaggcgg      60
ttagccctgt tccacgaacc caggagaact gctggccaga ttaattagac attgctatgg    120
```

-continued

```
gagacgtgta aacacactac ttatcattga tgcatatata aaaccatttt attttcgcta      180
ttatttcaga ggaagcgcct ctgatttgtt tcttttttcc cttttgctc tttctggctg       240 tgtggtttgg agaaagcaca gttggagtag ccggttgcta aataagtccc gagcgcgagc     300
ggagacgatg cagcggagac tggttcagca gtggagcgtc gcggtgttcc tgctgagcta     360
cgcggtgccc tcctgcgggc gctcggtgga gggtctcagc cgccgcctca aaagagctgt     420
gtctgaacat cagctcctcc atgacaaggg gaagtccatc caagatttac ggcgacgatt    480
cttccttcac catctgatcg cagaaatcca cacagctgaa atcagagcta cctcggaggt     540
gtcccctaac tccaagccct ctcccaacac aaagaaccac cccgtccgat tgggtctga     600 tgatgagggc agatacctaa ctcaggaaac taacaaggtg gagacgtaca agagcagcc     660 gctcaagaca cctgggaaga aaagaaagg caagcccggg aaacgcaagg agcaggaaaa    720
gaaaaaacgg cgaactcgct ctgcctggtt agactctgga gtgactggga gtgggctaga   780
aggggaccac ctgtctgaca cctccacaac gtcgctggag ctcgattcac ggaggcattg   840
aaattttcag cagagacctt ccaaggacat attgcaggat tctgtaatag tgaacatatg   900
gaaagtatta gaaatattta ttgtctgtaa atactgtaaa tgcattggaa taaaactgtc   960
tcccccattg ctctatgaaa ctgcacattg gtcattgtga atatttttt ttttgccaag    1020 gctaatccaa ttattattat cacatttacc ataatttatt ttgtccattg atgtatttat   1080
tttgtaaatg tatcttggtg ctgctgaatt tctatatttt ttgtaacata atgcacttta   1140
gatatacata tcaagtatgt tgataaatga cacaatgaag tgtctctatt ttgtggttga   1200
ttttaatgaa tgcctaaata taattatcca aattgatttt cctttgtgcc cgtaaaaata   1260 acagtattt aaatttgtaa agaatgtcta ataaatata atctaattac                1310
```

<210> SEQ ID NO 165
<211> LENGTH: 177
<212> TYPE: PRT
<213> ORGANISM: Homo sapien

<400> SEQUENCE: 165

```
Met Gln Arg Arg Leu Val Gln Gln Trp Ser Val Ala Val Phe Leu Leu
 1               5                  10                  15

Ser Tyr Ala Val Pro Ser Cys Gly Arg Ser Val Glu Gly Leu Ser Arg
            20                  25                  30

Arg Leu Lys Arg Ala Val Ser Glu His Gln Leu Leu His Asp Lys Gly
        35                  40                  45

Lys Ser Ile Gln Asp Leu Arg Arg Phe Phe Leu His His Leu Ile
    50                  55                  60

Ala Glu Ile His Thr Ala Glu Ile Arg Ala Thr Ser Glu Val Ser Pro
65                  70                  75                  80

Asn Ser Lys Pro Ser Pro Asn Thr Lys Asn His Pro Val Arg Phe Gly
                85                  90                  95

Ser Asp Asp Glu Gly Arg Tyr Leu Thr Gln Glu Thr Asn Lys Val Glu
            100                 105                 110

Thr Tyr Lys Glu Gln Pro Leu Lys Thr Pro Gly Lys Lys Lys Gly
        115                 120                 125

Lys Pro Gly Lys Arg Lys Glu Gln Glu Lys Lys Arg Arg Thr Arg
    130                 135                 140

Ser Ala Trp Leu Asp Ser Gly Val Thr Gly Ser Gly Leu Glu Gly Asp
145                 150                 155                 160

His Leu Ser Asp Thr Ser Thr Thr Ser Leu Glu Leu Asp Ser Arg Arg
```

|     |     |     |
| --- | --- | --- |
| 165 | 170 | 175 |

His

<210> SEQ ID NO 166
<211> LENGTH: 177
<212> TYPE: PRT
<213> ORGANISM: Homo sapien

<400> SEQUENCE: 166

| Met | Gln | Arg | Arg | Leu | Val | Gln | Gln | Trp | Ser | Val | Ala | Val | Phe | Leu | Leu |
| --- | --- | --- | --- | --- | --- | --- | --- | --- | --- | --- | --- | --- | --- | --- | --- |
| 1 |  |  |  | 5 |  |  |  |  | 10 |  |  |  |  | 15 |  |

| Ser | Tyr | Ala | Val | Pro | Ser | Cys | Gly | Arg | Ser | Val | Glu | Gly | Leu | Ser | Arg |
| --- | --- | --- | --- | --- | --- | --- | --- | --- | --- | --- | --- | --- | --- | --- | --- |
|  |  |  | 20 |  |  |  |  | 25 |  |  |  |  | 30 |  |  |

| Arg | Leu | Lys | Arg | Ala | Val | Ser | Glu | His | Gln | Leu | Leu | His | Asp | Lys | Gly |
| --- | --- | --- | --- | --- | --- | --- | --- | --- | --- | --- | --- | --- | --- | --- | --- |
|  |  | 35 |  |  |  |  | 40 |  |  |  |  | 45 |  |  |  |

| Lys | Ser | Ile | Gln | Asp | Leu | Arg | Arg | Phe | Phe | Leu | His | His | Leu | Ile |
| --- | --- | --- | --- | --- | --- | --- | --- | --- | --- | --- | --- | --- | --- | --- |
| 50 |  |  |  |  | 55 |  |  |  |  | 60 |  |  |  |  |

| Ala | Glu | Ile | His | Thr | Ala | Glu | Ile | Arg | Ala | Thr | Ser | Glu | Val | Ser | Pro |
| --- | --- | --- | --- | --- | --- | --- | --- | --- | --- | --- | --- | --- | --- | --- | --- |
| 65 |  |  |  | 70 |  |  |  |  | 75 |  |  |  |  | 80 |  |

| Asn | Ser | Lys | Pro | Ser | Pro | Asn | Thr | Lys | Asn | His | Pro | Val | Arg | Phe | Gly |
| --- | --- | --- | --- | --- | --- | --- | --- | --- | --- | --- | --- | --- | --- | --- | --- |
|  |  |  | 85 |  |  |  |  | 90 |  |  |  |  | 95 |  |  |

| Ser | Asp | Asp | Glu | Gly | Arg | Tyr | Leu | Thr | Gln | Glu | Thr | Asn | Lys | Val | Glu |
| --- | --- | --- | --- | --- | --- | --- | --- | --- | --- | --- | --- | --- | --- | --- | --- |
|  |  |  | 100 |  |  |  |  | 105 |  |  |  |  | 110 |  |  |

| Thr | Tyr | Lys | Glu | Gln | Pro | Leu | Lys | Thr | Pro | Gly | Lys | Lys | Lys | Gly |
| --- | --- | --- | --- | --- | --- | --- | --- | --- | --- | --- | --- | --- | --- | --- |
|  |  | 115 |  |  |  |  | 120 |  |  |  |  | 125 |  |  |

| Lys | Pro | Gly | Lys | Arg | Lys | Glu | Gln | Glu | Lys | Lys | Lys | Arg | Arg | Thr | Arg |
| --- | --- | --- | --- | --- | --- | --- | --- | --- | --- | --- | --- | --- | --- | --- | --- |
|  | 130 |  |  |  |  | 135 |  |  |  |  | 140 |  |  |  |  |

| Ser | Ala | Trp | Leu | Asp | Ser | Gly | Val | Thr | Gly | Ser | Gly | Leu | Glu | Gly | Asp |
| --- | --- | --- | --- | --- | --- | --- | --- | --- | --- | --- | --- | --- | --- | --- | --- |
| 145 |  |  |  |  | 150 |  |  |  |  | 155 |  |  |  |  | 160 |

| His | Leu | Ser | Asp | Thr | Ser | Thr | Thr | Ser | Leu | Glu | Leu | Asp | Ser | Arg | Arg |
| --- | --- | --- | --- | --- | --- | --- | --- | --- | --- | --- | --- | --- | --- | --- | --- |
|  |  |  |  | 165 |  |  |  |  | 170 |  |  |  |  | 175 |  |

His

<210> SEQ ID NO 167
<211> LENGTH: 3362
<212> TYPE: DNA
<213> ORGANISM: Homo sapien

<400> SEQUENCE: 167

| cacaatgtat | gcagcaggct | cagtgtgagt | gaactggagg | cttctctaca | acatgaccca | 60 |
| --- | --- | --- | --- | --- | --- | --- |
| aaggagcatt | gcaggtccta | tttgcaacct | gaagtttgtg | actctcctgg | ttgccttaag | 120 |
| ttcagaactc | ccattcctgg | gagctggagt | acagcttcaa | gacaatgggt | ataatggatt | 180 |
| gctcattgca | attaatcctc | aggtacctga | gaatcagaac | ctcatctcaa | acattaagga | 240 |
| aatgataact | gaagcttcat | tttacctatt | taatgctacc | aagagaagag | tattttttcag | 300 |
| aaatataaag | attttaatac | ctgccacatg | gaaagctaat | aataacagca | aaataaaaca | 360 |
| agaatcatat | gaaaaggcaa | atgtcatagt | gactgactgg | tatggggcac | atggagatga | 420 |
| tccatacacc | ctacaataca | gagggtgtgg | aaaagaggga | aaatacattc | atttcacacc | 480 |
| taatttccta | ctgaatgata | acttaacagc | tggctacgga | tcacgaggcc | gagtgtttgt | 540 |
| ccatgaatgg | gcccacctcc | gttgggggtgt | gttcgatgag | tataacaatg | acaaaccttt | 600 |
| ctacataaat | gggcaaaatc | aaattaaagt | gacaaggtgt | tcatctgaca | tcacaggcat | 660 |
| ttttgtgtgt | gaaaaaggtc | cttgcccccca | agaaaactgt | attattagta | agcttttttaa | 720 |

-continued

| | | |
|---|---|---|
| agaaggatgc accttatct acaatagcac ccaaaatgca actgcatcaa taatgttcat | 780 |
| gcaaagttta tcttctgtgg ttgaattttg taatgcaagt acccacaacc aagaagcacc | 840 |
| aaacctacag aaccagatgt gcagcctcag aagtgcatgg gatgtaatca cagactctgc | 900 |
| tgactttcac cacagctttc ccatgaacgg gactgagctt ccacctcctc ccacattctc | 960 |
| gcttgtagag gctggtgaca aagtggtctg tttagtgctg gatgtgtcca gcaagatggc | 1020 |
| agaggctgac agactccttc aactacaaca agccgcagaa ttttatttga tgcagattgt | 1080 |
| tgaaattcat accttcgtgg gcattgccag tttcgacagc aaaggagaga tcagagccca | 1140 |
| gctacaccaa attaacagca atgatgatcg aaagttgctg gtttcatatc tgcccaccac | 1200 |
| tgtatcagct aaaacagaca tcagcatttg ttcagggctt aagaaaggat ttgaggtggt | 1260 |
| tgaaaaactg aatggaaaag cttatggctc tgtgatgata ttagtgacca gcggagatga | 1320 |
| taagcttctt ggcaattgct tacccactgt gctcagcagt ggttcaacaa ttcactccat | 1380 |
| tgccctgggt tcatctgcag ccccaaatct ggaggaatta tcacgtctta caggaggttt | 1440 |
| aaagttcttt gttccagata tatcaaactc caatagcatg attgatgctt tcagtagaat | 1500 |
| ttcctctgga actggagaca ttttccagca acatattcag cttgaaagta caggtgaaaa | 1560 |
| tgtcaaacct caccatcaat tgaaaaacac agtgactgtg gataatactg tgggcaacga | 1620 |
| cactatgttt ctagttacgt ggcaggccag tggtcctcct gagattatat tatttgatcc | 1680 |
| tgatggacga aaatactaca caaataattt tatcaccaat ctaactttc ggacagctag | 1740 |
| tctttggatt ccaggaacag ctaagcctgg gcactggact tacaccctga tgtgttcca | 1800 |
| ccatgcaaaa ttattgacct ggaagctgta aagtagaag aggaattgac cctatcttgg | 1860 |
| acagcacctg gagaagactt tgatcagggc caggctacaa gctatgaaat aagaatgagt | 1920 |
| aaaagtctac agaatatcca agatgacttt aacaatgcta ttttagtaaa tacatcaaag | 1980 |
| cgaaatcctc agcaagctgg catcagggag atatttacgt tctcaccca aatttccacg | 2040 |
| aatggacctg aacatcagcc aaatggagaa acacatgaaa gccacagaat ttatgttgca | 2100 |
| atacgagcaa tggataggaa ctccttacag tctgctgtat ctaacattgc ccaggcgcct | 2160 |
| ctgtttattc ccccccaattc tgatcctgta cctgccagag attatcttat attgaaagga | 2220 |
| gttttaacag caatgggttt gataggaatc atttgcctta ttatagttgt gacacatcat | 2280 |
| actttaagca ggaaaaagag agcagacaag aaagagaatg gaacaaaatt attataaata | 2340 |
| aatatccaaa gtgtcttcct tcttagatat aagacccatg gccttcgact acaaaaacat | 2400 |
| actaacaaag tcaaattaac atcaaaactg tattaaaatg cattgagttt ttgtacaata | 2460 |
| cagataagat ttttacatgg tagatcaaca aattctttt ggggtagat tagaaaaccc | 2520 |
| ttacactttg gctatgaaca aataataaaa attattcttt aaagtaatgt ctttaaaggc | 2580 |
| aaagggaagg gtaaagtcgg accagtgtca aggaaagttt gttttattga ggtgaaaaa | 2640 |
| tagccccaag cagagaaaag gagggtaggt ctgcattata actgtctgtg tgaagcaatc | 2700 |
| atttagttac tttgattaat ttttcttttc tccttatctg tgcagaacag gttgcttgtt | 2760 |
| tacaactgaa gatcatgcta tatttcatat atgaagcccc taatgcaaag ctctttacct | 2820 |
| cttgctattt tgttatatat attacagatg aaatctcact gctaatgctc agagatcttt | 2880 |
| tttcactgta agaggtaacc tttaacaata tgggtattac ctttgtctct tcataccggt | 2940 |
| tttatgacaa aggtctattg aatttatttg tttgtaagtt tctactccca tcaaagcagc | 3000 |
| tttctaagtt attgccttgg ttattatgga tgatagttat agcccttata atgccttaac | 3060 |
| taaggaagaa aagatgttat tctgagtttg ttttaataca tatatgaaca tatagttta | 3120 |

```
ttcaattaaa ccaaagaaga ggtcagcagg gagatactaa cctttggaaa tgattagctg    3180
gctctgtttt ttggttaaat aagagtcttt aatcctttct ccatcaagag ttacttacca    3240
agggcagggg aaggggata tagaggtcac aaggaaataa aaatcatctt tcatctttaa     3300
ttttactcct tcctcttatt tttttaaaag attatcgaac aataaaatca tttgcctttt    3360
tt                                                                   3362

<210> SEQ ID NO 168
<211> LENGTH: 2784
<212> TYPE: DNA
<213> ORGANISM: Homo sapien

<400> SEQUENCE: 168
tctgcatcca tattgaaaac ctgacacaat gtatgcagca ggctcagtgt gagtgaactg      60
gaggcttctc tacaacatga cccaaaggag cattgcaggt cctatttgca acctgaagtt    120
tgtgactctc ctggttgcct taagttcaga actcccattc ctgggagctg gagtacagct    180
tcaagacaat gggtataatg gattgctcat tgcaattaat cctcaggtac ctgagaatca    240
gaacctcatc tcaaacatta aggaaatgat aactgaagct tcatttttacc tatttaatgc   300 taccaagaga agagtatttt tcagaaatat aaagatttta atacctgcca catggaaagc    360
taataataac agcaaaataa aacaagaatc atatgaaaag gcaaatgtca tagtgactga    420
ctggtatggg gcacatggag atgatccata caccctacaa tacagagggt gtggaaaaga    480
gggaaaatac attcatttca cacctaattt cctactgaat gataacttaa cagctggcta    540
cggatcacga ggccgagtgt ttgtccatga atgggcccac ctccgttggg gtgtgttcga    600
tgagtataac aatgacaaac ctttctacat aaatgggcaa aatcaaatta agtgacaag    660 gtgttcatct gacatcacag gcattttttgt gtgtgaaaaa ggtccttgcc cccaagaaaa    720
ctgtattatt agtaagcttt ttaaagaagg atgcaccttt atctacaata gcacccaaaa    780
tgcaactgca tcaataatgt tcatgcaaag tttatcttct gtggttgaat tttgtaatgc    840
aagtacccac aaccaagaag caccaaacct acagaaccag atgtgcagcc tcagaagtgc    900
atgggatgta atcacagact ctgctgactt tcaccagc tttcccatga acgggactga     960
gcttccacct cctcccacat tctcgcttgt agaggctggt gacaaagtgg tctgtttagt    1020
gctggatgtg tccagcaaga tggcagaggc tgacagactc cttcaactac aacaagccgc    1080
agaattttat ttgatgcaga ttgttgaaat tcataccttc gtgggcattg ccagtttcga    1140
cagcaaagga gagatcagag cccagctaca ccaaattaac agcaatgatg atcgaaagtt    1200
gctggtttca tatctgccca ccactgtatc agctaaaaca gacatcagca tttgttcagg    1260
gcttaagaaa ggatttgagg tggttgaaaa actgaatgga aaagcttatg gctctgtgat    1320
gatattagtg accagcggag atgataagct tcttggcaat tgcttaccca ctgtgctcag    1380
cagtggttca acaattcact ccattgccct gggttcatct gcagcccaa atctggagga    1440 attatcacgt cttacaggag gtttaaagtt ctttgttcca gatatatcaa actccaatag    1500
catgattgat gctttcagta gaattttcctc tggaactgga gacattttcc agcaacatat    1560
tcagcttgaa agtacaggtg aaaatgtcaa acctcaccat caattgaaaa acacagtgac    1620
tgtggataat actgtgggca cgacactat gttctagtt acgtggcagg ccagtggtcc     1680
tcctgagatt atattatttg atcctgatgg acgaaaatac tacacaaata tttttatcac    1740
caatctaact tttcggacag ctagtctttg gattccagga acagctaagc ctgggcactg    1800
```

-continued

```
gacttacacc ctgaacaata cccatcattc tctgcaagcc ctgaaagtga cagtgacctc    1860
tcgcgcctcc aactcagctg tgcccccagc cactgtggaa gcctttgtgg aaagagacag    1920
cctccatttt cctcatcctg tgatgattta tgccaatgtg aaacagggat tttatcccat    1980
tcttaatgcc actgtcactg ccacagttga gccagagact ggagatcctg ttacgctgag    2040
actccttgat gatggagcag gtgctgatgt tataaaaaat gatggaattt actcgaggta    2100 tttttttctcc tttgctgcaa atggtagata tagcttgaaa gtgcatgtca atcactctcc    2160
cagcataagc accccagccc actctattcc agggagtcat gctatgtatg taccaggtta    2220
cacagcaaac ggtaatattc agatgaatgc tccaaggaaa tcagtaggca gaaatgagga    2280
ggagcgaaag tggggcttta gccgagtcag ctcaggaggc tccttttcag tgctgggagt    2340
tccagctggc ccccaccctg atgtgtttcc accatgcaaa attattgacc tggaagctgt    2400
aaatagaaga ggaattgacc ctatcttgga cagcacctgg agaagacttt gatcagggcc    2460
aggctacaag ctatgaaata gaatgagta aaagtctaca gaatatccaa gatgacttta    2520
acaatgctat tttagtaaat acatcaaagc gaaatcctca gcaagctggc atcagggaga    2580
tatttacgtt ctcaccccaa atttccacga atggacctga acatcagcca aatggagaaa    2640
cacatgaaag ccacagaatt tatgttgcaa tacgagcaat ggataggaac tccttacagt    2700
ctgctgtatc taacattgcc caggcgcctc tgtttattcc ccccaattct gatcctgtac    2760
ctgccagaga ttatcttata ttga                                          2784
```

<210> SEQ ID NO 169  
<211> LENGTH: 592  
<212> TYPE: PRT  
<213> ORGANISM: Homo sapien

<400> SEQUENCE: 169

```
Met Thr Gln Arg Ser Ile Ala Gly Pro Ile Cys Asn Leu Lys Phe Val
  1               5                  10                  15

Thr Leu Val Ala Leu Ser Ser Glu Leu Pro Phe Leu Gly Ala Gly
             20                  25                  30

Val Gln Leu Gln Asp Asn Gly Tyr Asn Gly Leu Leu Ile Ala Ile Asn
         35                  40                  45

Pro Gln Val Pro Glu Asn Gln Asn Leu Ile Ser Asn Ile Lys Glu Met
     50                  55                  60

Ile Thr Glu Ala Ser Phe Tyr Leu Phe Asn Ala Thr Lys Arg Arg Val
 65                  70                  75                  80

Phe Phe Arg Asn Ile Lys Ile Leu Ile Pro Ala Thr Trp Lys Ala Asn
                 85                  90                  95

Asn Asn Ser Lys Ile Lys Gln Glu Ser Tyr Glu Lys Ala Asn Val Ile
            100                 105                 110

Val Thr Asp Trp Tyr Gly Ala His Gly Asp Asp Pro Tyr Thr Leu Gln
        115                 120                 125

Tyr Arg Gly Cys Gly Lys Glu Gly Lys Tyr Ile His Phe Thr Pro Asn
    130                 135                 140

Phe Leu Leu Asn Asp Asn Leu Thr Ala Gly Tyr Gly Ser Arg Gly Arg
145                 150                 155                 160

Val Phe Val His Glu Trp Ala His Leu Arg Trp Gly Val Phe Asp Glu
                165                 170                 175

Tyr Asn Asn Asp Lys Pro Phe Tyr Ile Asn Gly Gln Asn Gln Ile Lys
            180                 185                 190

Val Thr Arg Cys Ser Ser Asp Ile Thr Gly Ile Phe Val Cys Glu Lys
```

```
                195                 200                 205
Gly Pro Cys Pro Gln Glu Asn Cys Ile Ile Ser Lys Leu Phe Lys Glu
        210                 215                 220
Gly Cys Thr Phe Ile Tyr Asn Ser Thr Gln Asn Ala Thr Ala Ser Ile
225                 230                 235                 240
Met Phe Met Gln Ser Leu Ser Ser Val Val Glu Phe Cys Asn Ala Ser
                245                 250                 255
Thr His Asn Gln Glu Ala Pro Asn Leu Gln Asn Gln Met Cys Ser Leu
                260                 265                 270
Arg Ser Ala Trp Asp Val Ile Thr Asp Ser Ala Asp Phe His His Ser
                275                 280                 285
Phe Pro Met Asn Gly Thr Glu Leu Pro Pro Pro Thr Phe Ser Leu
                290                 295                 300
Val Glu Ala Gly Asp Lys Val Val Cys Leu Val Leu Asp Val Ser Ser
305                 310                 315                 320
Lys Met Ala Glu Ala Asp Arg Leu Leu Gln Leu Gln Ala Glu
                325                 330                 335
Phe Tyr Leu Met Gln Ile Val Glu Ile His Thr Phe Val Gly Ile Ala
                340                 345                 350
Ser Phe Asp Ser Lys Gly Glu Ile Arg Ala Gln Leu His Gln Ile Asn
        355                 360                 365
Ser Asn Asp Asp Arg Lys Leu Leu Val Ser Tyr Leu Pro Thr Thr Val
        370                 375                 380
Ser Ala Lys Thr Asp Ile Ser Ile Cys Ser Gly Leu Lys Lys Gly Phe
385                 390                 395                 400
Glu Val Val Glu Lys Leu Asn Gly Lys Ala Tyr Gly Ser Val Met Ile
                405                 410                 415
Leu Val Thr Ser Gly Asp Asp Lys Leu Leu Gly Asn Cys Leu Pro Thr
                420                 425                 430
Val Leu Ser Ser Gly Ser Thr Ile His Ser Ile Ala Leu Gly Ser Ser
                435                 440                 445
Ala Ala Pro Asn Leu Glu Glu Leu Ser Arg Leu Thr Gly Gly Leu Lys
        450                 455                 460
Phe Phe Val Pro Asp Ile Ser Asn Ser Asn Ser Met Ile Asp Ala Phe
465                 470                 475                 480
Ser Arg Ile Ser Ser Gly Thr Gly Asp Ile Phe Gln Gln His Ile Gln
                485                 490                 495
Leu Glu Ser Thr Gly Glu Asn Val Lys Pro His His Gln Leu Lys Asn
                500                 505                 510
Thr Val Thr Val Asp Asn Thr Val Gly Asn Asp Thr Met Phe Leu Val
                515                 520                 525
Thr Trp Gln Ala Ser Gly Pro Pro Glu Ile Ile Leu Phe Asp Pro Asp
        530                 535                 540
Gly Arg Lys Tyr Tyr Thr Asn Asn Phe Ile Thr Asn Leu Thr Phe Arg
545                 550                 555                 560
Thr Ala Ser Leu Trp Ile Pro Gly Thr Ala Lys Pro Gly His Trp Thr
                565                 570                 575
Tyr Thr Leu Met Cys Phe His His Ala Lys Leu Leu Thr Trp Lys Leu
                580                 585                 590

<210> SEQ ID NO 170
<211> LENGTH: 791
<212> TYPE: PRT
<213> ORGANISM: Homo sapien
```

<400> SEQUENCE: 170

| | | | | | | | | | | | | | | |
|---|---|---|---|---|---|---|---|---|---|---|---|---|---|---|
| Met | Thr | Gln | Arg | Ser | Ile | Ala | Gly | Pro | Ile | Cys | Asn | Leu | Lys | Phe | Val |
| 1 | | | | 5 | | | | | 10 | | | | | 15 | |
| Thr | Leu | Leu | Val | Ala | Leu | Ser | Ser | Glu | Leu | Pro | Phe | Leu | Gly | Ala | Gly |
| | | | 20 | | | | | 25 | | | | | 30 | | |
| Val | Gln | Leu | Gln | Asp | Asn | Gly | Tyr | Asn | Gly | Leu | Leu | Ile | Ala | Ile | Asn |
| | | 35 | | | | | 40 | | | | | 45 | | | |
| Pro | Gln | Val | Pro | Glu | Asn | Gln | Asn | Leu | Ile | Ser | Asn | Ile | Lys | Glu | Met |
| | 50 | | | | | 55 | | | | | 60 | | | | |
| Ile | Thr | Glu | Ala | Ser | Phe | Tyr | Leu | Phe | Asn | Ala | Thr | Lys | Arg | Arg | Val |
| 65 | | | | | 70 | | | | | 75 | | | | | 80 |
| Phe | Phe | Arg | Asn | Ile | Lys | Ile | Leu | Ile | Pro | Ala | Thr | Trp | Lys | Ala | Asn |
| | | | | 85 | | | | | 90 | | | | | 95 | |
| Asn | Asn | Ser | Lys | Ile | Lys | Gln | Glu | Ser | Tyr | Glu | Lys | Ala | Asn | Val | Ile |
| | | | 100 | | | | | 105 | | | | | 110 | | |
| Val | Thr | Asp | Trp | Tyr | Gly | Ala | His | Gly | Asp | Asp | Pro | Tyr | Thr | Leu | Gln |
| | | 115 | | | | | 120 | | | | | 125 | | | |
| Tyr | Arg | Gly | Cys | Gly | Lys | Glu | Gly | Lys | Tyr | Ile | His | Phe | Thr | Pro | Asn |
| | 130 | | | | | 135 | | | | | 140 | | | | |
| Phe | Leu | Leu | Asn | Asp | Asn | Leu | Thr | Ala | Gly | Tyr | Gly | Ser | Arg | Gly | Arg |
| 145 | | | | | 150 | | | | | 155 | | | | | 160 |
| Val | Phe | Val | His | Glu | Trp | Ala | His | Leu | Arg | Trp | Gly | Val | Phe | Asp | Glu |
| | | | | 165 | | | | | 170 | | | | | 175 | |
| Tyr | Asn | Asn | Asp | Lys | Pro | Phe | Tyr | Ile | Asn | Gly | Gln | Asn | Gln | Ile | Lys |
| | | | 180 | | | | | 185 | | | | | 190 | | |
| Val | Thr | Arg | Cys | Ser | Ser | Asp | Ile | Thr | Gly | Ile | Phe | Val | Cys | Glu | Lys |
| | | 195 | | | | | 200 | | | | | 205 | | | |
| Gly | Pro | Cys | Pro | Gln | Glu | Asn | Cys | Ile | Ile | Ser | Lys | Leu | Phe | Lys | Glu |
| | 210 | | | | | 215 | | | | | 220 | | | | |
| Gly | Cys | Thr | Phe | Ile | Tyr | Asn | Ser | Thr | Gln | Asn | Ala | Thr | Ala | Ser | Ile |
| 225 | | | | | 230 | | | | | 235 | | | | | 240 |
| Met | Phe | Met | Gln | Ser | Leu | Ser | Ser | Val | Val | Glu | Phe | Cys | Asn | Ala | Ser |
| | | | | 245 | | | | | 250 | | | | | 255 | |
| Thr | His | Asn | Gln | Glu | Ala | Pro | Asn | Leu | Gln | Asn | Gln | Met | Cys | Ser | Leu |
| | | | 260 | | | | | 265 | | | | | 270 | | |
| Arg | Ser | Ala | Trp | Asp | Val | Ile | Thr | Asp | Ser | Ala | Asp | Phe | His | His | Ser |
| | | 275 | | | | | 280 | | | | | 285 | | | |
| Phe | Pro | Met | Asn | Gly | Thr | Glu | Leu | Pro | Pro | Pro | Thr | Phe | Ser | Leu |
| | 290 | | | | | 295 | | | | | 300 | | | | |
| Val | Glu | Ala | Gly | Asp | Lys | Val | Val | Cys | Leu | Val | Leu | Asp | Val | Ser | Ser |
| 305 | | | | | 310 | | | | | 315 | | | | | 320 |
| Lys | Met | Ala | Glu | Ala | Asp | Arg | Leu | Leu | Gln | Leu | Gln | Gln | Ala | Ala | Glu |
| | | | | 325 | | | | | 330 | | | | | 335 | |
| Phe | Tyr | Leu | Met | Gln | Ile | Val | Glu | Ile | His | Thr | Phe | Val | Gly | Ile | Ala |
| | | | 340 | | | | | 345 | | | | | 350 | | |
| Ser | Phe | Asp | Ser | Lys | Gly | Glu | Ile | Arg | Ala | Gln | Leu | His | Gln | Ile | Asn |
| | | 355 | | | | | 360 | | | | | 365 | | | |
| Ser | Asn | Asp | Asp | Arg | Lys | Leu | Leu | Val | Ser | Tyr | Leu | Pro | Thr | Thr | Val |
| | 370 | | | | | 375 | | | | | 380 | | | | |
| Ser | Ala | Lys | Thr | Asp | Ile | Ser | Ile | Cys | Ser | Gly | Leu | Lys | Lys | Gly | Phe |
| 385 | | | | | 390 | | | | | 395 | | | | | 400 |
| Glu | Val | Val | Glu | Lys | Leu | Asn | Gly | Lys | Ala | Tyr | Gly | Ser | Val | Met | Ile |

```
                        405                 410                 415
    Leu Val Thr Ser Gly Asp Asp Lys Leu Leu Gly Asn Cys Leu Pro Thr
                    420                 425                 430
    Val Leu Ser Ser Gly Ser Thr Ile His Ser Ile Ala Leu Gly Ser Ser
                435                 440                 445
    Ala Ala Pro Asn Leu Glu Glu Leu Ser Arg Leu Thr Gly Gly Leu Lys
    450                 455                 460
    Phe Phe Val Pro Asp Ile Ser Asn Ser Asn Ser Met Ile Asp Ala Phe
    465                 470                 475                 480
    Ser Arg Ile Ser Ser Gly Thr Gly Asp Ile Phe Gln Gln His Ile Gln
                    485                 490                 495
    Leu Glu Ser Thr Gly Glu Asn Val Lys Pro His His Gln Leu Lys Asn
                500                 505                 510
    Thr Val Thr Val Asp Asn Thr Val Gly Asn Asp Thr Met Phe Leu Val
                515                 520                 525
    Thr Trp Gln Ala Ser Gly Pro Pro Glu Ile Ile Leu Phe Asp Pro Asp
            530                 535                 540
    Gly Arg Lys Tyr Tyr Thr Asn Asn Phe Ile Thr Asn Leu Thr Phe Arg
    545                 550                 555                 560
    Thr Ala Ser Leu Trp Ile Pro Gly Thr Ala Lys Pro Gly His Trp Thr
                    565                 570                 575
    Tyr Thr Leu Asn Asn Thr His His Ser Leu Gln Ala Leu Lys Val Thr
                580                 585                 590
    Val Thr Ser Arg Ala Ser Asn Ser Ala Val Pro Pro Ala Thr Val Glu
                595                 600                 605
    Ala Phe Val Glu Arg Asp Ser Leu His Phe Pro His Pro Val Met Ile
    610                 615                 620
    Tyr Ala Asn Val Lys Gln Gly Phe Tyr Pro Ile Leu Asn Ala Thr Val
    625                 630                 635                 640
    Thr Ala Thr Val Glu Pro Glu Thr Gly Asp Pro Val Thr Leu Arg Leu
                    645                 650                 655
    Leu Asp Asp Gly Ala Gly Ala Asp Val Ile Lys Asn Asp Gly Ile Tyr
                660                 665                 670
    Ser Arg Tyr Phe Phe Ser Phe Ala Ala Asn Gly Arg Tyr Ser Leu Lys
                675                 680                 685
    Val His Val Asn His Ser Pro Ser Ile Ser Thr Pro Ala His Ser Ile
    690                 695                 700
    Pro Gly Ser His Ala Met Tyr Val Pro Gly Tyr Thr Ala Asn Gly Asn
    705                 710                 715                 720
    Ile Gln Met Asn Ala Pro Arg Lys Ser Val Gly Arg Asn Glu Glu Glu
                    725                 730                 735
    Arg Lys Trp Gly Phe Ser Arg Val Ser Ser Gly Gly Ser Phe Ser Val
                740                 745                 750
    Leu Gly Val Pro Ala Gly Pro His Pro Asp Val Phe Pro Pro Cys Lys
                755                 760                 765
    Ile Ile Asp Leu Glu Ala Val Asn Arg Arg Gly Ile Asp Pro Ile Leu
    770                 775                 780
    Asp Ser Thr Trp Arg Arg Leu
    785                 790

<210> SEQ ID NO 171
    <211> LENGTH: 1491
    <212> TYPE: DNA
    <213> ORGANISM: Homo sapien
```

<400> SEQUENCE: 171

```
cctcctgcca gccaagtgaa gacatgctta cttcccctcc accttccttc atgatgtggg    60
aagagtgctg caacccagcc ctagccaacg ccgcatgaga gggagtgtgc cgagggcttc   120
tgagaaggtt tctctcacat ctagaaagaa gcgcttaaga tgtggcagcc ctcttcttc    180
aagtggctct tgtcctgttg ccctgggagt tctcaaattg ctgcagcagc ctccacccag   240
cctgaggatg acatcaatac acagaggaag aagagtcagg aaaagatgag agaagttaca   300
gactctcctg ggcgaccccg agagcttacc attcctcaga cttcttcaca tggtgctaac   360
agatttgttc ctaaaagtaa agctctagag gccgtcaaat tggcaataga agccgggttc   420
caccatattg attctgcaca tgtttacaat aatgaggagc aggttggact ggccatccga   480
agcaagattg cagatggcag tgtgaagaga gaagacatat tctacacttc aaagctttgg   540
agcaattccc atcgaccaga gttggtccga ccagccttgg aaaggtcact gaaaaatctt   600
caattggact atgttgacct ctatcttatt cattttccag tgtctgtaaa gccaggtgag   660
gaagtgatcc caaagatga aaatggaaaa atactatttg acacagtgga tctctgtgcc   720
acatgggagg ccatggagaa gtgtaaagat gcaggattgg ccaagtccat cggggtgtcc   780
aacttcaacc acaggctgct ggagatgatc ctcaacaagc cagggctcaa gtacaagcct   840
gtctgcaacc aggtggaatg tcatccttac ttcaaccaga gaaactgct ggatttctgc    900
aagtcaaaag acattgttct ggttgcctat agtgctctgg gatcccatcg agaagaacca   960
tgggtggacc cgaactcccc ggtgctcttg gaggacccag tcctttgtgc cttggcaaaa  1020
aagcacaagc gaaccccagc cctgattgcc ctgcgctacc agctgcagcg tggggttgtg  1080
gtcctggcca agagctacaa tgagcagcgc atcagacaga acgtgcaggt gtttgaattc  1140
cagttgactt cagaggagat gaaagccata gatggcctaa acagaaatgt gcgatatttg  1200
acccttgata ttttgctgg cccccctaat tatccatttt ctgatgaata ttaacatgga   1260
gggcattgca tgaggtctgc cagaaggccc tgcgtgtgga tggtgacaca gaggatggct  1320
ctatgctggt gactggacac atcgcctctg gttaaatctc tcctgcttgg cgacttcagt  1380
aagctacagc taagcccatc ggccggaaaa gaaagacaat aattttgttt ttcattttga  1440
aaaaattaaa tgctctctcc taaagattct tcacctaaaa aaaaaaaaa a            1491
```

<210> SEQ ID NO 172
<211> LENGTH: 364
<212> TYPE: PRT
<213> ORGANISM: Homo sapien

<400> SEQUENCE: 172

```
Met Trp Gln Pro Leu Phe Phe Lys Trp Leu Leu Ser Cys Cys Pro Gly
 1               5                  10                  15

Ser Ser Gln Ile Ala Ala Ala Ser Thr Gln Pro Glu Asp Asp Ile
            20                  25                  30

Asn Thr Gln Arg Lys Lys Ser Gln Glu Lys Met Arg Glu Val Thr Asp
        35                  40                  45

Ser Pro Gly Arg Pro Arg Glu Leu Thr Ile Pro Gln Thr Ser Ser His
    50                  55                  60

Gly Ala Asn Arg Phe Val Pro Lys Ser Lys Ala Leu Glu Ala Val Lys
65                  70                  75                  80

Leu Ala Ile Glu Ala Gly Phe His His Ile Asp Ser Ala His Val Tyr
                85                  90                  95
```

```
Asn Asn Glu Glu Gln Val Gly Leu Ala Ile Arg Ser Lys Ile Ala Asp
            100                 105                 110
Gly Ser Val Lys Arg Glu Asp Ile Phe Tyr Thr Ser Lys Leu Trp Ser
        115                 120                 125
Asn Ser His Arg Pro Glu Leu Val Arg Pro Ala Leu Glu Arg Ser Leu
    130                 135                 140
Lys Asn Leu Gln Leu Asp Tyr Val Asp Leu Tyr Leu Ile His Phe Pro
145                 150                 155                 160
Val Ser Val Lys Pro Gly Glu Glu Val Ile Pro Lys Asp Glu Asn Gly
                165                 170                 175
Lys Ile Leu Phe Asp Thr Val Asp Leu Cys Ala Thr Trp Glu Ala Met
            180                 185                 190
Glu Lys Cys Lys Asp Ala Gly Leu Ala Lys Ser Ile Gly Val Ser Asn
        195                 200                 205
Phe Asn His Arg Leu Leu Glu Met Ile Leu Asn Lys Pro Gly Leu Lys
    210                 215                 220
Tyr Lys Pro Val Cys Asn Gln Val Glu Cys His Pro Tyr Phe Asn Gln
225                 230                 235                 240
Arg Lys Leu Leu Asp Phe Cys Lys Ser Lys Asp Ile Val Leu Val Ala
                245                 250                 255
Tyr Ser Ala Leu Gly Ser His Arg Glu Glu Pro Trp Val Asp Pro Asn
            260                 265                 270
Ser Pro Val Leu Leu Glu Asp Pro Val Leu Cys Ala Leu Ala Lys Lys
        275                 280                 285
His Lys Arg Thr Pro Ala Leu Ile Ala Leu Arg Tyr Gln Leu Gln Arg
    290                 295                 300
Gly Val Val Val Leu Ala Lys Ser Tyr Asn Glu Gln Arg Ile Arg Gln
305                 310                 315                 320
Asn Val Gln Val Phe Glu Phe Gln Leu Thr Ser Glu Glu Met Lys Ala
                325                 330                 335
Ile Asp Gly Leu Asn Arg Asn Val Arg Tyr Leu Thr Leu Asp Ile Phe
            340                 345                 350
Ala Gly Pro Pro Asn Tyr Pro Phe Ser Asp Glu Tyr
        355                 360

<210> SEQ ID NO 173
<211> LENGTH: 1988
<212> TYPE: DNA
<213> ORGANISM: Homo sapiens

<400> SEQUENCE: 173
cgggagccgc ctccccgcgg cctcttcgct tttgtggcgg cgcccgcgct cgcaggccac    60
tctctgctgt cgcccgtccc gcgcgctcct ccgacccgct ccgctccgct ccgctcggcc   120
ccgcgccgcc cgtcaacatg atccgctgcg gcctggcctg cgagcgctgc cgctggatcc   180
tgcccctgct cctactcagc gccatcgcct tcgacatcat cgcgctggcc ggccgcggct   240
ggttgcagtc tagcgaccac ggccagacgt cctcgctgtg gtggaaatgc tcccaagagg   300
gcggcggcag cgggtcctac gaggagggct gtcagagcct catggagtac gcgtggggta   360
gagcagcggc tgccatgctc ttctgtggct tcatcatcct ggtgatctgt ttcatccctct   420
ccttcttcgc cctctgtgga ccccagatgc ttgtcttcct gagagtgatt ggaggtctcc   480
ttgccttggc tgctgtgttc cagatcatct ccctggtaat ttaccccgtg aagtacaccc   540
agaccttcac ccttcatgcc aaccctgctg tcacttacat ctataactgg gcctacggct   600
```

```
ttgggtgggc agccacgatt atcctgatcg gctgtgcctt cttcttctgc tgcctcccca    660
actacgaaga tgaccttctg ggcaatgcca agcccaggta cttctacaca tctgcctaac    720
ttgggaatga atgtgggaga aaatcgctgc tgctgagatg gactccagaa gaagaaactg    780
tttctccagg cgactttgaa cccattttt ggcagtgttc atattattaa actagtcaaa    840
aatgctaaaa taatttggga gaaatatttt tttaagtagt gttatagttt catgtttatc    900
ttttattatg ttttgtgaag ttgtgtcttt tcactaatta cctatactat gccaatattt    960
ccttatatct atccataaca tttatactac atttgtaaga gaatatgcac gtgaaactta   1020
acactttata aggtaaaaat gaggtttcca agatttaata atctgatcaa gttcttgtta   1080
tttccaaata gaatggactt ggtctgttaa gggctaagga gaagaggaag ataaggttaa   1140
aagttgttaa tgaccaaaca ttctaaaaga aatgcaaaaa aaagtttat tttcaagcct    1200 tcgaactatt taaggaaagc aaaatcattt cctaaatgca tatcatttgt gagaatttct   1260
cattaatatc ctgaatcatt catttcagct aaggcttcat gttgactcga tatgtcatct   1320
aggaaagtac tatttcatgg tccaaacctg ttgccatagt tggtaaggct ttcctttaag   1380
tgtgaaatat ttagatgaaa ttttctcttt taaagttctt tatagggtta gggtgtggga   1440
aaatgctata ttaataaatc tgtagtgttt tgtgtttata tgttcagaac cagagtagac   1500
tggattgaaa gatggactgg gtctaattta tcatgactga tagatctggt taagttgtgt   1560
agtaaagcat taggagggtc attcytgtca caaaagtgcc actaaaacag cctcaggaga   1620
ataaatgact tgcttttcta aatctcaggt ttatctgggc tctatcatat agacaggctt   1680
ctgatagttt gcarctgtaa gcagaaacct acatatagtt aaaatcctgg tctttcttgg   1740
taaacagatt ttaaatgtct gatataaaac atgccacagg agaattcggg gatttgagtt   1800
tctctgaata gcatatatat gatgcatcgg ataggtcatt atgattttt accatttcga   1860 cttacataat gaaaaccaat tcattttaaa tatcagatta ttattttgta agttgtggaa   1920
aaagctaatt gtagttttca ttatgaagtt ttcccaataa accaggtatt ctaaaaaaaa   1980
aaaaaaaa                                                            1988
```

<210> SEQ ID NO 174
<211> LENGTH: 238
<212> TYPE: PRT
<213> ORGANISM: Homo sapiens

<400> SEQUENCE: 174

```
Gly Ala Ala Ser Pro Arg Pro Leu Arg Phe Cys Gly Gly Ala Arg Ala
                 5                  10                  15

Arg Arg Pro Leu Ser Ala Val Ala Arg Pro Ala Arg Ser Ser Asp Pro
             20                  25                  30

Leu Arg Ser Ala Pro Leu Gly Pro Ala Pro Val Asn Met Ile Arg
         35                  40                  45

Cys Gly Leu Ala Cys Glu Arg Cys Arg Trp Ile Leu Pro Leu Leu Leu
     50                  55                  60

Leu Ser Ala Ile Ala Phe Asp Ile Ile Ala Leu Ala Gly Arg Gly Trp
 65                  70                  75                  80

Leu Gln Ser Ser Asp His Gly Gln Thr Ser Ser Leu Trp Trp Lys Cys
                 85                  90                  95

Ser Gln Glu Gly Gly Gly Ser Gly Ser Tyr Glu Glu Gly Cys Gln Ser
            100                 105                 110

Leu Met Glu Tyr Ala Trp Gly Arg Ala Ala Ala Ala Met Leu Phe Cys
        115                 120                 125
```

```
Gly Phe Ile Ile Leu Val Ile Cys Phe Ile Leu Ser Phe Phe Ala Leu
    130                 135                 140
Cys Gly Pro Gln Met Leu Val Phe Leu Arg Val Ile Gly Gly Leu Leu
145                 150                 155                 160
Ala Leu Ala Ala Val Phe Gln Ile Ile Ser Leu Val Ile Tyr Pro Val
                165                 170                 175
Lys Tyr Thr Gln Thr Phe Thr Leu His Ala Asn Pro Ala Val Thr Tyr
                180                 185                 190
Ile Tyr Asn Trp Ala Tyr Gly Phe Gly Trp Ala Ala Thr Ile Ile Leu
            195                 200                 205
Ile Gly Cys Ala Phe Phe Cys Cys Leu Pro Asn Tyr Glu Asp Asp
    210                 215                 220
Leu Leu Gly Asn Ala Lys Pro Arg Tyr Phe Tyr Thr Ser Ala
225                 230                 235
```

<210> SEQ ID NO 175
<211> LENGTH: 4181
<212> TYPE: DNA
<213> ORGANISM: Homo sapiens
<220> FEATURE:
<221> NAME/KEY: unsure
<222> LOCATION: (3347)
<223> OTHER INFORMATION: n=A,T,C or G
<221> NAME/KEY: unsure
<222> LOCATION: (3502)
<223> OTHER INFORMATION: n=A,T,C or G
<221> NAME/KEY: unsure
<222> LOCATION: (3506)
<223> OTHER INFORMATION: n=A,T,C or G
<221> NAME/KEY: unsure
<222> LOCATION: (3520)
<223> OTHER INFORMATION: n=A,T,C or G
<221> NAME/KEY: unsure
<222> LOCATION: (3538)
<223> OTHER INFORMATION: n=A,T,C or G
<221> NAME/KEY: unsure
<222> LOCATION: (3549)
<223> OTHER INFORMATION: n=A,T,C or G
<221> NAME/KEY: unsure
<222> LOCATION: (3646)
<223> OTHER INFORMATION: n=A,T,C or G
<221> NAME/KEY: unsure
<222> LOCATION: (3940)
<223> OTHER INFORMATION: n=A,T,C or G
<221> NAME/KEY: unsure
<222> LOCATION: (3968)
<223> OTHER INFORMATION: n=A,T,C or G
<221> NAME/KEY: unsure
<222> LOCATION: (3974)
<223> OTHER INFORMATION: n=A,T,C or G
<221> NAME/KEY: unsure
<222> LOCATION: (4036)
<223> OTHER INFORMATION: n=A,T,C or G
<221> NAME/KEY: unsure
<222> LOCATION: (4056)
<223> OTHER INFORMATION: n=A,T,C or G
<221> NAME/KEY: unsure
<222> LOCATION: (4062)
<223> OTHER INFORMATION: n=A,T,C or G
<221> NAME/KEY: unsure
<222> LOCATION: (4080)
<223> OTHER INFORMATION: n=A,T,C or G
<221> NAME/KEY: unsure
<222> LOCATION: (4088)
<223> OTHER INFORMATION: n=A,T,C or G
<221> NAME/KEY: unsure
<222> LOCATION: (4115)
<223> OTHER INFORMATION: n=A,T,C or G

<400> SEQUENCE: 175

-continued

```
ggtggatgcg tttgggttgt agctaggctt tttctttttct ttctctttta aaacacatct      60
agacaaggaa aaacaagcc tcggatctga tttttcactc ctcgttcttg tgcttggttc       120
ttactgtgtt tgtgtatttt aaaggcgaga agacgagggg aacaaaacca gctggatcca      180
tccatcaccg tgggtggttt taattttttcg ttttttctcg ttatttttttt ttaaacaacc    240
actcttcaca atgaacaaac tgtatatcgg aaacctcagc gagaacgccg cccctcgga      300
cctagaaagt atcttcaagg acgccaagat cccggtgtcg ggaccctttcc tggtgaagac    360
tggctacgcg ttcgtggact gcccggacga gagctgggcc ctcaaggcca tcgaggcgct    420
ttcaggtaaa atagaactgc acgggaaacc catagaagtt gagcactcgg tcccaaaaag    480
gcaaaggatt cggaaacttc agatacgaaa tatcccgcct catttacagt gggaggtgct    540
ggatagttta ctagtccagt atggagtggt ggagagctgt gagcaagtga acactgactc    600
ggaaactgca gttgtaaatg taacctattc cagtaaggac caagctagac aagcactaga    660
caaactgaat ggatttcagt tagagaattt caccttgaaa gtagcctata tccctgatga    720
aatggccgcc cagcaaaacc ccttgcagca gccccgaggt cgccggggggc ttgggcagag   780
gggctcctca aggcagggggt ctccaggatc cgtatccaag cagaaaccat gtgatttgcc   840
tctgcgcctg ctggttccca cccaatttgt tggagccatc ataggaaaag aaggtgccac    900
cattcggaac atcaccaaac agacccagtc taaaatcgat gtccaccgta aagaaaatgc    960
gggggctgct gagaagtcga ttactatcct ctctactcct gaaggcacct ctgcggcttg  1020
taagtctatt ctggagatta tgcataagga agctcaagat ataaaattca cagaagagat   1080
cccccttgaag attttagctc ataataactt tgttggacgt cttattggta agaaggaag   1140
aaatcttaaa aaaattgagc aagacacaga cactaaaatc acgatatctc cattgcagga  1200
attgacgctg tataatccag aacgcactat tacagttaaa ggcaatgttg agacatgtgc  1260
caaagctgag gaggagatca tgaagaaaat cagggagtct tatgaaaatg atattgcttc  1320
tatgaatctt caagcacatt taattcctgg attaaatctg aacgccttgg gtctgttccc  1380
acccacttca gggatgccac ctcccacctc agggcccct tcagccatga ctcctcccta   1440
cccgcagttt gagcaatcag aaacggagac tgttcatcag tttatcccag ctctatcagt  1500
cggtgccatc atcggcaagc agggccagca catcaagcag cttctcgct ttgctggagc   1560
ttcaattaag attgctccag cggaagcacc agatgctaaa gtgaggatgg tgattatcac  1620
tggaccacca gaggctcagt tcaaggctca gggaagaatt tatggaaaaa ttaaagaaga  1680
aaactttgtt agtcctaaag aagaggtgaa acttgaagct catatcagag tgccatcctt  1740
tgctgctggc agagttattg gaaaggagg caaaacggtg aatgaacttc agaatttgtc   1800
aagtgcagaa gttgttgtcc ctcgtgacca gacacctgat gagaatgacc aagtggttgt  1860
caaaataact ggtcacttct atgcttgcca ggttgcccag agaaaaattc aggaaattct  1920
gactcaggta aagcagcacc aacaacagaa ggctctgcaa agtggaccac ctcagtcaag  1980
acggaagtaa aggctcagga acagcccac cacagaggca gatgccaaac caaagacaga  2040
ttgcttaacc aacagatggg cgctgacccc ctatccagaa tcacatgcac aagttttttac 2100
ctagccagtt gtttctgagg accaggcaac ttttgaactc ctgtctctgt gagaatgtat  2160
actttatgct ctctgaaatg tatgacaccc agctttaaaa caaacaaaca aacaaacaaa  2220
aaaagggtgg ggggagggag gaaagagaag agctctgcac ttccctttgt tgtagtctca  2280
cagtataaca gatattctaa ttcttcttaa tattcccca taatgccaga aattggctta   2340
atgatgcttt cactaaattc atcaaataga ttgctcctaa atccaattgt taaaattgga  2400
```

```
tcagaataat tatcacagga acttaaatgt taagccatta gcatagaaaa actgttctca    2460 gtttttatttt tacctaacac taacatgagt aacctaaggg aagtgctgaa tggtgttggc    2520 agggtatta aacgtgcatt tttactcaac tacctcaggt attcagtaat acaatgaaaa     2580
gcaaaattgt tcctttttt tgaaaatttt atatacttta taatgataga agtccaaccg     2640 tttttaaaa aataaattta aaatttaaca gcaatcagct aacaggcaaa ttaagatttt     2700
tacttctggc tggtgacagt aaagctggaa aattaatttc agggtttttt gaggcttttg    2760
acacagttat tagttaaatc aaatgttcaa aaatacggag cagtgcctag tatctggaga   2820
gcagcactac catttattct ttcatttata gttgggaaag tttttgacgg tactaacaaa   2880
gtggtcgcag gagattttgg aacggctggt ttaaatggct tcaggagact tcagtttttt   2940
gtttagctac atgattgaat gcataataaa tgctttgtgc ttctgactat caatacctaa   3000
agaaagtgca tcagtgaaga gatgcaagac tttcaactga ctggcaaaaa gcaagcttta   3060
gcttgtctta taggatgctt agtttgccac tacacttcag accaatggga cagtcataga   3120
tggtgtgaca gtgtttaaac gcaacaaaag gctacatttc catggggcca gcactgtcat   3180
gagcctcact aagctatttt gaagattttt aagcactgat aaattaaaaa aaaaaaaaa   3240 aaattagact ccaccttaag tagtaaagta taacaggatt tctgtatact gtgcaatcag   3300
ttctttgaaa aaaagtcaa agatagaga atacaagaaa agttttnggg atataatttg    3360
aatgactgtg aaaacatatg acctttgata acgaactcat ttgctcactc cttgacagca   3420
aagcccagta cgtacaattg tgttgggtgt gggtggtctc caaggccacg ctgctctctg   3480
aattgatttt ttgagttttg gnttgnaaga tgatcacagn catgttacac tgatcttnaa   3540
ggacatatnt tataaccctt taaaaaaaaa atcccctgcc tcattcttat ttcgagatga   3600
atttcgatac agactagatg tctttctgaa gatcaattag acattntgaa aatgatttaa   3660
agtgttttcc ttaatgttct ctgaaaacaa gtttcttttg tagttttaac caaaaaagtg   3720 cccttttgt cactggtttc tcctagcatt catgatttt ttttcacaca atgaattaaa    3780
attgctaaaa tcatggactg gctttctggt tggatttcag gtaagatgtg tttaaggcca   3840
gagcttttct cagtatttga ttttttttccc caatatttga tttttttaaaa atatacacat  3900 aggagctgca tttaaaacct gctggtttaa attctgtcan atttcacttc tagcctttta   3960
gtatggcnaa tcanaattta cttttactta agcatttgta atttggagta tctggtacta   4020
gctaagaaat aattcnataa ttgagttttg tactcnccaa anatgggtca ttcctcatgn   4080
ataatgtncc cccaatgcag cttcattttc caganacctt gacgcaggat aaatttttc   4140 atcatttagg tccccaaaaa aaaaaaaaaa aaaaaaaaa a                        4181
```

<210> SEQ ID NO 176
<211> LENGTH: 579
<212> TYPE: PRT
<213> ORGANISM: Homo sapiens

<400> SEQUENCE: 176

```
Met Asn Lys Leu Tyr Ile Gly Asn Leu Ser Glu Asn Ala Ala Pro Ser
              5                  10                  15

Asp Leu Glu Ser Ile Phe Lys Asp Ala Lys Ile Pro Val Ser Gly Pro
         20                  25                  30

Phe Leu Val Lys Thr Gly Tyr Ala Phe Val Asp Cys Pro Asp Glu Ser
     35                  40                  45

Trp Ala Leu Lys Ala Ile Glu Ala Leu Ser Gly Lys Ile Glu Leu His
```

-continued

```
            50                  55                  60
Gly Lys Pro Ile Glu Val Glu His Ser Val Pro Lys Arg Gln Arg Ile
 65                  70                  75                  80

Arg Lys Leu Gln Ile Arg Asn Ile Pro Pro His Leu Gln Trp Glu Val
                 85                  90                  95

Leu Asp Ser Leu Leu Val Gln Tyr Gly Val Val Glu Ser Cys Glu Gln
                100                 105                 110

Val Asn Thr Asp Ser Glu Thr Ala Val Val Asn Val Thr Tyr Ser Ser
                115                 120                 125

Lys Asp Gln Ala Arg Gln Ala Leu Asp Lys Leu Asn Gly Phe Gln Leu
130                 135                 140

Glu Asn Phe Thr Leu Lys Val Ala Tyr Ile Pro Asp Glu Met Ala Ala
145                 150                 155                 160

Gln Gln Asn Pro Leu Gln Gln Pro Arg Gly Arg Arg Gly Leu Gly Gln
                165                 170                 175

Arg Gly Ser Ser Arg Gln Gly Ser Pro Gly Ser Val Ser Lys Gln Lys
                180                 185                 190

Pro Cys Asp Leu Pro Leu Arg Leu Leu Val Pro Thr Gln Phe Val Gly
                195                 200                 205

Ala Ile Ile Gly Lys Glu Gly Ala Thr Ile Arg Asn Ile Thr Lys Gln
                210                 215                 220

Thr Gln Ser Lys Ile Asp Val His Arg Lys Glu Asn Ala Gly Ala Ala
225                 230                 235                 240

Glu Lys Ser Ile Thr Ile Leu Ser Thr Pro Glu Gly Thr Ser Ala Ala
                245                 250                 255

Cys Lys Ser Ile Leu Glu Ile Met His Lys Glu Ala Gln Asp Ile Lys
                260                 265                 270

Phe Thr Glu Glu Ile Pro Leu Lys Ile Leu Ala His Asn Asn Phe Val
                275                 280                 285

Gly Arg Leu Ile Gly Lys Glu Gly Arg Asn Leu Lys Lys Ile Glu Gln
                290                 295                 300

Asp Thr Asp Thr Lys Ile Thr Ile Ser Pro Leu Gln Glu Leu Thr Leu
305                 310                 315                 320

Tyr Asn Pro Glu Arg Thr Ile Thr Val Lys Gly Asn Val Glu Thr Cys
                325                 330                 335

Ala Lys Ala Glu Glu Glu Ile Met Lys Lys Ile Arg Glu Ser Tyr Glu
                340                 345                 350

Asn Asp Ile Ala Ser Met Asn Leu Gln Ala His Leu Ile Pro Gly Leu
                355                 360                 365

Asn Leu Asn Ala Leu Gly Leu Phe Pro Pro Thr Ser Gly Met Pro Pro
                370                 375                 380

Pro Thr Ser Gly Pro Pro Ser Ala Met Thr Pro Pro Tyr Pro Gln Phe
385                 390                 395                 400

Glu Gln Ser Glu Thr Glu Thr Val His Gln Phe Ile Pro Ala Leu Ser
                405                 410                 415

Val Gly Ala Ile Ile Gly Lys Gln Gly Gln His Ile Lys Gln Leu Ser
                420                 425                 430

Arg Phe Ala Gly Ala Ser Ile Lys Ile Ala Pro Ala Glu Ala Pro Asp
                435                 440                 445

Ala Lys Val Arg Met Val Ile Ile Thr Gly Pro Pro Glu Ala Gln Phe
                450                 455                 460

Lys Ala Gln Gly Arg Ile Tyr Gly Lys Ile Lys Glu Glu Asn Phe Val
465                 470                 475                 480
```

```
Ser Pro Lys Glu Glu Val Lys Leu Glu Ala His Ile Arg Val Pro Ser
                485                 490                 495

Phe Ala Ala Gly Arg Val Ile Gly Lys Gly Gly Lys Thr Val Asn Glu
            500                 505                 510

Leu Gln Asn Leu Ser Ser Ala Glu Val Val Pro Arg Asp Gln Thr
        515                 520                 525

Pro Asp Glu Asn Asp Gln Val Val Lys Ile Thr Gly His Phe Tyr
    530                 535                 540

Ala Cys Gln Val Ala Gln Arg Lys Ile Gln Glu Ile Leu Thr Gln Val
545                 550                 555                 560

Lys Gln His Gln Gln Gln Lys Ala Leu Gln Ser Gly Pro Pro Gln Ser
                565                 570                 575

Arg Arg Lys

<210> SEQ ID NO 177
<211> LENGTH: 401
<212> TYPE: DNA
<213> ORGANISM: Homo sapiens

<400> SEQUENCE: 177
atgccccgta aatgtcttca gtgttcttca gggtagttgg gatctcaaaa gatttggttc      60
agatccaaac aaatacacat tctgtgtttt agctcagtgt tttctaaaaa agaaactgc     120
cacacagcaa aaaattgttt actttgttgg acaaaccaaa tcagttctca aaaaatgacc    180
ggtgcttata aaaagttata aatatcgagt agctctaaaa caaaccacct gaccaagagg    240
gaagtgagct tgtgcttagt atttacattg gatgccagtt ttgtaatcac tgacttatgt    300
gcaaactggt gcagaaattc tataaactct ttgctgtttt tgatacctgc tttttgtttc    360
attttgtttt gttttgtaaa aatgataaaa cttcagaaaa t                        401

<210> SEQ ID NO 178
<211> LENGTH: 561
<212> TYPE: DNA
<213> ORGANISM: Homo sapiens

<400> SEQUENCE: 178
acgcctttca agggtgtacg caaagcactc attgataccc ttttggatgg ctatgaaaca      60
gcccgctatg ggacaggggt ctttggccag aatgagtacc tacgctatca ggaggccctg     120
agtgagctgg ccactgcggt taaagcacga attgggagct ctcagcgaca tcaccagtca     180
gcagccaaag acctaactca gtcccctgag gtctccccaa caaccatcca ggtgacatac     240
ctcccctcca gtcagaagag taaacgtgcc aagcacttcc ttgaattgaa gagctttaag     300
gataactata acacattgga gagtactctg tgacggagct gaaggactct tgccgtagat     360
taagccagtc agttgcaatg tgcaagacag gctgcttgcc gggccgccct cggaacatct     420
ggcccagcag gcccagactg tatccatcca agttcccgtt gtatccagag ttcttagagc     480
ttgtgtctaa agggtaattc cccaacccct ccttatgagc atttttagaa cattggctaa     540
gactattttc ccccagtagc g                                               561

<210> SEQ ID NO 179
<211> LENGTH: 521
<212> TYPE: DNA
<213> ORGANISM: Homo sapiens

<400> SEQUENCE: 179
```

```
cccaacgcgt tgcaaatat tccctggta gcctacttcc ttaccccga atattggtaa      60 gatcgagcaa tggcttcagg acatgggttc tcttctcctg tgatcattca agtgctcact    120
gcatgaagac tggcttgtct cagtgtttca acctcaccag gctgtctct tggtccacac    180 ctcgctccct gttagtgccg tatgacagcc ccatcaaat gaccttggcc aagtcacggt    240
ttctctgtgg tcaaggttgg ttggctgatt ggtggaaagt agggtggacc aaaggaggcc    300
acgtgagcag tcagcaccag ttctgcacca gcagcgcctc cgtcctagtg ggtgttcctg    360
tttctcctgg ccctgggtgg gctagggcct gattcgggaa gatgcctttg cagggagggg    420
aggataagtg ggatctacca attgattctg gcaaaacaat ttctaagatt tttttgcttt    480
atgtgggaaa cagatctaaa tctcatttta tgctgtattt t                        521

<210> SEQ ID NO 180
<211> LENGTH: 417
<212> TYPE: DNA
<213> ORGANISM: Homo sapiens

<400> SEQUENCE: 180
ggtggaattc gccgaagatg gcggaggtgc aggtcctggt gcttgatggt cgaggccatc     60
tcctgggccg cctggcggcc atcgtggcta acaggtact gctgggccgg aagtggtgg     120 tcgtacgctg tgaaggcatc aacatttctg gcaatttcta cagaaacaag ttgaagtacc    180
tggctttcct ccgcaagcgg atgaacacca accttcccg aggcccctac cacttccggg    240 ccccagccg catcttctgg cggaccgtgc gaggtatgct gccccacaaa accaagcgag    300
gccaggccgc tctggaccgt ctcaaggtgt tgacggcat cccaccgccc tacgacaaga    360 aaagcggat ggtggttcct gctgccctca aggtcgtgcg tctgaagcct acaagaa       417

<210> SEQ ID NO 181
<211> LENGTH: 283
<212> TYPE: DNA
<213> ORGANISM: Homo sapiens
<220> FEATURE:
<221> NAME/KEY: unsure
<222> LOCATION: (35)
<223> OTHER INFORMATION: n=A,T,C or G

<400> SEQUENCE: 181
gatttcttct aaataggatg taaaacttct ttcanattac tcttcctcag tcctgcctgc     60
caagaactca agtgtaactg tgataaaata accttcca ggtatattgg caggtatgtg    120
tgtaatctca gaatacacag gtgacataga tatgatatga caactggtaa tggtggattc    180
atttacattg tttacacttc tatgaccagg ccttaaggga aggtcagttt tttaaaaaac    240
caagtagtgt cttcctacct atctccagat acatgtcaaa aaa                     283

<210> SEQ ID NO 182
<211> LENGTH: 401
<212> TYPE: DNA
<213> ORGANISM: Homo sapiens

<400> SEQUENCE: 182
atattcttgc tgcttatgca gctgacattg ttgccctccc taaagcaacc aagtagcctt     60
tatttcccac agtgaaagaa aacgctggcc tatcagttac attacaaaag gcagatttca    120
agaggattga gtaagtagtt ggatggcttt cataaaaaca agaattcaag aagaggattc    180
atgctttaag aaacatttgt tatacattcc tcacaaatta tacctgggat aaaaactatg    240
tagcaggcag tgtgttttcc ttccatgtct ctctgcacta cctgcagtgt gtcctctgag    300
```

```
gctgcaagtc tgtcctatct gaattcccag cagaagcact aagaagctcc accctatcac      360
ctagcagata aaactatggg gaaaacttaa atctgtgcat a                           401
```

<210> SEQ ID NO 183
<211> LENGTH: 366
<212> TYPE: DNA
<213> ORGANISM: Homo sapiens
<220> FEATURE:
<221> NAME/KEY: unsure
<222> LOCATION: (325)
<223> OTHER INFORMATION: n=A,T,C or G

<400> SEQUENCE: 183

```
accgtgtcca gttttttaga acccttgtta gccagaccga ggtgtcctgg tcaccgtttc       60
accatcatgc tttgatgttc ccctgtcttt ctctcttctg ctctcaagag caaaggttaa      120
tttaaggaca aagatgaagt cactgtaaac taatctgtca ttgttttttac cttcctttc      180 tttttcagtg cagaaattaa agtaagtat aaagcaccgt gattgggagt gtttttgcgt      240
gtgtcggaat cactggtaaa tgttggctga aacaatccc tcccttgca cttgtgaaaa        300 cactttgagc gctttaagag attanccctga gaataatta aatatctttt ctcttcaaaa     360
aaaaaa                                                                 366
```

<210> SEQ ID NO 184
<211> LENGTH: 370
<212> TYPE: DNA
<213> ORGANISM: Homo sapiens

<400> SEQUENCE: 184

```
tcttacttca aagaaaaat aaacataaaa ataagttgc tggttcctaa caggaaaaat         60
tttaataatt gtactgagag aaactgctta cgtacacatt gcagatcaaa tatttggagt      120
taaaatgtta gtctacatag atgggtgatt gtaactttat tgccattaaa agatttcaaa      180
ttgcattcat gcttctgtgt acacataatg aaaaatgggc aaataatgaa gatctctcct     240
tcagtctgct ctgtttaatt ctgctgtctg ctcttctcta atgctgcgtc cctaattgta     300
cacagtttag tgatatctag gagtataaag ttgtcgccca tcaataaaaa tcacaaagtt     360
ggtttaaaaa                                                            370
```

<210> SEQ ID NO 185
<211> LENGTH: 107
<212> TYPE: DNA
<213> ORGANISM: Homo sapiens

<400> SEQUENCE: 185

```
ctcatattat tttccttttg agaaattgga aactctttct gttgctatta tattaataaa       60
gttggtgttt attttctggt agtcaccttc cccatttaaa aaaaaaa                   107
```

<210> SEQ ID NO 186
<211> LENGTH: 309
<212> TYPE: DNA
<213> ORGANISM: Homo sapiens

<400> SEQUENCE: 186

```
gaaaggatgg ctctggttgc cacagagctg ggacttcatg ttcttctaga gagggccaca       60
agagggccac aggggtggcc gggagttgtc agctgatgcc tgctgagagg caggaattgt      120
gccagtgagt gacagtcatg agggagtgtc tcttcttggg gaggaaagaa ggtagagcct     180
```

```
ttctgtctga atgaaaggcc aaggctacag tacagggccc cgccccagcc agggtgttaa    240
tgcccacgta gtggaggcct ctggcagatc ctgcattcca aggtcactgg actgtacgtt    300
tttatggtt                                                           309
```

<210> SEQ ID NO 187
<211> LENGTH: 477
<212> TYPE: DNA
<213> ORGANISM: Homo sapiens

<400> SEQUENCE: 187

```
ttcagtccta gcaagaagcg agaattctga gatcctccag aaagtcgagc agcacccacc     60
tccaacctcg ggccagtgtc ttcaggcttt actggggacc tgcgagctgg cctaatgtgg    120
tggcctgcaa gccaggccat ccctgggcgc cacagacgag ctccgagcca ggtcaggctt    180
cggaggccac aagctcagcc tcaggcccag gcactgattg tggcagaggg gccactaccc    240
aaggtctagc taggcccaag acctagttac ccagacagtg agaagcccct ggaaggcaga    300
aaagttggga gcatggcaga cagggaaggg aaacattttc agggaaaaga catgtatcac    360
atgtcttcag aagcaagtca ggtttcatgt aaccgagtgt cctcttgcgt gtccaaaagt    420
agcccagggc tgtagcacag gcttcacagt gattttgtgt tcagccgtga gtcacac      477
```

<210> SEQ ID NO 188
<211> LENGTH: 220
<212> TYPE: DNA
<213> ORGANISM: Homo sapiens

<400> SEQUENCE: 188

```
taaatatggt agatattaat attcctctta gatgaccagt gattccaatt gtcccaagtt     60
ttaaataagt accctgtgag tatgagataa attagtgaca atcagaacaa gtttcagtat    120
cagatgttca agaggaagtt gctattgcat tgattttaat atttgtacat aaacactgat    180 tttttttgagc attattttgt atttgttgta ctttaatacc                        220
```

<210> SEQ ID NO 189
<211> LENGTH: 417
<212> TYPE: DNA
<213> ORGANISM: Homo sapiens
<220> FEATURE:
<221> NAME/KEY: unsure
<222> LOCATION: (76)
<223> OTHER INFORMATION: n=A,T,C or G
<221> NAME/KEY: unsure
<222> LOCATION: (77)
<223> OTHER INFORMATION: n=A,T,C or G

<400> SEQUENCE: 189

```
accatcttga cagaggatac atgctcccaa aacgtttgtt accacactta aaaatcactg     60
ccatcattaa gcatcnnttt caaaattata gccattcatg atttactttt tccagatgac    120
tatcattatt ctagtccttt gaatttgtaa ggggaaaaaa aacaaaaaca aaaacttacg    180
atgcactttt ctccagcaca tcagatttca aattgaaaat taaagacatg ctatggtaat    240
gcacttgcta gtactacaca ctttgtacaa caaaaaacag aggcaagaaa caacggaaag    300
agaaaagcct tcctttgttg gcccttaaac tgagtcaaga tctgaaatgt agagatgatc    360
tctgacgata cctgtatgtt cttattgtgt aaataaaatt gctggtatga aatgaca      417
```

<210> SEQ ID NO 190
<211> LENGTH: 497
<212> TYPE: DNA

<213> ORGANISM: Homo sapiens

<400> SEQUENCE: 190

| | | | | | |
|---|---|---|---|---|---|
| gcactgcggc | gctctcccgt | cccgcggtgg | ttgctgctgc | tgccgctgct | gctgggcctg | 60 |
| aacgcaggag | ctgtcattga | ctggcccaca | gaggagggca | aggaagtatg | ggattatgtg | 120 |
| acggtccgca | aggatgccta | catgttctgg | tggctctatt | atgccaccaa | ctcctgcaag | 180 |
| aacttctcag | aactgcccct | ggtcatgtgg | cttcagggcg | gtccaggcgg | ttctagcact | 240 |
| ggatttggaa | actttgagga | aattgggccc | cttgacagtg | atctcaaacc | acggaaaacc | 300 |
| acctggctcc | aggctgccag | tctcctattt | gtggataatc | ccgtgggcac | tgggttcagt | 360 |
| tatgtgaatg | gtagtggtgc | ctatgccaag | gacctggcta | tggtggcttc | agacatgatg | 420 |
| gttctcctga | agaccttctt | cagttgccac | aaagaattcc | agacagttcc | attctacatt | 480 |
| ttctcagagt | cctatgg | | | | | 497 |

<210> SEQ ID NO 191
<211> LENGTH: 175
<212> TYPE: DNA
<213> ORGANISM: Homo sapiens

<400> SEQUENCE: 191

| | | | | | |
|---|---|---|---|---|---|
| atgttgaata | ttttgcttat | taactttgtt | tattgtcttc | tccctcgatt | agaatattag | 60 |
| ctacttgagt | acaaggattt | gagcctgtta | cattcactgc | tgaattttag | gctcctggaa | 120 |
| gatacccagc | attcaataga | gaccacacaa | taaatatatg | tcaaataaaa | aaaaa | 175 |

<210> SEQ ID NO 192
<211> LENGTH: 526
<212> TYPE: DNA
<213> ORGANISM: Homo sapiens

<400> SEQUENCE: 192

| | | | | | |
|---|---|---|---|---|---|
| agtaaacatt | attatttttt | ttatatttgc | aaaggaaaca | tatctaatcc | ttcctataga | 60 |
| aagaacagta | ttgctgtaat | tccttttctt | ttcttcctca | tttcctctgc | cccttaaaag | 120 |
| attgaagaaa | gagaaacttg | tcaactcata | tccacgttat | ctagcaaagt | acataagaat | 180 |
| ctatcactaa | gtaatgtatc | cttcagaatg | tgttggttta | ccagtgacac | cccatattca | 240 |
| tcacaaaatt | aaagcaagaa | gtccatagta | atttatttgc | taatagtgga | ttttttaatgc | 300 |
| tcagagtttc | tgaggtcaaa | ttttatcttt | tcacttacaa | gctctatgat | cttaaataat | 360 |
| ttacttaatg | tattttggtg | tattttcctc | aaattaatat | tggtgttcaa | gactatatct | 420 |
| aattcctctg | atcactttga | gaaacaaact | tttattaaat | gtaaggcact | tttctatgaa | 480 |
| ttttaaatat | aaaaataaat | attgttctga | ttattactga | aaaaaa | | 526 |

<210> SEQ ID NO 193
<211> LENGTH: 553
<212> TYPE: DNA
<213> ORGANISM: Homo sapiens
<220> FEATURE:
<221> NAME/KEY: unsure
<222> LOCATION: (290)
<223> OTHER INFORMATION: n=A,T,C or G
<221> NAME/KEY: unsure
<222> LOCATION: (300)
<223> OTHER INFORMATION: n=A,T,C or G
<221> NAME/KEY: unsure
<222> LOCATION: (411)
<223> OTHER INFORMATION: n=A,T,C or G
<221> NAME/KEY: unsure
<222> LOCATION: (441)

<223> OTHER INFORMATION: n=A,T,C or G

<400> SEQUENCE: 193

| | |
|---|---|
| tccattgtgg tggaattcgc tctctggtaa aggcgtgcag gtgttggccg cggcctctga | 60 |
| gctgggatga gccgtgctcc cggtggaagc aagggagccc agccggagcc atggccagta | 120 |
| cagtggtagc agttggactg accattgctg ctgcaggatt gcaggccgt tacgttttgc | 180 |
| aagccatgaa gcatatggag cctcaagtaa acaagtttt tcaaagccta ccaaaatctg | 240 |
| ccttcagtgg tggctattat agaggtgggt ttgaacccaa aatgacaaan cgggaagcan | 300 |
| cattaatact aggtgtaagc cctactgcca ataaagggaa aataagagat gctcatcgac | 360 |
| gaattatgct tttaaatcat cctgacaaag gaggatctcc ttatatagca nccaaaatca | 420 |
| atgaagctaa agatttacta naaggtcaag ctaaaaaatg aagtaaatgt atgatgaatt | 480 |
| ttaagttcgt attagtttat gtatatgagt actaagtttt tataataaaa tgcctcagag | 540 |
| ctacaatttt aaa | 553 |

<210> SEQ ID NO 194
<211> LENGTH: 320
<212> TYPE: DNA
<213> ORGANISM: Homo sapiens

<400> SEQUENCE: 194

| | |
|---|---|
| cccttcccaa tccatcagta aagaccccat ctgccttgtc catgccgttt cccaacaggg | 60 |
| atgtcacttg atatgagaat ctcaaatctc aatgccttat aagcattcct tcctgtgtcc | 120 |
| attaagactc tgataattgt ctcccctcca taggaatttc tcccaggaaa gaatatatc | 180 |
| cccatctccg tttcatatca gaactaccgt ccccgatatt cccttcagag agattaaaga | 240 |
| ccagaaaaaa gtgagcctct tcatctgcac ctgtaatagt ttcagttcct attttcttcc | 300 |
| attgacccat atttataccct | 320 |

<210> SEQ ID NO 195
<211> LENGTH: 320
<212> TYPE: DNA
<213> ORGANISM: Homo sapiens
<220> FEATURE:
<221> NAME/KEY: unsure
<222> LOCATION: (203)
<223> OTHER INFORMATION: n=A,T,C or G
<221> NAME/KEY: unsure
<222> LOCATION: (218)
<223> OTHER INFORMATION: n=A,T,C or G

<400> SEQUENCE: 195

| | |
|---|---|
| aagcatgacc tgggaaatg gtcagacctt gtattgtgtt tttggccttg aaagtagcaa | 60 |
| gtgaccagaa tctgccatgg caacaggctt taaaaagac ccttaaaaag acactgtctc | 120 |
| aactgtggtg ttagcaccag ccagctctct gtacatttgc tagcttgtag ttttctaaga | 180 |
| ctgagtaaac ttcttatttt tanaaagggg aggctggntt gtaactttcc ttgtacttaa | 240 |
| ttgggtaaaa gtcttttcca caaaccacca tctattttgt gaactttgtt agtcatcttt | 300 |
| tatttggtaa attatgaact | 320 |

<210> SEQ ID NO 196
<211> LENGTH: 357
<212> TYPE: DNA
<213> ORGANISM: Homo sapiens
<220> FEATURE:
<221> NAME/KEY: unsure
<222> LOCATION: (36)

<223> OTHER INFORMATION: n=A,T,C or G

<400> SEQUENCE: 196

```
atataaaata atacgaaact ttaaaaagca ttggantgtc agtatgttga atcagtagtt      60
tcactttaac tgtaaacaat ttcttaggac accatttggg ctagtttctg tgtaagtgta     120
aatactacaa aaacttattt atactgttct tatgtcattt gttatattca tagatttata     180
tgatgatatg acatctggct aaaaagaaat tattgcaaaa ctaaccacta tgtacttttt     240
tataaatact gtatggacaa aaaatggcat tttttatatt aaattgttta gctctggcaa     300
aaaaaaaaaa ttttaagagc tggtactaat aaaggattat tatgactgtt aaaaaaa       357
```

<210> SEQ ID NO 197
<211> LENGTH: 565
<212> TYPE: DNA
<213> ORGANISM: Homo sapiens
<220> FEATURE:
<221> NAME/KEY: unsure
<222> LOCATION: (27)
<223> OTHER INFORMATION: n=A,T,C or G

<400> SEQUENCE: 197

```
tcagctgagt accatcagga tatttanccc tttaagtgct gttttgggag tagaaaacta      60
aagcaacaat acttcctctt gacagctttg attggaatgg ggttattaga tcattcacct     120
tggtcctaca cttttttagga tgcttggtga acataacacc acttataatg aacatccctg    180
gttcctatat tttgggctat gtgggtagga attgttactt gttactgcag cagcagccc     240
agaaagtaag cccagggctt cagatctaag ttagtccaaa agctaaatga tttaaagtca    300
agttgtaatg ctaggcataa gcactctata atacattaaa ttataggccg agcaattagg    360
gaatgtttct gaaacattaa acttgtattt atgtcactaa aattctaaca caaacttaaa    420
aaatgtgtct catacatatg ctgtactagg cttcatcatg catttctaaa tttgtgtatg    480
atttgaatat atgaaagaat ttatacaaga gtgttattta aaattattaa aaataaatgt    540
atataatttg tacctattgt aaaaa                                           565
```

<210> SEQ ID NO 198
<211> LENGTH: 484
<212> TYPE: DNA
<213> ORGANISM: Homo sapiens

<400> SEQUENCE: 198

```
tatgtaagta ttggtgtctg ctttaaaaaa ggagacccag acttcacctg tccttttaa      60
acatttgaga acagtgttac tctgagcagt tgggccacct tcacttatc cgacagctga     120
ctgttggatg tgtccattgt cgccagtttg gctgttgccc ggacaggaca ggacctccat    180
tgggcgcagc agcaggtggc agggtgtgg cttgaggtgg gtggcagcgt ctggtcctcc     240
tctctggtgc tttctgagag ggtctctaaa gcagagtgtg gttggcctgg gggaaggcag    300
agcacgtatt tctcccctct agtacctctg catttgtgag tgttccctct ggctttctga    360
agggcagcag actcttgagt atactgcaga ggacatgctt tatcagtagg tcctgagggc    420
tccagggget caactgacca agtaacacag aagttggggt atgtggccta tttgggtcgg    480
aaac                                                                 484
```

<210> SEQ ID NO 199
<211> LENGTH: 429
<212> TYPE: DNA
<213> ORGANISM: Homo sapiens

```
<220> FEATURE:
<221> NAME/KEY: unsure
<222> LOCATION: (77)
<223> OTHER INFORMATION: n=A,T,C or G
<221> NAME/KEY: unsure
<222> LOCATION: (88)
<223> OTHER INFORMATION: n=A,T,C or G
<221> NAME/KEY: unsure
<222> LOCATION: (134)
<223> OTHER INFORMATION: n=A,T,C or G
<221> NAME/KEY: unsure
<222> LOCATION: (151)
<223> OTHER INFORMATION: n=A,T,C or G
<221> NAME/KEY: unsure
<222> LOCATION: (189)
<223> OTHER INFORMATION: n=A,T,C or G
<221> NAME/KEY: unsure
<222> LOCATION: (227)
<223> OTHER INFORMATION: n=A,T,C or G
<221> NAME/KEY: unsure
<222> LOCATION: (274)
<223> OTHER INFORMATION: n=A,T,C or G
<221> NAME/KEY: unsure
<222> LOCATION: (319)
<223> OTHER INFORMATION: n=A,T,C or G

<400> SEQUENCE: 199
gcttatgttt tttgttttaa cttttgtttt ttaacattta gaatattaca ttttgtatta      60
tacagtacct ttctcanaca ttttgtanaa ttcatttcgg cagctcacta ggattttgct     120
gaacattaaa aagngtgata gcgatattag ngccaatcaa atggaaaaaa ggtagtctta     180
ataaacaana cacaacgttt ttatacaaca tactttaaaa tattaanaaa actccttaat     240
attgtttcct attaagtatt attctttggg caanattttc tgatgctttt gattttctct    300
caatttagca tttgctttng gttttttttct ctatttagca ttctgttaag gcacaaaaac   360
tatgtactgt atgggaaatg ttgtaaatat tacctttttcc acattttaaa cagacaactt   420
tgaatccaa                                                             429

<210> SEQ ID NO 200
<211> LENGTH: 279
<212> TYPE: DNA
<213> ORGANISM: Homo sapiens

<400> SEQUENCE: 200
gcttttttga ggaattacag ggaagctcct ggaattgtac atggatatct ttatccctag      60
ggggaaatca aggagctggg caccoctaat tctttatgga agtgtttaaa actattttaa     120
ttttattaca agtattacta gagtagtggt tctactctaa gatttcaaaa gtgcatttaa     180
aatcatacat gttcccgcct gcaaatatat tgttattttg gtggagaaaa aaatagtata     240
ttctacataa aaaattaaag atattaacta agaaaaaaa                             279

<210> SEQ ID NO 201
<211> LENGTH: 569
<212> TYPE: DNA
<213> ORGANISM: Homo sapiens

<400> SEQUENCE: 201
taggtcagta tttttagaaa ctcttaatag ctcatactct tgataccaaa agcagccctg      60
attgttaaag cacacacctg cacaagaagc agtgatggtt gcatttacat ttcctgggtg    120
cacaaaaaaa aattctcaaa aagcaaggac ttacgctttt tgcaaagcct ttgagaagtt    180
actggatcat aggaagctta taacaagaat ggaagattct taaataactc actttctttg   240
gtatccagta acagtagatg ttcaaaatat gtagctgatt aataccagca ttgtgaacgc   300
```

```
tgtacaacct tgtggttatt actaagcaag ttactactag cttctgaaaa gtagcttcat    360
aattaatgtt atttatacac tgccttccat gactttact ttgccctaag ctaatctcca    420
aaatctgaaa tgctactcca atatcagaaa aaaggggga ggtggaatta tatttcctgt    480
gattttaaga gtacagagaa tcatgcacat ctctgattag ttcatatatg tctagtgtgt    540
aataaaagtc aaagatgaac tctcaaaaa                                       569

<210> SEQ ID NO 202
<211> LENGTH: 501
<212> TYPE: DNA
<213> ORGANISM: Homo sapiens

<400> SEQUENCE: 202
attaataggc ttaataattg ttggcaagga tccttttgct ttctttggca tgcaagctcc     60
tagcatctgg cagtggggcc aagaaaataa ggtttatgca tgtatgatgg ttttcttctt    120
gagcaacatg attgagaacc agtgtatgtc aacaggtgca tttgagataa ctttaaatga    180
tgtacctgtg tggtctaagc tggaatctgg tcaccttcca tccatgcaac aacttgttca    240
aattcttgac aatgaaatga agctcaatgt gcatatggat tcaatcccac accatcgatc    300
atagcaccac ctatcagcac tgaaaactct tttgcattaa gggatcattg caagagcagc    360
gtgactgaca ttatgaaggc ctgtactgaa gacagcaagc tgttagtaca gaccagatgc    420
tttcttggca ggctcgttgt acctcttgga aaacctcaat gcaagatagt gtttcagtgc    480
tggcatattt tggaattctg c                                              501

<210> SEQ ID NO 203
<211> LENGTH: 261
<212> TYPE: DNA
<213> ORGANISM: Homo sapiens
<220> FEATURE:
<221> NAME/KEY: unsure
<222> LOCATION: (36)
<223> OTHER INFORMATION: n=A,T,C or G
<221> NAME/KEY: unsure
<222> LOCATION: (96)
<223> OTHER INFORMATION: n=A,T,C or G

<400> SEQUENCE: 203
gacaagctcc tggtcttgag atgtcttctc gttaangaga tgggccttttt ggaggtaaag     60 gataaaatga atgagttctg tcatgattca ctattntata acttgcatga cctttactgt    120
gttagctctt tgaatgttct tgaaatttta gactttcttt gtaaacaaat gatatgtcct    180
tatcattgta taaaagctgt tatgtgcaac agtgtggaga ttccttgtct gatttaataa    240
aatacttaaa cactgaaaaa a                                              261

<210> SEQ ID NO 204
<211> LENGTH: 421
<212> TYPE: DNA
<213> ORGANISM: Homo sapiens

<400> SEQUENCE: 204
agcatctttt ctacaacgtt aaaattgcag aagtagctta tcattaaaaa acaacaacaa     60
caacaataac aataaatcct aagtgtaaat cagttattct acccctacc aaggatatca    120 gcctgttttt ttccttttttt ctcctgggaa taattgtggg cttcttccca aatttctaca    180 gcctcttcc tcttctcatg cttgagcttc cctgtttgca cgcatgcgtg tgcaggactg    240
gcttgtgtgc ttggactcgg ctccaggtgg aagcatgctt tcccttgtta ctgttggaga    300
```

```
aactcaaacc ttcaagccct aggtgtagcc attttgtcaa gtcatcaact gtattttgt      360 actggcatta acaaaaaaag aagataaaat attgtaccat taaactttaa taaaacttta      420
a                                                                      421

<210> SEQ ID NO 205
<211> LENGTH: 460
<212> TYPE: DNA
<213> ORGANISM: Homo sapiens

<400> SEQUENCE: 205
tactctcaca atgaaggacc tggaatgaaa atctgtgtc taaacaagtc ctctttagat       60
tttagtgcaa atccagagcc agcgtcggtt gcctcgagta attctttcat gggtacctt      120 ggaaaagctc tcaggagacc tcacctagat gcctattcaa gctttggaca gccatcagat     180
tgtcagccaa gagcctttta tttgaaagct cattcttccc cagacttgga ctctgggtca     240
gaggaagatg ggaaagaaag gacagatttt caggaagaaa atcacatttg tacctttaaa     300
cagactttag aaaactacag gactccaaat tttcagtctt atgacttgga cacatagact     360
gaatgagacc aaaggaaaag cttaacatac tacctcaagg tgaactttta tttaaaagag     420
agagaatctt atgttttta aatggagtta tgaattttaa                            460

<210> SEQ ID NO 206
<211> LENGTH: 481
<212> TYPE: DNA
<213> ORGANISM: Homo sapiens

<400> SEQUENCE: 206
tgtggtggaa ttcgggacgc ccccagaccc tgactttttc ctgcgtgggc cgtctcctcc      60
tgcggaagca gtgacctctg accctggtg accttcgctt tgagtgcctt ttgaacgctg     120
gtcccgcggg acttggtttt tcaagctct gtctgtccaa agacgctccg gtcgaggtcc     180
cgcctgccct gggtggatac ttgaacccca gacgcccctc tgtgctgctg tgtccggagg     240
cggccttccc atctgcctgc ccacccggag ctctttccgc cggcgcaggg tcccaagccc     300
acctcccgcc ctcagtcctg cggtgtgcgt ctgggcacgt cctgcacaca caatgcaagt     360
cctggcctcc gcgcccgccc gcccacgcga gccgtacccg ccgccaactc tgttatttat     420
ggtgtgaccc cctggaggtg ccctcggccc accggggcta tttattgttt aatttatttg     480
t                                                                      481

<210> SEQ ID NO 207
<211> LENGTH: 605
<212> TYPE: DNA
<213> ORGANISM: Homo sapiens

<400> SEQUENCE: 207 acccttttg gattcagggc tcctcacaat taaaatgagt gtaatgaaac aagtgaaaa        60 tatagaagca tcccttttgta tactgttttg ctacttacag tgtacttggc attgcttat     120 ctcactggat tctcacggta ggatttctga gatcttaatc taagctccaa agttgtctac     180
ttttttgatc ctagggtgct ccttttgttt tacagagcag ggtcacttga tttgctagct     240
ggtggcagaa ttggcaccat tacccaggtc tgactgacca ccagtcagag gcactttatt     300
tgtatcatga aatgatttga aatcattgta agcagcgaa gtctgataat gaatgccagc      360
tttccttgtg ctttgataac aaagactcca atattctgg agaacctgga taaagttttg     420
```

-continued

| | |
|---|---|
| aagggctaga ttgggatttg aagacaaaat tgtaggaaat cttacatttt tgcaataaca | 480 |
| aacattaatg aaagcaaaac attataaaag taattttaat tcaccacata cttatcaatt | 540 |
| tcttgatgct tccaaatgac atctaccaga tatggttttg tggacatctt tttctgttta | 600 |
| cataa | 605 |

<210> SEQ ID NO 208
<211> LENGTH: 655
<212> TYPE: DNA
<213> ORGANISM: Homo sapiens

<400> SEQUENCE: 208

| | |
|---|---|
| ggcgttgttc tggattcccg tcgtaactta aagggaaact ttcacaatgt ccggagccct | 60 |
| tgatgtcctg caaatgaagg aggaggatgt ccttaagttc cttgcagcag gaacccactt | 120 |
| aggtggcacc aatcttgact tccagatgga acagtacatc tataaaagga aaagtgatgg | 180 |
| catctatatc ataaatctca agaggacctg ggagaagctt ctgctggcag ctcgtgcaat | 240 |
| tgttgccatt gaaaacctg ctgatgtcag tgttatatcc tccaggaata ctggccagag | 300 |
| ggctgtgctg aagtttgctg ctgccactgg agccactcca attgctggcc gcttcactcc | 360 |
| tggaaccttc actaaccaga tccaggcagc cttcgggag ccacggcttc ttgtggttac | 420 |
| tgaccccagg gctgaccacc agcctctcac ggaggcatct tatgttaacc tacctaccat | 480 |
| tgcgctgtgt aacacagatt ctcctctgcg ctatgtggac attgccatcc catgcaacaa | 540 |
| caagggagct cactcagtgg gtttgatgtg gtggatgctg gctcgggaag ttctgcgcat | 600 |
| gcgtggcacc atttcccgtg aacacccatg ggaggtcatg cctgatctgt acttc | 655 |

<210> SEQ ID NO 209
<211> LENGTH: 621
<212> TYPE: DNA
<213> ORGANISM: Homo sapiens

<400> SEQUENCE: 209

| | |
|---|---|
| catttagaac atggttatca tccaagacta ctctaccctg caacattgaa ctcccaagag | 60 |
| caaatccaca ttcctcttga gttctgcagc ttctgtgtaa atagggcagc tgtcgtctat | 120 |
| gccgtagaat cacatgatct gaggaccatt catggaagct gctaaatagc ctagtctggg | 180 |
| gagtcttcca taaagttttg catggagcaa acaaacagga ttaaactagg tttggttcct | 240 |
| tcagccctct aaaagcatag ggcttagcct gcaggcttcc ttgggctttc tctgtgtgtg | 300 |
| tagttttgta aacactatag catctgttaa gatccagtgt ccatggaaac cttcccacat | 360 |
| gccgtgactc tggactatat cagttttggg aaagcagggt tcctctgcct gctaacaagc | 420 |
| ccacgtggac cagtctgaat gtctttcctt tacacctatg tttttaaata gtcaaacttc | 480 |
| aagaaacaat ctaaacaagt ttctgttgca tatgtgtttg tgaacttgta tttgtattta | 540 |
| gtaggcttct atattgcatt taacttgttt ttgtaactcc tgattcttcc ttttcggata | 600 |
| ctattgatga ataaagaaat t | 621 |

<210> SEQ ID NO 210
<211> LENGTH: 533
<212> TYPE: DNA
<213> ORGANISM: Homo sapiens
<220> FEATURE:
<221> NAME/KEY: unsure
<222> LOCATION: (20)
<223> OTHER INFORMATION: n=A,T,C or G
<221> NAME/KEY: unsure
<222> LOCATION: (21)

<223> OTHER INFORMATION: n=A,T,C or G
<221> NAME/KEY: unsure
<222> LOCATION: (61)
<223> OTHER INFORMATION: n=A,T,C or G

<400> SEQUENCE: 210

| | | | | | |
|---|---|---|---|---|---|
| cgccttgggg | agccggcggn | ngagtccggg | acgtggagac | ccggggtccc | ggcagccggg | 60 |
| nggcccgcgg | gcccagggtg | gggatgcacc | gccgcgggt | gggagctggc | gccatcgcca | 120 |
| agaagaaact | tgcagaggcc | aagtataagg | agcgagggac | ggtcttggct | gaggaccagc | 180 |
| tagcccagat | gtcaaagcag | ttggacatgt | tcaagaccaa | cctggaggaa | tttgccagca | 240 |
| aacacaagca | ggagatccgg | aagaatcctg | agttccgtgt | gcagttccag | gacatgtgtg | 300 |
| caaccattgg | cgtggatccg | ctggcctctg | gaaaaggatt | tggtctgag | atgctgggcg | 360 |
| tgggggactt | ctattacgaa | ctaggtgtcc | aaattatcga | agtgtgcctg | gcgctgaagc | 420 |
| atcggaatgg | aggtctgata | actttggagg | aactacatca | acaggtgttg | aagggaaggg | 480 |
| gcaagttcgc | ccaggatgtc | agtcaagatg | acctgatcag | agccatcaag | aaa | 533 |

<210> SEQ ID NO 211
<211> LENGTH: 451
<212> TYPE: DNA
<213> ORGANISM: Homo sapiens

<400> SEQUENCE: 211

| | | | | | |
|---|---|---|---|---|---|
| ttagcttgag | ccgagaacga | ggcgagaaag | ctggagaccg | aggagaccgc | ctagagcgga | 60 |
| gtgaacgggg | aggggaccgt | ggggaccggc | ttgatcgtgc | gcggacacct | gctaccaagc | 120 |
| ggagcttcag | caaggaagtg | gaggagcgga | gtagagaacg | gccctcccag | cctgaggggc | 180 |
| tgcgcaaggc | agctagcctc | acggaggatc | gggaccgtgg | gcgggatgcc | gtgaagcgag | 240 |
| aagctgccct | accccagtg | agccccctga | aggcggctct | ctctgaggag | gagttagaga | 300 |
| agaaatccaa | ggctatcatt | gaggaatatc | tccatctcaa | tgacatgaaa | gaggcagtcc | 360 |
| agtgcgtgca | ggagctggcc | tcaccctcct | tgctcttcat | cttttgtacgg | catggtgtcg | 420 |
| agtctacgct | ggagcgcagt | gccattgctc | g | | | 451 |

<210> SEQ ID NO 212
<211> LENGTH: 471
<212> TYPE: DNA
<213> ORGANISM: Homo sapiens
<220> FEATURE:
<221> NAME/KEY: unsure
<222> LOCATION: (54)
<223> OTHER INFORMATION: n=A,T,C or G

<400> SEQUENCE: 212

| | | | | | |
|---|---|---|---|---|---|
| gtgattattc | ttgatcaggg | agaagatcat | ttagatttgt | tttgcattcc | ttanaatgga | 60 |
| gggcaacatt | ccacagctgc | cctggctgtg | atgagtgtcc | ttgcagggc | cggagtagga | 120 |
| gcactggggt | gggggcggaa | ttgggggttac | tcgatgtaag | ggattccttg | ttgttgtgtt | 180 |
| gagatccagt | gcagttgtga | tttctgtgga | tcccagcttg | gttccaggaa | ttttgtgtga | 240 |
| ttggcttaaa | tccagttttc | aatcttcgac | agctgggctg | gaacgtgaac | tcagtagctg | 300 |
| aacctgtctg | acccggtcac | gttcttggat | cctcagaact | ctttgctctt | gtcgggtgg | 360 |
| gggtgggaac | tcacgtgggg | agcggtggct | gagaaaatgt | aaggattctg | gaatacatat | 420 |
| tccatgggac | tttccttccc | tctcctgctt | cctctttttcc | tgctccctaa | c | 471 |

<210> SEQ ID NO 213

```
<211> LENGTH: 511
<212> TYPE: DNA
<213> ORGANISM: Homo sapiens
<220> FEATURE:
<221> NAME/KEY: unsure
<222> LOCATION: (27)
<223> OTHER INFORMATION: n=A,T,C or G
<221> NAME/KEY: unsure
<222> LOCATION: (63)
<223> OTHER INFORMATION: n=A,T,C or G
<221> NAME/KEY: unsure
<222> LOCATION: (337)
<223> OTHER INFORMATION: n=A,T,C or G
<221> NAME/KEY: unsure
<222> LOCATION: (442)
<223> OTHER INFORMATION: n=A,T,C or G

<400> SEQUENCE: 213
ctaattagaa acttgctgta cttttntttt tcttttaggg gtcaaggacc ctctttatag    60
ctnccatttg cctacaataa attattgcag cagtttgcaa tactaaaata ttttttatag   120
actttatatt tttccttttg ataaagggat gctgcatagt agagttggtg taattaaact   180
atctcagccg tttccctgct ttcccttctg ctccatatgc ctcattgtcc ttccagggag   240
ctctttaat cttaaagttc tacatttcat gctcttagtc aaattctgtt acctttttaa    300
taactcttcc cactgcatat ttccatcttg aattggnggt tctaaattct gaaactgtag   360
ttgagataca gctatttaat atttctggga gatgtgcatc cctcttcttt gtggttgccc   420
aaggttgttt tgcgtaactg anactccttg atatgcttca gagaatttag gcaaacactg   480
gccatggccg tgggagtact gggagtaaaa t                                  511

<210> SEQ ID NO 214
<211> LENGTH: 521
<212> TYPE: DNA
<213> ORGANISM: Homo sapiens

<400> SEQUENCE: 214
agcattgcca aataatccct aattttccac taaaaatata atgaaatgat gttaagcttt    60
ttgaaaagtt taggttaaac ctactgttgt tagattaatg tatttgttgc ttcccttat   120
ctggaatgtg gcattagctt ttttatttta accctcttta attcttattc aattccatga   180
cttaaggttg gagagctaaa cactgggatt tttggataac agactgacag ttttgcataa   240
ttataatcgg cattgtacat agaaaggata tggctacctt ttgttaaatc tgcactttct   300
aaatatcaaa aaagggaaat gaagtataaa tcaattttg tataatctgt ttgaaacatg    360
agttttattt gcttaatatt agggctttgc ccctttctg taagtctctt gggatcctgt    420
gtagaagctg ttctcattaa acaccaaaca gttaagtcca ttctctggta ctagctacaa   480
attcggtttc atattctact taacaattta aataaactga a                       521

<210> SEQ ID NO 215
<211> LENGTH: 381
<212> TYPE: DNA
<213> ORGANISM: Homo sapiens
<220> FEATURE:
<221> NAME/KEY: unsure
<222> LOCATION: (17)
<223> OTHER INFORMATION: n=A,T,C or G
<221> NAME/KEY: unsure
<222> LOCATION: (20)
<223> OTHER INFORMATION: n=A,T,C or G
<221> NAME/KEY: unsure
<222> LOCATION: (60)
<223> OTHER INFORMATION: n=A,T,C or G
<221> NAME/KEY: unsure
```

```
<222> LOCATION: (61)
<223> OTHER INFORMATION: n=A,T,C or G
<221> NAME/KEY: unsure
<222> LOCATION: (365)
<223> OTHER INFORMATION: n=A,T,C or G

<400> SEQUENCE: 215
gagcggagag cggaccngtn agagccctga gcagccccac cgccgccgcc ggcctagttn    60
ncatcacacc ccgggaggag ccgcagctgc cgcagccggc cccagtcacc atcaccgcaa   120
ccatgagcag cgaggccgag acccagcagc cgccgccgcc cccccccgcc gccccgccc    180
tcagcgccgc cgacaccaag cccggcacta cgggcagcgg cgcagggagc ggtggcccgg   240
gcggcctcac atcggcggcg cctgccgcg ggacaagaa ggtcatcgca cgaaggttt    300
tgggaacagt aaaatggttc aatgtaagga acggatatgg tttcatcaac aggaatgaca   360
ccaangaaga tgtatttgta c                                             381

<210> SEQ ID NO 216
<211> LENGTH: 425
<212> TYPE: DNA
<213> ORGANISM: Homo sapiens

<400> SEQUENCE: 216
ttactaacta ggtcattcaa ggaagtcaag ttaacttaaa catgtcacct aaatgcactt    60
gatggtgttg aaatgtccac cttcttaaat ttttaagatg aacttagttc taagaagat   120
aacaggccaa tcctgaaggt actccctgtt tgctgcagaa tgtcagatat tttggatgtt   180
gcataagagt cctatttgcc ccagttaatt caacttttgt ctgcctgttt tgtggactgg   240
ctggctctgt tagaactctg tccaaaaagt gcatggaata taacttgtaa agcttcccac   300
aattgacaat atatatgcat gtgtttaaac caaatccaga aagcttaaac aatagagctg   360
cataatagta tttattaaag aatcacaact gtaaacatga gaataactta aggattctag   420
tttag                                                               425

<210> SEQ ID NO 217
<211> LENGTH: 181
<212> TYPE: DNA
<213> ORGANISM: Homo sapiens

<400> SEQUENCE: 217
gagaaaccaa atgataggtt gtagagcctg atgactccaa acaaagccat cacccgcatt    60
cttcctcctt cttctggtgc tacagctcca agggcccttc accttcatgt ctgaaatgga   120
actttggctt tttcagtgga agaatatgtt gaaggtttca ttttgttcta gaaaaaaaaa   180
a                                                                   181

<210> SEQ ID NO 218
<211> LENGTH: 405
<212> TYPE: DNA
<213> ORGANISM: Homo sapiens

<400> SEQUENCE: 218
caggccttcc agttcactga caaacatggg gaagtgtgcc cagctggctg gaaacctggc    60
agtgatacca tcaagcctga tgtccaaaag agcaaagaat atttctccaa gcagaagtga   120
gcgctgggct gttttagtgc caggctgcg tgggcagcca tgagaacaaa acctcttctg   180
tatttttttt ttccattagt aaaacacaag acttcagatt cagccgaatt gtggtgtctt   240
acaaggcagg cctttcctac aggggtgga gagaccagcc tttcttcctt tggtaggaat   300
```

```
ggcctgagtt ggcgttgtgg gcaggctact ggtttgtatg atgtattagt agagcaaccc    360
attaatcttt tgtagtttgt attaaacttg aactgagaaa aaaaa                     405

<210> SEQ ID NO 219
<211> LENGTH: 216
<212> TYPE: DNA
<213> ORGANISM: Homo sapiens
<220> FEATURE:
<221> NAME/KEY: unsure
<222> LOCATION: (207)
<223> OTHER INFORMATION: n=A,T,C or G
<221> NAME/KEY: unsure
<222> LOCATION: (210)
<223> OTHER INFORMATION: n=A,T,C or G

<400> SEQUENCE: 219
actccaagag ttagggcagc agagtggagc gatttagaaa gaacatttta aaacaatcag     60
ttaatttacc atgtaaaatt gctgtaaatg ataatgtgta cagattttct gttcaaatat    120
tcaattgtaa acttcttgtt aagactgtta cgtttctatt gcttttgtat gggatattgc    180
aaaaataaaa aggaaagaac cctcttnaan aaaaaa                              216

<210> SEQ ID NO 220
<211> LENGTH: 380
<212> TYPE: DNA
<213> ORGANISM: Homo sapiens

<400> SEQUENCE: 220
cttacaaatt gcccccatgt gtaggggaca cagaacccct tgagaaaact tagatttttg     60
tctgtacaaa gtctttgcct ttttccttct tcatttttt ccagtacatt aaatttgtca    120
atttcatctt tgagggaaac tgattagatg ggttgtgttt gtgttctgat ggagaaaaca   180 gcacccccaag gactcagaag atgattttaa cagttcagaa cagatgtgtg caatattggt    240
gcatgtaata atgttgagtg gcagtcaaaa gtcatgattt ttatcttagt tcttcattac    300
tgcattgaaa aggaaaaacct gtctgagaaa atgcctgaca gtttaattta aaactatggt    360
gtaagtcttt gacaaaaaaa                                                380

<210> SEQ ID NO 221
<211> LENGTH: 398
<212> TYPE: DNA
<213> ORGANISM: Homo sapiens

<400> SEQUENCE: 221
ggttagtaag ctgtcgactt tgtaaaaaag ttaaaaatga aaaaaaaagg aaaaatgaat     60
tgtatattta atgaatgaac atgtacaatt tgccactggg aggaggttcc tttttgttgg    120
gtgagtctgc aagtgaattt cactgatgtt gatattcatt gtgtgtagtt ttatttcggt    180
cccagccccg tttccttttta ttttggagct aatgccagct gcgtgtctag ttttgagtgc    240
agtaaaatag aatcagcaaa tcactcttat ttttcatcct ttttccggtat tttttgggtt   300 gtttctgtgg gagcagtgta caccaactct tcctgtatat tgccttttg ctggaaaatg    360 ttgtatgttg aataaaattt tctataaaaa ttaaaaaa                             398

<210> SEQ ID NO 222
<211> LENGTH: 301
<212> TYPE: DNA
<213> ORGANISM: Homo sapiens
<220> FEATURE:
<221> NAME/KEY: unsure
```

```
<222> LOCATION: (49)
<223> OTHER INFORMATION: n=A,T,C or G
<221> NAME/KEY: unsure
<222> LOCATION: (64)
<223> OTHER INFORMATION: n=A,T,C or G

<400> SEQUENCE: 222
ttcgataatt gatctcatgg gctttccctg gaggaaaggt ttttttgnt gtttattttt      60 taanaacttg aaacttgtaa actgagatgt ctgtagcttt tttgcccatc tgtagtgtat    120
gtgaagattt caaaacctga gagcactttt tctttgttta gaattatgag aaaggcacta    180
gatgacttta ggatttgcat ttttcccttt attgcctcat ttcttgtgac gccttgttgg    240
ggagggaaat ctgtttattt tttcctacaa ataaaaagct aagattctat atcgcaaaaa    300
a                                                                    301

<210> SEQ ID NO 223
<211> LENGTH: 200
<212> TYPE: DNA
<213> ORGANISM: Homo sapiens

<400> SEQUENCE: 223
gtaagtgctt aggaagaaac tttgcaaaca tttaatgagg atacactgtt cattttaaa     60 attccttcac actgtaattt aatgtgtttt atattctttt gtagtaaaac aacataactc   120
agatttctac aggagacagt ggttttattt ggattgtctt ctgtaatagg tttcaataaa   180
gctggatgaa cttaaaaaaa                                                200

<210> SEQ ID NO 224
<211> LENGTH: 385
<212> TYPE: DNA
<213> ORGANISM: Homo sapiens

<400> SEQUENCE: 224
gaaaggtttg atccggactc aaagaaagca aggagtgtg agccgccatc tgctggagca     60
gctgtaactg caagacctgg acaagagatt cgtcagcgaa ctgcagctca agaaaccttt   120
tctccaacac cagcaagccc taaccagggc cctcctccac aagttccagt atctcctgga   180
ccaccaaagg acagttctgc ccctggtgga ccccagaaa ggactgttac tccagcccta   240
tcatcaaatg tgttaccaag acatcttgga tcccctgcta cttcagtgcc tggaatgggt   300
aaacagagca ttaatgtta tttacagttt atattgtttt ctctggttac caataaaacg    360
ggccattttc aggtggtaaa aaaaa                                          385

<210> SEQ ID NO 225
<211> LENGTH: 560
<212> TYPE: PRT
<213> ORGANISM: Homo sapien

<400> SEQUENCE: 225

Met Glu Cys Leu Tyr Tyr Phe Leu Gly Phe Leu Leu Ala Ala Arg
 1               5                  10                  15

Leu Pro Leu Asp Ala Ala Lys Arg Phe His Asp Val Leu Gly Asn Glu
            20                  25                  30

Arg Pro Ser Ala Tyr Met Arg Glu His Asn Gln Leu Asn Gly Trp Ser
        35                  40                  45

Ser Asp Glu Asn Asp Trp Asn Glu Lys Leu Tyr Pro Val Trp Lys Arg
    50                  55                  60

Gly Asp Met Arg Trp Lys Asn Ser Trp Lys Gly Gly Arg Val Gln Ala
```

```
              65                  70                  75                  80
Val Leu Thr Ser Asp Ser Pro Ala Leu Val Gly Ser Asn Ile Thr Phe
                85                  90                  95
Ala Val Asn Leu Ile Phe Pro Arg Cys Gln Lys Glu Asp Ala Asn Gly
               100                 105                 110
Asn Ile Val Tyr Glu Lys Asn Cys Arg Asn Glu Ala Gly Leu Ser Ala
               115                 120                 125
Asp Pro Tyr Val Tyr Asn Trp Thr Ala Trp Ser Glu Asp Ser Asp Gly
130                 135                 140
Glu Asn Gly Thr Gly Gln Ser His His Asn Val Phe Pro Asp Gly Lys
145                 150                 155                 160
Pro Phe Pro His His Pro Gly Trp Arg Arg Trp Asn Phe Ile Tyr Val
               165                 170                 175
Phe His Thr Leu Gly Gln Tyr Phe Gln Lys Leu Gly Arg Cys Ser Val
               180                 185                 190
Arg Val Ser Val Asn Thr Ala Asn Val Thr Leu Gly Pro Gln Leu Met
               195                 200                 205
Glu Val Thr Val Tyr Arg Arg His Gly Arg Ala Tyr Val Pro Ile Ala
210                 215                 220
Gln Val Lys Asp Val Tyr Val Val Thr Asp Gln Ile Pro Val Phe Val
225                 230                 235                 240
Thr Met Phe Gln Lys Asn Asp Arg Asn Ser Ser Asp Glu Thr Phe Leu
               245                 250                 255
Lys Asp Leu Pro Ile Met Phe Asp Val Leu Ile His Asp Pro Ser His
               260                 265                 270
Phe Leu Asn Tyr Ser Thr Ile Asn Tyr Lys Trp Ser Phe Gly Asp Asn
               275                 280                 285
Thr Gly Leu Phe Val Ser Thr Asn His Thr Val Asn His Thr Tyr Val
               290                 295                 300
Leu Asn Gly Thr Phe Ser Leu Asn Leu Thr Val Lys Ala Ala Ala Pro
305                 310                 315                 320
Gly Pro Cys Pro Pro Pro Pro Pro Pro Arg Pro Ser Lys Pro Thr
               325                 330                 335
Pro Ser Leu Gly Pro Ala Gly Asp Asn Pro Leu Glu Leu Ser Arg Ile
               340                 345                 350
Pro Asp Glu Asn Cys Gln Ile Asn Arg Tyr Gly His Phe Gln Ala Thr
               355                 360                 365
Ile Thr Ile Val Glu Gly Ile Leu Glu Val Asn Ile Ile Gln Met Thr
370                 375                 380
Asp Val Leu Met Pro Val Pro Trp Pro Glu Ser Ser Leu Ile Asp Phe
385                 390                 395                 400
Val Val Thr Cys Gln Gly Ser Ile Pro Thr Glu Val Cys Thr Ile Ile
               405                 410                 415
Ser Asp Pro Thr Cys Glu Ile Thr Gln Asn Thr Val Cys Ser Pro Val
               420                 425                 430
Asp Val Asp Glu Met Cys Leu Leu Thr Val Arg Arg Thr Phe Asn Gly
               435                 440                 445
Ser Gly Thr Tyr Cys Val Asn Leu Thr Leu Gly Asp Asp Thr Ser Leu
               450                 455                 460
Ala Leu Thr Ser Thr Leu Ile Ser Val Pro Asp Arg Asp Pro Ala Ser
465                 470                 475                 480
Pro Leu Arg Met Ala Asn Ser Ala Leu Ile Ser Val Gly Cys Leu Ala
               485                 490                 495
```

```
Ile Phe Val Thr Val Ile Ser Leu Leu Val Tyr Lys Lys His Lys Glu
                500                 505                 510
Tyr Asn Pro Ile Glu Asn Ser Pro Gly Asn Val Val Arg Ser Lys Gly
            515                 520                 525
Leu Ser Val Phe Leu Asn Arg Ala Lys Ala Val Phe Phe Pro Gly Asn
        530                 535                 540
Gln Glu Lys Asp Pro Leu Leu Lys Asn Gln Glu Phe Lys Gly Val Ser
545                 550                 555                 560

<210> SEQ ID NO 226
<211> LENGTH: 9
<212> TYPE: PRT
<213> ORGANISM: Homo sapien

<400> SEQUENCE: 226

Ile Leu Ile Pro Ala Thr Trp Lys Ala
1               5

<210> SEQ ID NO 227
<211> LENGTH: 9
<212> TYPE: PRT
<213> ORGANISM: Homo sapien

<400> SEQUENCE: 227

Phe Leu Leu Asn Asp Asn Leu Thr Ala
1               5

<210> SEQ ID NO 228
<211> LENGTH: 9
<212> TYPE: PRT
<213> ORGANISM: Homo sapien

<400> SEQUENCE: 228

Leu Leu Gly Asn Cys Leu Pro Thr Val
1               5

<210> SEQ ID NO 229
<211> LENGTH: 10
<212> TYPE: PRT
<213> ORGANISM: Homo sapien

<400> SEQUENCE: 229

Lys Leu Leu Gly Asn Cys Leu Pro Thr Val
1               5                   10

<210> SEQ ID NO 230
<211> LENGTH: 10
<212> TYPE: PRT
<213> ORGANISM: Homo sapien

<400> SEQUENCE: 230

Arg Leu Thr Gly Gly Leu Lys Phe Phe Val
1               5                   10

<210> SEQ ID NO 231
<211> LENGTH: 9
<212> TYPE: PRT
<213> ORGANISM: Homo sapien

<400> SEQUENCE: 231

Ser Leu Gln Ala Leu Lys Val Thr Val
1               5
```

<210> SEQ ID NO 232
<211> LENGTH: 20
<212> TYPE: PRT
<213> ORGANISM: Homo sapiens

<400> SEQUENCE: 232

Ala Gly Ala Asp Val Ile Lys Asn Asp Gly Ile Tyr Ser Arg Tyr Phe
                5                   10                  15
Phe Ser Phe Ala
            20

<210> SEQ ID NO 233
<211> LENGTH: 21
<212> TYPE: PRT
<213> ORGANISM: Homo sapiens

<400> SEQUENCE: 233

Phe Phe Ser Phe Ala Ala Asn Gly Arg Tyr Ser Leu Lys Val His Val
                5                   10                  15
Asn His Ser Pro Ser
            20

<210> SEQ ID NO 234
<211> LENGTH: 20
<212> TYPE: PRT
<213> ORGANISM: Homo sapiens

<400> SEQUENCE: 234

Phe Leu Val Thr Trp Gln Ala Ser Gly Pro Pro Glu Ile Ile Leu Phe
                5                   10                  15
Asp Pro Asp Gly
            20

<210> SEQ ID NO 235
<211> LENGTH: 20
<212> TYPE: PRT
<213> ORGANISM: Homo sapiens

<400> SEQUENCE: 235

Leu Gln Ser Ala Val Ser Asn Ile Ala Gln Ala Pro Leu Phe Ile Pro
                5                   10                  15
Pro Asn Ser Asp
            20

<210> SEQ ID NO 236
<211> LENGTH: 20
<212> TYPE: PRT
<213> ORGANISM: Homo sapiens

<400> SEQUENCE: 236

Ile Gln Asp Asp Phe Asn Asn Ala Ile Leu Val Asn Thr Ser Lys Arg
                5                   10                  15
Asn Pro Gln Gln
            20

<210> SEQ ID NO 237
<211> LENGTH: 21
<212> TYPE: PRT
<213> ORGANISM: Homo sapiens

<400> SEQUENCE: 237

Arg Asn Ser Leu Gln Ser Ala Val Ser Asn Ile Ala Gln Ala Pro Leu

```
                      5                  10                  15
Phe Ile Pro Pro Asn
            20

<210> SEQ ID NO 238
<211> LENGTH: 20
<212> TYPE: PRT
<213> ORGANISM: Homo sapiens

<400> SEQUENCE: 238

Thr His Glu Ser His Arg Ile Tyr Val Ala Ile Arg Ala Met Asp Arg
                      5                  10                  15
Asn Ser Leu Gln
            20

<210> SEQ ID NO 239
<211> LENGTH: 20
<212> TYPE: PRT
<213> ORGANISM: Homo sapiens

<400> SEQUENCE: 239

Arg Asn Pro Gln Gln Ala Gly Ile Arg Glu Ile Phe Thr Phe Ser Pro
                      5                  10                  15
Gln Ile Ser Thr
            20

<210> SEQ ID NO 240
<211> LENGTH: 21
<212> TYPE: PRT
<213> ORGANISM: Homo sapiens

<400> SEQUENCE: 240

Gly Gln Ala Thr Ser Tyr Glu Ile Arg Met Ser Lys Ser Leu Gln Asn
                      5                  10                  15
Ile Gln Asp Asp Phe
            20

<210> SEQ ID NO 241
<211> LENGTH: 20
<212> TYPE: PRT
<213> ORGANISM: Homo sapiens

<400> SEQUENCE: 241

Glu Arg Lys Trp Gly Phe Ser Arg Val Ser Ser Gly Gly Ser Phe Ser
                      5                  10                  15
Val Leu Gly Val
            20

<210> SEQ ID NO 242
<211> LENGTH: 20
<212> TYPE: PRT
<213> ORGANISM: Homo sapiens

<400> SEQUENCE: 242

Gly Ser His Ala Met Tyr Val Pro Gly Tyr Thr Ala Asn Gly Asn Ile
                      5                  10                  15
Gln Met Asn Ala
            20

<210> SEQ ID NO 243
<211> LENGTH: 20
<212> TYPE: PRT
```

<213> ORGANISM: Homo sapiens

<400> SEQUENCE: 243

Val Asn His Ser Pro Ser Ile Ser Thr Pro Ala His Ser Ile Pro Gly
                 5                  10                  15
Ser His Ala Met
            20

<210> SEQ ID NO 244
<211> LENGTH: 20
<212> TYPE: PRT
<213> ORGANISM: Homo sapiens

<400> SEQUENCE: 244

Ala Val Pro Pro Ala Thr Val Glu Ala Phe Val Glu Arg Asp Ser Leu
                 5                  10                  15
His Phe Pro His
            20

<210> SEQ ID NO 245
<211> LENGTH: 20
<212> TYPE: PRT
<213> ORGANISM: Homo sapiens

<400> SEQUENCE: 245

Lys Pro Gly His Trp Thr Tyr Thr Leu Asn Asn Thr His His Ser Leu
                 5                  10                  15
Gln Ala Leu Lys
            20

<210> SEQ ID NO 246
<211> LENGTH: 20
<212> TYPE: PRT
<213> ORGANISM: Homo sapiens

<400> SEQUENCE: 246

Asn Leu Thr Phe Arg Thr Ala Ser Leu Trp Ile Pro Gly Thr Ala Lys
                 5                  10                  15
Pro Gly His Trp
            20

<210> SEQ ID NO 247
<211> LENGTH: 20
<212> TYPE: PRT
<213> ORGANISM: Homo sapiens

<400> SEQUENCE: 247

Leu His Phe Pro His Pro Val Met Ile Tyr Ala Asn Val Lys Gln Gly
                 5                  10                  15
Phe Tyr Pro Ile
            20

<210> SEQ ID NO 248
<211> LENGTH: 20
<212> TYPE: PRT
<213> ORGANISM: Homo sapiens

<400> SEQUENCE: 248

Pro Glu Thr Gly Asp Pro Val Thr Leu Arg Leu Leu Asp Asp Gly Ala
                 5                  10                  15
Gly Ala Asp Val
            20

```
<210> SEQ ID NO 249
<211> LENGTH: 20
<212> TYPE: PRT
<213> ORGANISM: Homo sapiens

<400> SEQUENCE: 249

Gly Phe Tyr Pro Ile Leu Asn Ala Thr Val Thr Ala Thr Val Glu Pro
 1               5                  10                  15

Glu Thr Gly Asp
            20

<210> SEQ ID NO 250
<211> LENGTH: 20
<212> TYPE: PRT
<213> ORGANISM: Homo sapiens

<400> SEQUENCE: 250

Phe Asp Pro Asp Gly Arg Lys Tyr Tyr Thr Asn Asn Phe Ile Thr Asn
 1               5                  10                  15

Leu Thr Phe Arg
            20

<210> SEQ ID NO 251
<211> LENGTH: 20
<212> TYPE: PRT
<213> ORGANISM: Homo sapiens

<400> SEQUENCE: 251

Leu Gln Ala Leu Lys Val Thr Val Thr Ser Arg Ala Ser Asn Ser Ala
 1               5                  10                  15

Val Pro Pro Ala
            20

<210> SEQ ID NO 252
<211> LENGTH: 153
<212> TYPE: PRT
<213> ORGANISM: Homo sapien

<400> SEQUENCE: 252

Met Ala Ser Val Arg Val Ala Ala Tyr Phe Glu Asn Phe Leu Ala Ala
 1               5                  10                  15

Trp Arg Pro Val Lys Ala Ser Asp Gly Asp Tyr Tyr Thr Leu Ala Val
                20                  25                  30

Pro Met Gly Asp Val Pro Met Asp Gly Ile Ser Val Ala Asp Ile Gly
            35                  40                  45

Ala Ala Val Ser Ser Ile Phe Asn Ser Pro Glu Glu Phe Leu Gly Lys
        50                  55                  60

Ala Val Gly Leu Ser Ala Glu Leu Thr Ile Gln Gln Tyr Ala Asp
65                  70                  75                  80

Val Leu Ser Lys Ala Leu Gly Lys Glu Val Arg Asp Ala Lys Ile Thr
                85                  90                  95

Pro Glu Ala Phe Glu Lys Leu Gly Phe Pro Ala Ala Lys Glu Ile Ala
            100                 105                 110

Asn Met Cys Arg Phe Tyr Glu Met Lys Pro Asp Arg Asp Val Asn Leu
        115                 120                 125

Thr His Gln Leu Asn Pro Lys Val Lys Ser Phe Ser Gln Phe Ile Ser
    130                 135                 140

Glu Asn Gln Gly Ala Phe Lys Gly Met
```

<210> SEQ ID NO 253
<211> LENGTH: 462
<212> TYPE: DNA
<213> ORGANISM: Homo sapien

<400> SEQUENCE: 253

| | | | | | |
|---|---|---|---|---|---|
| atggccagtg | tccgcgtggc | ggcctacttt | gaaaactttc | tcgcggcgtg | gcggcccgtg | 60 |
| aaagcctctg | atggagatta | ctacaccttg | gctgtaccga | tgggagatgt | accaatggat | 120 |
| ggtatctctg | ttgctgatat | tggagcagcc | gtctctagca | ttttttaattc | tccagaggaa | 180 |
| tttttaggca | aggccgtggg | gctcagtgca | aagcactaa | caatacagca | atatgctgat | 240 |
| gttttgtcca | aggctttggg | gaaagaagtc | cgagatgcaa | agattacccc | ggaagctttc | 300 |
| gagaagctgg | gattccctgc | agcaaaggaa | atagccaata | tgtgtcgttt | ctatgaaatg | 360 |
| aagccagacc | gagatgtcaa | tctcacccac | caactaaatc | ccaaagtcaa | aagcttcagc | 420 |
| cagtttatct | cagagaacca | gggagccttc | aagggcatgt | ag | | 462 |

<210> SEQ ID NO 254
<211> LENGTH: 8031
<212> TYPE: DNA
<213> ORGANISM: Homo sapien

<400> SEQUENCE: 254

| | | | | | |
|---|---|---|---|---|---|
| ggcgaatgg | gacgcgccct | gtagcggcgc | attaagcgcg | gcgggtgtgg | tggttacgcg | 60 |
| agcgtgacc | gctacacttg | ccagcgccct | agcgcccgct | cctttcgctt | tcttcccttc | 120 |
| tttctcgcc | acgttcgccg | gctttccccg | tcaagctcta | aatcggggc | tcccttttagg | 180 |
| ttccgattt | agtgctttac | ggcacctcga | ccccaaaaaa | cttgattagg | gtgatggttc | 240 |
| cgtagtggg | ccatcgccct | gatagacggt | ttttcgccct | ttgacgttgg | agtccacgtt | 300 |
| tttaatagt | ggactcttgt | tccaaactgg | aacaacactc | aaccctatct | cggtctattc | 360 |
| tttgattta | taagggattt | tgccgatttc | ggcctattgg | ttaaaaaatg | agctgattta | 420 |
| caaaaattt | aacgcgaatt | ttaacaaaat | attaacgttt | acaatttcag | gtggcacttt | 480 |
| cggggaaat | gtgcgcggaa | cccctatttg | tttatttttc | taaatacatt | caaatatgta | 540 |
| ccgctcatg | aattaattct | tagaaaaact | catcgagcat | caaatgaaac | tgcaatttat | 600 |
| catatcagg | attatcaata | ccatattttt | gaaaagccg | tttctgtaat | gaaggagaaa | 660 |
| ctcaccgag | gcagttccat | aggatggcaa | gatcctggta | tcggtctgcg | attccgactc | 720 |
| tccaacatc | aatacaacct | attaatttcc | cctcgtcaaa | aataaggtta | tcaagtgaga | 780 |
| atcaccatg | agtgacgact | gaatccggtg | agaatggcaa | aagtttatgc | atttctttcc | 840 |
| gacttgttc | aacaggccag | ccattacgct | cgtcatcaaa | atcactcgca | tcaaccaaac | 900 |
| gttattcat | tcgtgattgc | gcctgagcga | gacgaaatac | gcgatcgctg | ttaaaaggac | 960 |
| attacaaac | aggaatcgaa | tgcaaccggc | gcaggaacac | tgccagcgca | tcaacaatat | 1020 |
| ttcacctga | atcaggatat | tcttctaata | cctggaatgc | tgttttcccg | gggatcgcag | 1080 |
| ggtgagtaa | ccatgcatca | tcaggagtac | ggataaaatg | cttgatggtc | ggaagaggca | 1140 |
| aaattccgt | cagccagttt | agtctgacca | tctcatctgt | aacatcattg | gcaacgctac | 1200 |
| tttgccatg | tttcagaaac | aactctggcg | catcgggctt | cccatacaat | cgatagattg | 1260 |
| cgcacctga | ttgcccgaca | ttatcgcgag | cccatttata | cccatataaa | tcagcatcca | 1320 |
| gttggaatt | taatcgcggc | ctagagcaag | acgtttcccg | ttgaatatgg | ctcataacac | 1380 |

-continued

```
ccttgtatt actgtttatg taagcagaca gttttattgt tcatgaccaa aatcccttaa      1440 gtgagtttt cgttccactg agcgtcagac cccgtagaaa agatcaaagg atcttcttga      1500 atccttttt ttctgcgcgt aatctgctgc ttgcaaacaa aaaaaccacc gctaccagcg      1560 tggtttgtt tgccggatca agagctacca actctttttc cgaaggtaac tggcttcagc      1620 gagcgcaga taccaaatac tgtccttcta gtgtagccgt agttaggcca ccacttcaag      1680 actctgtag caccgcctac atacctcgct ctgctaatcc tgttaccagt ggctgctgcc      1740 gtggcgata agtcgtgtct taccgggttg gactcaagac gatagttacc ggataaggcg      1800 agcggtcgg gctgaacggg gggttcgtgc acacagccca gcttggagcg aacgacctac      1860 ccgaactga gatacctaca gcgtgagcta tgagaaagcg ccacgcttcc cgaagggaga      1920 aggcggaca ggtatccggt aagcggcagg gtcggaacag gagagcgcac gagggagctt      1980
caggggggaa acgcctggta tctttatagt cctgtcgggt ttcgccacct ctgacttgag      2040 gtcgatttt tgtgatgctc gtcagggggg cggagcctat ggaaaaacgc cagcaacgcg      2100 cctttttac ggttcctggc cttttgctgg ccttttgctc acatgttctt tcctgcgtta      2160 ccctgatt ctgtggataa ccgtattacc gcctttgagt gagctgatac cgctcgccgc      2220 gccgaacga ccgagcgcag cgagtcagtg agcgaggaag cggaagagcg cctgatgcgg      2280
atttttctcc ttacgcatct gtgcggtatt tcacaccgca tatatggtgc actctcagta      2340 aatctgctc tgatgccgca tagttaagcc agtatacact ccgctatcgc tacgtgactg      2400 gtcatggct gcgccccgac acccgccaac acccgctgac gcgccctgac gggcttgtct      2460 ctcccggca tccgcttaca gacaagctgt gaccgtctcc gggagctgca tgtgtcagag      2520 ttttcaccg tcatcaccga aacgcgcgag gcagctgcgg taaagctcat cagcgtggtc      2580 tgaagcgat tcacagatgt ctgcctgttc atccgcgtcc agctcgttga gtttctccag      2640 agcgttaat gtctggcttc tgataaagcg ggccatgtta agggcggttt tttcctgttt      2700 gtcactgat gcctccgtgt aagggggatt tctgttcatg ggggtaatga taccgatgaa      2760 cgagagagg atgctcacga tacgggttac tgatgatgaa catgcccggt tactggaacg      2820 tgtgagggt aaacaactgg cggtatggat gcggcgggac cagagaaaaa tcactcaggg      2880 caatgccag cgcttcgtta atacagatgt aggtgttcca cagggtagcc agcagcatcc      2940 gcgatgcag atccggaaca taatggtgca gggcgctgac ttccgcgttt ccagacttta      3000 gaaacacgg aaaccgaaga ccattcatgt tgttgctcag gtcgcagacg ttttgcagca      3060 cagtcgctt cacgttcgct cgcgtatcgg tgattcattc tgctaaccag taaggcaacc      3120 cgccagcct agccgggtcc tcaacgacag gagcacgatc atgcgcaccc gtggggccgc      3180 atgccggcg ataatggcct gcttctcgcc gaaacgtttg gtggcgggac cagtgacgaa      3240 gcttgagcg agggcgtgca agattccgaa taccgcaagc gacaggccga tcatcgtcgc      3300 ctccagcga aagcggtcct cgccgaaaat gacccagagc gctgccggca cctgtcctac      3360 agttgcatg ataaagaaga cagtcataag tgcggcgacg atagtcatgc cccgcgccca      3420 cggaaggag ctgactgggt tgaaggctct caagggcatc ggtcgagatc ccggtgccta      3480 tgagtgagc taacttacat taattgcgtt gcgctcactg cccgctttcc agtcgggaaa      3540 ctgtcgtgc cagctgcatt aatgaatcgg ccaacgcgcg gggagaggcg gtttgcgtat      3600 gggcgccag ggtggttttt cttttcacca gtgagacggg caacagctga ttgcccttca      3660 cgcctggcc ctgagagagt tgcagcaagc ggtccacgct ggtttgcccc agcaggcgaa      3720
```

```
atcctgttt  gatggtggtt  aacggcggga  tataacatga  gctgtcttcg  gtatcgtcgt   3780
tcccactac  cgagatatcc  gcaccaacgc  gcagcccgga  ctcggtaatg  gcgcgcattg   3840
gcccagcgc  catctgatcg  ttggcaacca  gcatcgcagt  gggaacgatg  ccctcattca   3900
catttgcat  ggtttgttga  aaaccggaca  tggcactcca  gtcgccttcc  cgttccgcta   3960
cggctgaat  ttgattgcga  gtgagatatt  tatgccagcc  agccagacgc  agacgcgccg   4020
gacagaact  taatgggccc  gctaacagcg  cgatttgctg  gtgacccaat  gcgaccagat   4080
ctccacgcc  cagtcgcgta  ccgtcttcat  gggagaaaat  aatactgttg  atgggtgtct   4140
gtcagagac  atcaagaaat  aacgccggaa  cattagtgca  ggcagcttcc  acagcaatgg   4200
atcctggtc  atccagcgga  tagttaatga  tcagcccact  gacgcgttgc  gcgagaagat   4260
gtgcaccgc  cgctttacag  gcttcgacgc  cgcttcgttc  taccatcgac  accaccacgc   4320
ggcacccag  ttgatcggcg  cgagatttaa  tcgccgcgac  aatttgcgac  ggcgcgtgca   4380
ggccagact  ggaggtggca  acgccaatca  gcaacgactg  tttgcccgcc  agttgttgtg   4440
cacgcggtt  gggaatgtaa  ttcagctccg  ccatcgccgc  ttccactttt  tcccgcgttt   4500
cgcagaaac  gtggctggcc  tggttcacca  cgcgggaaac  ggtctgataa  gagacaccgg   4560
atactctgc  gacatcgtat  aacgttactg  gtttcacatt  caccaccctg  aattgactct   4620
ttccgggcg  ctatcatgcc  ataccgcgaa  aggttttgcg  ccattcgatg  gtgtccggga   4680
ctcgacgct  ctcccttatg  cgactcctgc  attaggaagc  agcccagtag  taggttgagg   4740
cgttgagca  ccgccgccgc  aaggaatggt  gcatgcaagg  agatggcgcc  caacagtccc   4800
cggccacgg  ggcctgccac  catacccacg  ccgaaacaag  cgctcatgag  cccgaagtgg   4860
gagcccgat  cttcccatc   ggtgatgtcg  gcgatatagg  cgccagcaac  cgcacctgtg   4920
cgccggtga  tgccggccac  gatgcgtccg  gcgtagagga  tcgagatctc  gatcccgcga   4980
attaatacg  actcactata  ggggaattgt  gagcggataa  caattcccct  ctagaaataa   5040
tttgtttaa  ctttaagaag  gagatataca  tatgcagcat  caccaccatc  accacggagt   5100
cagcttcaa  gacaatgggt  ataatggatt  gctcattgca  attaatcctc  aggtacctga   5160
aatcagaac  ctcatctcaa  acattaagga  aatgataact  gaagcttcat  tttacctatt   5220
aatgctacc  aagagaagag  tattttttcag  aaatataaag  attttaatac  ctgccacatg   5280
aaagctaat  aataacagca  aaataaaaca  agaatcatat  gaaaaggcaa  atgtcatagt   5340
actgactgg  tatggggcac  atggagatga  tccatacacc  ctacaataca  gagggtgtgg   5400
aaagaggga  aaatacattc  atttcacacc  taatttccta  ctgaatgata  acttaacagc   5460
ggctacgga  tcacgaggcc  gagtgtttgt  ccatgaatgg  gcccacctcc  gttggggtgt   5520
ttcgatgag  tataacaatg  acaaaccttt  ctacataaat  gggcaaaatc  aaattaaagt   5580
acaaggtgt  tcatctgaca  tcacaggcat  ttttgtgtgt  gaaaaaggtc  cttgccccca   5640
gaaaactgt  attattagta  agcttttttaa  agaaggatgc  acctttatct  acaatagcac   5700
caaaatgca  actgcatcaa  taatgttcat  gcaaagttta  tcttctgtgg  ttgaattttg   5760
aatgcaagt  acccacaacc  aagaagcacc  aaacctacag  aaccagatgt  gcagcctcag   5820
agtgcatgg  gatgtaatca  cagactctgc  tgactttcac  cacagctttc  catgaacgg    5880
actgagctt  ccacctcctc  ccacattctc  gcttgtagag  gctggtgaca  agtggtctg    5940
ttagtgctg  gatgtgtcca  gcaagatggc  agaggctgac  agactcctcc  aactacaaca   6000
gccgcagaa  ttttatttga  tgcagattgt  tgaaattcat  accttcgtgg  gcattgccag   6060
ttcgacagc  aaaggagaga  tcagagccca  gctacaccaa  attaacagca  atgatgatcg   6120
```

```
aagttgctg gtttcatatc tgcccaccac tgtatcagct aaaacagaca tcagcatttg      6180 tcagggctt aagaaaggat ttgaggtggt tgaaaaactg aatggaaaag cttatggctc      6240 gtgatgata ttagtgacca gcggagatga taagcttctt ggcaattgct tacccactgt      6300 ctcagcagt ggttcaacaa ttcactccat tgccctgggt tcatctgcag ccccaaatct      6360 gaggaatta tcacgtctta caggaggttt aaagttcttt gttccagata tatcaaactc      6420 aatagcatg attgatgctt tcagtagaat ttcctctgga actggagaca ttttccagca      6480 catattcag cttgaaagta caggtgaaaa tgtcaaacct caccatcaat tgaaaaacac      6540 gtgactgtg gataatactg tgggcaacga cactatgttt ctagttacgt ggcaggccag      6600 ggtcctcct gagattatat tatttgatcc tgatggacga aaatactaca caaataattt      6660 atcaccaat ctaacttttc ggacagctag tctttggatt ccaggaacag ctaagcctgg      6720 cactggact tacaccctga acaatacccca tcattctctg caagccctga agtgacagt      6780 acctctcgc gcctccaact cagctgtgcc cccagccact gtggaagcct tgtggaaag      6840 gacagcctc cattttcctc atcctgtgat gatttatgcc aatgtgaaac agggatttta      6900 cccattctt aatgccactg tcactgccac agttgagcca gagactggag atcctgttac      6960 ctgagactc cttgatgatg gagcaggtgc tgatgttata aaaaatgatg gaatttactc      7020 aggtatttt ttctcctttg ctgcaaatgg tagatatagc ttgaaagtgc atgtcaatca      7080 tctcccagc ataagcaccc cagcccactc tattccaggg agtcatgcta tgtatgtacc      7140 ggttacaca gcaaacggta atattcagat gaatgctcca aggaaatcag taggcagaaa      7200 gaggaggag cgaaagtggg gctttagccg agtcagctca ggaggctcct tttcagtgct      7260 ggagttcca gctggccccc accctgatgt gtttccacca tgcaaaatta ttgacctgga      7320 gctgtaaaa gtagaagagg aattgaccct atcttggaca gcacctggag aagactttga      7380 cagggccag gctacaagct atgaaataag aatgagtaaa agtctacaga atatccaaga      7440 gactttaac aatgctattt tagtaaatac atcaaagcga aatcctcagc aagctggcat      7500 agggagata tttacgttct caccccaaat ttccacgaat ggacctgaac atcagccaaa      7560 ggagaaaca catgaaagcc acagaattta tgttgcaata cgagcaatgg ataggaactc      7620 ttacagtct gctgtatcta acattgccca ggcgcctctg tttattcccc ccaattctga      7680 cctgtacct gccagagatt atcttatatt gaaaggagtt ttaacagcaa tgggtttgat      7740 ggaatcatt tgccttatta tagttgtgac acatcatact ttaagcagga aaaagagagc      7800 gacaagaaa gagaatggaa caaaattatt ataatgaatt ctgcagatat ccatcacact      7860 gcggccgct cgagcaccac caccaccacc actgagatcc ggctgctaac aaagcccgaa      7920 ggaagctga gttggctgct gccaccgctg agcaataact agcataaccc cttggggcct      7980 taaacgggt cttgagggt tttttgctga aaggaggaac tatatccgga t               8031
```

<210> SEQ ID NO 255
<211> LENGTH: 401
<212> TYPE: DNA
<213> ORGANISM: Homo sapien
<220> FEATURE:
<221> NAME/KEY: misc_feature
<222> LOCATION: (1)...(401)
<223> OTHER INFORMATION: n = A,T,C or G

<400> SEQUENCE: 255

```
gtggccagng actagaaggc gaggcgccgc gggaccatgg cggcggcggc ggacgagcgg       60
```

```
agtccanagg acggagaaga cgaggaagag gaggagcagt tggttctggt ggaattatca    120
ggaattattg attcagactt cctctcaaaa tgtgaaaata aatgcaaggt tttgggcatt    180
gacactgaga ggcccattct gcaagtggac agctgtgtct ttgctgggga gtatgaagac    240
actctangga cctgtgttat atttgaagaa aatgntnaac atgctgatac agaaggcaat    300
aataaaacag tgctaaaata taaatgccat acaatgaaga agctcagcat gacaagaact    360
ctcctgacag agaagaagga aggagaagaa aacatangtg g                       401
```

<210> SEQ ID NO 256
<211> LENGTH: 401
<212> TYPE: DNA
<213> ORGANISM: Homo sapien
<220> FEATURE:
<221> NAME/KEY: misc_feature
<222> LOCATION: (1)...(401)
<223> OTHER INFORMATION: n = A,T,C or G

<400> SEQUENCE: 256

```
tggtggncct gggatgggga accgcggtgg cttccgngga ggtttcggca ntggcatccg    60 gggccgggt cgcggccgng gacggggccg gggccnangc cgnnganctc gcggangcaa    120
ggccgaggat aaggagtgga tgcccgtcac caacttgggc cgcttgncca aggacatgaa    180
nancaagccc ctgnaggaga tctatntctt cttccctgcc ccattaagga atcaagagat    240
catttgattt cttcctgggg gcctctctca aggataaggt ttttgaagat tatgccagtg    300
canaaannan accccgttgc ccngtccatc tncacccaac ncttccaagg gcnattttg     360 tttaggcctc attncngggg ggaaccttaa cccaatttgg g                       401
```

<210> SEQ ID NO 257
<211> LENGTH: 401
<212> TYPE: DNA
<213> ORGANISM: Homo sapien
<220> FEATURE:
<221> NAME/KEY: misc_feature
<222> LOCATION: (1)...(401)
<223> OTHER INFORMATION: n = A,T,C or G

<400> SEQUENCE: 257

```
atgtatgtaa aacacttcat aaaatgtaaa gggctataac aaatatgtta taagtgatt    60 ctctcagccc tgaggtatac agaatcattt gcctcagact gctgttggat tttaaaattt    120
ttaaaatatc tgctaagtaa tttgctatgt cttctcccac actatcaata tgcctgcttc    180
taacaggctc cccactttct tttaatgtgc tgttatgagc tttggacatg agataaccgt    240
gcctgttcag agtgtctaca gtaagagctg gacaaactct ggagggacac agtctttgag    300
acagctcttt tggttgcttt ccacttttct gaaaggttca cagtaacctt ctagataata    360
gaaactccca gttaaagcct angctancaa ttttttttag t                       401
```

<210> SEQ ID NO 258
<211> LENGTH: 401
<212> TYPE: DNA
<213> ORGANISM: Homo sapien

<400> SEQUENCE: 258

```
ggagcgctag gtcggtgtac gaccgagatt agggtgcgtg ccagctccgg gaggccgcgg    60
tgaggggccg ggcccaagct gccgacccga gccgatcgtc agggtcgcca gcgcctcagc    120
tctgtggagg agcagcagta gtcggagggt gcaggatatt agaaatggct actccccagt    180
caattttcat ctttgcaatc tgcattttaa tgataacaga attaattctg gcctcaaaaa    240
```

```
gctactatga tatcttaggt gtgccaaaat cggcatcaga gcgccaaatc aagaaggcct      300
ttcacaagtt ggccatgaag taccaccctg acaaaaataa gacccagatg ctgaagcaaa      360
attcagagag attgcagaag catatgaaac actctcagat g                         401

<210> SEQ ID NO 259
<211> LENGTH: 401
<212> TYPE: DNA
<213> ORGANISM: Homo sapien

<400> SEQUENCE: 259
attgggtttg gagggaggat gatgacagag gaatgcccct tggccatcac ggttttgatt      60
ctccagaata ttgtgggttt gatcatcaat gcagtcatgt taggctgcat tttcatgaaa     120
acagctcagg ctcacagaag ggcagaaact ttgattttca gccgccatgc tgtgattgcc     180
gtccgaaatg gcaagctgtg cttcatgttc cgagtgggtg acctgaggaa aagcatgatc     240
attagtgcct ctgtgcgcat ccaggtggtc aagaaaacaa ctacacctga aggggaggtg     300
gttcctattc accaactgga cattcctgtt gataacccaa tcgagagcaa taacattttt     360
ctggtggccc ctttgatcat ctgccacgtg attgacaagc g                         401

<210> SEQ ID NO 260
<211> LENGTH: 363
<212> TYPE: DNA
<213> ORGANISM: Homo sapien
<220> FEATURE:
<221> NAME/KEY: misc_feature
<222> LOCATION: (1)...(363)
<223> OTHER INFORMATION: n = A,T,C or G

<400> SEQUENCE: 260
aggaganang gaggggggana tgaataggga tggagaggga natagtggat gagcagggca     60
canggagagg aancagaaag gagaggcaag acagggagac acacancaca nangangana    120
caggtggggg ctgggtggg gcatggagag cctttnangt cncccaggcc accctgctct      180
cgctggnctg ttgaaaccca ctccatggct tcctgccact gcagttgggc ccagggctgg     240
cttattnctg gaatgcaagt ggctgtggct tggagcctcc cctctggnnn anggaaannn     300
attgctccct tatctgcttg gaatatctga gttttttccan cccggaaata aaacacacac    360
aca                                                                   363

<210> SEQ ID NO 261
<211> LENGTH: 401
<212> TYPE: DNA
<213> ORGANISM: Homo sapien
<220> FEATURE:
<221> NAME/KEY: misc_feature
<222> LOCATION: (1)...(401)
<223> OTHER INFORMATION: n = A,T,C or G

<400> SEQUENCE: 261
cggctctccg ccgctctccc ggggtttcgg ggcacttggg tcccacagtc tggtcctgct      60
tcaccttccc ctgacctgag tagtcgccat ggcacaggtt ctcagaggca ctgngactga    120
cttccctgga tttgatgagc gggctgatgc anaaactctt cggaaggcta tgaaaggctt    180
gggcacagat gaggagagca tcctgactct gttgacatcc gaagtaatg ctcagcgcca     240 ggaaatctct gcagctttta agactctgtt tggcagggat cttctggatg acctgaaatc    300
agaactaact ggaaaatttg aaaaattaat tgtggctctg atgaaaccct ctcggcttta    360
```

```
tgatgcttat gaactgaaac atgccttgaa gggagctgga a                          401
```

<210> SEQ ID NO 262
<211> LENGTH: 401
<212> TYPE: DNA
<213> ORGANISM: Homo sapien
<220> FEATURE:
<221> NAME/KEY: misc_feature
<222> LOCATION: (1)...(401)
<223> OTHER INFORMATION: n = A,T,C or G

<400> SEQUENCE: 262

```
agtctanaac atttctaata ttttgngctt tcatatatca aaggagatta tgtgaaacta     60
tttttaaata ctgtaaagtg acatatagtt ataagatata tttctgtaca gtagagaaag    120
agtttataac atgaagaata ttgtaccatt atacattttc attctcgatc tcataagaaa    180
ttcaaaagaa taatgataga ggtgaaaata tgtttacttt ctctaaatca agcctagttg    240
tcaactcaaa aattatgntg catagtttta ttttgaattt aggttttggg actacttttt    300
tccancttca atgagaaaat aaaatctaca actcaggagt tactacagaa gttctaanta    360
tttttttgct aannagcnaa aaatataaac atatgaaaat g                        401
```

<210> SEQ ID NO 263
<211> LENGTH: 401
<212> TYPE: DNA
<213> ORGANISM: Homo sapien
<220> FEATURE:
<221> NAME/KEY: misc_feature
<222> LOCATION: (1)...(401)
<223> OTHER INFORMATION: n = A,T,C or G

<400> SEQUENCE: 263

```
ctgtccgacc aagagaggcc ggccgagccc gaggcttggg cttttgcttt ctggcggagg     60
gatctgcggc ggtttaggag gcggcgctga tcctgggagg aagaggcagc tacgcggcg    120
gcggcggtgg cggctagggc ggcggcgaat aaaggggccg ccgccgggtg atgcggtgac    180
cactgcggca ggcccaggag ctgagtgggc cccggccctc agcccgtccc gncgacccg    240
cttttcctcaa ctctccatct tctcctgccg accgagatcg ccgaggcggn ctcaggctcc    300
ctancccctt ccccgtccct tccccncccc cgtccccgcc ccggggccg ccgccacccg    360
cctcccacca tggctctgaa ganaatccac aaggaattga a                        401
```

<210> SEQ ID NO 264
<211> LENGTH: 401
<212> TYPE: DNA
<213> ORGANISM: Homo sapien

<400> SEQUENCE: 264

```
aacaccagcc actccaggac ccctgaaggc ctctaccagg tcaccagtgt tctgcgccta     60
aagccacccc ctggcagaaa cttcagctgt gtgttctgga atactcacgt gagggaactt    120
actttggcca gcattgacct tcaaagtcag atggaaccca ggacccatcc aacttggctg    180
cttcacattt tcatcccctc ctgcatcatt gctttcattt tcatagccac agtgatagcc    240
ctaagaaaac aactctgtca aaagctgtat tcttcaaaag acacaacaaa aagacctgtc    300
accacaacaa agagggaagt gaacagtgct gtgaatctga acctgtggtc ttgggagcca    360
gggtgacctg atatgacatc taaagaagct tctggactct g                        401
```

<210> SEQ ID NO 265
<211> LENGTH: 271

```
<212> TYPE: DNA
<213> ORGANISM: Homo sapien
<220> FEATURE:
<221> NAME/KEY: misc_feature
<222> LOCATION: (1)...(271)
<223> OTHER INFORMATION: n = A,T,C or G

<400> SEQUENCE: 265
gccacttcct gtggacatgg gcagagcgct gctgccagtt cctggtagcc ttgaccacna     60
cgctgggggg tctttgtgat ggtcatgggt ctcatttgca cttggggtg tgggattcaa    120 gttagaagtt tctagatctg gccgggcgca gtggctcaca cctgtaatcc cagcacttta   180
ggaggctgag gcaggcggat catgaggtca ggagatcgag accgtcctgg ctaacacagt   240 gaaacccgt ctctactaaa aatacaaaaa a                                   271

<210> SEQ ID NO 266
<211> LENGTH: 401
<212> TYPE: DNA
<213> ORGANISM: Homo sapien
<220> FEATURE:
<221> NAME/KEY: misc_feature
<222> LOCATION: (1)...(401)
<223> OTHER INFORMATION: n = A,T,C or G

<400> SEQUENCE: 266
attcataaat ttagctgaaa gatactgatt caatttgtat acagngaata taaatgagac     60
gacagcaaaa ttttcatgaa atgtaaaata tttttatagt ttgttcatac tatatgaggt   120
tctattttaa atgactttct ggattttaaa aaatttcttt aaatacaatc attttttgtaa  180 tatttatttt atgcttatga tctagataat tgcagaatat cattttatct gactctgtct   240
tcataagaga gctgtggccg aattttgaac atctgttata gggagtgatc aaattagaag   300
gcaatgtgga aaaacaattc tgggaaagat ttctttatat gaagtccctg ccactagcca   360
gccatcctaa ttgatgaaag ttatctgttc acaggcctgc a                       401

<210> SEQ ID NO 267
<211> LENGTH: 401
<212> TYPE: DNA
<213> ORGANISM: Homo sapien
<220> FEATURE:
<221> NAME/KEY: misc_feature
<222> LOCATION: (1)...(401)
<223> OTHER INFORMATION: n = A,T,C or G

<400> SEQUENCE: 267
gaagaggcat cacctgatcc cggagacctt tggagttaag aggcggcgga agcgagggcc     60
tgtggagtcg gatcctcttc ggggtgagcc agggtcggcg cgcgcggctg tctcanaact   120
catgcagctg ttcccgcgag gcctgtttga ggacgcgctg ccgcccatcg tgctgaggag   180
ccaggtgtac agccttgtgc ctgacaggac cgtggccgac cggcagctga aggagcttca   240
agagcanggg gagacaaaat cgtccagctg ggcttcnact tggatgccca tggaanttat   300
tctttcnctt ganggactta cnngggaccc aagaanccct tncaagggc ccttngtgga    360 tgggncccga aaccccnnta tttgcccttg gggggnccca a                       401

<210> SEQ ID NO 268
<211> LENGTH: 223
<212> TYPE: DNA
<213> ORGANISM: Homo sapien

<400> SEQUENCE: 268
```

```
tcgccatgtt ggccaggctg gtcttgaact cctgacttta agtgatccac ccgcctcaac      60
ctcccaaagt gctgggatta caggtgtgag ccaccgcgcc tggcctgata catactttta     120
gaatcaagta gtcacgcact ttttctgttc attttcctaa aaagtaaata tacaaatgtt     180 ttgtttttg ttttttttgt ttgtttgttt ctgttttttt ttt                       223
```

<210> SEQ ID NO 269
<211> LENGTH: 401
<212> TYPE: DNA
<213> ORGANISM: Homo sapien

<400> SEQUENCE: 269

```
actatgtaaa ccacattgta cttttttta ctttggcaac aaatatttat acatacaaga      60
tgctagttca tttgaatatt ctcccaact tatccaagga tctccagctc taacaaaatg     120
gtttattttt atttaaatgt caatagttgt ttttaaaat ccaaatcaga ggtgcaggcc     180
accagttaaa tgccgtctat caggttttgt gccttaagag actacagagt caaagctcat     240
ttttaaagga gtaggacaaa gttgtcacag gttttgttg ttgtttttat tgcccccaaa     300
attacatgtt aatttccatt tatatcaggg attctattta cttgaagact gtgaagttgc     360
cattttgtct cattgttttc tttgacataa ctaggatcca t                        401
```

<210> SEQ ID NO 270
<211> LENGTH: 401
<212> TYPE: DNA
<213> ORGANISM: Homo sapien
<220> FEATURE:
<221> NAME/KEY: misc_feature
<222> LOCATION: (1)...(401)
<223> OTHER INFORMATION: n = A,T,C or G

<400> SEQUENCE: 270

```
tggctgttga ttcacctcag cactgcttgg tatctgcacc ctacctctct ttagaggctg      60
ccttgtcaac tgaaaaatgc acctgacttc gagcaagact ctttccttag gttctggatc     120
tgtttgagcc ccatggcact gagctggaat ctgagggtct tgttccaagg atgtgatgat     180
gtgggagaat gttctttgaa agagcagaaa tccagtctgc atggaaacag cctgtagagn     240
agaagtttcc agtgataagt gttcactgtt ctaaggaggg acaccacagc tacctgaatt     300
ttcccaaaat gagtgcttct gtgcgttaca actggccttt gtacttgact gtgatgactt     360
tgttttttct tttcaattct anatgaacat gggaaaaaat g                        401
```

<210> SEQ ID NO 271
<211> LENGTH: 329
<212> TYPE: DNA
<213> ORGANISM: Homo sapien

<400> SEQUENCE: 271

```
ccacagcctc caagtcaggt ggggtggagt cccagagctg cacagggttt ggcccaagtt      60
tctaagggag gcacttcctc ccctcgccca tcagtgccag ccctgctgg ctggtgcctg     120 agcccctcag acagccccct gccccgcagg cctgccttct cagggacttc tgcggggcct     180
gaggcaagcc atggagtgag acccaggagc cggacacttc tcaggaaatg gcttttccca     240 accccagcc cccacccggt ggttcttcct gttctgtgac tgtgtatagt gccaccacag     300
cttatggcat ctcattgagg acaaaaaaa                                      329
```

<210> SEQ ID NO 272
<211> LENGTH: 401

```
<212> TYPE: DNA
<213> ORGANISM: Homo sapien
<220> FEATURE:
<221> NAME/KEY: misc_feature
<222> LOCATION: (1)...(401)
<223> OTHER INFORMATION: n = A,T,C or G

<400> SEQUENCE: 272
nggctgntaa cntcggaggt nacttcctgg actatcctgg agaccccctc cgcttccacg      60
nncatnatat cnctcatngc tgggcccntn angacacnat cccactccaa cacctgngng     120
atgctggncn cctnggaacc ancntcagaa ngaccctgnt cntntgtnnt ccgcaanctg     180
aagnnaangc gggntacacc tncntgcant ggnccacnct gcnggnaact ntacacacct     240
acgggatgtg gctgcgccan gagccaagag cntttctgga tgattcccca gcctcttgnn     300
agggantcta caacattgct nnntacccttt ntccnncngc nnntnntgga ntacaggngn    360
tnntaacact acatcttttt tactgcnccn tncttggtgg g                        401

<210> SEQ ID NO 273
<211> LENGTH: 401
<212> TYPE: DNA
<213> ORGANISM: Homo sapien
<220> FEATURE:
<221> NAME/KEY: misc_feature
<222> LOCATION: (1)...(401)
<223> OTHER INFORMATION: n = A,T,C or G

<400> SEQUENCE: 273
cagcaccatg aagatcaaga tcatcgcacc cccagagcgc aagtactcgg tgtggatcgg      60
tggctccatc ctggcctcac tgtccaccttt ccagcagatg tggattagca agcaggagta    120
cgacgagtcg ggcccctcca tcgtccaccg caaatgcttc taaacggact cagcagatgc    180
gtagcatttg ctgcatgggt taattgagaa tagaaatttg cccctggcaa atgcacacac    240
ctcatgctag cctcacgaaa ctggaataag ccttcgaaaa gaaattgtcc ttgaagcttg    300
tatctgatat cagcactgga ttgtagaact tgttgctgat tttgaccttg tattgaagtt    360
aactgttccc cttggtatta acgtgtcagg gctgagtgnt c                       401

<210> SEQ ID NO 274
<211> LENGTH: 401
<212> TYPE: DNA
<213> ORGANISM: Homo sapien

<400> SEQUENCE: 274
ccacccacac ccaccgcgcc ctcgttcgcc tcttctccgg gagccagtcc gcgccaccgc      60
cgccgcccag gccatcgcca ccctccgcag ccatgtccac caggtccgtg tcctcgtcct    120
cctaccgcag gatgttcggc ggcccgggca ccgcgagccg gccgagctcc agccggagct    180
acgtgactac gtccacccgc acctacagcc tgggcagcgc gctgcgcccc agcaccagcc    240
gcagcctcta cgcctcgtcc ccgggcggcg tgtatgccac gcgctcctct gccgtgcgcc    300
tgcggagcag cgtgcccggg gtgcggctcc tgcaggactc ggtggacttc tcgctggccg    360
acgccatcaa caccgagttc aagaacaccc gcaccaacga g                        401

<210> SEQ ID NO 275
<211> LENGTH: 401
<212> TYPE: DNA
<213> ORGANISM: Homo sapien

<400> SEQUENCE: 275
```

```
ccacttccac cactttgtgg agcagtgcct tcagcgcaac ccggatgcca ggtatccctg      60
ctggcctggg cctgggcttc gggagagcag aggtgctca ggagggtaag gccagggtgt     120
gaagggactt acctcccaaa ggttctgcag gggaatctgg agctacacac aggagggatc    180
agctcctggg tgtgtcagag gccagcctgg ggagctctgg ccactgcttc ccatgagctg    240
agggagaggg agaggggacc cgaggctgag gcataagtgg caggatttcg ggaagctggg    300
gacacggcag tgatgctgcg gtctctcctc cccttccct ccaggcccag tgccagcacc     360
ctcctgaacc actctttctt caagcagatc aagcgacgtg c                        401
```

<210> SEQ ID NO 276
<211> LENGTH: 401
<212> TYPE: DNA
<213> ORGANISM: Homo sapien
<220> FEATURE:
<221> NAME/KEY: misc_feature
<222> LOCATION: (1)...(401)
<223> OTHER INFORMATION: n = A,T,C or G

<400> SEQUENCE: 276

```
tctgatattg ntaccettga gccacctaag ttagaagaaa ttggaaatca agaagttgtc     60
attgttgaag aagcacagag ttcagaagac tttaacatgg gctcttcctc tagcagccag    120
tatactttct gtcagccaga aactgtattt tcatctcagc ctagtgatga tgaatcaagt    180
agtgatgaaa ccagtaatca gcccagtcct gcctttagac gacgccgtgc taggaagaag    240
accgtttctg cttcagaatc tgaagaccgg ctagttggtg aacaagaaac tgaaccttct    300
aaggagttga gtaaacgtca gttcagtagt ggtctcaata agtgtgttat acttgctttg    360
gtgattgcaa tcagcatggg atttggccat ttctatggca c                        401
```

<210> SEQ ID NO 277
<211> LENGTH: 401
<212> TYPE: DNA
<213> ORGANISM: Homo sapien
<220> FEATURE:
<221> NAME/KEY: misc_feature
<222> LOCATION: (1)...(401)
<223> OTHER INFORMATION: n = A,T,C or G

<400> SEQUENCE: 277

```
aactttggca acatatctca gcaaaaacta cagctatgtt attcatgcca aaataaaagc     60
tgtgcagagg agtggctgca atgaggtcac aacggtggtg gatgtaaaag agatcttcaa    120
gtcctcatca cccatccctc gaactcaagt cccgctcatt acaaattctt cttgccagtg    180
tccacacatc ctgcccatc aagatgttct catcatgtgt tacgagnggc gctcaaggat     240
gatgcttctt gaaaattgct tagttgaaaa atggagagat cagcttagta aaagatccat    300
acagtgggaa gagaggctgc aggaacagcg ganaacagtt caggacaaga agaaaacagc    360
cgggcgcacc agtcgtagta atccccccaa accaagggaa                           401
```

<210> SEQ ID NO 278
<211> LENGTH: 401
<212> TYPE: DNA
<213> ORGANISM: Homo sapien
<220> FEATURE:
<221> NAME/KEY: misc_feature
<222> LOCATION: (1)...(401)
<223> OTHER INFORMATION: n = A,T,C or G

<400> SEQUENCE: 278

```
aatgagtgtg agaccacaaa tgaatgccgg gaggatgaaa tgtgttggaa ttatcatggc     60
```

| | |
|---|---|
| ggcttccgtt gttatccacg aaatccttgt caagatccct acattctaac accagagaac | 120 |
| cgatgtgttt gcccagtctc aaatgccatg tgccgagaac tgccccagtc aatagtctac | 180 |
| aaatacatga gcatccgatc tgataggtct gtgccatcag acatcttcca gatacaggcc | 240 |
| acaactattt atgccaacac catcaatact tttcggatta aatctggaaa tgaaaatgga | 300 |
| gagtctacct acgacaacaa anccctgtaa gtcaatgct tgtgctcgtg aagncattat | 360 |
| caggaccaag agaacatatc gtggacctgg agatgctgac a | 401 |

<210> SEQ ID NO 279
<211> LENGTH: 401
<212> TYPE: DNA
<213> ORGANISM: Homo sapien
<220> FEATURE:
<221> NAME/KEY: misc_feature
<222> LOCATION: (1)...(401)
<223> OTHER INFORMATION: n = A,T,C or G

<400> SEQUENCE: 279

| | |
|---|---|
| aaattattgc ctctgataca tacctaagtn aacanaacat taatacctaa gtaaacataa | 60 |
| cattacttgg agggttgcag nttctaantg aaactgtatt tgaaactttt aagtatactt | 120 |
| taggaaacaa gcatgaacgg cagtctagaa taccagaaac atctacttgg gtagcttggn | 180 |
| gccattatcc tgtggaatct gatatgtctg gnagcatgtc attgatggga catgaagaca | 240 |
| tctttggaaa tgatgagatt atttcctgtg ttaaaaaaaa aaaaaatctt aaattcctac | 300 |
| aatgtgaaac tgaaactaat aattttgatc ctgatgtatg ggacagcgta tctgtaccag | 360 |
| gctctaaata acaaaagnta gggngacaag nacatgttcc t | 401 |

<210> SEQ ID NO 280
<211> LENGTH: 326
<212> TYPE: DNA
<213> ORGANISM: Homo sapien

<400> SEQUENCE: 280

| | |
|---|---|
| gaagtggaat tgtataattc aattcgataa ttgatctcat gggctttccc tggaggaaag | 60 |
| gtttttttg ttgttttttt tttaagaact tgaaacttgt aaactgagat gtctgtagct | 120 |
| tttttgccca tctgtagtgt atgtgaagat ttcaaaacct gagagcactt tttctttgtt | 180 |
| tagaattatg agaaaggcac tagatgactt taggatttgc atttttccct ttattgcctc | 240 |
| atttcttgtg acgccttgtt ggggagggaa atctgtttat tttttcctac aaataaaaag | 300 |
| ctaagattct atatcgcaaa aaaaaa | 326 |

<210> SEQ ID NO 281
<211> LENGTH: 374
<212> TYPE: DNA
<213> ORGANISM: Homo sapien

<400> SEQUENCE: 281

| | |
|---|---|
| caacgcgttt gcaaatattc ccctggtagc ctacttcctt accccgaat attggtaaga | 60 |
| tcgagcaatg gcttcaggac atgggttctc ttctcctgtg atcattcaag tgctcactgc | 120 |
| atgaagactg gcttgtctca gtgtttcaac ctcaccaggg ctgtctcttg gtccacacct | 180 |
| cgctccctgt tagtgccgta tgacagcccc catcaaatga ccttggccaa gtcacggttt | 240 |
| ctctgtggtc aaggttggtt ggctgattgg tggaaagtag ggtggaccaa aggaggccac | 300 |
| gtgagcagtc agcaccagtt ctgcaccagc agcgcctccg tcctagtggg tgttcctgtt | 360 |

```
tctcctggcc ctgg                                                           374
```

<210> SEQ ID NO 282
<211> LENGTH: 404
<212> TYPE: DNA
<213> ORGANISM: Homo sapien
<220> FEATURE:
<221> NAME/KEY: misc_feature
<222> LOCATION: (1)...(404)
<223> OTHER INFORMATION: n = A,T,C or G

<400> SEQUENCE: 282

```
agtgtggtgg aattcccgca tcctanncgc cgactcacac aaggcagagt ngccatggag   60
aaaattccag tgtcagcatt cttgctcctt gtggccctct cctacactct ggccagagat  120
accacagtca aacctgnagc caaaaaggac acaaggact  ctcgacccaa actgccccan  180
accctctcca gaggttgggg tgaccaactc atctggactc anacatatga agaagctcta  240
tataaatcca agacaagcaa caaacccttg atgattattc atcacttgga tgagtgccca  300
cacagtcaag ctttaaagaa agtgtttgct gaaaataaag aaatccagaa attggcagag  360
cagtttgtcc tcctcaatct ggtttatgaa acaactgaca aaca                   404
```

<210> SEQ ID NO 283
<211> LENGTH: 184
<212> TYPE: DNA
<213> ORGANISM: Homo sapien
<220> FEATURE:
<221> NAME/KEY: misc_feature
<222> LOCATION: (1)...(184)
<223> OTHER INFORMATION: n = A,T,C or G

<400> SEQUENCE: 283

```
agtgtggtgg aattcacttg cttaanttgt gggcaaaaga gaaaagaag gattgatcag    60
agcattgtgc aatacagttt cattaactcc ttccctcgct cccccaaaaa tttgaatttt  120
tttttcaaca ctcttacacc tgttatggaa aatgtcaacc tttgtaagaa aaccaaaata  180
aaaa                                                               184
```

<210> SEQ ID NO 284
<211> LENGTH: 421
<212> TYPE: DNA
<213> ORGANISM: Homo sapien
<220> FEATURE:
<221> NAME/KEY: misc_feature
<222> LOCATION: (1)...(421)
<223> OTHER INFORMATION: n = A,T,C or G

<400> SEQUENCE: 284

```
ctattaatcc tgccacaata tttttaatta cgtacaaaga tctgacatgt cacccaggga   60
cccatttcac ccactgctct gtttggccgc cagtcttttg tctctctctt cagcaatggt  120
gaggcggata ccctttcctc ggggaanana aatccatggt ttgttgccct tgccaataac  180
aaaaatgttg gaaagtcgag tgcaaagct  gttgccattg gcatctttca cgtgaaccac  240
gtcaaaagat ccagggtgcc tctctctgtt ggtgatcaca ccaattcttc ctaggttagc  300
acctccagtc accatacaca ggttaccagt gtcgaacttg atgaaatcag taatcttgcc  360
agtctctaaa tcaatctgaa tggtatcatt caccttgatg aggggatcgg ggtagcggat  420
g                                                                  421
```

<210> SEQ ID NO 285
<211> LENGTH: 361

```
<212> TYPE: DNA
<213> ORGANISM: Homo sapien
<220> FEATURE:
<221> NAME/KEY: misc_feature
<222> LOCATION: (1)...(361)
<223> OTHER INFORMATION: n = A,T,C or G

<400> SEQUENCE: 285
ctgggtggta actctttatt tcattgtccg gaanaaagat gggagtggga acagggtgga      60
cactgtgcag gcttcagctt ccactccggg caggattcag gctatctggg accgcaggga    120
ctgccaggtg cacagccctg gctcccgagg caggcaggca aggtgacggg actggaagcc    180
cttttcanag ccttggagga gctggtccgt ccacaagcaa tgagtgccac tctgcagttt    240
gcaggggatg gataaacagg gaaacactgt gcattcctca cagccaacag tgtaggtctt    300
ggtgaagccc cggcgctgag ctaagctcag gctgttccag ggagccacga aactgcaggt    360
a                                                                     361

<210> SEQ ID NO 286
<211> LENGTH: 336
<212> TYPE: DNA
<213> ORGANISM: Homo sapien
<220> FEATURE:
<221> NAME/KEY: misc_feature
<222> LOCATION: (1)...(336)
<223> OTHER INFORMATION: n = A,T,C or G

<400> SEQUENCE: 286
tttgagtggc agcgccttta tttgtggggg ccttcaaggn agggtcgtgg ggggcagcgg      60 ggaggaaanag ccganaaact gtgtgaccgg ggcctcaggt ggtgggcatt gggggctcct    120
cttgcanatg cccattggca tcaccggtgc agccattggt ggcagcgggt accggtcctt    180
tcttgttcaa catagggtag gtggcagcca cgggtccaac tcgcttgagg ctgggccctg    240
ggcgctccat tttgtgttcc angagcatgt ggttctgtgg cgggagcccc acgcaggccc    300
tgaggatgtt ctcgatgcag ctgcgctggc ggaaaa                              336

<210> SEQ ID NO 287
<211> LENGTH: 301
<212> TYPE: DNA
<213> ORGANISM: Homo sapien
<220> FEATURE:
<221> NAME/KEY: misc_feature
<222> LOCATION: (1)...(301)
<223> OTHER INFORMATION: n = A,T,C or G

<400> SEQUENCE: 287
tgggtaccaa atttntttat ttgaaggaat ggnacaaatc aaanaactta agnggatgtt      60
ttggtacaac ttatanaaaa ggnaaaggaa accccaacat gcatgcnctg ccttggngac    120
cagggaagtc accccacggc tatggggaaa ttancccgag gcttanctt cattatcact     180 gtctcccagg gngngcttgt caaaaanata ttccnccaag ccaaattcgg gcgctcccat    240
nttgcncaag ttggtcacgt ggtcacccaa ttctttgatg gctttcacct gctcattcag    300
g                                                                     301

<210> SEQ ID NO 288
<211> LENGTH: 358
<212> TYPE: DNA
<213> ORGANISM: Homo sapien
<220> FEATURE:
<221> NAME/KEY: misc_feature
<222> LOCATION: (1)...(358)
```

<223> OTHER INFORMATION: n = A,T,C or G

<400> SEQUENCE: 288

| aagtttttaa actttttatt tgcatattaa aaaaattgng cattccaata attaaaatca | 60 |
| tttgaacaaa aaaaaaaatg gcactctgat taaactgcat tacagcctgc aggacacctt | 120 |
| gggccagctt ggttttactc tanatttcac tgtcgtccca ccccacttct tccaccccac | 180 |
| ttcttccttc accaacatgc aagttctttc cttccctgcc agccanatag atagacagat | 240 |
| gggaaaggca ggcgcggcct tcgttgtcag tagttctttg atgtgaaagg ggcagcacag | 300 |
| tcatttaaac ttgatccaac ctctttgcat cttacaaagt taaacagcta aaagaagt | 358 |

<210> SEQ ID NO 289
<211> LENGTH: 462
<212> TYPE: DNA
<213> ORGANISM: Homo sapien
<220> FEATURE:
<221> NAME/KEY: misc_feature
<222> LOCATION: (1)...(462)
<223> OTHER INFORMATION: n = A,T,C or G

<400> SEQUENCE: 289

| ggcatcagaa atgctgttta tttctctgct gctcccaagc tggctggcct ttgcagagga | 60 |
| gcagacaaca gatgcatagt tggggananaaa gggaggacag gttccaggat agagggtgca | 120 |
| ggctgaggga ggaagggtaa naggaaggaa ggccatcctg gatccccaca tttcagtctc | 180 |
| anatgaggac aaagggactc ccaagccccc aaatcatcan aaaacaccaa ggagcaggag | 240 |
| gagcttgagc aggccccagg gagcctcana gccataccag ccactgtcta cttcccatcc | 300 |
| tcctctccca ttccctgtct gcttcanacc acctcccagc taagcccag ctccattccc | 360 |
| ccaatcctgg cccttgccag cttgacagtc acagtgcctg gaattccacc actgaggctt | 420 |
| ctcccagttg gattaggacg tcgccctgtt agcatgctgc cc | 462 |

<210> SEQ ID NO 290
<211> LENGTH: 481
<212> TYPE: DNA
<213> ORGANISM: Homo sapien
<220> FEATURE:
<221> NAME/KEY: misc_feature
<222> LOCATION: (1)...(481)
<223> OTHER INFORMATION: n = A,T,C or G

<400> SEQUENCE: 290

| tactttccta aactttatta agaaaaaag caataagcaa tggnggtaaa tctctanaac | 60 |
| atacccaatt ttctgggctt cctcccccga gaatgtgaca ttttgatttc caaacatgcc | 120 |
| anaagtgtat ggttcccaac tgtactaaag taggtganaa gctgaagtcc tcaagtgttc | 180 |
| atcttccaac ttttcccagt ctgtggtctg tctttggatc agcaataatt gcctgaacag | 240 |
| ctactatggc ttcgttgatt tttgtctgta gctctctgag ctcctctatg tgcagcaatc | 300 |
| gcanaatttg agcagcttca ttaanaactg catctcctgt gtcaaaacca anatatgtt | 360 |
| tgtctaaagc aacaggtaag ccctcttttg tttgatttgc cttancaact gcatcctgtg | 420 |
| tcaggcgctc ctgaaccaaa atccgaattg ccttaagcat taccaggtaa tcatcatgac | 480 |
| g | 481 |

<210> SEQ ID NO 291
<211> LENGTH: 381
<212> TYPE: DNA
<213> ORGANISM: Homo sapien
<220> FEATURE:
<221> NAME/KEY: misc_feature
<222> LOCATION: (1)...(381)
<223> OTHER INFORMATION: n = A,T,C or G

<400> SEQUENCE: 291

| | | | | | |
|---|---|---|---|---|---|
| tcatagtaat | gtaaaaccat | ttgtttaatt | ctaaatcaaa | tcactttcac | aacagtgaaa | 60 |
| attagtgact | ggttaaggng | tgccactgta | catatcatca | ttttctgact | ggggtcagga | 120 |
| cctggtccta | gtccacaagg | gtggcaggag | gagggtggag | gctaanaaca | cagaaaacac | 180 |
| acaaanaaa | ggaaagctgc | cttggcanaa | ggatgaggng | gtgagcttgc | cgaaggatgg | 240 |
| tgggaagggg | gctccctgtt | ggggccgagc | caggagtccc | aagtcagctc | tcctgcctta | 300 |
| cttagctcct | ggcanagggt | gagtggggac | ctacgaggtt | caaaatcaaa | tggcatttgg | 360 |
| ccagcctggc | tttactaaca | g | | | | 381 |

<210> SEQ ID NO 292
<211> LENGTH: 371
<212> TYPE: DNA
<213> ORGANISM: Homo sapien
<220> FEATURE:
<221> NAME/KEY: misc_feature
<222> LOCATION: (1)...(371)
<223> OTHER INFORMATION: n = A,T,C or G

<400> SEQUENCE: 292

| | | | | | |
|---|---|---|---|---|---|
| gaaaaaataa | tccgtttaat | tgaaaaacct | gnaggatact | attccactcc | cccanatgag | 60 |
| gaggctgagg | anaccaaacc | cctacatcac | ctcgtagcca | cttctgatac | tcttcacgag | 120 |
| gcagcaggca | aagacaattc | ccaaaacctc | nacaaaagca | attccaaggg | ctgctgcagc | 180 |
| taccaccanc | acattttttcc | tcagccagcc | cccaatcttc | tccacacagc | cctccttatg | 240 |
| gatcgccttc | tcgttgaaat | taatcccaca | gcccacagta | acattaatgc | ancaggagtc | 300 |
| ggggactcgg | ttcttcgaca | tggaagggat | tttctcccaa | tctgtgtagt | tagcagcccc | 360 |
| acagcactta | a | | | | | 371 |

<210> SEQ ID NO 293
<211> LENGTH: 361
<212> TYPE: DNA
<213> ORGANISM: Homo sapien
<220> FEATURE:
<221> NAME/KEY: misc_feature
<222> LOCATION: (1)...(361)
<223> OTHER INFORMATION: n = A,T,C or G

<400> SEQUENCE: 293

| | | | | | |
|---|---|---|---|---|---|
| gatttaaaag | aaaacacttt | attgttcagc | aattaaaagt | tagccaaata | tgtatttttc | 60 |
| tccataattt | attgngatgt | tatcaacatc | aagtaaaatg | ctcattttca | tcatttgctt | 120 |
| ctgttcatgt | tttcttgaac | acgtcttcaa | ttttccttcc | aaaatgctgc | atgccacact | 180 |
| tgaggtaacg | aagcanaagt | atttttaaac | atgacagcta | anaacattca | tctacagcaa | 240 |
| cctatatgct | caatacatgc | cgcgtgatcc | tagtagtttt | ttcacaacct | tctacaagtt | 300 |
| tttggaaaac | atctgttatg | atgactttca | tacaccttca | cctcaaaggc | tttcttgcac | 360 |
| c | | | | | | 361 |

<210> SEQ ID NO 294
<211> LENGTH: 391
<212> TYPE: DNA
<213> ORGANISM: Homo sapien
<220> FEATURE:

<221> NAME/KEY: misc_feature
<222> LOCATION: (1)...(391)
<223> OTHER INFORMATION: n = A,T,C or G

<400> SEQUENCE: 294

| | |
|---|---|
| tattttaaag tttaattatg attcanaaaa aatcgagcga ataactttct ctgaaaaaat | 60 |
| atattgactc tgtatanacc acagttattg gggganaagg gctggtaggt taaattatcc | 120 |
| tatttttat tctgaaaatg atattaatan aaagtcccgt ttccagtctg attataaaga | 180 |
| tacatatgcc caaaatggct ganaataaat acaacaggaa atgcaaaagc tgtaaagcta | 240 |
| agggcatgca ananaaaatc tcanaatacc caaagnggca acaaggaacg tttggctgga | 300 |
| atttgaagtt atttcagtca tctttgtctt tggctccatg tttcaggatg cgtgtgaact | 360 |
| cgatgtaatt gaaattcccc tttttatcaa t | 391 |

<210> SEQ ID NO 295
<211> LENGTH: 343
<212> TYPE: DNA
<213> ORGANISM: Homo sapien
<220> FEATURE:
<221> NAME/KEY: misc_feature
<222> LOCATION: (1)...(343)
<223> OTHER INFORMATION: n = A,T,C or G

<400> SEQUENCE: 295

| | |
|---|---|
| ttcttttgtt ttattgataa cagaaactgt gcataattac agatttgatg aggaatctgc | 60 |
| aaataataaa gaatgtgtct actgccagca aaatacaatt attccatgcc ctctcaacat | 120 |
| acaaatatag agttcttcac accanatggc tctggtgtaa caaagccatt ttanatgttt | 180 |
| aattgtgctt ctacaaaacc ttcanagcat gaggtagttt cttttaccta cnatattttc | 240 |
| cacatttcca ttattacact tttagtgagc taaaatcctt ttaacatagc ctgcggatga | 300 |
| tctttcacaa aagccaagcc tcatttacaa agggtttatt tct | 343 |

<210> SEQ ID NO 296
<211> LENGTH: 241
<212> TYPE: DNA
<213> ORGANISM: Homo sapien
<220> FEATURE:
<221> NAME/KEY: misc_feature
<222> LOCATION: (1)...(241)
<223> OTHER INFORMATION: n = A,T,C or G

<400> SEQUENCE: 296

| | |
|---|---|
| ttcttggata ttggttgttt ttgtgaaaaa gtttttgttt ttcttctcag tcaactgaat | 60 |
| tatttctcta ctttgccctc ctgatgccca catgananaa cttaanataa tttctaacag | 120 |
| cttccacttt ggaaaaaaaa aaaacctgtt ttcctcatgg aacccagga gttgaaagtg | 180 |
| gatanatcgc tctcaaaatc taaggctctg ttcagcttta cattatgtta cctgacgttt | 240 |
| t | 241 |

<210> SEQ ID NO 297
<211> LENGTH: 391
<212> TYPE: DNA
<213> ORGANISM: Homo sapien
<220> FEATURE:
<221> NAME/KEY: misc_feature
<222> LOCATION: (1)...(391)
<223> OTHER INFORMATION: n = A,T,C or G

<400> SEQUENCE: 297

| | |
|---|---|
| gttgtggctg anaatgctgg agatgctcag ttctctccct cacaaggtag gccacaaatt | 60 | cttggtggtg ccctcacatc tggggtcttc aggcaccagc catgcctgcc gaggagtgct      120 gtcaggacan accatgtccg tgctaggccc aggcacagcc caaccactcc tcatccaagt      180 ctctcccagg tttctggtcc cgatgggcaa ggatgacccc tccagtggct ggtaccccac      240 catcccacta cccctcacat gctctcactc tccatcaggt ccccaatcct ggcttccctc      300 ttcacgaact ctcaaagaaa aggaaggata aaacctaaat aaaccagaca gaagcagctc      360 tggaaaagta caaaaagaca gccagaggtg t      391

<210> SEQ ID NO 298
<211> LENGTH: 321
<212> TYPE: DNA
<213> ORGANISM: Homo sapien
<220> FEATURE:
<221> NAME/KEY: misc_feature
<222> LOCATION: (1)...(321)
<223> OTHER INFORMATION: n = A,T,C or G

<400> SEQUENCE: 298
caagccaaac tgtntccagc tttattaaan atactttcca taaacaatca tggtatttca      60
ggcaggacat gggcanacaa tcgttaacag tatacaacaa ctttcaaact cccttnttca      120
atggactacc aaaaatcaaa aagccactat aaaacccaat gaagtcttca tctgatgctc      180
tgaacaggga aagtttaaag ngagggttga catttcacat ttagcatgtt gtttaacaac      240
ttttcacaag ccgaccctga ctttcaggaa gtgaaatgaa aatggcanaa tttatctgaa      300
natccacaat ctaaaaatgg a      321

<210> SEQ ID NO 299
<211> LENGTH: 401
<212> TYPE: DNA
<213> ORGANISM: Homo sapien
<220> FEATURE:
<221> NAME/KEY: misc_feature
<222> LOCATION: (1)...(401)
<223> OTHER INFORMATION: n = A,T,C or G

<400> SEQUENCE: 299
tatcataaag agtgttgaag tttatttatt atagcaccat tgagacattt tgaaattgga      60
attggtaaaa aaataaaaca aaaagcattt gaattgtatt tggnggaaca gcaaaaaaag      120
agaagtatca tttttctttg tcaaattata ctgtttccaa acattttgga aataaataac      180
tggaattttg tcggtcactt gcactggttg acaagattag aacaagagga acacatatgg      240
agttaaattt ttttttgttgg gatttcanat agagtttggt ttataaaaag caaacagggc      300
caacgtccac accaaattct tgatcaggac caccaatgtc atagggngca atatctacaa      360
taggtagtct cacagccttg cgtgttcgat attcaaagac t      401

<210> SEQ ID NO 300
<211> LENGTH: 188
<212> TYPE: DNA
<213> ORGANISM: Homo sapien
<220> FEATURE:
<221> NAME/KEY: misc_feature
<222> LOCATION: (1)...(188)
<223> OTHER INFORMATION: n = A,T,C or G

<400> SEQUENCE: 300
tgaatgcttt gtcatattaa gaaagttaaa gtgcaataat gtttgaanac aataagtggt      60
ggtgtatctt gtttctaata agataaactt ttttgtcttt gctttatctt attagggagt      120

```
tgtatgtcag tgtataaaac atactgtgtg gtataacagg cttaataaat tctttaaaag    180
gaaaaaaa                                                             188

<210> SEQ ID NO 301
<211> LENGTH: 291
<212> TYPE: DNA
<213> ORGANISM: Homo sapien

<400> SEQUENCE: 301
aagattttgt tttattttat tatggctaga aagacactgt tatagccaaa atcggcaatg     60
acactaaaga aatcctctgt gcttttcaat atgcaaatat atttcttcca agagttgccc    120
tggtgtgact tcaagagttc atgttaactt cttttctgga aacttccttt tcttagttgt    180
tgtattcttg aagagcctgg gccatgaaga gcttgcctaa gttttgggca gtgaactcct    240
tgatgttctg gcagtaagtg tttatctggc ctgcaatgag cagcgagtcc a             291

<210> SEQ ID NO 302
<211> LENGTH: 341
<212> TYPE: DNA
<213> ORGANISM: Homo sapien
<220> FEATURE:
<221> NAME/KEY: misc_feature
<222> LOCATION: (1)...(341)
<223> OTHER INFORMATION: n = A,T,C or G

<400> SEQUENCE: 302
tgatttttca taattttatt aaatnatcac tgggaaaact aatggttcgc gtatcacaca     60
attacactac aatctgatag gagtggtaaa accagccaat ggaatccagg taaagtacaa    120
aaacgccacc ttttattgtc ctgtcttatt tctcgggaag gagggttcta ctttacacat    180
ttcatgagcc agcagtggac ttgagttaca atgtgtaggt tccttgtggt tatagctgca    240
gaagaagcca tcaaattctt gaggacttga catctctcgg aaagaagcaa actagtggat    300
cccccgggct gcaggaattc gatatcaagc ttatcgatac c                        341

<210> SEQ ID NO 303
<211> LENGTH: 361
<212> TYPE: DNA
<213> ORGANISM: Homo sapien
<220> FEATURE:
<221> NAME/KEY: misc_feature
<222> LOCATION: (1)...(361)
<223> OTHER INFORMATION: n = A,T,C or G

<400> SEQUENCE: 303
tgcagacagt aaatnaattt tatttgngtt cacagaacat actaggcgat ctcgacagtc     60
gctccgtgac agcccaccaa cccccaaccc tntacctcgc agccaccta aaggcgactt    120 caanaanatg gaaggatctc acggatctca ttcctaatgg tccgccgaag tctcacacag    180
tanacagacg gagttganat gctggaggat gcagtcacct cctaaactta cgacccacca    240
ccanacttca tcccagccgg gacgtcctcc cccacccgag tcctcccat ttcttctcct     300 actttgccgc agtccaggn gtcctgcttc caccagtccc acaaagctca ataaatacca    360
a                                                                    361

<210> SEQ ID NO 304
<211> LENGTH: 301
<212> TYPE: DNA
<213> ORGANISM: Homo sapien
<220> FEATURE:
<221> NAME/KEY: misc_feature
```

<222> LOCATION: (1)...(301)
<223> OTHER INFORMATION: n = A,T,C or G

<400> SEQUENCE: 304
ctctttacaa cagcctttat ttncggccct tgatcctgct cggatgctgg tggaggccct     60
tagctccgcc cgccaggctc tgtgccgcct ccccgcaggc gcanattcat gaacacggtg    120 ctcagggget tgaggccgta ctcccccagc gggagctggt cctccagggg cttcccctcg    180
aaggtcagcc anaacaggtc gtcctgcaca ccctccagcc cgctcacttg ctgcttcagg    240
tgggccacgg tctgcgtcag ccgcacctcg taggtgctgc tgcggccctt gttattcctc    300
a                                                                    301

<210> SEQ ID NO 305
<211> LENGTH: 331
<212> TYPE: DNA
<213> ORGANISM: Homo sapien
<220> FEATURE:
<221> NAME/KEY: misc_feature
<222> LOCATION: (1)...(331)
<223> OTHER INFORMATION: n = A,T,C or G

<400> SEQUENCE: 305
ganaggctag taacatcagt tttattgggt tggggnggca accatagcct ggctgggggn     60
ggggctggcc ctcacaggtt gttgagttcc agcagggtct ggtccaaggt ctggtgaatc    120
tcgacgttct cctccttggc actggccaag gtctcttcta ggtcatcgat ggttttctcc    180
aactttgcca canacctctc ggcaaactct gctcgggtct cancctcctt cagcttctcc    240
tccaacagtt tgatctcctc ttcatattta tcttctttgg gggaatactc ctcctctgag    300
gccatcaggg acttgagggc ctggtccatg g                                   331

<210> SEQ ID NO 306
<211> LENGTH: 457
<212> TYPE: DNA
<213> ORGANISM: Homo sapien

<400> SEQUENCE: 306
aatatgtaaa ggtaataact tttattatat taaagacaat gcaaacgaaa acagaattg      60 agcagtgcaa aatttaaagg actgttttgt tctcaaagtt gcaagtttca agccaaaag    120 aattatatgt atcaaatata taagtaaaaa aaagttagac tttcaagcct gtaatcccag    180
cactttggga ggctgaggca ggtggatcac taacattaaa aagacaacat tagattttgt    240
cgatttatag caattttata aatatataac tttgtcactt ggatcctgaa gcaaaataat    300
aaagtgaatt tgggattttt gtacttggta aaaagtttaa caccctaaat tcacaactag    360
tggatccccc gggctgcagg aattcgatat caagcttatc gataccgtcg acctcgaggg    420
ggggcccggt acccaattcg ccctatagtg agtcgta                             457

<210> SEQ ID NO 307
<211> LENGTH: 491
<212> TYPE: DNA
<213> ORGANISM: Homo sapien

<400> SEQUENCE: 307
gtgcttggac ggaacccggc gctcgttccc caccccggcc ggccgcccat agccagccct     60
ccgtcacctc ttcaccgcac cctcggactg cccaaggcc cccgccgccg ctccagcgcc    120
gcgcagccac cgccgccgcc gccgcctctc cttagtcgcc gccatgacga ccgcgtccac    180

-continued

| | |
|---|---|
| ctcgcaggtg cgccagaact accaccagga ctcagaggcc gccatcaacc gccagatcaa | 240 |
| cctggagctc tacgcctcct acgtttacct gtccatgtct tactactttg accgcgatga | 300 |
| tgtggctttg aagaactttg ccaaatactt tcttcaccaa tctcatgagg agagggaaca | 360 |
| tgctgagaaa ctgatgaagc tgcagaacca acgaggtggc cgaatcttcc ttcaggatat | 420 |
| caagaaacca gactgtgatg actgggagag cgggctgaat gcaatggagt gtgcattaca | 480 |
| tttggaaaaa a | 491 |

<210> SEQ ID NO 308
<211> LENGTH: 421
<212> TYPE: DNA
<213> ORGANISM: Homo sapien

<400> SEQUENCE: 308

| | |
|---|---|
| ctcagcgctt cttctttctt ggtttgatcc tgactgctgt catggcgtgc cctctggaga | 60 |
| aggccctgga tgtgatggtg tccaccttcc acaagtactc gggcaaagag ggtgacaagt | 120 |
| tcaagctcaa caagtcagaa ctaaaggagc tgctgacccg ggagctgccc agcttcttgg | 180 |
| ggaaaaggac agatgaagct gctttccaga agctgatgag caacttggac agcaacaggg | 240 |
| acaacgaggt ggacttccaa gagtactgtg tcttcctgtc ctgcatcgcc atgatgtgta | 300 |
| acgaattctt tgaaggcttc ccagataagc agcccaggaa gaaatgaaaa ctcctctgat | 360 |
| gtggttgggg ggtctgccag ctggggcccct ccctgtcgcc agtgggcact ttttttttttc | 420 |
| c | 421 |

<210> SEQ ID NO 309
<211> LENGTH: 321
<212> TYPE: DNA
<213> ORGANISM: Homo sapien

<400> SEQUENCE: 309

| | |
|---|---|
| accaaatggc ggatgacgcc ggtgcagcgg gggggcccgg gggccctggt ggccctggga | 60 |
| tggggaaccg cggtggcttc cgcggaggtt tcggcagtgg catccggggc cggggtcgcg | 120 |
| gccgtggacg gggccggggc cgaggccgcg gagctcgcgg aggcaaggcc gaggataagg | 180 |
| agtggatgcc cgtcaccaag ttgggccgct tggtcaagga catgaagatc aagtccctgg | 240 |
| aggagatcta tctcttctcc ctgcccatta ggaatcaga gatcattgat tcttcctgg | 300 |
| gggcctctct caaggatgag g | 321 |

<210> SEQ ID NO 310
<211> LENGTH: 381
<212> TYPE: DNA
<213> ORGANISM: Homo sapien

<400> SEQUENCE: 310

| | |
|---|---|
| ttaaccagcc atattggctc aataaatagc ttcggtaagg agttaatttc cttctagaaa | 60 |
| tcagtgccta ttttttcctgg aaactcaatt ttaaatagtc caattccatc tgaagccaag | 120 |
| ctgttgtcat tttcattcgg tgacattctc tcccatgaca cccagaaggg gcagaagaac | 180 |
| cacatttttc atttatagat gtttgcatcc tttgtattaa aattattttg aagggggttgc | 240 |
| ctcattggat ggcttttttt ttttttcctcc agggagaagg ggagaaatgt acttggaaat | 300 |
| taatgtatgt ttcacatctct ttgcaaattc ctgtacatag agatatattt tttaagtgtg | 360 |
| aatgtaacaa catactgtga a | 381 |

```
<210> SEQ ID NO 311
<211> LENGTH: 538
<212> TYPE: DNA
<213> ORGANISM: Homo sapien

<400> SEQUENCE: 311
tttgaattta caccaagaac ttctcaataa aagaaaatca tgaatgctcc acaatttcaa      60
cataccacaa gagaagttaa tttcttaaca ttgtgttcta tgattatttg taagaccttc     120
accaagttct gatatctttt aaagacatag ttcaaaattg cttttgaaaa tctgtattct     180
tgaaaatatc cttgttgtgt attaggtttt taaataccag ctaaaggatt acctcactga     240
gtcatcagta ccctcctatt cagctcccca agatgatgtg ttttgctta ccctaagaga     300
ggttttcttc ttattttag ataattcaag tgcttagata aattatgttt tctttaagtg     360
tttatggtaa actcttttaa agaaaattta atatgttata gctgaatctt tttggtaact     420
ttaaatcttt atcatagact ctgtacatat gttcaaatta gctgcttgcc tgatgtgtgt     480
atcatcggtg ggatgacaga acaaacatat ttatgatcat gaataatgtg ctttgtaa      538

<210> SEQ ID NO 312
<211> LENGTH: 176
<212> TYPE: DNA
<213> ORGANISM: Homo sapien

<400> SEQUENCE: 312
ggaggagcag ctgagagata gggtcagtga atgcggttca gcctgctacc tctcctgtct      60
tcatagaacc attgccttag aattattgta tgacacgttt tttgttggtt aagctgtaag     120
gttttgttct ttgtgaacat gggtattttg aggggagggt ggagggagta gggaag          176

<210> SEQ ID NO 313
<211> LENGTH: 396
<212> TYPE: DNA
<213> ORGANISM: Homo sapien

<400> SEQUENCE: 313
ccagcacccc caggccctgg ggacctgggt ttctcagact gccaaagaag ccttgccatc      60
tggcgctccc atggctcttg caacatctcc ccttcgtttt tgagggggtc atgccggggg     120
agccaccagc ccctcactgg gttcggagga gagtcaggaa gggccaagca cgacaaagca     180
gaaacatcgg atttgggaa cgcgtgtcaa tcccttgtgc cgcagggctg ggcgggagag     240
actgttctgt tccttgtgta actgtgttgc tgaaagacta cctcgttctt gtcttgatgt     300
gtcaccgggg caactgcctg gggcgggga tgggggcagg gtggaagcgg ctccccattt     360
tataccaaag gtgctacatc tatgtgatgg gtgggg                                396

<210> SEQ ID NO 314
<211> LENGTH: 311
<212> TYPE: DNA
<213> ORGANISM: Homo sapien

<400> SEQUENCE: 314
cctcaacatc ctcagagagg actggaagcc agtccttacg ataaactcca taatttatgg      60
cctgcagtat ctcttcttgg agcccaaccc cgaggaccca ctgaacaagg aggccgcaga     120
ggtcctgcag aacaaccggc ggctgtttga gcagaacgtg cagcgctcca tgcggggtgg     180
ctacatcggc tccaccctact ttgagcgctg cctgaaatag ggttggcgca tacccacccc     240
cgccacggcc acaagccctg gcatcccctg caaatatttta ttgggggcca tgggtagggg     300
```

```
tttgggggc g                                                              311
```

<210> SEQ ID NO 315
<211> LENGTH: 336
<212> TYPE: DNA
<213> ORGANISM: Homo sapien

<400> SEQUENCE: 315

```
tttagaacat ggttatcatc caagactact ctaccctgca acattgaact cccaagagca        60
aatccacatt cctcttgagt tctgcagctt ctgtgtaaat agggcagctg tcgtctatgc       120
cgtagaatca catgatctga ggaccattca tggaagctgc taaatagcct agtctgggga       180
gtcttccata aagttttgca tggagcaaac aaacaggatt aaactaggtt tggttccttc       240
agccctctaa aagcataggg cttagcctgc aggcttcctt gggctttctc tgtgtgtgta       300
gttttgtaaa cactatagca tctgttaaga tccagt                                  336
```

<210> SEQ ID NO 316
<211> LENGTH: 436
<212> TYPE: DNA
<213> ORGANISM: Homo sapien

<400> SEQUENCE: 316

```
aacatggtct gcgtgcctta agagagacgc ttcctgcaga acaggacctg actacaaaga        60
atgtttccat tggaattgtt ggtaaagact tggagtttac aatctatgat gatgatgatg       120
tgtctccatt cctggaaggt cttgaagaaa gaccacagag aaaggcacag cctgctcaac       180
ctgctgatga acctgcagaa aaggctgatg aaccaatgga acattaagtg ataagccagt       240
ctatatatgt attatcaaat atgtaagaat acaggcacca catactgatg acaataatct       300
atactttgaa ccaaaagttg cagagtggtg gaatgctatg ttttaggaat cagtccagat       360
gtgagttttt tccaagcaac ctcactgaaa cctatataat ggaatacatt tttctttgaa       420
agggtctgta taatca                                                        436
```

<210> SEQ ID NO 317
<211> LENGTH: 196
<212> TYPE: DNA
<213> ORGANISM: Homo sapien

<400> SEQUENCE: 317

```
tattccttgt gaagatgata tactatttt gttaagcgtg tctgtattta tgtgtgagga        60
gctgctggct tgcagtgcgc gtgcacgtgg agagctggtg cccggagatt ggacggcctg       120
atgctccctc ccctgccctg gtccagggaa gctggccgag ggtcctggct cctgaggggc       180
atctgcccct ccccca                                                        196
```

<210> SEQ ID NO 318
<211> LENGTH: 381
<212> TYPE: DNA
<213> ORGANISM: Homo sapien
<220> FEATURE:
<221> NAME/KEY: misc_feature
<222> LOCATION: (1)...(381)
<223> OTHER INFORMATION: n = A,T,C or G

<400> SEQUENCE: 318

```
gacgcttnng ccgtaacgat gatcggagac atcctgctgt tcgggacgtt gctgatgaat        60
gccggggcgg tgctgaactt taagctgaaa aagaaggaca cncagggctt tggggaggag       120
tncaggagc ccaacacagg tgacaacatc cgggaattct tgctgancct cagatacttt       180
```

```
cnaatcttca tcnccctgtg aacatcttc atgatgttct gcatgattgt gctgntcggc      240
tcttgaatcc cancgatgaa accannaact cactttcccg ggatgccgan tctccattcc      300
tccattcctg atgacttcaa naatgttttt gaccaaaaaa ccgacaacct tcccagaaag      360
tccaagctcg tggtgggngg a                                                381
```

<210> SEQ ID NO 319
<211> LENGTH: 506
<212> TYPE: DNA
<213> ORGANISM: Homo sapien

<400> SEQUENCE: 319

```
ctaagcttta cgaatggggt gacaacttat gataaaaact agagctagtg aattagccta       60
tttgtaaata cctttgttat aattgatagg atacatcttg acatggaat tgttaagcca       120 cctctgagca gtgtatgtca ggacttgttc attaggttgg cagcagaggg gcagaaggaa      180
ttatacaggt agagatgtat gcagatgtgt ccatatatgt ccatatttac attttgatag      240
ccattgatgt atgcatctct ggctgtact ataagaacac attaattcaa tggaaataca      300
ctttgctaat attttaatgg tatagatctg ctaatgaatt ctcttaaaaa catactgtat      360
tctgttgctg tgtgtttcat tttaaattga gcattaaggg aatgcagcat ttaaatcaga      420
actctgccaa tgcttttatc tagaggcgtg ttgccatttt tgtcttatat gaaatttctg      480
tcccaagaaa ggcaggatta catctt                                           506
```

<210> SEQ ID NO 320
<211> LENGTH: 351
<212> TYPE: DNA
<213> ORGANISM: Homo sapien

<400> SEQUENCE: 320

```
ctgacctgca ggacgaaacc atgaagagcc tgatccttct tgccatcctg gccgccttag       60
cggtagtaac tttgtgttat gaatcacatg aaagcatgga atcttatgaa cttaatccct      120
tcattaacag gagaaatgca aataccttca tatcccctca gcagagatgg agagctaaag      180
tccaagagag gatccgagaa cgctctaagc ctgtccacga gctcaatagg gaagcctgtg      240
atgactacag actttgcgaa cgctacgcca tggtttatgg atacaatgct gcctataatc      300
gctacttcag gaagcgccga gggaccaaat gagactgagg gaagaaaaaa a              351
```

<210> SEQ ID NO 321
<211> LENGTH: 421
<212> TYPE: DNA
<213> ORGANISM: Homo sapien

<400> SEQUENCE: 321

```
ctcggaggcg ttcagctgct tcaagatgaa gctgaacatc tccttcccag ccactggctg       60
ccagaaactc attgaagtgg acgatgaacg caaacttcgt actttctatg agaagcgtat      120
ggccacagaa gttgctgctg acgctctggg tgaagaatgg aagggttatg tggtccgaat      180
cagtggtggg aacgacaaac aaggtttccc catgaagcag ggtgtcttga cccatggccg      240
tgtccgcctc ctactgagta agggcattc tgttacaga ccaaggagaa ctggagaaag      300
aaagagaaaa tcagttcgtg gttgcattgt ggatgcaaat ctgagcgttc tcaacttggt      360
tattgtaaaa aaaggagaga aggatattcc tggactgact gatactacag tgcctcgccg      420
c                                                                      421
```

<210> SEQ ID NO 322
<211> LENGTH: 521
<212> TYPE: DNA
<213> ORGANISM: Homo sapien

<400> SEQUENCE: 322

| | | | | | |
|---|---|---|---|---|---|
| agcagctctc | ctgccacagc | tcctcacccc | ctgaaaatgt | tcgcctgctc | caagtttgtc | 60 |
| tccactccct | ccttggtcaa | gagcacctca | cagctgctga | gccgtccgct | atctgcagtg | 120 |
| gtgctgaaac | gaccggagat | actgacagat | gagagcctca | gcagcttggc | agtctcatgt | 180 |
| cccccttacct | cacttgtctc | tagccgcagc | ttccaaacca | gcgccatttc | aagggacatc | 240 |
| gacacagcag | ccaagttcat | tggagctggg | gctgccacag | ttggggtggc | tggttctggg | 300 |
| gctgggattg | gaactgtgtt | tgggagcctc | atcattggtt | atgccaggaa | cccttctctg | 360 |
| aagcaacagc | tcttctccta | cgccattctg | ggctttgccc | tctcggaggc | catggggctc | 420 |
| ttttgtctga | tggtagcctt | tctcatcctc | tttgccatgt | gaaggagccg | tctccacctc | 480 |
| ccatagttct | cccgcgtctg | gttggccccg | tgtgttcctt | t | | 521 |

<210> SEQ ID NO 323
<211> LENGTH: 435
<212> TYPE: DNA
<213> ORGANISM: Homo sapien

<400> SEQUENCE: 323

| | | | | | |
|---|---|---|---|---|---|
| ccgaggtcgc | acgcgtgaga | cttctccgcc | gcagacgccg | ccgcgatgcg | ctacgtcgcc | 60 |
| tcctacctgc | tggctgccct | aggggggcaac | tcctccccca | gcgccaagga | catcaagaag | 120 |
| atcttggaca | gcgtgggtat | cgaggcggac | gacgaccggc | tcaacaaggt | tatcagtgag | 180 |
| ctgaatggaa | aaacattga | agacgtcatt | gcccagggta | ttggcaagct | tgccagtgta | 240 |
| cctgctggtg | gggctgtagc | cgtctctgct | gccccaggct | ctgcagcccc | tgctgctggt | 300 |
| tctgccccctg | ctgcagcaga | ggagaagaaa | gatgagaaga | aggaggagtc | tgaagagtca | 360 |
| gatgatgaca | tgggatttgg | ccttttttgat | taaattcctg | ctccccctgca | aataaagcct | 420 |
| ttttacacat | ctcaa | | | | | 435 |

<210> SEQ ID NO 324
<211> LENGTH: 521
<212> TYPE: DNA
<213> ORGANISM: Homo sapien

<400> SEQUENCE: 324

| | | | | | |
|---|---|---|---|---|---|
| aggagatcga | ctttcggtgc | ccgcaagacc | agggctggaa | cgccgagatc | acgctgcaga | 60 |
| tggtgcagta | caagaatcgt | caggccatcc | tggcggtcaa | atccacgcgg | cagaagcagc | 120 |
| agcacctggt | ccagcagcag | ccccccctcgc | agccgcagcc | gcagccgcag | ctccagcccc | 180 |
| aaccccagcc | tcagcctcag | ccgcaacccc | agccccaatc | acaacccccag | cctcagcccc | 240 |
| aacccaagcc | tcagccccag | cagctccacc | cgtatccgca | tccacatcca | catccacact | 300 |
| ctcatcctca | ctcgcacccca | caccctcacc | cgcacccgca | tccgcaccaa | ataccgcacc | 360 |
| cacacccaca | gccgcactcg | cagccgcacg | ggcaccggct | tctccgcagc | acctccaact | 420 |
| ctgcctgaaa | ggggcagctc | ccgggcaaga | caaggttttg | aggacttgag | gaagtgggac | 480 |
| gagcacattt | ctattgtctt | cacttggatc | aaaagcaaaa | c | | 521 |

<210> SEQ ID NO 325
<211> LENGTH: 451

```
<212> TYPE: DNA
<213> ORGANISM: Homo sapien

<400> SEQUENCE: 325
attttcattt ccattaacct ggaagctttc atgaatattc tcttctttta aaacatttta      60
acattattta aacagaaaaa gatgggctct ttctggttag ttgttacatg atagcagaga     120 tattttact tagattactt tgggaatgag agattgttgt cttgaactct ggcactgtac     180
agtgaatgtg tctgtagttg tgttagtttg cattaagcat gtataacatt caagtatgtc     240
atccaaataa gaggcatata cattgaattg tttttaatcc tctgacaagt tgactcttcg     300 accccaccc ccacccaaga cattttaata gtaaatagag agagagaa gagttaatga       360 acatgaggta gtgttccact ggcaggatga cttttcaata gctcaaatca atttcagtgc     420
ctttatcact tgaattatta acttaatttg a                                    451

<210> SEQ ID NO 326
<211> LENGTH: 421
<212> TYPE: DNA
<213> ORGANISM: Homo sapien
<220> FEATURE:
<221> NAME/KEY: misc_feature
<222> LOCATION: (1)...(421)
<223> OTHER INFORMATION: n = A,T,C or G

<400> SEQUENCE: 326
cgcggtcgta agggctgagg attttggtc cgcacgctcc tgctcctgac tcaccgctgt       60
tcgctctcgc cgaggaacaa gtcggtcagg aagcccgcgc gcaacagcca tggcttttaa     120
ggataccgga aaaacacccg tggagccgga ggtggcaatt caccgaattc gaatcaccct     180
aacaagccgc aacgtaaaat ccttggaaaa ggtgtgtgct gacttgataa gaggcgcaaa     240
agaaaagaat ctcaaagtga aaggaccagt tcgaatgcct accaagactt tgagantcac     300
tacaagaaaa actccttgtg gtgaaggttc taagacgtgg gatcgtttcc agatgagaat     360
tcacaagcga ctcattgact tgcacagtcc ttctgagatt gttaagcaga ttacttccat     420
c                                                                    421

<210> SEQ ID NO 327
<211> LENGTH: 456
<212> TYPE: DNA
<213> ORGANISM: Homo sapien

<400> SEQUENCE: 327
atcttgacga ggctgcggtg tctgctgcta ttctccgagc ttcgcaatgc cgcctaagga      60
cgacaagaag aagaaggacg ctggaaagtc ggccaagaaa gacaaagacc cagtgaacaa     120
atccgggggc aaggccaaaa agaagaagtg gtccaaaggc aaagttcggg acaagctcaa     180
taacttagtc ttgttttgaca aagctaccta tgataaactc tgtaaggaag ttcccaacta     240
taaacttata accccagctg tggtctctga gagactgaag attcgaggct ccctggccag     300 ggcagcccctt caggagctcc ttagtaaagg acttatcaaa ctggtttcaa agcacagagc     360
tcaagtaatt tacaccagaa ataccaaggg tggagatgct ccagctgctg gtgaagatgc     420
atgaataggt ccaaccagct gtacatttgg aaaaat                                456

<210> SEQ ID NO 328
<211> LENGTH: 471
<212> TYPE: DNA
<213> ORGANISM: Homo sapien
```

<400> SEQUENCE: 328

```
gtggaagtga catcgtcttt aaaccctgcg tggcaatccc tgacgcaccg ccgtgatgcc      60
cagggaagac agggcgacct ggaagtccaa ctacttcctt aagatcatcc aactattgga     120
tgattatccg aaatgtttca ttgtgggagc agacaatgtg ggctccaagc agatgcagca     180
gatccgcatg tcccttcgcg ggaaggctgt ggtgctgatg gcaagaaca ccatgatgcg      240
caaggccatc cgagggcacc tggaaaacaa cccagctctg gagaaactgc tgcctcatat     300
ccggggggaat gtgggctttg tgttcaccaa ggaggacctc actgagatca gggacatgtt   360
gctggccaat aaggtgccag ctgctgcccg tgctggtgcc attgccccat gtgaagtcac     420
tgtgccagcc cagaacactg gtctcgggcc cgagaagacc tccttttttcc a             471
```

<210> SEQ ID NO 329
<211> LENGTH: 278
<212> TYPE: DNA
<213> ORGANISM: Homo sapien
<220> FEATURE:
<221> NAME/KEY: misc_feature
<222> LOCATION: (1)...(278)
<223> OTHER INFORMATION: n = A,T,C or G

<400> SEQUENCE: 329

```
gtttaaactt aagcttggta ccgagctcgg atccactagt ccagtgtggt ggaattctag      60
aaattgagat gccccccccag gccagcaaat gttccttttt gttcaaagtc tattttatt    120
ccttgatatt tttctttttt tttttttttt ttgnggatgg ggacttgtga attttctaa     180
aggtgctatt taacatggga gganagcgtg tgcggctcca gcccagcccg ctgctcactt    240
tccaccctct ctccacctgc ctctggcttc tcaggcct                              278
```

<210> SEQ ID NO 330
<211> LENGTH: 338
<212> TYPE: DNA
<213> ORGANISM: Homo sapien

<400> SEQUENCE: 330

```
ctcaggcttc aacatcgaat acgccgcagg ccccttcgcc ctattcttca tagccgaata      60
cacaaacatt attataataa acaccctcac cactacaatc ttcctaggaa caacatatga     120
cgcactctcc cctgaactct acacaacata ttttgtcacc aagaccctac ttctaacctc    180
cctgttctta tgaattcgaa cagcataccc ccgattccgc tacgaccaac tcatacacct    240
cctatgaaaa aacttcctac cactcaccct agcattactt atatgatatg tctccatacc   300
cattacaatc tccagcattc cccctcaaac ctaaaaaa                              338
```

<210> SEQ ID NO 331
<211> LENGTH: 2820
<212> TYPE: DNA
<213> ORGANISM: Homo sapiens

<400> SEQUENCE: 331

```
tggcaaaatc ctggagccag aagaaaggac agcagcattg atcaatctta cagctaacat      60
gttgtacctg gaaaacaatg cccagactca atttagtgag ccacagtaca cgaacctggg    120
gctcctgaac agcatggacc agcagattcg gaacggctcc tcgtccacca gtccctataa   180
cacagaccac gcgcagaaca gcgtcacggc gccctcgccc tacgcacagc ccagccccac   240
cttcgatgct ctctctccat caccgccat cccctccaac accgactacc caggcccgca   300
cagttccgac gtgtccttcc agcagtcgag caccgccaag tcggccacct ggacgtattc   360
```

-continued

```
cactgaactg aagaaactct actgccaaat tgcaaagaca tgccccatcc agatcaaggt    420
gatgacccca cctcctcagg gagctgttat ccgcgccatg cctgtctaca aaaaagctga    480
gcacgtcacg gaggtggtga agcggtgccc caaccatgag ctgagccgtg agttcaacga    540
gggacagatt gcccctccta gtcatttgat tcgagtagag gggaacagcc atgcccagta    600
tgtagaagat cccatcacag gaagacagag tgtgctggta ccttatgagc caccccaggt    660
tggcactgaa ttcacgacag tcttgtacaa tttcatgtgt aacagcagtt gtgttggagg    720
gatgaaccgc cgtccaattt taatcattgt tactctggaa accagagatg ggcaagtcct    780
gggccgacgc tgctttgagg cccggatctg tgcttgccca ggaagagaca ggaaggcgga    840
tgaagatagc atcagaaagc agcaagtttc ggacagtaca agaacggtg atggtacgaa     900 gcgcccgttt cgtcagaaca cacatggtat ccagatgaca tccatcaaga acgaagatc     960 cccagatgat gaactgttat acttaccagt gaggggccgt gagacttatg aaatgctgtt   1020
gaagatcaaa gagtccctgg aactcatgca gtaccttcct cagcacacaa ttgaaacgta   1080
caggcaacag caacagcagc agcaccagca cttacttcag aaacagacct caatacagtc   1140
tccatcttca tatggtaaca gctccccacc tctgaacaaa atgaacagca tgaacaagct   1200
gccttctgtg agccagctta tcaaccctca gcagcgcaac gccctcactc ctacaaccat   1260
tcctgatggc atgggagcca acattccat gatgggcacc cacatgccaa tggctggaga    1320
catgaatgga ctcagcccca cccaggcact ccctccccca ctctccatgc catccacctc   1380
ccactgcaca ccccccacctc cgtatcccac agattgcagc attgtcagtt tcttagcgag   1440
gttgggctgt tcatcatgtc tggactattt cacgacccag gggctgacca ccatctatca   1500
gattgagcat tactccatgg atgatctggc aagtctgaaa atccctgagc aatttcgaca   1560
tgcgatctgg aagggcatcc tggaccaccg gcagctccac gaattctcct cccctctca    1620 tctcctgcgg accccaagca gtgcctctac agtcagtgtg ggctccagtg agacccgggg   1680
tgagcgtgtt attgatgctg tgcgattcac cctccgccag accatctctt cccaccccg    1740 agatgagtgg aatgacttca actttgacat ggatgctcgc cgcaataagc aacagcgcat   1800
caaagaggag ggggagtgag cctcaccatg tgagctcttc ctatccctct cctaactgcc   1860 agcccctaa aagcactcct gcttaatctt caaagccttc tccctagctc ctcccttcc     1920 tcttgtctga tttcttaggg gaaggagaag taagaggcta cctcttacct aacatctgac   1980
ctggcatcta attctgattc tggctttaag ccttcaaaac tatagcttgc agaactgtag   2040
ctgccatggc taggtagaag tgagcaaaaa agagttgggt gtctccttaa gctgcagaga   2100
tttctcattg acttttataa agcatgttca cccttatagt ctaagactat atatataaat   2160
gtataaatat acagtataga tttttgggtg gggggcattg agtattgttt aaaatgtaat   2220
ttaaatgaaa gaaaattgag ttgcacttat tgaccatttt ttaatttact tgttttggat   2280
ggcttgtcta tactccttcc cttaagggt atcatgtatg gtgataggta tctagagctt    2340
aatgctacat gtgagtgcga tgatgtacag attctttcag ttctttggat tctaaataca   2400
tgccacatca aacctttgag tagatccatt tccattgctt attatgtagg taagactgta   2460
gatatgtatt ctttttctcag tgttggtata ttttatatta ctgacatttc ttctagtgat   2520
gatggttcac gttggggtga tttaatccag ttataagaag aagttcatgt ccaaacggtc   2580
ctctttagtt tttggttggg aatgaggaaa attcttaaaa ggcccatagc agccagttca   2640
aaaacacccg acgtcatgta tttgagcata tcagtaaccc ccttaaattt aatacccaga   2700
```

| | |
|---|---|
| tacettatct tacaatgttg attgggaaaa catttgctgc ccattacaga ggtattaaaa | 2760 |
| ctaaatttca ctactagatt gactaactca aatacacatt tgctactgtt gtaagaattc | 2820 |

<210> SEQ ID NO 332
<211> LENGTH: 2270
<212> TYPE: DNA
<213> ORGANISM: Homo sapiens

<400> SEQUENCE: 332

| | |
|---|---|
| tcgttgatat caaagacagt tgaaggaaat gaattttgaa acttcacggt gtgccaccct | 60 |
| acagtactgc cctgacccttt acatccagcg tttcgtagaa acccagctca tttctcttgg | 120 |
| aaagaaagtt attaccgatc caccatgtcc cagagcacac agacaaatga attcctcagt | 180 |
| ccagaggttt tccagcatat ctgggatttt ctggaacagc ctatatgttc agttcagccc | 240 |
| attgacttga actttgtgga tgaaccatca gaagatggtg cgacaaacaa gattgagatt | 300 |
| agcatggact gtatccgcat gcaggactcg gacctgagtg accccatgtg gccacagtac | 360 |
| acgaacctgg ggctcctgaa cagcatggac cagcagattc agaacggctc ctcgtccacc | 420 |
| agtccctata acacagacca cgcgcagaac agcgtcacgg cgccctcgcc ctacgcacag | 480 |
| cccagctcca ccttcgatgc tctctctcca tcacccgcca tccctccaa caccgactac | 540 |
| ccaggcccgc acagtttcga cgtgtccttc cagcagtcga gcaccgccaa gtcggccacc | 600 |
| tggacgtatt ccactgaact gaagaaactc tactgccaaa ttgcaaagac atgccccatc | 660 |
| cagatcaagg tgatgacccc acctcctcag ggagctgtta ccgcgccat gcctgtctac | 720 |
| aaaaaagctg agcacgtcac ggaggtggtg aagcggtgcc ccaaccatga gctgagccgt | 780 |
| gaattcaacg agggacagat tgcccctcct agtcatttga ttcgagtaga ggggaacagc | 840 |
| catgcccagt atgtagaaga tcccatcaca ggaagacaga gtgtgctggt accttatgag | 900 |
| ccaccccagg ttggcactga attcacgaca gtcttgtaca atttcatgtg taacagcagt | 960 |
| tgtgttggag ggatgaaccg ccgtccaatt ttaatcattg ttactctgga aaccagagat | 1020 |
| gggcaagtcc tgggccgacg ctgctttgag gcccggatct gtgcttgccc aggaagagac | 1080 |
| aggaaggcgg atgaagatag catcagaaag cagcaagttt cggacagtac aaagaacggt | 1140 |
| gatggtacga agcgcccgtt tcgtcagaac acacatggta tccagatgac atccatcaag | 1200 |
| aaacgaagat ccccagatga tgaactgtta tacttaccag tgaggggccg tgagacttat | 1260 |
| gaaatgctgt tgaagatcaa agagtccctg gaactcatgc agtaccttcc tcagcacaca | 1320 |
| attgaaacgt acaggcaaca gcaacagcag cagcaccagc acttacttca gaaacagacc | 1380 |
| tcaatacagt ctccatcttc atatggtaac agctccccac ctctgaacaa aatgaacagc | 1440 |
| atgaacaagc tgccttctgt gagccagctt atcaaccctc agcagcgcaa cgccctcact | 1500 |
| cctacaacca ttcctgatgg catgggagcc aacattccca tgatgggcac ccacatgcca | 1560 |
| atggctggag acatgaatgg actcagcccc acccaggcac tccctccccc actctccatg | 1620 |
| ccatccacct cccactgcac acccccacct ccgtatccaa cagattgcag cattgtcggt | 1680 |
| ttcttagcga ggttgggctg ttcatcatgt ctggactatt tcacgaccca ggggctgacc | 1740 |
| accatctatc agattgagca ttactccatg gatgatctgg caagtctgaa aatccctgag | 1800 |
| caatttcgac atgcgatctg gaagggcatc ctggaccacc ggcagctcca cgaattctcc | 1860 |
| tccccttctc atctcctgcg gaccccaagc agtgcctcta cagtcagtgt gggctccagt | 1920 |
| gagacccggg gtgagcgtgt tattgatgct gtgcgattca ccctccgcca gaccatctct | 1980 |
| ttcccacccc gagatgagtg gaatgacttc aactttgaca tggatgctcg ccgcaataag | 2040 |

-continued

| | |
|---|---|
| caacagcgca tcaaagagga gggggagtga gcctcaccat gtgagctctt cctatccctc | 2100 |
| tcctaactgc cagcccccta aaagcactcc tgcttaatct tcaaagcctt ctccctagct | 2160 |
| cctccccttc ctcttgtctg atttcttagg ggaaggagaa gtaagaggct acctcttacc | 2220 |
| taacatctga cctggcatct aattctgatt ctggctttaa gccttcaaaa | 2270 |

<210> SEQ ID NO 333
<211> LENGTH: 2816
<212> TYPE: DNA
<213> ORGANISM: Homo sapiens

<400> SEQUENCE: 333

| | |
|---|---|
| tcgttgatat caaagacagt tgaaggaaat gaattttgaa acttcacggt gtgccaccct | 60 |
| acagtactgc cctgacccett acatccagcg tttcgtagaa acccagctca tttctcttgg | 120 |
| aaagaaagtt attaccgatc caccatgtcc cagagcacac agacaaatga attcctcagt | 180 |
| ccagaggttt tccagcatat ctgggatttt ctggaacagc ctatatgttc agttcagccc | 240 |
| attgacttga actttgtgga tgaaccatca gaagatggtg cgacaaacaa gattgagatt | 300 |
| agcatggact gtatccgcat gcaggactcg gacctgagtg accccatgtg gccacagtac | 360 |
| acgaacctgg ggctcctgaa cagcatggac cagcagattc agaacggctc ctcgtccacc | 420 |
| agtccctata acacagacca cgcgcagaac agcgtcacgg cgccctcgcc ctacgcacag | 480 |
| cccagctcca ccttcgatgc tctctctcca tcacccgcca tcccctccaa caccgactac | 540 |
| ccaggcccgc acagtttcga cgtgtccttc cagcagtcga gcaccgccaa gtcggccacc | 600 |
| tggacgtatt ccactgaact gaagaaactc tactgccaaa ttgcaaagac atgccccatc | 660 |
| cagatcaagg tgatgacccc acctcctcag ggagctgtta tccgcgccat gcctgtctac | 720 |
| aaaaaagctg agcacgtcac ggaggtggtg aagcggtgcc ccaaccatga gctgagccgt | 780 |
| gaattcaacg agggacagat tgcccctcct agtcatttga ttcgagtaga ggggaacagc | 840 |
| catgcccagt atgtagaaga tcccatcaca ggaagacaga gtgtgctggt acctatgag | 900 |
| ccacccagg ttggcactga attcacgaca gtcttgtaca atttcatgtg taacagcagt | 960 |
| tgtgttggag ggatgaaccg ccgtccaatt ttaatcattg ttactctgga aaccagagat | 1020 |
| gggcaagtcc tgggccgacg ctgctttgag gcccggatct gtgcttgccc aggaagagac | 1080 |
| aggaaggcgg atgaagatag catcagaaag cagcaagttt cggacagtac aaagaacggt | 1140 |
| gatggtacga agcgcccgtt tcgtcagaac acacatggta tccagatgac atccatcaag | 1200 |
| aaacgaagat ccccagatga tgaactgtta tacttaccag tgaggggccg tgagacttat | 1260 |
| gaaatgctgt tgaagatcaa agagtccctg gaactcatgc agtaccttcc tcagcacaca | 1320 |
| attgaaacgt acaggcaaca gcaacagcag cagcaccagc acttacttca gaaacatctc | 1380 |
| ctttcagcct gcttcaggaa tgagcttgtg gagccccgga gagaaactcc aaaacaatct | 1440 |
| gacgtcttct ttagacattc aagcccccca aaccgatcag tgtacccata gagccctatc | 1500 |
| tctatatttt aagtgtgtgt gttgtatttc catgtgtata tgtgagtgtg tgtgtgtgta | 1560 |
| tgtgtgtgcg tgtgtatcta gccctcataa acaggacttg aagacacttt ggctcagaga | 1620 |
| cccaactgct caaaggcaca aagccactag tgagagaatc ttttgaaggg actcaaacct | 1680 |
| ttacaagaaa ggatgttttc tgcagatttt gtatccttag accggccatt ggtgggtgag | 1740 |
| gaaccactgt gtttgtctgt gagctttctg ttgtttcctg ggagggaggg gtcaggtggg | 1800 |
| gaaaggggca ttaagatgtt tattggaacc cttttctgtc ttcttctgtt gttttctaa | 1860 |

```
aattcacagg gaagcttttg agcaggtctc aaacttaaga tgtcttttta agaaaaggag    1920
aaaaaagttg ttattgtctg tgcataagta agttgtaggt gactgagaga ctcagtcaga    1980
cccttttaat gctggtcatg taataatatt gcaagtagta agaaacgaag gtgtcaagtg    2040
tactgctggg cagcgaggtg atcattacca aaagtaatca actttgtggg tggagagttc    2100
tttgtgagaa cttgcattat ttgtgtcctc ccctcatgtg taggtagaac atttcttaat    2160
gctgtgtacc tgcctctgcc actgtatgtt ggcatctgtt atgctaaagt ttttcttgta    2220
catgaaaccc tggaagacct actacaaaaa aactgttgtt tggcccccat agcaggtgaa    2280
ctcattttgt gcttttaata gaaagacaaa tccacccag taatattgcc cttacgtagt    2340
tgtttaccat tattcaaagc tcaaaataga atttgaagcc ctctcacaaa atctgtgatt    2400
aatttgctta attagagctt ctatccctca agcctaccta ccataaaacc agccatatta    2460
ctgatactgt tcagtgcatt tagccaggag acttacgttt tgagtaagtg agatccaagc    2520
agacgtgtta aaatcagcac tcctggactg gaaattaaag attgaaaggg tagactactt    2580
ttcttttttt tactcaaaag tttagagaat ctctgtttct ttccatttta aaaacatatt    2640
ttaagataat agcataaaga ctttaaaaat gttcctcccc tccatcttcc cacacccagt    2700
caccagcact gtattttctg tcaccaagac aatgatttct tgttattgag ctgttgctt    2760
ttgtggatgt gtgattttaa ttttcaataa acttttgcat cttggtttaa aagaaa        2816

<210> SEQ ID NO 334
<211> LENGTH: 2082
<212> TYPE: DNA
<213> ORGANISM: Homo sapiens

<400> SEQUENCE: 334
agatgctaca gcgactgcac acccaggctg tatgatacag cctattgctc ccgggctgca     60
aacctgtcca gcatgtgatg tggtgggata ctgaattgaa taccgaatac tgtaggcaat    120
tgtaacacag tggtaagtct ttgtgtatct aaacatagct aaacaccaaa aggtatagta    180
agaatatggt attataatct tatggaacta tcattgtata tgtggtttgt caaccagaat    240
gtagttatac agcacaggac tgtgcttatg atgtgccaag cacagctctc agtactaact    300
cctttaatct tcatatcaac cctaggaggt aacttcttaa gtagattcat attgtaaggg    360
tctcggggtg ggggggttgg caaaatcctg gagccagaag aaaggacagc agcattgatc    420
aatcttacag ctaacatgtt gtacctggaa acaatgccc agactcaatt tagtgagcca    480
cagtacacga acctggggct cctgaacagc atggaccagc agattcagaa cggctcctcg    540
tccaccagtc cctataacac agaccacgcg cagaacagcg tcacggcgcc ctcgccctac    600
gcacagccca gctccacctt cgatgctctc tctccatcac ccgccatccc ctccaacacc    660
gactacccag gcccgcacag tttcgacgtg tccttccagc agtcgagcac cgccaagtcg    720
gccacctgga cgtattccac tgaactgaag aaactctact gccaaattgc aaagacatgc    780
cccatccaga tcaaggtgat gaccccacct cctcagggag ctgttatccg cgccatgcct    840
gtctacaaaa aagctgagca cgtcacggag gtggtgaagc ggtgccccaa ccatgagctg    900
agccgtgaat tcaacgaggg acagattgcc cctcctagtc atttgattcg agtagagggg    960
aacagccatg cccagtatgt agaagatccc atcacaggaa gacagagtgt gctggtacct   1020
tatgagccac cccaggttgg cactgaattc acgacagtct tgtacaattt catgtgtaac   1080
agcagttgtg ttggagggat gaaccgccgt ccaattttaa tcattgttac tctggaaacc   1140
agagatgggc aagtcctggg ccgacgctgc tttgaggccc ggatctgtgc ttgcccagga   1200
```

| | |
|---|---|
| agagacagga aggcggatga agatagcatc agaaagcagc aagtttcgga cagtacaaag | 1260 |
| aacggtgatg gtacgaagcg cccgtctcgt cagaacacac atggtatcca gatgacatcc | 1320 |
| atcaagaaac gaagatcccc agatgatgaa ctgttatact taccagtgag gggccgtgag | 1380 |
| acttatgaaa tgctgttgaa gatcaaagag tccctggaac tcatgcagta ccttcctcag | 1440 |
| cacacaattg aaacgtacag gcaacagcaa cagcagcagc accagcactt acttcagaaa | 1500 |
| cagtgagtgt atcaacgtgt cattttagga ggcatgagtg acggtgactt tatttggatc | 1560 |
| agcaataggg tgattgatga gcaatgtgga acataatggg agatagcaga ttgtcataga | 1620 |
| ttcagatgac ctggtatggc aaccctcttt cagttgcaac ctttttttacg tgtcttatta | 1680 |
| taaccttccc ttcagaattc cacttatgtt ctgaaattaa atacaaacca tttctggtga | 1740 |
| attacaaaga aactcacact aacagttctc ttctctatat gcctggtcca tacacactaa | 1800 |
| cagtaagtac acactctatt tggtagtgat gtgtatattt gaaaacatga aatcttttct | 1860 |
| catcccaatg gattgtctta taaatctcct gggatgcaca ctatccactt ttgggaataa | 1920 |
| cactgtagac cagggatagc aaataggctt tactataata taaagtgact tgtttgaatg | 1980 |
| ctgtaatgag aagaattctg agacctagtg catgataatt ggggaaatat ctgggtgcag | 2040 |
| aaggataagg tagcatcatg ttgccgtatt ttagcatctc tg | 2082 |

<210> SEQ ID NO 335
<211> LENGTH: 4849
<212> TYPE: DNA
<213> ORGANISM: Homo sapiens

<400> SEQUENCE: 335

| | |
|---|---|
| cgttgatatc aaagacagtt gaaggaaatg aattttgaaa cttcacggtg tgccacccta | 60 |
| cagtactgcc ctgaccctta catccagcgt ttcgtagaaa ccccagctca tttctcttgg | 120 |
| aaagaaagtt attaccgatc caccatgtcc cagagcacac agacaaatga attcctcagt | 180 |
| ccagaggttt tccagcatat ctgggatttt ctggaacagc ctatatgttc agttcagccc | 240 |
| attgacttga actttgtgga tgaaccatca gaagatggtg cgacaaacaa gattgagatt | 300 |
| agcatggact gtatccgcat gcaggactcg gacctgagtg accccatgtg gccacagtac | 360 |
| acgaacctgg ggctcctgaa cagcatggac cagcagattc agaacggctc ctcgtccacc | 420 |
| agtccctata acacgaccca cgcgcagaac agcgtcacgg cgccctcgcc ctacgcacag | 480 |
| cccagctcca ccttcgatgc tctctctcca tcacccgcca tccctccaa caccgactac | 540 |
| ccaggcccgc acagtttcga cgtgtccttc cagcagtcga gcaccgccaa gtcgccacc | 600 |
| tggacgtatt ccactgaact gaagaaactc tactgccaaa ttgcaaagac atgccccatc | 660 |
| cagatcaagg tgatgacccc acctcctcag ggagctgtta ccgcgccat gcctgtctac | 720 |
| aaaaaagctg agcacgtcac ggaggtggtg aagcggtgcc ccaaccatga gctgagccgt | 780 |
| gaattcaacg agggacagat tgcccctcct agtcatttga ttcgagtaga ggggaacagc | 840 |
| catgcccagt atgtagaaga tcccatcaca ggaagacaga gtgtgctggt accttatgag | 900 |
| ccaccccagg ttggcactga attcacgaca gtcttgtaca atttcatgtg taacagcagt | 960 |
| tgtgttggag ggatgaaccg ccgtccaatt ttaatcattg ttactctgga aaccagagat | 1020 |
| gggcaagtcc tgggccgacg ctgctttgag gcccggatct gtgcttgccc aggaagagac | 1080 |
| aggaaggcg atgaagatag catcagaaag cagcaagttt cggacagtac aaagaacggt | 1140 |
| gatggtacga agcgcccgtt tcgtcagaac acacatggta tccagatgac atccatcaag | 1200 |

-continued

```
aaacgaagat cccagatga tgaactgtta tacttaccag tgagggggccg tgagacttat    1260
gaaatgctgt tgaagatcaa agagtccctg gaactcatgc agtaccttcc tcagcacaca    1320
attgaaacgt acaggcaaca gcaacagcag cagcaccagc acttacttca gaaacagacc    1380
tcaatacagt ctccatcttc atatggtaac agctccccac ctctgaacaa aatgaacagc    1440
atgaacaagc tgccttctgt gagccagctt atcaaccctc agcagcgcaa cgccctcact    1500
cctacaacca ttcctgatgg catgggagcc aacattccca tgatgggcac ccacatgcca    1560
atggctggag acatgaatgg actcagcccc acccaggcac tccctccccc actctccatg    1620
ccatccacct cccagtgcac accccacct ccgtatccca cagattgcag cattgtcagt    1680
ttcttagcga ggttgggctg ttcatcatgt ctggactatt tcacgaccca ggggctgacc    1740
accatctatc agattgagca ttactccatg gatgatctgg caagtctgaa atccctgag    1800
caatttcgac atgcgatctg gaagggcatc ctggaccacc ggcagctcca cgaattctcc    1860
tccccttctc atctcctgcg gacccccaagc agtgcctcta cagtcagtgt gggctccagt    1920
gagacccggg gtgagcgtgt tattgatgct gtgcgattca ccctccgcca gaccatctct    1980
ttcccacccc gagatgagtg gaatgacttc aactttgaca tggatgctcg ccgcaataag    2040
caacagcgca tcaaagagga gggggagtga gcctcaccat gtgagctctt cctatccctc    2100
tcctaactgc cagcycccta aaagcactcc tgcttaatct tcaaagcctt ctccctagct    2160
cctcccttc ctcttgtctg atttcttagg ggaaggagaa gtaagaggct acctcttacc    2220
taacatctga cctggcatct aattctgatt ctggctttaa gccttcaaaa ctatagcttg    2280
cagaactgta gctgccatgg ctaggtagaa gtgagcaaaa aagagttggg tgtctcctta    2340
agctgcagag atttctcatt gacttttata aagcatgttc acccttatag tctaagacta    2400
tatatataaa tgtataaata tacagtatag attttttgggt gggggggcatt gagtattgtt    2460
taaaatgtaa tttaaatgaa agaaaattga gttgcactta ttgaccattt tttaatttac    2520
ttgttttgga tggcttgtct atactccttc ccttaagggg tatcatgtat ggtgataggt    2580
atctagagct taatgctaca tgtgagtgac gatgatgtac agattctttc agttctttgg    2640
attctaaata catgccacat caaacctttg agtagatcca tttccattgc ttattatgta    2700
ggtaagactg tagatatgta ttcttttctc agtgttggta tattttatat tactgacatt    2760
tcttctagtg atgatggttc acgttgggt gatttaatcc agttataaga agaagttcat    2820
gtccaaacgt cctctttagt ttttggttgg gaatgaggaa aattcttaaa aggcccatag    2880
cagccagttc aaaaacaccc gacgtcatgt atttgagcat atcagtaacc cccttaaatt    2940
taataccaga taccttatct tacaatattg attgggaaaa catttgctgc cattacagag    3000
gtattaaaac taaatttcac tactagattg actaactcaa atacacattt gctactgttg    3060
taagaattct gattgatttg attgggatga atgccatcta tctagttcta acagtgaagt    3120
tttactgtct attaatattc agggtaaata ggaatcattc agaaatgttg agtctgtact    3180
aaacagtaag atatctcaat gaaccataaa ttcaactttg taaaaatctt ttgaagcata    3240
gataatattg tttggtaaat gtttcttttg tttggtaaat gtttctttta aagaccctcc    3300
tattctataa aactctgcat gtagaggctt gtttaccttt ctctctctaa ggtttacaat    3360
aggagtggtg atttgaaaaa tataaaatta tgagattggt tttcctgtgg cataaattgc    3420
atcactgtat cattttctttt tttaaccggt aagagtttca gtttgttgga aagtaactgt    3480
gagaacccag tttcccgtcc atctccctta gggactaccc atagacatga aggtccccca    3540
cagagcaaga gataagtctt tcatggctgc tgttgcttaa accacttaaa cgaagagttc    3600
```

```
ccttgaaact ttgggaaaac atgttaatga caatattcca gatctttcag aaatataaca    3660
catttttttg catgcatgca aatgagctct gaaatcttcc catgcattct ggtcaagggc    3720
tgtcattgca cataagcttc cattttaatt ttaaagtgca aagggccag cgtggctcta     3780 aaaggtaatg tgtggattgc ctctgaaaag tgtgtatata ttttgtgtga aattgcatac    3840
tttgtatttt gattattttt tttttcttct tgggatagtg ggatttccag aaccacactt    3900 gaaaccttt tttatcgttt ttgtattttc atgaaaatac catttagtaa gaataccaca    3960
tcaaataaga aataatgcta caattttaag aggggaggga agggaaagtt tttttttatt    4020
atttttttaa aattttgtat gttaaagaga atgagtcctt gatttcaaag ttttgttgta    4080
cttaaatggt aataagcact gtaaacttct gcaacaagca tgcagctttg caacccatt    4140 aaggggaaga atgaaagctg ttccttggtc ctagtaagaa gacaaactgc ttcccttact    4200
ttgctgaggg tttgaataaa cctaggactt ccgagctatg tcagtactat tcaggtaaca    4260
ctagggcctt ggaaattcct gtactgtgtc tcatggattt ggcactagcc aaagcgaggc    4320
acccttactg gcttacctcc tcatggcagc ctactctcct tgagtgtatg agtagccagg    4380
gtaaggggta aaaggatagt aagcatagaa accactagaa agtgggctta atggagttct    4440
tgtggcctca gctcaatgca gttagctgaa gaattgaaaa gttttttgttt ggagacgttt    4500 ataaacagaa atggaaagca gagttttcat taaatccttt tacctttttt ttttcttggt    4560
aatcccctaa aataacagta tgtgggatat tgaatgttaa agggatattt tttttctatt    4620
atttttataa ttgtacaaaa ttaagcaaat gttaaaagtt ttatatgctt tattaatgtt    4680
ttcaaaaggt attatacatg tgatacattt tttaagcttc agttgcttgt cttctggtac    4740
tttctgttat gggcttttgg ggagccagaa gccaatctac aatctctttt tgtttgccag    4800
gacatgcaat aaaatttaaa aataaataa aaactaatta agaaataaa                 4849
```

<210> SEQ ID NO 336
<211> LENGTH: 1386
<212> TYPE: DNA
<213> ORGANISM: Homo sapiens

<400> SEQUENCE: 336

```
atgttgtacc tggaaaacaa tgcccagact caatttagtg agccacagta cacgaacctg      60
gggctcctga acagcatgga ccagcagatt cagaacggct cctcgtccac cagtccctat     120
aacacagacc acgcgcagaa cagcgtcacg gcgcccctcgc cctacgcaca gcccagctcc    180
accttcgatg ctctctctcc atcacccgcc atcccctcca acaccgacta cccaggcccg     240
cacagtttcg acgtgtcctt ccagcagtcg agcaccgcca agtcggccac ctggacgtat    300
tccactgaac tgaagaaact ctactgccaa attgcaaaga catgccccat ccagatcaag    360
gtgatgaccc cacctcctca gggagctgtt atccgcgcca tgcctgtcta caaaaaagct    420
gagcacgtca cggaggtggt gaagcggtgc cccaaccatg agctgagccg tgaattcaac    480
gagggacaga ttgcccctcc tagtcatttg attcgagtag aggggaacag ccatgcccag    540
tatgtagaag atcccatcac aggaagacag agtgtgctgg taccttatga gccaccccag    600
gttggcactg aattcacgac agtccttgtac aatttcatgt gtaacagcag ttgtgttgga    660
gggatgaacc gccgtccaat tttaatcatt gttactctgg aaaccagaga tgggcaagtc    720
ctgggccgac gctgctttga ggcccggatc tgtgcttgcc aggaagaga caggaaggcg     780 gatgaagata gcatcagaaa gcagcaagtt tcggacagta caaagaacgg tgatggtacg    840
```

-continued

```
aagcgcccgt tcgtcagaa cacacatggt atccagatga catccatcaa gaaacgaaga      900
tccccagatg atgaactgtt atacttacca gtgagggcc gtgagactta tgaaatgctg      960
ttgaagatca aagagtccct ggaactcatg cagtaccttc ctcagcacac aattgaaacg     1020
tacaggcaac agcaacagca gcagcaccag cacttacttc agaaacagac ctcaatacag    1080
tctccatctt catatggtaa cagctcccca cctctgaaca aaatgaacag catgaacaag    1140
ctgccttctg tgagccagct tatcaaccct cagcagcgca acgccctcac tcctacaacc    1200
attcctgatg gcatgggagc caacattccc atgatgggca cccacatgcc aatggctgga    1260
gacatgaatg gactcagccc cacccaggca ctccctcccc cactctccat gccatccacc    1320
tcccactgca cacccccacc tccgtatccc acagattgca gcattgtcag gatctggcaa    1380
gtctga                                                               1386
```

<210> SEQ ID NO 337
<211> LENGTH: 1551
<212> TYPE: DNA
<213> ORGANISM: Homo sapiens

<400> SEQUENCE: 337

```
atgtcccaga gcacacagac aaatgaattc ctcagtccag aggttttcca gcatatctgg       60
gattttctgg aacagcctat atgttcagtt cagcccattg acttgaactt tgtggatgaa      120
ccatcagaag atggtgcgac aaacaagatt gagattagca tggactgtat ccgcatgcag      180
gactcggacc tgagtgaccc catgtggcca cagtacacga acctggggct cctgaacagc      240
atggaccagc agattcagaa cggctcctcg tccaccagtc cctataacac agaccacgcg      300
cagaacagcg tcacggcgcc ctcgccctac gcacagccca gctccacctt cgatgctctc      360
tctccatcac ccgccatccc ctcaacacc gactacccag gccgcacag tttcgacgtg       420 tccttccagc agtcgagcac cgccaagtcg gccacctgga cgtattccac tgaactgaag      480
aaactctact gccaaattgc aaagacatgc cccatccaga tcaaggtgat gaccccacct      540
cctcagggag ctgttatccg cgccatgcct gtctacaaaa agctgagca cgtcacggag       600 gtggtgaagc ggtgcccca ccatgagctg agccgtgaat caacgaggg acagattgcc       660 cctcctagtc atttgattcg agtagagggg aacagccatg cccagtatgt agaagatccc      720
atcacaggaa gacagagtgt gctggtacct tatgagccac cccaggttgg cactgaattc      780
acgacagtct tgtacaattt catgtgtaac agcagttgtg ttggagggat gaaccgccgt      840 ccaatttta tcattgttac tctggaaacc agagatgggc aagtcctggg ccgacgctgc      900
tttgaggccc ggatctgtgc ttgcccagga agagacagga aggcggatga agatagcatc      960
agaaagcagc aagtttcgga cagtacaaag aacggtgatg gtacgaagcg cccgtttcgt     1020
cagaacacac atggtatcca gatgacatcc atcaagaaac gaagatcccc agatgatgaa     1080
ctgttatact accagtgag gggccgtgag acttatgaaa tgctgttgaa gatcaaagag    1140
tccctggaac tcatgcagta ccttcctcag cacacaattg aaacgtacag gcaacagcaa    1200
cagcagcagc accagcactt acttcagaaa cagacctcaa tacagtctcc atcttcatat    1260
ggtaacagct ccccacctct gaacaaaatg aacagcatga acaagctgcc ttctgtgagc    1320
cagcttatca accctcagca gcgcaacgcc ctcactccta caaccattcc tgatggcatg    1380
ggagccaaca ttcccatgat gggcacccac atgccaatgg ctggagacat gaatggactc    1440
agccccaccc aggcactccc tcccccactc tccatgccat ccacctccca ctgcacaccc    1500
ccacctccgt atcccacaga ttgcagcatt gtcaggatct ggcaagtctg a             1551
```

-continued

```
<210> SEQ ID NO 338
<211> LENGTH: 586
<212> TYPE: PRT
<213> ORGANISM: Homo sapiens

<400> SEQUENCE: 338
```

Met Leu Tyr Leu Glu Asn Asn Ala Gln Thr Gln Phe Ser Glu Pro Gln
                  5                  10                  15

Tyr Thr Asn Leu Gly Leu Leu Asn Ser Met Asp Gln Gln Ile Arg Asn
             20                  25                  30

Gly Ser Ser Thr Ser Pro Tyr Asn Thr Asp His Ala Gln Asn Ser
         35                  40                  45

Val Thr Ala Pro Ser Pro Tyr Ala Gln Pro Ser Pro Thr Phe Asp Ala
 50                  55                  60

Leu Ser Pro Ser Pro Ala Ile Pro Ser Asn Thr Asp Tyr Pro Gly Pro
 65                  70                  75                  80

His Ser Ser Asp Val Ser Phe Gln Gln Ser Ser Thr Ala Lys Ser Ala
                 85                  90                  95

Thr Trp Thr Tyr Ser Thr Glu Leu Lys Lys Leu Tyr Cys Gln Ile Ala
                100                 105                 110

Lys Thr Cys Pro Ile Gln Ile Lys Val Met Thr Pro Pro Pro Gln Gly
            115                 120                 125

Ala Val Ile Arg Ala Met Pro Val Tyr Lys Lys Ala Glu His Val Thr
130                 135                 140

Glu Val Val Lys Arg Cys Pro Asn His Glu Leu Ser Arg Glu Phe Asn
145                 150                 155                 160

Glu Gly Gln Ile Ala Pro Pro Ser His Leu Ile Arg Val Glu Gly Asn
                165                 170                 175

Ser His Ala Gln Tyr Val Glu Asp Pro Ile Thr Gly Arg Gln Ser Val
            180                 185                 190

Leu Val Pro Tyr Glu Pro Pro Gln Val Gly Thr Glu Phe Thr Thr Val
        195                 200                 205

Leu Tyr Asn Phe Met Cys Asn Ser Ser Cys Val Gly Gly Met Asn Arg
    210                 215                 220

Arg Pro Ile Leu Ile Ile Val Thr Leu Glu Thr Arg Asp Gly Gln Val
225                 230                 235                 240

Leu Gly Arg Arg Cys Phe Glu Ala Arg Ile Cys Ala Cys Pro Gly Arg
                245                 250                 255

Asp Arg Lys Ala Asp Glu Asp Ser Ile Arg Lys Gln Gln Val Ser Asp
            260                 265                 270

Ser Thr Lys Asn Gly Asp Gly Thr Lys Arg Pro Phe Arg Gln Asn Thr
        275                 280                 285

His Gly Ile Gln Met Thr Ser Ile Lys Lys Arg Arg Ser Pro Asp Asp
    290                 295                 300

Glu Leu Leu Tyr Leu Pro Val Arg Gly Arg Glu Thr Tyr Glu Met Leu
305                 310                 315                 320

Leu Lys Ile Lys Glu Ser Leu Glu Leu Met Gln Tyr Leu Pro Gln His
                325                 330                 335

Thr Ile Glu Thr Tyr Arg Gln Gln Gln Gln Gln His Gln His Leu
            340                 345                 350

Leu Gln Lys Gln Thr Ser Ile Gln Ser Pro Ser Ser Tyr Gly Asn Ser
        355                 360                 365

Ser Pro Pro Leu Asn Lys Met Asn Ser Met Asn Lys Leu Pro Ser Val

-continued

```
            370                 375                 380
Ser Gln Leu Ile Asn Pro Gln Gln Arg Asn Ala Leu Thr Pro Thr Thr
385                 390                 395                 400

Ile Pro Asp Gly Met Gly Ala Asn Ile Pro Met Met Gly Thr His Met
                405                 410                 415

Pro Met Ala Gly Asp Met Asn Gly Leu Ser Pro Thr Gln Ala Leu Pro
                420                 425                 430

Pro Pro Leu Ser Met Pro Ser Thr Ser His Cys Thr Pro Pro Pro Pro
                435                 440                 445

Tyr Pro Thr Asp Cys Ser Ile Val Ser Phe Leu Ala Arg Leu Gly Cys
                450                 455                 460

Ser Ser Cys Leu Asp Tyr Phe Thr Thr Gln Gly Leu Thr Thr Ile Tyr
465                 470                 475                 480

Gln Ile Glu His Tyr Ser Met Asp Asp Leu Ala Ser Leu Lys Ile Pro
                485                 490                 495

Glu Gln Phe Arg His Ala Ile Trp Lys Gly Ile Leu Asp His Arg Gln
                500                 505                 510

Leu His Glu Phe Ser Ser Pro Ser His Leu Leu Arg Thr Pro Ser Ser
                515                 520                 525

Ala Ser Thr Val Ser Val Gly Ser Ser Glu Thr Arg Gly Glu Arg Val
                530                 535                 540

Ile Asp Ala Val Arg Phe Thr Leu Arg Gln Thr Ile Ser Phe Pro Pro
545                 550                 555                 560

Arg Asp Glu Trp Asn Asp Phe Asn Phe Asp Met Asp Ala Arg Arg Asn
                565                 570                 575

Lys Gln Gln Arg Ile Lys Glu Glu Gly Glu
                580                 585

<210> SEQ ID NO 339
<211> LENGTH: 641
<212> TYPE: PRT
<213> ORGANISM: Homo sapiens

<400> SEQUENCE: 339

Met Ser Gln Ser Thr Gln Thr Asn Glu Phe Leu Ser Pro Glu Val Phe
                5                   10                  15

Gln His Ile Trp Asp Phe Leu Glu Gln Pro Ile Cys Ser Val Gln Pro
                20                  25                  30

Ile Asp Leu Asn Phe Val Asp Glu Pro Ser Glu Asp Gly Ala Thr Asn
            35                  40                  45

Lys Ile Glu Ile Ser Met Asp Cys Ile Arg Met Gln Asp Ser Asp Leu
50                  55                  60

Ser Asp Pro Met Trp Pro Gln Tyr Thr Asn Leu Gly Leu Leu Asn Ser
65                  70                  75                  80

Met Asp Gln Gln Ile Gln Asn Gly Ser Ser Ser Thr Ser Pro Tyr Asn
                85                  90                  95

Thr Asp His Ala Gln Asn Ser Val Thr Ala Pro Ser Pro Tyr Ala Gln
                100                 105                 110

Pro Ser Ser Thr Phe Asp Ala Leu Ser Pro Ser Pro Ala Ile Pro Ser
                115                 120                 125

Asn Thr Asp Tyr Pro Gly Pro His Ser Phe Asp Val Ser Phe Gln Gln
                130                 135                 140

Ser Ser Thr Ala Lys Ser Ala Thr Trp Thr Tyr Ser Thr Glu Leu Lys
145                 150                 155                 160
```

-continued

```
Lys Leu Tyr Cys Gln Ile Ala Lys Thr Cys Pro Ile Gln Ile Lys Val
                165                 170                 175

Met Thr Pro Pro Gln Gly Ala Val Ile Arg Ala Met Pro Val Tyr
            180                 185                 190

Lys Lys Ala Glu His Val Thr Glu Val Val Lys Arg Cys Pro Asn His
        195                 200                 205

Glu Leu Ser Arg Glu Phe Asn Glu Gly Gln Ile Ala Pro Pro Ser His
    210                 215                 220

Leu Ile Arg Val Glu Gly Asn Ser His Ala Gln Tyr Val Glu Asp Pro
225                 230                 235                 240

Ile Thr Gly Arg Gln Ser Val Leu Val Pro Tyr Glu Pro Pro Gln Val
                245                 250                 255

Gly Thr Glu Phe Thr Thr Val Leu Tyr Asn Phe Met Cys Asn Ser Ser
            260                 265                 270

Cys Val Gly Gly Met Asn Arg Arg Pro Ile Leu Ile Ile Val Thr Leu
        275                 280                 285

Glu Thr Arg Asp Gly Gln Val Leu Gly Arg Arg Cys Phe Glu Ala Arg
    290                 295                 300

Ile Cys Ala Cys Pro Gly Arg Asp Arg Lys Ala Asp Glu Asp Ser Ile
305                 310                 315                 320

Arg Lys Gln Gln Val Ser Asp Ser Thr Lys Asn Gly Asp Gly Thr Lys
                325                 330                 335

Arg Pro Phe Arg Gln Asn Thr His Gly Ile Gln Met Thr Ser Ile Lys
            340                 345                 350

Lys Arg Arg Ser Pro Asp Asp Glu Leu Leu Tyr Leu Pro Val Arg Gly
        355                 360                 365

Arg Glu Thr Tyr Glu Met Leu Leu Lys Ile Lys Glu Ser Leu Glu Leu
    370                 375                 380

Met Gln Tyr Leu Pro Gln His Thr Ile Glu Thr Tyr Arg Gln Gln Gln
385                 390                 395                 400

Gln Gln Gln His Gln His Leu Leu Gln Lys Gln Thr Ser Ile Gln Ser
                405                 410                 415

Pro Ser Ser Tyr Gly Asn Ser Ser Pro Leu Asn Lys Met Asn Ser
            420                 425                 430

Met Asn Lys Leu Pro Ser Val Ser Gln Leu Ile Asn Pro Gln Gln Arg
        435                 440                 445

Asn Ala Leu Thr Pro Thr Thr Ile Pro Asp Gly Met Gly Ala Asn Ile
    450                 455                 460

Pro Met Met Gly Thr His Met Pro Met Ala Gly Asp Met Asn Gly Leu
465                 470                 475                 480

Ser Pro Thr Gln Ala Leu Pro Pro Leu Ser Met Pro Ser Thr Ser
            485                 490                 495

His Cys Thr Pro Pro Pro Tyr Pro Thr Asp Cys Ser Ile Val Gly
        500                 505                 510

Phe Leu Ala Arg Leu Gly Cys Ser Ser Cys Leu Asp Tyr Phe Thr Thr
    515                 520                 525

Gln Gly Leu Thr Thr Ile Tyr Gln Ile Glu His Tyr Ser Met Asp Asp
530                 535                 540

Leu Ala Ser Leu Lys Ile Pro Glu Gln Phe Arg His Ala Ile Trp Lys
545                 550                 555                 560

Gly Ile Leu Asp His Arg Gln Leu His Glu Phe Ser Ser Pro Ser His
                565                 570                 575

Leu Leu Arg Thr Pro Ser Ser Ala Ser Thr Val Ser Val Gly Ser Ser
```

-continued

```
                    580                 585                 590
Glu Thr Arg Gly Glu Arg Val Ile Asp Ala Val Arg Phe Thr Leu Arg
                595                 600                 605

Gln Thr Ile Ser Phe Pro Pro Arg Asp Glu Trp Asn Asp Phe Asn Phe
            610                 615                 620

Asp Met Asp Ala Arg Arg Asn Lys Gln Gln Arg Ile Lys Glu Glu Gly
625                 630                 635                 640

Glu

<210> SEQ ID NO 340
<211> LENGTH: 448
<212> TYPE: PRT
<213> ORGANISM: Homo sapiens

<400> SEQUENCE: 340

Met Ser Gln Ser Thr Gln Thr Asn Glu Phe Leu Ser Pro Glu Val Phe
                  5                  10                  15

Gln His Ile Trp Asp Phe Leu Glu Gln Pro Ile Cys Ser Val Gln Pro
             20                  25                  30

Ile Asp Leu Asn Phe Val Asp Glu Pro Ser Glu Asp Gly Ala Thr Asn
         35                  40                  45

Lys Ile Glu Ile Ser Met Asp Cys Ile Arg Met Gln Asp Ser Asp Leu
     50                  55                  60

Ser Asp Pro Met Trp Pro Gln Tyr Thr Asn Leu Gly Leu Leu Asn Ser
 65                  70                  75                  80

Met Asp Gln Gln Ile Gln Asn Gly Ser Ser Ser Thr Ser Pro Tyr Asn
                 85                  90                  95

Thr Asp His Ala Gln Asn Ser Val Thr Ala Pro Ser Pro Tyr Ala Gln
            100                 105                 110

Pro Ser Ser Thr Phe Asp Ala Leu Ser Pro Ser Pro Ala Ile Pro Ser
        115                 120                 125

Asn Thr Asp Tyr Pro Gly Pro His Ser Phe Asp Val Ser Phe Gln Gln
    130                 135                 140

Ser Ser Thr Ala Lys Ser Ala Thr Trp Thr Tyr Ser Thr Glu Leu Lys
145                 150                 155                 160

Lys Leu Tyr Cys Gln Ile Ala Lys Thr Cys Pro Ile Gln Ile Lys Val
                165                 170                 175

Met Thr Pro Pro Pro Gln Gly Ala Val Ile Arg Ala Met Pro Val Tyr
            180                 185                 190

Lys Lys Ala Glu His Val Thr Glu Val Val Lys Arg Cys Pro Asn His
        195                 200                 205

Glu Leu Ser Arg Glu Phe Asn Glu Gly Gln Ile Ala Pro Pro Ser His
    210                 215                 220

Leu Ile Arg Val Glu Gly Asn Ser His Ala Gln Tyr Val Glu Asp Pro
225                 230                 235                 240

Ile Thr Gly Arg Gln Ser Val Leu Val Pro Tyr Glu Pro Pro Gln Val
                245                 250                 255

Gly Thr Glu Phe Thr Thr Val Leu Tyr Asn Phe Met Cys Asn Ser Ser
            260                 265                 270

Cys Val Gly Gly Met Asn Arg Arg Pro Ile Leu Ile Ile Val Thr Leu
        275                 280                 285

Glu Thr Arg Asp Gly Gln Val Leu Gly Arg Arg Cys Phe Glu Ala Arg
    290                 295                 300

Ile Cys Ala Cys Pro Gly Arg Asp Arg Lys Ala Asp Glu Asp Ser Ile
```

-continued

```
            305                 310                 315                 320

Arg Lys Gln Gln Val Ser Asp Ser Thr Lys Asn Gly Asp Gly Thr Lys
                325                 330                 335

Arg Pro Phe Arg Gln Asn Thr His Gly Ile Gln Met Thr Ser Ile Lys
                340                 345                 350

Lys Arg Arg Ser Pro Asp Asp Glu Leu Leu Tyr Leu Pro Val Arg Gly
                355                 360                 365

Arg Glu Thr Tyr Glu Met Leu Leu Lys Ile Lys Glu Ser Leu Glu Leu
                370                 375                 380

Met Gln Tyr Leu Pro Gln His Thr Ile Glu Thr Tyr Arg Gln Gln Gln
385                 390                 395                 400

Gln Gln Gln His Gln His Leu Leu Gln Lys His Leu Leu Ser Ala Cys
                405                 410                 415

Phe Arg Asn Glu Leu Val Glu Pro Arg Arg Glu Thr Pro Lys Gln Ser
                420                 425                 430

Asp Val Phe Phe Arg His Ser Lys Pro Pro Asn Arg Ser Val Tyr Pro
                435                 440                 445

<210> SEQ ID NO 341
<211> LENGTH: 356
<212> TYPE: PRT
<213> ORGANISM: Homo sapiens

<400> SEQUENCE: 341

Met Leu Tyr Leu Glu Asn Asn Ala Gln Thr Gln Phe Ser Glu Pro Gln
                  5                  10                  15

Tyr Thr Asn Leu Gly Leu Leu Asn Ser Met Asp Gln Gln Ile Gln Asn
                 20                  25                  30

Gly Ser Ser Ser Thr Ser Pro Tyr Asn Thr Asp His Ala Gln Asn Ser
             35                  40                  45

Val Thr Ala Pro Ser Pro Tyr Ala Gln Pro Ser Ser Thr Phe Asp Ala
         50                  55                  60

Leu Ser Pro Ser Pro Ala Ile Pro Ser Asn Thr Asp Tyr Pro Gly Pro
 65                  70                  75                  80

His Ser Phe Asp Val Ser Phe Gln Gln Ser Ser Thr Ala Lys Ser Ala
                 85                  90                  95

Thr Trp Thr Tyr Ser Thr Glu Leu Lys Lys Leu Tyr Cys Gln Ile Ala
                100                 105                 110

Lys Thr Cys Pro Ile Gln Ile Lys Val Met Thr Pro Pro Gln Gly
            115                 120                 125

Ala Val Ile Arg Ala Met Pro Val Tyr Lys Lys Ala Glu His Val Thr
        130                 135                 140

Glu Val Val Lys Arg Cys Pro Asn His Glu Leu Ser Arg Glu Phe Asn
145                 150                 155                 160

Glu Gly Gln Ile Ala Pro Pro Ser His Leu Ile Arg Val Glu Gly Asn
                165                 170                 175

Ser His Ala Gln Tyr Val Glu Asp Pro Ile Thr Gly Arg Gln Ser Val
            180                 185                 190

Leu Val Pro Tyr Glu Pro Pro Gln Val Gly Thr Glu Phe Thr Thr Val
        195                 200                 205

Leu Tyr Asn Phe Met Cys Asn Ser Ser Cys Val Gly Gly Met Asn Arg
    210                 215                 220

Arg Pro Ile Leu Ile Ile Val Thr Leu Glu Thr Arg Asp Gly Gln Val
225                 230                 235                 240
```

-continued

```
Leu Gly Arg Arg Cys Phe Glu Ala Arg Ile Cys Ala Cys Pro Gly Arg
                245                 250                 255

Asp Arg Lys Ala Asp Glu Asp Ser Ile Arg Lys Gln Gln Val Ser Asp
            260                 265                 270

Ser Thr Lys Asn Gly Asp Gly Thr Lys Arg Pro Ser Arg Gln Asn Thr
        275                 280                 285

His Gly Ile Gln Met Thr Ser Ile Lys Lys Arg Ser Pro Asp Asp
    290                 295                 300

Glu Leu Leu Tyr Leu Pro Val Arg Gly Arg Glu Thr Tyr Glu Met Leu
305                 310                 315                 320

Leu Lys Ile Lys Glu Ser Leu Glu Leu Met Gln Tyr Leu Pro Gln His
                325                 330                 335

Thr Ile Glu Thr Tyr Arg Gln Gln Gln Gln Gln His Gln His Leu
                340                 345                 350

Leu Gln Lys Gln
        355

<210> SEQ ID NO 342
<211> LENGTH: 680
<212> TYPE: PRT
<213> ORGANISM: Homo sapiens

<400> SEQUENCE: 342

Met Asn Phe Glu Thr Ser Arg Cys Ala Thr Leu Gln Tyr Cys Pro Asp
                5                   10                  15

Pro Tyr Ile Gln Arg Phe Val Glu Thr Pro Ala His Phe Ser Trp Lys
            20                  25                  30

Glu Ser Tyr Tyr Arg Ser Thr Met Ser Gln Ser Thr Gln Thr Asn Glu
        35                  40                  45

Phe Leu Ser Pro Glu Val Phe Gln His Ile Trp Asp Phe Leu Glu Gln
    50                  55                  60

Pro Ile Cys Ser Val Gln Pro Ile Asp Leu Asn Phe Val Asp Glu Pro
65                  70                  75                  80

Ser Glu Asp Gly Ala Thr Asn Lys Ile Glu Ile Ser Met Asp Cys Ile
                85                  90                  95

Arg Met Gln Asp Ser Asp Leu Ser Asp Pro Met Trp Pro Gln Tyr Thr
            100                 105                 110

Asn Leu Gly Leu Leu Asn Ser Met Asp Gln Gln Ile Gln Asn Gly Ser
        115                 120                 125

Ser Ser Thr Ser Pro Tyr Asn Thr Asp His Ala Gln Asn Ser Val Thr
    130                 135                 140

Ala Pro Ser Pro Tyr Ala Gln Pro Ser Ser Thr Phe Asp Ala Leu Ser
145                 150                 155                 160

Pro Ser Pro Ala Ile Pro Ser Asn Thr Asp Tyr Pro Gly Pro His Ser
                165                 170                 175

Phe Asp Val Ser Phe Gln Gln Ser Ser Thr Ala Lys Ser Ala Thr Trp
            180                 185                 190

Thr Tyr Ser Thr Glu Leu Lys Lys Leu Tyr Cys Gln Ile Ala Lys Thr
        195                 200                 205

Cys Pro Ile Gln Ile Lys Val Met Thr Pro Pro Gln Gly Ala Val
    210                 215                 220

Ile Arg Ala Met Pro Val Tyr Lys Lys Ala Glu His Val Thr Glu Val
225                 230                 235                 240

Val Lys Arg Cys Pro Asn His Glu Leu Ser Arg Glu Phe Asn Glu Gly
                245                 250                 255
```

-continued

```
Gln Ile Ala Pro Pro Ser His Leu Ile Arg Val Glu Gly Asn Ser His
            260                 265                 270

Ala Gln Tyr Val Glu Asp Pro Ile Thr Gly Arg Gln Ser Val Leu Val
        275                 280                 285

Pro Tyr Glu Pro Pro Gln Val Gly Thr Glu Phe Thr Thr Val Leu Tyr
    290                 295                 300

Asn Phe Met Cys Asn Ser Ser Cys Val Gly Met Asn Arg Arg Pro
305                 310                 315                 320

Ile Leu Ile Ile Val Thr Leu Glu Thr Arg Asp Gly Gln Val Leu Gly
                325                 330                 335

Arg Arg Cys Phe Glu Ala Arg Ile Cys Ala Cys Pro Gly Arg Asp Arg
            340                 345                 350

Lys Ala Asp Glu Asp Ser Ile Arg Lys Gln Gln Val Ser Asp Ser Thr
        355                 360                 365

Lys Asn Gly Asp Gly Thr Lys Arg Pro Phe Arg Gln Asn Thr His Gly
    370                 375                 380

Ile Gln Met Thr Ser Ile Lys Lys Arg Ser Pro Asp Asp Glu Leu
385                 390                 395                 400

Leu Tyr Leu Pro Val Arg Gly Arg Glu Thr Tyr Glu Met Leu Leu Lys
                405                 410                 415

Ile Lys Glu Ser Leu Glu Leu Met Gln Tyr Leu Pro Gln His Thr Ile
            420                 425                 430

Glu Thr Tyr Arg Gln Gln Gln Gln Gln His Gln His Leu Leu Gln
        435                 440                 445

Lys Gln Thr Ser Ile Gln Ser Pro Ser Ser Tyr Gly Asn Ser Ser Pro
    450                 455                 460

Pro Leu Asn Lys Met Asn Ser Met Asn Lys Leu Pro Ser Val Ser Gln
465                 470                 475                 480

Leu Ile Asn Pro Gln Gln Arg Asn Ala Leu Thr Pro Thr Thr Ile Pro
                485                 490                 495

Asp Gly Met Gly Ala Asn Ile Pro Met Met Gly Thr His Met Pro Met
            500                 505                 510

Ala Gly Asp Met Asn Gly Leu Ser Pro Thr Gln Ala Leu Pro Pro Pro
        515                 520                 525

Leu Ser Met Pro Ser Thr Ser Gln Cys Thr Pro Pro Pro Tyr Pro
    530                 535                 540

Thr Asp Cys Ser Ile Val Ser Phe Leu Ala Arg Leu Gly Cys Ser Ser
545                 550                 555                 560

Cys Leu Asp Tyr Phe Thr Thr Gln Gly Leu Thr Thr Ile Tyr Gln Ile
                565                 570                 575

Glu His Tyr Ser Met Asp Asp Leu Ala Ser Leu Lys Ile Pro Glu Gln
            580                 585                 590

Phe Arg His Ala Ile Trp Lys Gly Ile Leu Asp His Arg Gln Leu His
        595                 600                 605

Glu Phe Ser Ser Pro Ser His Leu Leu Arg Thr Pro Ser Ser Ala Ser
    610                 615                 620

Thr Val Ser Val Gly Ser Ser Glu Thr Arg Gly Glu Arg Val Ile Asp
625                 630                 635                 640

Ala Val Arg Phe Thr Leu Arg Gln Thr Ile Ser Phe Pro Pro Arg Asp
                645                 650                 655

Glu Trp Asn Asp Phe Asn Phe Asp Met Asp Ala Arg Arg Asn Lys Gln
            660                 665                 670
```

```
Gln Arg Ile Lys Glu Glu Gly Glu
        675             680
```

<210> SEQ ID NO 343
<211> LENGTH: 461
<212> TYPE: PRT
<213> ORGANISM: Homo sapiens

<400> SEQUENCE: 343

```
Met Leu Tyr Leu Glu Asn Asn Ala Gln Thr Gln Phe Ser Glu Pro Gln
              5                  10                  15

Tyr Thr Asn Leu Gly Leu Leu Asn Ser Met Asp Gln Gln Ile Gln Asn
             20                  25                  30

Gly Ser Ser Thr Ser Pro Tyr Asn Thr Asp His Ala Gln Asn Ser
         35                  40                  45

Val Thr Ala Pro Ser Pro Tyr Ala Gln Pro Ser Ser Thr Phe Asp Ala
     50                  55                  60

Leu Ser Pro Ser Pro Ala Ile Pro Ser Asn Thr Asp Tyr Pro Gly Pro
 65                  70                  75                  80

His Ser Phe Asp Val Ser Phe Gln Gln Ser Ser Thr Ala Lys Ser Ala
                 85                  90                  95

Thr Trp Thr Tyr Ser Thr Glu Leu Lys Lys Leu Tyr Cys Gln Ile Ala
            100                 105                 110

Lys Thr Cys Pro Ile Gln Ile Lys Val Met Thr Pro Pro Gln Gly
        115                 120                 125

Ala Val Ile Arg Ala Met Pro Val Tyr Lys Lys Ala Glu His Val Thr
    130                 135                 140

Glu Val Val Lys Arg Cys Pro Asn His Glu Leu Ser Arg Glu Phe Asn
145                 150                 155                 160

Glu Gly Gln Ile Ala Pro Pro Ser His Leu Ile Arg Val Glu Gly Asn
                165                 170                 175

Ser His Ala Gln Tyr Val Glu Asp Pro Ile Thr Gly Arg Gln Ser Val
            180                 185                 190

Leu Val Pro Tyr Glu Pro Pro Gln Val Gly Thr Glu Phe Thr Thr Val
        195                 200                 205

Leu Tyr Asn Phe Met Cys Asn Ser Ser Cys Val Gly Gly Met Asn Arg
    210                 215                 220

Arg Pro Ile Leu Ile Ile Val Thr Leu Glu Thr Arg Asp Gly Gln Val
225                 230                 235                 240

Leu Gly Arg Arg Cys Phe Glu Ala Arg Ile Cys Ala Cys Pro Gly Arg
                245                 250                 255

Asp Arg Lys Ala Asp Glu Asp Ser Ile Arg Lys Gln Gln Val Ser Asp
            260                 265                 270

Ser Thr Lys Asn Gly Asp Gly Thr Lys Arg Pro Phe Arg Gln Asn Thr
        275                 280                 285

His Gly Ile Gln Met Thr Ser Ile Lys Lys Arg Arg Ser Pro Asp Asp
    290                 295                 300

Glu Leu Leu Tyr Leu Pro Val Arg Gly Arg Glu Thr Tyr Glu Met Leu
305                 310                 315                 320

Leu Lys Ile Lys Glu Ser Leu Glu Leu Met Gln Tyr Leu Pro Gln His
                325                 330                 335

Thr Ile Glu Thr Tyr Arg Gln Gln Gln Gln Gln His Gln His Leu
            340                 345                 350

Leu Gln Lys Gln Thr Ser Ile Gln Ser Pro Ser Ser Tyr Gly Asn Ser
        355                 360                 365
```

-continued

Ser Pro Pro Leu Asn Lys Met Asn Ser Met Asn Lys Leu Pro Ser Val
        370                 375                 380

Ser Gln Leu Ile Asn Pro Gln Gln Arg Asn Ala Leu Thr Pro Thr Thr
385                 390                 395                 400

Ile Pro Asp Gly Met Gly Ala Asn Ile Pro Met Met Gly Thr His Met
                405                 410                 415

Pro Met Ala Gly Asp Met Asn Gly Leu Ser Pro Thr Gln Ala Leu Pro
                420                 425                 430

Pro Pro Leu Ser Met Pro Ser Thr Ser His Cys Thr Pro Pro Pro Pro
        435                 440                 445

Tyr Pro Thr Asp Cys Ser Ile Val Arg Ile Trp Gln Val
        450                 455                 460

<210> SEQ ID NO 344
<211> LENGTH: 516
<212> TYPE: PRT
<213> ORGANISM: Homo sapiens

<400> SEQUENCE: 344

Met Ser Gln Ser Thr Gln Thr Asn Glu Phe Leu Ser Pro Glu Val Phe
                5                   10                  15

Gln His Ile Trp Asp Phe Leu Glu Gln Pro Ile Cys Ser Val Gln Pro
            20                  25                  30

Ile Asp Leu Asn Phe Val Asp Glu Pro Ser Glu Asp Gly Ala Thr Asn
        35                  40                  45

Lys Ile Glu Ile Ser Met Asp Cys Ile Arg Met Gln Asp Ser Asp Leu
    50                  55                  60

Ser Asp Pro Met Trp Pro Gln Tyr Thr Asn Leu Gly Leu Leu Asn Ser
65                  70                  75                  80

Met Asp Gln Gln Ile Gln Asn Gly Ser Ser Ser Thr Ser Pro Tyr Asn
                85                  90                  95

Thr Asp His Ala Gln Asn Ser Val Thr Ala Pro Ser Pro Tyr Ala Gln
            100                 105                 110

Pro Ser Ser Thr Phe Asp Ala Leu Ser Pro Ser Pro Ala Ile Pro Ser
        115                 120                 125

Asn Thr Asp Tyr Pro Gly Pro His Ser Phe Asp Val Ser Phe Gln Gln
    130                 135                 140

Ser Ser Thr Ala Lys Ser Ala Thr Trp Thr Tyr Ser Thr Glu Leu Lys
145                 150                 155                 160

Lys Leu Tyr Cys Gln Ile Ala Lys Thr Cys Pro Ile Gln Ile Lys Val
                165                 170                 175

Met Thr Pro Pro Pro Gln Gly Ala Val Ile Arg Ala Met Pro Val Tyr
            180                 185                 190

Lys Lys Ala Glu His Val Thr Glu Val Val Lys Arg Cys Pro Asn His
        195                 200                 205

Glu Leu Ser Arg Glu Phe Asn Glu Gly Gln Ile Ala Pro Pro Ser His
    210                 215                 220

Leu Ile Arg Val Glu Gly Asn Ser His Ala Gln Tyr Val Glu Asp Pro
225                 230                 235                 240

Ile Thr Gly Arg Gln Ser Val Leu Val Pro Tyr Glu Pro Pro Gln Val
                245                 250                 255

Gly Thr Glu Phe Thr Thr Val Leu Tyr Asn Phe Met Cys Asn Ser Ser
            260                 265                 270

Cys Val Gly Gly Met Asn Arg Arg Pro Ile Leu Ile Ile Val Thr Leu

```
                275                 280                 285
Glu Thr Arg Asp Gly Gln Val Leu Gly Arg Arg Cys Phe Glu Ala Arg
            290                 295                 300
Ile Cys Ala Cys Pro Gly Arg Asp Arg Lys Ala Asp Glu Asp Ser Ile
305                 310                 315                 320
Arg Lys Gln Gln Val Ser Asp Ser Thr Lys Asn Gly Asp Gly Thr Lys
                325                 330                 335
Arg Pro Phe Arg Gln Asn Thr His Gly Ile Gln Met Thr Ser Ile Lys
            340                 345                 350
Lys Arg Arg Ser Pro Asp Asp Glu Leu Leu Tyr Leu Pro Val Arg Gly
                355                 360                 365
Arg Glu Thr Tyr Glu Met Leu Leu Lys Ile Lys Glu Ser Leu Glu Leu
            370                 375                 380
Met Gln Tyr Leu Pro Gln His Thr Ile Glu Thr Tyr Arg Gln Gln Gln
385                 390                 395                 400
Gln Gln Gln His Gln His Leu Leu Gln Lys Gln Thr Ser Ile Gln Ser
                405                 410                 415
Pro Ser Ser Tyr Gly Asn Ser Ser Pro Leu Asn Lys Met Asn Ser
            420                 425                 430
Met Asn Lys Leu Pro Ser Val Ser Gln Leu Ile Asn Pro Gln Gln Arg
            435                 440                 445
Asn Ala Leu Thr Pro Thr Thr Ile Pro Asp Gly Met Gly Ala Asn Ile
450                 455                 460
Pro Met Met Gly Thr His Met Pro Met Ala Gly Asp Met Asn Gly Leu
465                 470                 475                 480
Ser Pro Thr Gln Ala Leu Pro Pro Pro Leu Ser Met Pro Ser Thr Ser
                485                 490                 495
His Cys Thr Pro Pro Pro Tyr Pro Thr Asp Cys Ser Ile Val Arg
                500                 505                 510
Ile Trp Gln Val
        515

<210> SEQ ID NO 345
<211> LENGTH: 1800
<212> TYPE: DNA
<213> ORGANISM: Homo sapiens

<400> SEQUENCE: 345
gcgcctcatt gccactgcag tgactaaagc tgggaagacg ctggtcagtt cacctgcccc     60
actggttgtt tttaaacaa attctgatac aggcgacatc ctcactgacc gagcaaagat    120
tgacattcgt atcatcactg tgcaccattg gcttctaggc actccagtgg ggtaggagaa    180
ggaggtctga aaccctcgca gagggatctt gccctcattc tttgggtctg aaacactggc    240
agtcgttgga aacaggactc aggataaaac cagcgcaatg gattggggga cgctgcacac    300
tttcatcggg ggtgtcaaca aacactccac cagcatcggg aaggtgtgga tcacagtcat    360
ctttattttc cgagtcatga tcctagtggt ggctgcccag gaagtgtggg gtgacgagca    420
agaggacttc gtctgcaaca cactgcaacc gggatgcaaa aatgtgtgct atgaccactt    480
tttcccggtg tcccacatcc ggctgtgggc cctccagctg atcttcgtct ccaccccagc    540
gctgctggtg gccatgcatg tggcctacta caggcacgaa accactcgca agttcaggcg    600
aggagagaag aggaatgatt tcaaagacat agaggacatt aaaaagcaca aggttcggat    660
agaggggtcg ctgtggtgga cgtacaccag cagcatcttt ttccgaatca tctttgaagc    720
```

-continued

```
agcctttatg tatgtgtttt acttccttta caatgggtac cacctgccct gggtgttgaa    780
atgtgggatt gacccctgcc ccaaccttgt tgactgcttt atttctaggc aacagagaa     840
gaccgtgttt accattttta tgatttctgc gtctgtgatt tgcatgctgc ttaacgtggc    900
agagttgtgc tacctgctgc tgaaagtgtg ttttaggaga tcaaagagag cacagacgca    960
aaaaaatcac cccaatcatg ccctaaagga gagtaagcag aatgaaatga atgagctgat   1020
ttcagatagt ggtcaaaatg caatcacagg tttcccaagc taaacatttc aaggtaaaat   1080
gtagctgcgt cataaggaga cttctgtctt ctccagaagg caataccaac ctgaaagttc   1140
cttctgtagc ctgaagagtt tgtaaatgac tttcataata aatagacact tgagttaact   1200
ttttgtagga tacttgctcc attcatacac aacgtaatca aatatgtggt ccatctctga   1260
aaacaagaga ctgcttgaca aaggagcatt gcagtcactt tgacaggttc cttttaagtg   1320
gactctctga caaagtgggt actttctgaa aatttatata actgttgttg ataaggaaca   1380
tttatccagg aattgatacg tttattagga aaagatattt ttataggctt ggatgttttt   1440
agttccgact ttgaatttat ataaagtatt tttataatga ctggtcttcc ttacctggaa   1500
aaacatgcga tgttagtttt agaattacac cacaagtatc taaatttcca acttacaaag   1560
ggtcctatct tgtaaatatt gttttgcatt gtctgttggc aaatttgtga actgtcatga   1620
tacgcttaag gtgggaaagt gttcattgca caatatattt ttactgcttt ctgaatgtag   1680
acggaacagt gtggaagcag aaggcttttt taactcatcc gtttggccga tcgttgcaga   1740
ccactgggag atgtggatgt ggttgcctcc ttttgctcgt ccccgtggct taacccttct   1800
```

<210> SEQ ID NO 346
<211> LENGTH: 261
<212> TYPE: PRT
<213> ORGANISM: Homo sapiens

<400> SEQUENCE: 346

```
Met Asp Trp Gly Thr Leu His Thr Phe Ile Gly Gly Val Asn Lys His
                  5                  10                  15

Ser Thr Ser Ile Gly Lys Val Trp Ile Thr Val Ile Phe Ile Phe Arg
             20                  25                  30

Val Met Ile Leu Val Val Ala Ala Gln Glu Val Trp Gly Asp Glu Gln
         35                  40                  45

Glu Asp Phe Val Cys Asn Thr Leu Gln Pro Gly Cys Lys Asn Val Cys
     50                  55                  60

Tyr Asp His Phe Phe Pro Val Ser His Ile Arg Leu Trp Ala Leu Gln
 65                  70                  75                  80

Leu Ile Phe Val Ser Thr Pro Ala Leu Leu Val Ala Met His Val Ala
                 85                  90                  95

Tyr Tyr Arg His Glu Thr Thr Arg Lys Phe Arg Arg Gly Glu Lys Arg
            100                 105                 110

Asn Asp Phe Lys Asp Ile Glu Asp Ile Lys Lys His Lys Val Arg Ile
        115                 120                 125

Glu Gly Ser Leu Trp Trp Thr Tyr Thr Ser Ser Ile Phe Phe Arg Ile
    130                 135                 140

Ile Phe Glu Ala Ala Phe Met Tyr Val Phe Tyr Phe Leu Tyr Asn Gly
145                 150                 155                 160

Tyr His Leu Pro Trp Val Leu Lys Cys Gly Ile Asp Pro Cys Pro Asn
                165                 170                 175

Leu Val Asp Cys Phe Ile Ser Arg Pro Thr Glu Lys Thr Val Phe Thr
            180                 185                 190
```

```
Ile Phe Met Ile Ser Ala Ser Val Ile Cys Met Leu Leu Asn Val Ala
            195                 200                 205

Glu Leu Cys Tyr Leu Leu Lys Val Cys Phe Arg Arg Ser Lys Arg
    210                 215                 220

Ala Gln Thr Gln Lys Asn His Pro Asn His Ala Leu Lys Glu Ser Lys
225                 230                 235                 240

Gln Asn Glu Met Asn Glu Leu Ile Ser Asp Ser Gly Gln Asn Ala Ile
                245                 250                 255

Thr Gly Phe Pro Ser
            260

<210> SEQ ID NO 347
<211> LENGTH: 1740
<212> TYPE: DNA
<213> ORGANISM: Homo sapiens

<400> SEQUENCE: 347
atgaacaaac tgtatatcgg aaacctcagc gagaacgccg cccccctcgga cctagaaagt      60 atcttcaagg acgccaagat cccggtgtcg ggacccttcc tggtgaagac tggctacgcg     120
ttcgtggact gcccggacga gagctgggcc ctcaaggcca tcgaggcgct ttcaggtaaa     180
atagaactgc acgggaaacc catagaagtt gagcactcgg tcccaaaaag gcaaaggatt     240
cggaaacttc agatacgaaa tatcccgcct catttacagt gggaggtgct ggatagttta     300
ctagtccagt atggagtggt ggagagctgt gagcaagtga acactgactc ggaaactgca     360
gttgtaaatg taacctattc cagtaaggac caagctagac aagcactaga caaactgaat     420
ggatttcagt tagagaattt caccttgaaa gtagcctata tccctgatga aacggccgcc     480
cagcaaaacc ccttgcagca gccccgaggt cgccgggggc ttgggcagag gggctcctca     540
aggcaggggt ctccaggatc cgtatccaag cagaaaccat gtgatttgcc tctgcgcctg     600
ctggttccca cccaatttgt tggagccatc ataggaaaag aaggtgccac cattcggaac     660
atcaccaaac agacccagtc taaatcgat gtccaccgta agaaaatgc ggggctgct      720 gagaagtcga ttactatcct ctctactcct gaaggcacct ctgcggcttg taagtctatt     780
ctggagatta tgcataagga agctcaagat ataaaattca cagaagagat ccccttgaag     840
attttagctc ataataactt tgttggacgt cttattggta agaaggaag aaatcttaaa     900 aaaattgagc aagacacaga cactaaaatc acgatatctc cattgcagga attgacgctg     960
tataatccag aacgcactat tacagttaaa ggcaatgttg agacatgtgc caaagctgag    1020
gaggagatca tgaagaaaat cagggagtct tatgaaaatg atattgcttc tatgaatctt    1080
caagcacatt taattcctgg attaaatctg aacgccttgg gtctgttccc acccacttca    1140
gggatgccac ctcccacctc agggcccccct tcagccatga ctcctcccta cccgcagttt    1200
gagcaatcag aaacggagac tgttcatctg tttatcccag ctctatcagt cggtgccatc    1260
atcggcaagc agggccagca catcaagcag ctttctcgct tgctggagc ttcaattaag    1320 attgctccag cggaagcacc agatgctaaa gtgaggatgg tgattatcac tggaccacca    1380
gaggctcagt tcaaggctca gggaagaatt tatggaaaaa ttaaagaaga aactttgtt    1440 agtcctaaag aagaggtgaa acttgaagct catatcagag tgccatcctt tgctgctggc    1500
agagttattg gaaaggagg caaaacggta atgaacttc agaatttgtc aagtgcagaa    1560
gttgttgtcc ctcgtgacca gacacctgat gagaatgacc aagtggttgt caaaataact    1620
ggtcacttct atgcttgcca ggttgcccag agaaaaattc aggaaattct gactcaggta    1680
```

-continued aagcagcacc aacaacagaa ggctctgcaa agtggaccac ctcagtcaag acggaagtaa    1740

<210> SEQ ID NO 348
<211> LENGTH: 579
<212> TYPE: PRT
<213> ORGANISM: Homo sapiens

<400> SEQUENCE: 348

```
Met Asn Lys Leu Tyr Ile Gly Asn Leu Ser Glu Asn Ala Ala Pro Ser
                  5                  10                  15

Asp Leu Glu Ser Ile Phe Lys Asp Ala Lys Ile Pro Val Ser Gly Pro
             20                  25                  30

Phe Leu Val Lys Thr Gly Tyr Ala Phe Val Asp Cys Pro Asp Glu Ser
         35                  40                  45

Trp Ala Leu Lys Ala Ile Glu Ala Leu Ser Gly Lys Ile Glu Leu His
     50                  55                  60

Gly Lys Pro Ile Glu Val Glu His Ser Val Pro Lys Arg Gln Arg Ile
 65                  70                  75                  80

Arg Lys Leu Gln Ile Arg Asn Ile Pro Pro His Leu Gln Trp Glu Val
                 85                  90                  95

Leu Asp Ser Leu Leu Val Gln Tyr Gly Val Val Glu Ser Cys Glu Gln
            100                 105                 110

Val Asn Thr Asp Ser Glu Thr Ala Val Val Asn Val Thr Tyr Ser Ser
        115                 120                 125

Lys Asp Gln Ala Arg Gln Ala Leu Asp Lys Leu Asn Gly Phe Gln Leu
    130                 135                 140

Glu Asn Phe Thr Leu Lys Val Ala Tyr Ile Pro Asp Glu Thr Ala Ala
145                 150                 155                 160

Gln Gln Asn Pro Leu Gln Gln Pro Arg Gly Arg Arg Gly Leu Gly Gln
                165                 170                 175

Arg Gly Ser Ser Arg Gln Gly Ser Pro Gly Ser Val Ser Lys Gln Lys
            180                 185                 190

Pro Cys Asp Leu Pro Leu Arg Leu Val Pro Thr Gln Phe Val Gly
        195                 200                 205

Ala Ile Ile Gly Lys Glu Gly Ala Thr Ile Arg Asn Ile Thr Lys Gln
    210                 215                 220

Thr Gln Ser Lys Ile Asp Val His Arg Lys Glu Asn Ala Gly Ala Ala
225                 230                 235                 240

Glu Lys Ser Ile Thr Ile Leu Ser Thr Pro Glu Gly Thr Ser Ala Ala
                245                 250                 255

Cys Lys Ser Ile Leu Glu Ile Met His Lys Glu Ala Gln Asp Ile Lys
            260                 265                 270

Phe Thr Glu Glu Ile Pro Leu Lys Ile Leu Ala His Asn Asn Phe Val
        275                 280                 285

Gly Arg Leu Ile Gly Lys Glu Gly Arg Asn Leu Lys Lys Ile Glu Gln
    290                 295                 300

Asp Thr Asp Thr Lys Ile Thr Ile Ser Pro Leu Gln Glu Leu Thr Leu
305                 310                 315                 320

Tyr Asn Pro Glu Arg Thr Ile Thr Val Lys Gly Asn Val Glu Thr Cys
                325                 330                 335

Ala Lys Ala Glu Glu Glu Ile Met Lys Lys Ile Arg Glu Ser Tyr Glu
            340                 345                 350

Asn Asp Ile Ala Ser Met Asn Leu Gln Ala His Leu Ile Pro Gly Leu
        355                 360                 365
```

```
Asn Leu Asn Ala Leu Gly Leu Phe Pro Pro Thr Ser Gly Met Pro Pro
    370                 375                 380

Pro Thr Ser Gly Pro Pro Ser Ala Met Thr Pro Pro Tyr Pro Gln Phe
385                 390                 395                 400

Glu Gln Ser Glu Thr Glu Thr Val His Leu Phe Ile Pro Ala Leu Ser
                405                 410                 415

Val Gly Ala Ile Ile Gly Lys Gln Gly Gln His Ile Lys Gln Leu Ser
            420                 425                 430

Arg Phe Ala Gly Ala Ser Ile Lys Ile Ala Pro Ala Glu Ala Pro Asp
        435                 440                 445

Ala Lys Val Arg Met Val Ile Ile Thr Gly Pro Pro Glu Ala Gln Phe
    450                 455                 460

Lys Ala Gln Gly Arg Ile Tyr Gly Lys Ile Lys Glu Glu Asn Phe Val
465                 470                 475                 480

Ser Pro Lys Glu Glu Val Lys Leu Glu Ala His Ile Arg Val Pro Ser
                485                 490                 495

Phe Ala Ala Gly Arg Val Ile Gly Lys Gly Gly Lys Thr Val Asn Glu
            500                 505                 510

Leu Gln Asn Leu Ser Ser Ala Glu Val Val Val Pro Arg Asp Gln Thr
        515                 520                 525

Pro Asp Glu Asn Asp Gln Val Val Val Lys Ile Thr Gly His Phe Tyr
    530                 535                 540

Ala Cys Gln Val Ala Gln Arg Lys Ile Gln Glu Ile Leu Thr Gln Val
545                 550                 555                 560

Lys Gln His Gln Gln Gln Lys Ala Leu Gln Ser Gly Pro Pro Gln Ser
                565                 570                 575

Arg Arg Lys

<210> SEQ ID NO 349
<211> LENGTH: 207
<212> TYPE: DNA
<213> ORGANISM: Homo sapiens

<400> SEQUENCE: 349
atgtggcagc ccctcttctt caagtggctc ttgtcctgtt gccctgggag ttctcaaatt    60
gctgcagcag cctccaccca gcctgaggat gacatcaata cacagaggaa gagagtcag   120 gaaaagatga gagaagttac agactctcct gggcgacccc gagagcttac cattcctcag   180
acttcttcac atggtgctaa cagattt                                      207

<210> SEQ ID NO 350
<211> LENGTH: 69
<212> TYPE: PRT
<213> ORGANISM: Homo sapiens

<400> SEQUENCE: 350

Met Trp Gln Pro Leu Phe Phe Lys Trp Leu Leu Ser Cys Cys Pro Gly
                5                   10                  15

Ser Ser Gln Ile Ala Ala Ala Ala Ser Thr Gln Pro Glu Asp Asp Ile
            20                  25                  30

Asn Thr Gln Arg Lys Lys Ser Gln Glu Lys Met Arg Glu Val Thr Asp
        35                  40                  45
```

```
                                    -continued
Ser Pro Gly Arg Pro Arg Glu Leu Thr Ile Pro Gln Thr Ser Ser His
    50                  55                  60
Gly Ala Asn Arg Phe
65
```